(12) United States Patent
Schoenfisch et al.

(10) Patent No.: US 11,026,965 B2
(45) Date of Patent: Jun. 8, 2021

(54) NITRIC OXIDE-RELEASING CYCLODEXTRINS AS BIODEGRADABLE ANTIBACTERIAL SCAFFOLDS AND METHODS PERTAINING THERETO

(71) Applicant: The University of North Carolina at Chapel Hill, Chapel Hill, NC (US)

(72) Inventors: Mark H. Schoenfisch, Chapel Hill, NC (US); Haibao Jin, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/459,015

(22) Filed: Jul. 1, 2019

(65) Prior Publication Data

US 2019/0343869 A1    Nov. 14, 2019

Related U.S. Application Data

(63) Continuation of application No. PCT/US2019/021051, filed on Mar. 6, 2019.

(60) Provisional application No. 62/639,119, filed on Mar. 6, 2018.

(51) Int. Cl.
| | |
|---|---|
| *C08B 37/16* | (2006.01) |
| *A61K 31/724* | (2006.01) |
| *A61K 47/69* | (2017.01) |
| *A61P 35/00* | (2006.01) |

(52) U.S. Cl.
CPC ........ *A61K 31/724* (2013.01); *A61K 47/6951* (2017.08); *A61P 35/00* (2018.01); *C08B 37/0012* (2013.01)

(58) Field of Classification Search
CPC ...... A61K 31/724; A61K 47/56; A61K 47/61; A61K 47/6951; C08B 37/0012
See application file for complete search history.

(56) References Cited

U.S. PATENT DOCUMENTS

| | | | |
|---|---|---|---|
| 4,169,079 A * | 9/1979 | Tabushi | ............. C08B 37/0012 502/402 |
| 5,234,933 A | 8/1993 | Marnett et al. | |
| 5,326,902 A | 7/1994 | Seipp et al. | |
| 5,525,357 A | 6/1996 | Keefer et al. | |
| 5,574,027 A | 11/1996 | Bernstein | |
| 5,632,981 A | 5/1997 | Saavedra et al. | |
| 5,650,442 A | 7/1997 | Mitchell et al. | |
| 5,650,447 A | 7/1997 | Keefer et al. | |
| 5,714,511 A | 2/1998 | Saavedra et al. | |
| 5,814,666 A | 9/1998 | Green et al. | |
| 5,840,759 A | 11/1998 | Mitchell et al. | |
| 5,910,316 A | 6/1999 | Keefer et al. | |
| 6,110,453 A | 8/2000 | Keefer et al. | |
| 6,121,441 A | 9/2000 | Simensen et al. | |
| 6,180,082 B1 | 1/2001 | Woltering et al. | |
| 6,200,558 B1 | 3/2001 | Saavedra et al. | |
| 6,261,594 B1 | 7/2001 | Smith et al. | |
| 6,451,337 B1 | 9/2002 | Smith et al. | |
| 6,911,433 B2 | 6/2005 | Saavedra et al. | |
| 7,553,656 B2 | 6/2009 | Gimmestad et al. | |
| 7,928,079 B2 | 4/2011 | Hrabie et al. | |
| 8,158,580 B2 | 4/2012 | Judice et al. | |
| 8,603,454 B2 | 12/2013 | Cheng et al. | |
| 8,815,831 B2 | 8/2014 | Onsoyen et al. | |
| 8,841,279 B2 | 9/2014 | Taylor et al. | |
| 8,987,215 B2 | 3/2015 | Taylor et al. | |
| 9,238,038 B2 | 1/2016 | Schoenfisch et al. | |
| 9,539,233 B2 | 1/2017 | Ohtake et al. | |
| 9,850,322 B2 | 12/2017 | Schoenfisch et al. | |
| 10,759,877 B2 | 9/2020 | Schoenfisch et al. | |
| 2001/0000039 A1 | 3/2001 | Toone et al. | |
| 2002/0122857 A1 | 9/2002 | Asai et al. | |
| 2003/0078365 A1 | 4/2003 | Stamler et al. | |
| 2003/0093143 A1 | 5/2003 | Zhao et al. | |
| 2004/0038947 A1 | 2/2004 | Wink et al. | |
| 2005/0009789 A1 | 1/2005 | Wink et al. | |
| 2005/0085413 A1 | 4/2005 | Jin et al. | |
| 2005/0228184 A1 | 10/2005 | Haj-Yehia | |
| 2005/0265956 A1 | 12/2005 | Liu et al. | |
| 2006/0199785 A1* | 9/2006 | Fahmi | ................ C08B 37/0009 514/58 |
| 2007/0243131 A1 | 10/2007 | Chen et al. | |
| 2008/0305004 A1 | 12/2008 | Anderson et al. | |
| 2009/0214618 A1 | 8/2009 | Schoenfisch et al. | |
| 2009/0222088 A1* | 9/2009 | Chen | ...................... A61L 31/10 623/11.11 |

(Continued)

FOREIGN PATENT DOCUMENTS

| | | |
|---|---|---|
| CA | 2205564 C | 7/2006 |
| CN | 101049513 A | 10/2007 |

(Continued)

OTHER PUBLICATIONS

Singh, M. et al "Biotechnological applications of cyclodextrins" Biothechnol. Adv., vol. 20, pp. 341-359. (Year: 2002).*
Vizitiu, D. et al "Binding phosphates to aminocyclodextrin . . . " J. Org. Chem., vol. 64, pp. 6235-6238. (Year: 1999).*
Schomburg, G. et al "Preparation, purification, and analysis . . . " J. High Res. Chromatog., vol. 15, pp. 579-584. (Year: 1992).*
Deng, W. et al "pH and cation-responsivie supramolecular gels . . . " Soft Matter, vol. 6, pp. 1884-1887. (Year: 2010).*
Davies, K. et al "Chemistry of the diazeniumdiolates . . . " JACS, vol. 123, pp. 5473-5481. (Year: 2001).*
Safdar, S. et al "Targeted diazeniumdiolates . . . " Int. J. Pharm., vol. 422, No. 1-2, pp. 264-270. (Year: 2012).*

(Continued)

*Primary Examiner* — Leigh C Maier
(74) *Attorney, Agent, or Firm* — Alston & Bird LLP

(57) ABSTRACT

Disclosed herein are cyclodextrin molecules covalently modified to store and release nitric oxide, as well as methods of making and uses thereof. The covalently modified cyclodextrin molecules may be tailored, in several embodiments, to release nitric oxide in a controlled manner and are useful for reduction and/or eradication of bacteria and for the treatment of disease.

23 Claims, 37 Drawing Sheets

(56) References Cited

U.S. PATENT DOCUMENTS

| | | |
|---|---|---|
| 2009/0232863 A1 | 9/2009 | Cheng et al. |
| 2010/0305062 A1 | 12/2010 | Onsoyen et al. |
| 2010/0305489 A1 | 12/2010 | Liu et al. |
| 2011/0002999 A1 | 1/2011 | Chen et al. |
| 2011/0150999 A1 | 6/2011 | Chu et al. |
| 2011/0218139 A1 | 9/2011 | Robinson et al. |
| 2012/0034169 A1 | 2/2012 | Schoenfisch et al. |
| 2012/0107229 A1 | 5/2012 | Huang et al. |
| 2013/0096078 A1 | 4/2013 | Yoon et al. |
| 2013/0196951 A1 | 8/2013 | Schoenfisch et al. |
| 2013/0337033 A1 | 12/2013 | Balkus, Jr. et al. |
| 2014/0256658 A1 | 9/2014 | Sinha et al. |
| 2015/0126467 A1 | 5/2015 | Onsøyen et al. |
| 2015/0225488 A1 | 8/2015 | Schoenfisch et al. |
| 2016/0185891 A1 | 6/2016 | Chambers et al. |
| 2016/0331777 A1 | 11/2016 | Dessen et al. |
| 2016/0346313 A1 | 12/2016 | Nordgard et al. |
| 2016/0361342 A1 | 12/2016 | Hansson et al. |
| 2017/0333456 A1 | 11/2017 | Miranda et al. |
| 2018/0055873 A1 | 3/2018 | Dessen et al. |
| 2019/0225747 A1 | 7/2019 | Schoenfisch et al. |
| 2019/0322770 A1 | 10/2019 | Schoenfisch et al. |
| 2020/0021657 A1 | 1/2020 | Brinkmann et al. |
| 2020/0030362 A1 | 1/2020 | Schoenfisch et al. |
| 2020/0216571 A1 | 7/2020 | Schoenfisch et al. |
| 2020/0332061 A1 | 10/2020 | Schoenfisch et al. |

FOREIGN PATENT DOCUMENTS

| | | | |
|---|---|---|---|
| CN | 102083862 A | 6/2011 | |
| CN | 106046382 A | 10/2016 | |
| EP | 0726768 B1 | 5/2000 | |
| EP | 2547660 B1 | 1/2015 | |
| EP | 3185853 A1 | 7/2017 | |
| IN | 2010DN04583 A | 11/2010 | |
| JP | 2001-524991 A | 12/2001 | |
| JP | 2002-518557 A | 6/2002 | |
| JP | 2005047979 A | 2/2005 | |
| JP | 4285775 B2 | 6/2009 | |
| NO | 20050480 A | 4/2005 | |
| WO | WO 93/25521 A1 | 12/1993 | |
| WO | WO 1996/015797 A1 | 5/1996 | |
| WO | 1996032136 A1 | 10/1996 | |
| WO | WO-9805689 A1 * | 2/1998 | ............ A61L 31/10 |
| WO | 1998013358 A1 | 4/1998 | |
| WO | WO 00/30658 A1 | 6/2000 | |
| WO | WO 2007/085254 A1 | 8/2007 | |
| WO | WO 2009/049208 A1 | 4/2009 | |
| WO | WO 2010/037179 A1 | 8/2010 | |
| WO | WO 2010/096320 A3 | 8/2010 | |
| WO | WO 2010/139957 A1 | 12/2010 | |
| WO | WO 2010/139958 A1 | 12/2010 | |
| WO | WO 2010/139959 A2 | 12/2010 | |
| WO | WO 2011/003172 A1 | 1/2011 | |
| WO | WO 2012/046994 A2 | 4/2012 | |
| WO | WO 2012/116177 A2 | 8/2012 | |
| WO | WO 2013/029009 A1 | 2/2013 | |
| WO | WO 2014/028847 A1 | 2/2014 | |
| WO | WO 2017/060388 A1 | 4/2017 | |
| WO | WO 2018/067838 A1 | 4/2018 | |
| WO | WO2018/127819 A1 | 7/2018 | |
| WO | WO 2018/178902 A1 | 10/2018 | |
| WO | WO 2019/099525 A1 | 5/2019 | |
| WO | WO 2019/173539 A1 | 9/2019 | |
| WO | WO 2020/139857 A1 | 7/2020 | |

OTHER PUBLICATIONS

Cutrone et al., "Mannoside and 1,2-mannobioside β-cyclodextrin-scaffolded NO-photodonors for targeting antibiotic resistant bacteria", Carbohydr. Polym, 199: 649-660, (2018).

Machelart et al., "Intrinsic Antibacterial Activity of Nanoparticles Made of β-Cyclodextrins Potentiates Their Effect as Drug Nanocarriers against Tuberculosis", ACS Nano, 13: 3992-4007, (2019).

WIPO Application No. PCT/US2019/021051, PCT International Search Report and Written Opinion of the International Searching Authority dated Jun. 21, 2019.

Benkovics et al., "A multifunctional β-cyclodextrin-conjugate photodelivering nitric oxide with fluorescence reporting," International Journal of Pharmaceutics, 531: 614-620 (2017).

Mourtzis et al., "Synthesis, characterization, and remarkable biological properties of cyclodextrins bearing guanidinoalkylamino and aminoalkylamino groups on their primary side," Chem. Eur. J., 14: 4188-4200 (2008).

Zhou et al., "Water-soluble poly(ethylenimine)-based nitric oxide donors: preparation, characterization, and potential application in hemodialysis," Biomacromolecules, 7: 2565-2574 (2006).

Piras et al., "S-Nitroso-Beta-Cyclodextrins as New Bimodal Carriers: Preparation, Detailed Characterization, Nitric-Oxide Release, and Molecular Encapsulation," Chemistry—An Asian Journal, 8:2768-2778 (2013).

Jin et al., "Nitric Oxide-Releasing Cyclodextrins," Journal of the American Chemical Society, 140: 14178-14184 (2018).

Ahonen et al., "Nitric oxide-releasing alginates as mucolytic agents," ACS Biomater. Sci. Eng., 5:3409-3418, (2019).

Ahonen et al., "Nitric oxide-releasing alginate as a biodegradable antibacterial scaffold," 253rd National Meeting of the American Chemical Society (ACS) on Advanced Materials, Technologies, Systems, and Processes; San Francisco, CA, Apr. 2-6, 2017—Abstracts of Papers, p. 600, (2017).

Allaker, R.P., "The use of Nanoparticles to Control Oral Biofilm formation," J Dent Res, 89(11):1175-1186, (2010).

Alnaief et al., "Preparation of biodegradable nanoporous microspherical aerogel based on alginate," Carbohydrate Polymers, 84(3):1011-1018, (2011).

Arulsamy, N. et al. "Multiplicity Control in the Polygeminal Diazeniumdiolation of Active Hydrogen Bearing Carbons: Chemistry of a New Type of Trianionic Molecular Propeller," S. J. Am. Chem. Soc., 123:10860-10869, (2001).

Backlund et al., "Antibacterial Efficacy of Exogenous Nitric Oxide on Periodontal Pathogens," J Dent Res, 93(11): 1089-1094, (2014).

Backlund et al., "Anti-biofilm action of nitric oxide-releasing alkyl-modified poly(amidoamine) dendrimers against Streptococcus mutans," Acta Biomaterialia, 29:198-205, (2016).

Backlund et al., "Kinetic-dependent Killing of Oral Pathogens with Nitric Oxide," J Dent Res, 94(8): 1092-1098, (2015).

Barraud et al., "Nitric Oxide: A Key Mediator of Biofilm Dispersal with Applications in Infectious Diseases," Curr. Pharm. Des., 21(1):31-42, (2015).

Barrud et al., "Involvement of Nitric Oxide in Biofilm Dispersal of Pseudomonas aeruglnosa,"Journal of Bacteriology, 188(21):7344-7353, (2006).

Beck et al., "Systemic Effects of Periodontitis: Epidemiology of Periodontal Disease and Cardiovascular Disease," J. Periodontol., 76(11)(Suppl.):2089-2100, (2005).

Belley, A. et al., "Assessment by time-kill methodology of the synergistic effects of oritavancin in combination with other antimicrobial agents against Staphylococcus aureus," Antimicrob. Agents Chemother., 52:3820-3822, (2008).

Bernkop-Schnurch et al., "Improvement in the mucoadhesive properties of alginate by the covalent attachment of cysteine," Journal of Controlled Release, 71(3):277-285, (2001).

Besinis et al., "Review of Nanomaterials in Dentistry: Interactions with the Oral Microenvironment, Clinical Applications, Hazards, and Benefits," ACS Nano, 9(3):2255-2289, (2015).

Beveridge, Terry J., "Structures of Gram-Negative Cell Walls and Their Derived Membrane Vesicles," Journal of Bacteriology, 181(16):4725-4733, (1999).

Bhardwaj, Atul, et al., "A diazen-1-ium-1, 2-diolate analog of 7-azabenzobicyclo [2.2.1] heptane: Synthesis, nitric oxide and nitroxyl release, in vitro hemodynamic, and anti-hypertensive studies," Bioorganic & Medicinal Chemistry Letters, 23(9):2769-2774, (2013).

Bjarnsholt et al., "Why chronic wounds will not heal: a novel hypothesis," Wound Rep Reg, 16:2-10, (2008).

(56) References Cited

OTHER PUBLICATIONS

Boas and Heegaard, "Dendrimers in drug research," Chem. Soc. Rev., 33(1):43-63, (2004).
Bogdan, Christian, "Nitric oxide and the immune response," Nat. Immunol., 2(10):907-916, (2001).
Bollenbach, T., "Antimicrobial interactions: mechanisms and implications for drug discovery and resistance evolution," Curr. Opin. Microbiol., 27:1-9, (2015).
Breed and Dotterrer, "The number of colonies allowable on satisfactory agar plates," J. Bacteriol. 1(3):321-331, (1916).
Calabretta et al., "Antibacterial activities of poly (amidoamine) dendrimers terminated with amino and poly (ethylene glycol) groups," Biomacromolecules, 8(6):1807-1811, (2007).
Caleffi-Ferracioli et al., "Fast detection of drug interaction in Mycobacterium tuberculosis by a checkerboard resazurin method," Tuberculosis, 93:660-663, (2013).
Caminade et al., "Dendrimers and hyperbranched polymers," Chem. Soc. Rev, 44(12):3870-3873, (2015).
Cao et al., "Synthesis and striking fluorescence properties of hyperbranched poly (amido amine)," J. Macromol. Sci. Pure Appl. Chem., 44(4):417-424, (2007).
Caraher, E. M. et al., "The effect of recombinant human lactoferrin on growth and the antibiotic susceptibility of the cystic fibrosis pathogen Burkholderia cepacia complex when cultured planktonically or as biofilms," J. Antimicrob. Chemother., 60:546-554, (2007).
Carl Mark et al "New methodologies in the construction of dendritic materials," Chem. Soc. Rev., 38(2):352-362, (2009).
Carlmark, A. et al., "Dendritic Architechtures Based on bis-MPA: Functional Polymeric Scaffolds for Application-Driven Research," Chem Soc Rev., 42:5858-79, (2013).
Carpenter et al., "Dual action antimicrobials: nitric oxide release from quaternary ammonium-functionalized silica nanoparticles," Biomacromolecules, 13(10):3334-3342, (2012).
Carpenter et al., "Nitric oxide release: Part II. Therapeutic applications," Chem. Soc. Rev., 41(10):3742-3752, (2012).
Centers for Disease Control, Antibiotic Resistance Threats in the United States, (2013).
Chakrapani, Harinath, et al., "Nitric oxide prodrugs: diazeniumdiolate anions of hindered secondary amines," Organic Letters, 9(22): 4551-4554, (2007).
Charbonneau et al., "Reduced chlorhexidine tooth stain coverage by sequential administration of monoperoxyphthalic acid in the beagle dog," J. Dent. Res., 76(9):1596-1601, (1997).
Chen et al., "Cytotoxicity, hemolysis, and acute in vivo toxicity of dendrimers based on melamine, candidate vehicles for drug delivery," J. Am. Chem. Soc., 126(32):10044-10048, (2004).
Chen et al., "Cariogenic Actinomyces Identified with a β-Glucosidase-Dependent Green Color Reaction to Gardenia jasminoides Extract," Journal of Clinical Microbology, 39(8):3009-3012, (2001).
Chen et al., "Hyperbranched glycoconjugated polymer from natural small molecule kanamycin as a safe and efficient gene vector," Polym. Chem., 2:2674-2682, (2011).
Chen et al., "Hyperbranched polymers from A2 +B 3 strategy: recent advances in description control of fine to pology," Polym. Chem., 7(22):3643-3663, (2016).
Chen et al., "Multifunctional Hyperbranched Glycoconjuated Polymers Based on Natural Aminoglycosides," Bioconjugate Chemistry, 23(6):1189-1199, (2012).
Chen et al., "Selective deprotection of the Cbz amine protecting group for the facile synthesis of kanamycin a dimers linked at N-3" position, Tetrahedron, 65(31)5922-5927, (2009).
Cheng et al., "Michael Addition Polymerization of Trifunctional Amine and Acrylic Monomer: A Versatile Platform for Development of Biomaterials ," Biomacromolecules, 17(10):3115-3126, (2016).
Ciacci, N., et al., "In vitro Synergism of Colistin and N-acetylcysteine against Stenotrophomonas maltophilia," Antibiotics, 8:101, (2019).

Ciofu, O. & Tolker-Nielsen, T., "Tolerance and Resistance of Pseudomonas aeruginosa Biofilms to Antimicrobial Agents—How P. aeruginosa Can Escape Antibiotics," Front. Microbiol., 10:913, (2019).
Cleland, W.W., "Diothiothreitol, A New Protective Reagent for SH Groups," Biochemical., 3(4):480-482, (1964).
Compound Summary, "PubChem Compound Summary for CID 65430: Gallium citrate ga-67," National Library of Medicine: National Center for Biotechnology Information, (Last accessed Aug. 7, 2020), https://pubchem.ncbi.nlm.nih.gov/compound/Gallium-citrate-ga-67.
Compound Summary, "Gallium citrate Ga-67," Drugbank, (Last accessed Aug. 6, 2020), https://www.drugbank.ca/drugs/DB06784.
Compound Summary, "PubChem Compound Summary for CID 61635, Gallium nitrate," National Library of Medicine: National Center for Biotechnology Information, (Last accessed Aug. 7, 2020) https://pubchem.ncbi.nlm.nih.gov/compound/61635.
Coneski and Scoenfisch, "Nitric oxide release: part III. Measurement and reporting," Chem. Soc. Rev, 41(10):3753-3758, (2012).
Coneski, "Design and Synthesis of Nitric Oxide Releasing Polymers for Biomedical Applications", pp. 122-127, (2010). [Retrieved from the Internet: URL:https://cdr.lib.unc.edu/indexablecontent/uuid:d84bce49-d4dd-4026-96a5-3ea9e82dee9c [retrieved on Oct. 9, 2015]].
Coneski, P.N. and Schoenfisch, M.H., "Synthesis of Nitric Oxide-Releasing Polyurethanes with S-Nitrosothiol-Containing Hard and Soft Segments," Polym Chem., 2(4):906-913, (2011).
Coneski, P.N. et al., "Degradable Nitric Oxide-Releasing Biomaterials via Post-Polymerization Functionalization of Cross-Linked Polyesters," Biomacromolecules, 11(11):3208-3215, (2010).
Cooke et al., "Nitric Oxide and Angiogenesis," Circulation, 105:2133-2135, (2002).
Cooke, John P., "NO and Angiogenesis," Atherosclerosis Suppl., 4(4):53-60, (2003).
Cullen, L. & McClean, S., "Bacterial adaptation during chronic respiratory infections," Pathogens, 4:66-89, (2015).
Da Silva et al., "Antimicrobial peptide control of pathogenic microorganisms of the oral cavity: A review of the literature," Peptides, 36(2):315-321, (2012).
Damodaran, V.B. and Reynolds, M.M., "Biodegradable S-Nitrosothiol Tethered Multiblock Polymer for Nitric Oxide Delivery," J Mater Chem., 21:5870-5872, (2011).
Davies et al., "Evolutionary diversification of Pseudomonas aeruginosa in an artificial sputum model," BMC Microbiol. 17:3, (2017).
Deupree, S. M. & Schoenfisch, M. H., "Morphological analysis of the antimicrobial action of nitric oxide on Gram-negative pathogens using atomic force microscopy," Acta Biomater., 5:1405-1415, (2009).
Draget et al., "Chemical, physical and biological properties of alginates and their biomedical implications," Food Hydrocolloids, 25(2):251-256, (2011).
Drug Development Pipeline Status, "Inhaled Gallium: Phase One", Cystic Fibrosis Foundation, (Last accessed Aug. 13, 2020), https://www.cff.org/Trials/Pipeline/details/10146/Inhaled-Gallium.
Duncan and Izzo, "Dendrimer biocompatibility and toxicity," Adv. Drug Deliv. Rev., 57(14):2215-2237, (2005).
Duong et al., "Functional gold nanoparticles for the storage and controlled release of nitric oxide: applications in biofilm dispersal and intracellular delivery," J. Mater. Chem. B-2, 2(31):5003-5011, (2014).
Duong et al., "Nanoparticle (Star Polymer) Delivery of Nitric Oxide Effectively Negates Pseudomonas aeruginosa Biofilm Formation," Biomacromolecules, 15(7):2583-2589, (2014).
Elion et al., "Antagonists of Nucleic, Acid Derivatives: VIII. Synergism in combinations of biochemically related antimetabolites," J. Biol. Chem., 208:477-488, (1954).
Fang, Ferric C., "Antimicrobial reactive oxygen and nitrogen species: concepts and controversies," Nat. Rev. Micro., 2(10):820-832, (2004).
Feliu, N. et al., "Stability and Biocompatibility of a Library of Polyester Dendrimers in Comparison to Polyamidoamine Dendrimers," Biomaterials., 33(7):1970-1981, (2012).

(56) References Cited

OTHER PUBLICATIONS

Fernandez-Barat, L. et al., "Phenotypic shift in Pseudomonas aeruginosa populations from cystic fibrosis lungs after 2-week antipseudomonal treatment," J. Cyst. Fibros., 16:222-229, (2017).
Friedman et al., "The negative impact of antibiotic resistance," Clin. Microbiol. Infect., 22:416-422, (2016).
Frost, M.C. and Meyerhoff, M.E., "Synthesis, Characterization, and Controlled Nitric Oxide Release from S-Nitrosothiol-Derivatized Fumed Silica Polyme Filler Particles," J Biomed Mater Res Part A., 72A(4):409-419, (2005).
Fu, et al., "Preparation and reversible photo-crosslinking/photocleavage behavior o 4-methylcoumarin functionalized hyperbranched polyester," Polymer, 49(23): 4981-4988, (2008).
Gabor, G. and Vincze A., "Determination of Thiols in Non-Aqueous Solutions," Anal Chim Acta., 92(2):429-431, (1977).
Gao and Koo, "Do catalytic nanoparticles offer an improved therapeutic strategy to combat dental biofilms!," Nanomed. Nanotech. Biol. Med., 12(4):275-279, (2017).
Gao and Yan, "Hyperbranched polymers: from synthesis to applications," Prog. Polym. Sci., 29(3):183-275, (2004).
Gao, Q, et al., "Synthesis and Characterization of Chitosan-Based Diazeniumdiolates. [Abstract]," Polymer Materials Science and Engineering, 24(12):415-421, (2008).
Ghosh, S. & Lapara, T. M., "The effects of subtherapeutic antibiotic use in farm animals on the proliferation and persistence of antibiotic resistance among soil bacteria," ISME J., 1:191-203, (2007).
Gibney et al., "Poly(ethylene imine)s as antimicrobial agents with selective activity," Macromol. Biosci., 12(9):1279-1289, (2012).
Gombotz et al., "Protein release from alginate matrices," Advanced Drug Delivery Reviews, 31(3):267-285, (1998).
Grabowski et al., "Toxicity of surface-modified PLGA nanoparticles toward lung alveolar epithelial cells," International Journal of Pharmaceutics, 454:686-694, (2013).
Haggie, P., and Lueck, J.(Eds), "Agenda for Cystic Fibrosis Foundation Research Conference," Cystic Fibrosis Foundation, (2019), https://www.cff.org/Research/Researcher-Resources/Cystic-Fibrosis-Foundation-Research-Conference/.
Hall, J. R. et al., "Mode of nitric oxide delivery affects antibacterial action," ACS Biomater. Sci. Eng., acsbiomaterials.9b01384 (2019).
Hall-Stoodley et al., "Bacterial Biofilms: from the Natural Enviorment to Infectious Diseases," Nat. Rev. Micro., 2:95-108, (2004).
Harrison et al., "Development of an ex vivo porcine lung model for studying growth Virulence, and signaling of pseudomonas aeruginosa," Infect. Immun., 82:3312-3323, (2014).
Helander, I. M. & Mattila-Sandholm, T. "Fluorometric assessment of Gram-negative bacterial permeabilization," J. Appl. Microbiol., 88:213-219, (2000).
Hetrick and Schoenfisch, "Analytical chemistry of nitric oxide," Annu. Rev. Anal. Chem., 2:409-433, (2009).
Hetrick et al., "Anti-biofilm efficacy of nitric oxide-releasing silica nanoparticles," Biomaterials, 30:2782-2789, (2009).
Hetrick et al., "Bactericidal Efficacy of Nitric-Oxide Releasing Silica Nanoparticles," ACS Nano, 2(2)235-246, (2008).
Hopkins, Sean, "Development of high capacity hyperbranched nitric oxide donors for controlling subcutaneous inflammation," Open Access Dissertation, Michigan Technological University, 154 pages, (2015).
Hossain et al., "Discovery of Two Bacterial Nitric Oxide-Responsive Proteins and Their Roles in Bacterial Biofilm Regulation," Acc. Chem. Res., 50(7):1633-1639, (2017).
Howlin, R. P., et al., "Low-Dose Nitric Oxide as Targeted Anti-biofilm Adjunctive Therapy to Treat Chronic Pseudomonas aeruginosa Infection in Cystic Fibrosis," Mol. Ther., 25:2104-2116, (2017).
Hrabie, Joseph A., et al., "New nitric oxide-releasing zwitterions derived from polyamines," the Journal of Organic Chemistry, 58(6):1472-1476, (1993).
Hu et al., "A smart aminoglycoside hydrogel with tunable gel degradation, on-demand drug release, and high antibacterial activity," Journal of Controlled Release, 247:145-152, (2017).
Huang et al., "Nitric oxide-loaded echogenic liposomes for nitric oxide delivery and inhibition of intimal hyperplasia," J. Am. Coll. Cardiol., 54(7):652-659, (2009).
Huang et al., "Reduction-responsive multifunctional hyperbranched polyaminoglycosides with excellent antibacterial activity, biocompatibility and gene transfection capability," Biomaterials, 106:134-143, (2016).
Hussain et al., "Glucocorticoids can affect Pseudomonas aeruginosa (ATCC 27853) internalization and intracellular calcium concentration in cystic fibrosis bronchial epithelial cells," Experimental Lung Research, 41(7):383-392, (2015).
Imfeld, T. "Chewing gum—facts and fiction: a review of gum-chewing and oral health," Crit. Rev. Oral. Biol. Med., 10(3):405-419, (1999).
Jin et al., "Biocompatible or biodegradable hyperbranched polymers: from self-assembly to cytomimetic applications," Chem. Soc. Rev., 41(18):5986-5997, (2012).
Jones et al., "Antimicrobial properties of nitric oxide and its application in antimicrobial formulations and medical devices," Appl. Microbiol. Biotechnol., 88(2):401-407, (2010).
Jones, C.G., "Chlorhexidine: is it still the gold standard?" Periodontology 2000, 15:55-62, (1997).
Kailasan et al., "Synthesis and characterization of thermoresponsive polyamidoamine—polyethylene glycol—poly (d, 1-lactide) core—shell nanoparticles," Acta Biomater. 6(3):1131- 1139, (2010).
Kaneko et al., "The transition metal gallium disrupts Pseudomonas aeruginosa iron metabolism and has antimicrobial and antibiofilm activity," The Journal of Clinical Investigations, 117(4):877-888, (2007).
Karatasos, K., "Self-Association and Complexation of the Anti-Cancer Drug Doxorubicin with PEGylated Hyperbranched Polyesters in an Aqueous Environment," J Phys Chem B., 117(8):2564-2575, (2013).
Kassebaum et al., "Global Burden of Untreated Caries: A Systematic Review and Metaregression," Journal of Dental Research, 94(5):650-658, (2015).
Keefer et al., "Chemistry of the Diazeniumdiolates I. Structural and Spectral Characteristics of the [N(O)NO]—Functional Group," Nitric Oxide, 5(4):377-394, (2001).
Keefer et al., "'NONOates' (1-Substituted Diazen- 1-ium-1,2-diolates) as Nitric Oxide Donors: Convenient Nitric Oxide Dosage Forms," Methods in Enzymology, 268:281-293, (1996).
Keefer, Larry K., "Fifty Years of Diazeniumdiolate Research. From Laboratory Curiosity to Broad-Spectrum Biomedical Advances," ACS Chemical Biology, 6(11):1147-1155, (2011).
Keefer, Larry K., "Nitric Oxide (NO)- and Nitroxyl (HNO)-Generating Diazeniumdiolates (NONOates): Emerging Commercial Opportunities," Current Topics in Medicinal Chemistry, 5(7):625-636, (2005).
Khalil et al., "Synergy between Polyethylenimine and Different Families of Antibiotics against a Resistant Clinical Isolate of Pseudomonas aeruginosa," Antimicrob. Agents Chemother., 52:1635-1641, (2008).
Khan et al., "Overcoming Drug Resistance with Alginate Oligosaccharides Able to Potentiate the Action of Selected Antibiotics," Antimicrobial Agents and Chemotherapy, 56(10):5134-5141, (2012).
Kim et al., "NONOates—polyethylenimine hydrogel for controlled nitric oxide release and cell proliferation modulation," Bioconjugate Chem., 22(6)1 031-1038, (2011).
Knop et al., "Poly(ethylene glycol) in drug delivery: pros and cons as well as potential alternatives," Angew. Chem. Int. Ed., 49(36):6288-6308, (2010).
Konter, Joerg, et al., "Synthesis of Diazen-1-ium-1, 2-diolates Monitored by the "NOtizer" Apparatus: Relationship between Formation Rates, Molecular Structure and the Release of Nitric Oxide," European Journal of Organic Chemistry, 2007(4): 616-624, (2007).
Kovach, K. et al., "Evolutionary adaptations of biofilms infecting cystic fibrosis lungs promote mechanical toughness by adjusting polysaccharide production," npj Biofilms Microbiomes, 3, (2017).
Kurniasih et al., "Dendritic nanocarriers based on hyperbranched polymers," Chem. Soc. Rev., 44(12):4145-4164, (2015).

(56) References Cited

OTHER PUBLICATIONS

Labena et al., "One-pot synthesize of dendritic hyperbranched PAMAM and assessment as a broad spectrum antimicrobial agent and anti-biofilm," Mater. Sci. Eng. C Mater. Biol. Appl., 58:1150-1159, (2016).
Lee et. al., "Alginate: properties and biomedical applications," Prog Polym Sci., 37(1):106-126 (2012)
Lenoir et al. "Polyolefin, matrixes with permanent antibacterial activity: preparation, antibacterial activity, and action mode of the active species," Biomacromolecules, 7(8):2291-2296, (2006).
Liakos et al., "All-natural composite wound dressing films of essential oils encapsulated in sodium alginate with antimicrobial properties," International Journal of Pharmaceutics, 463(2):137-145, (2014).
Liu et al., "Hollow double-layered polymer microspheres with pH and thermo-responsive properties as nitric oxide-releasing reservoirs," Polym. Chem., 6(17):3305-3314, (2015).
Liu et al., "Synergistic supramolecular encapsulation of amphiphilic hyperbranched polymer to dyes," Macromolecules, 39(23):8102-8111, (2006).
Liu, T. et al., "Hollow Polymer Nanoparticles with S-Nitrosothiols as Scaffolds for Nitric Oxide Release," J Colloid Interface Sci., 459:115-122, (2015).
Loesche et al., "Role of Streptococcus mutans in Human Dental Decay," Microbiological Reviews, 50(4):353-380, (1986).
Lowe et al., "Storage and delivery of nitric oxide via diazeniumdiolated metal organic framework," Micropor. Mesopor. Mat., 181:17-22, (2013).
Lu et al., "Nitric oxide-releasing amphiphilic poly(amidoamine) (PAMAM) dendrimers as antibacterial agents," Biomacromolecules, 14(10):3589-3598, (2013).
Lu et al., "Nitric oxide-releasing chitosan oligosaccharides as antibacterial agents," Biomaterials, 35(5):1716-1724, (2014).
Lu et al., "Structurally Diverse Nitric Oxide-Releasing Poly(propylene imine) Dendrimers," Chem. Mater., 23(18):4227-4233, (2011).
Lu, Y. et al., "Shape- and Nitric Oxide Flux-Dependent Bactericidal Activity of Nitric Oxide- Releasing Silica Nanorods," Small., 9(12):2189-2198, (2013).
Lu, Y. et al., "S-Nitrosothiol-Modified Nitric Oxide-Releasing Chitosan Oligosacccarides as Antibacterial Agents," Acta Biomater.,12:62-69, (2015).
Luo et al., "Nitric oxide: a newly discovered function on wound healing," Acta Pharmacol. Sin., 26(3):259-264, (2005).
Luo et al., "Poly (ethylene glycol)-conjugated Pamam dendrimer for biocompatible, high- efficiency Dna delivery," Macromolecules, 35(9):356-3462, (2002).
Lutzke, A.. et al., "Nitric Oxide-Releasing S-Nitrosated Derivatives of chitin and Chitosan for Biomedical Applications," J Mater Chem B., 2:7449-7458, (2014).
Lutzke, et al., "Nitric oxide release from a biodegradable cysteine-based polyphosphazene," Journal of Materials Chemistry B, 4(11): 1987-1988, (2016).
Macmicking et al., "Nitric oxide and macrophage function," Annu. Rev. Immunol, 15:323-350, (1997).
Madison, C.J., et al., "Gallium and Nitrite Have Synergistic Antimicrobial Activity," Cystic Fibrosis Conference: Scientific Session VIII: Novel Approaches for Treating Difficult Infections, Abstract, Jun. 26, 2019.
Malmstrom, E. et al., "Hyperbranched Aliphatic Polyesters," Macromolecules, 28(5):1698-1703, (1995).
Maragos, Chris M., et al., "Complexes of. NO with Nucleophiles as agents for the controlled biological release of nitric oxide. Vasorelaxent effects," Journal of Medicinal Chemistry, 34(11):3242-3247, (1991).
Martinez, J. L. & Baquero, F., "Mutation Frequencies and Antibiotic Resistance," Antimicrob. Agents Chemother., 44:1771-1777, (2000).
Matai et al., "Chemically Cross-Linked Hybrid Nanogels of Alginate and PAMAM Dendrimers as Efficient Anticancer Drug Delivery Vehicles," ACS Biomater. Sci. Eng., 2(2):213-223, (2016).

Mather et al., "Michael addition reactions in macromolecular design for emerging technologies," Prog. Polym. Sci., 31(5):487-531, (2006).
Mendelman, P. M. et al., "Aminoglycoside penetration, inactivation, and efficacy in cystic fibrosis sputum," Am. Rev. Respir. Dis., 132:761-765, (1985).
Miller et al., "Gaseous nitric oxide bactericidal activity retained during intermittent high-dose short duration exposure," Nitric Oxide, 20:16-23, (2009).
Miller et al., "Role of Oxidants in Microbial Pathophysiology," Clinical Microbiology Reviews, 10(1):1-18, (1997).
Miller, MR, and Megson, IL, "Recent developments in nitric oxide donor drugs," Br J Pharmacol.,151(3):305-321, (2007).
Minandri, F., "Promises and failures of gallium as an antibacterial agent," Future Microbiology, 9(3):379-397, (2014).
Moreno-Sastre et al., "Pulmonary delivery of tobramycin-loaded nanostructured lipid carriers for Pseudomonas aeruginosa infections associated with cystic fibrosis," International Journal of Pharmaceutics, 498:263-273, (2016).
Mulani et al., "Emerging Strategies to Combat Eskape Pathogens in the Era of Antimicrobial Resistance: A Review," Front. Microbiol., 10, (2019).
Muller, L. et al., "Human airway mucus alters susceptibility of Pseudomonas aeruginosa biofilms to tobramycin, but not colistin," J. Antimicrob. Chemother., 73:2762-2769, (2018).
Nair et al., "Biodegradable polymers as biomaterials," Prog. Polym. Sci., 32(8-9):762-798, (2007).
Nakamoto, H. and Bardwell, J.C.A., "Catalysis of Disulfide Bond Formation and Isomerization in the *Escherichia coli*Periplasm," Biochim Biophys Acta., 1694(1-3):111-119, (2004).
Nguyen et al., "Co-delivery of nitric oxide and antibiotic using polymeric nanoparticles," Chem Sci., 7(2):1016-1027, (2016).
Nichols et al., "Local delivery of nitric oxide: Targeted delivery of therapeutics to bone and connective tissues," Adv. Drug Delivery Rev, 64(12):1177-1188, (2012).
Nordgard et al., "Alterations in Mucus Barrier Function and Matrix Structure Induced by Guluronate Oligomers," Biomacromolecules, 15:2294-2300, (2014).
Nordgard et al., "Oligosaccharides As Modulators of Rheology in Complex Mucous Systems," Biomacromolecules, 12(8):3084-3090, (2011).
O'Halloran, T.V. And Culotta,"Metallochaperones, an Intercellular Shuttle Service for Metal Ions," J Biol Chem., 275(33):25057-25060, (2000).
Ohwada, Tomohiko, et al., "7-Azabicyclo [2.2.1] heptane as a structural motif to block mutagenicity of nitrosamines," Bioorganic & Medicinal Chemistry, 19(8): 2726-2741, (2011).
Park et al., "Nitric oxide integrated polyethylenimine-based triblock copolymer for efficient antibacterial activity," Biomaterials, 34(34):8766-8775, (2013).
Park et al., "Polydopamine Hollow Nanoparticle Functionalized with N-diazeniumdiolates as a Nitric Oxide Delivery Carrier for Antibacterial Therapy," Adv. Healthcare Mater., 5(16):2019- 2024, (2016).
Parzuchowski et al., "Synthesis and characterization of polymethacrylate-based nitric oxide donors," J. Am. Chem. Soc., 124(41):12182-12191, (2002).
Paster et al., "The breadth of bacterial diversity in the human periodontal pocket and other oral sites," Periodontology 2000, 42:80-87, (2006).
Paul et al., "Chitosan and Alginate Wound Dressings: A Short Review," Trends Biomater. Artif. Organs, 18(1):18-23, (2004).
Paula and Koo, "Nanosized building blocks for customizing novel antibiofilm approaches," J. Dent. Res., 96(2):128-136, (2017).
Petersen et al., "The global burden of oral diseases and risks to oral health," Bull. World Health Organ., 83(9):661-669, (2005).
Polizzi et al., "Water-Soluble Nitric Oxide-Releasing Gold Nanoparticles," Langmuir, 23:4938-4943, (2007).
Prabaharan, M. et al., "Amphiphilic Multi-Arm-Block Copolymer Conjugated with Doxorubicin via pH-Sensitive Hydrazone Bond for Tumor-Targeted Drug Delivery," Biomaterials., 30(29):5757-5766, (2009).

(56) References Cited

OTHER PUBLICATIONS

Pritchard et al., "A New Class of Safe Oligosaccharide Polymer Therapy to Modify the Mucus Barrier of Chronic Respiratory Disease," Molecular Pharmaceutics, 13(3):863-872, (2016).
Privett et al., "Examination of Bacterial Resistance to Exogenous Nitric Oxide," Nitric Oxide, 26:169-173, (2012).
Privett, B. J., et al., "Synergy of nitric oxide and silver sulfadiazine against gram- negative, gram-positive, and antibiotic-resistant pathogens," Mol. Pharm., 7:2289- 2296, (2010).
Product Overiew, "AR-501 (Gallium Citrate): Novel anti-infective for the growing problem of antibiotic resistance," Aridis Pharmaceuticals, (Last accessed Aug. 13, 2020), https://www.aridispharma.com/ar-501/.
Product Overview, "Ardis Pipeline: Blood Stream Infections: Product Candidates,"Andis Pharmaceuticals, (Last Accessed Aug. 13, 2020), https://www.aridispharma.com/ar-501/.
Pubchem CID 6032, "Kanamycin A," PubChem, NCBI, pp. 1-9, (2005).
Radvar et al., "Comparison of 3 periodontal local antibiotic therapies in persistent periodontal pockets," J. Periodontol., 67(9):860-865, (1996).
Ragheb, M. N. et al. "Inhibiting the Evolution of Antibiotic Resistance," Mol. Cell, 73:157-165.e5, (2019).
Rees et al., "Role of endothelium-derived nitric oxide in the regulation of blood pressure," Proc. Natl. Acad. Sci., 86(9):3375-3378, (1989).
Reighard et al., "Disruption and eradication of P. aeruginosa biofilms using nitric oxide- releasing chitosan oligosaccharides," Biofouling, 31:775-787, (2015).
Reighard, K. P. & Schoenfisch, M. H., "Antibacterial action of nitric oxide-releasing chitosan oligosaccharides against Pseudomonas aeruginosa under aerobic and anaerobic conditions," Antimicrob. Agents Chemother., 59:6506-6513, (2015).
Riccio and Schoenfisch, "Nitric oxide release: part I. Macromolecular scaffolds," Chem. Soc. Rev., 41(10):3731-3741, (2012).
Riccio, D.A. et al., "Photoinitiated Nitric Oxide-Releasing Tertiary S-Nitrosothiol-Modified Xerogels," ACS Appl Mater Interfaces., 4(2):796-804, (2012).
Riccio, D.A. et al., "Stober Synthesis of Nitric Oxide-Releasing S-Nitrosothiol-Modified Silica Particles," Chem Mater., 23(7):1727-1735, (2011).
Robson, Martin C., "Wound Infection: A Failure of Wound Healing Caused by an Imbalance of Bacteria," Surgical Clinics of North America, 77(3):637-650, (1997).
Rouillard, K. R., et al., "Exogenous Nitric Oxide Improves Antibiotic Susceptibility in Resistant Bacteria," Research Presentation: Univ. of North of Carolina Chapel Hill, (2019).
Roy, B. et al., New Thionitrates: Synthesis, Stability, and Nitric Oxide Generation, J Org Chem., 59(23):7019-7026, (1994).
Santajit, S. & Indrawattana, N., "Mechanisms of Antimicrobial Resistance in ESKAPE Pathogens," Biomed Res. Int., 2016:1-8, (2016).
Schaffer et al., "Nitric oxide regulates wound healing," J. Surg. Res., 63(1):237-240, (1996).
Schairer et al., "The potential of nitric oxide releasing therapies as antimicrobial agents," Virulence, 3:271-279, (2012).
Seabra, a.B. et al., "Antibacterial Nitric Oxide-Releasing Polyester for the Coating of Blood- Contacting Artificial Materials," Artif Organs, 34(7):E204-14, (2010).
Sen et al., "Periodontal Disease and Recurrent Vascular Events in Stroke/TIA Patients," J. Stroke Cerebrovasc Dis., 22(8):1420-1427, (2013).
Shah et al., "Synthesis of S-nitrosoglutathione-alginate for prolonged delivery of nitric oxide in intestines," Drug Deliv., 23(8):2927-2935, (2016).
Shin e al., "Inorganic/Organic Hybrid Silica Nanoparticles as a Nitric Oxide Delivery Scaffold," Chem. Mater., 20:239-249, (2008).
Shishido, S.M. And Oliveira, M.G., "Polyethylene Glycol Matrix Reduces the Rates of Photochemical and Thermal Release of Nitric Oxide from S-Nitroso-N-Acetylcysteine," Photochem Photobiol., 71(3):273-80, (2000).
Singh, Simrat Pal et al., "Rice Nivotianamine Synthase 2 expression improves dietary iron and zinc levels in wheat," Theoretical and Applied Genetics, 130(2): 283-292, (2017).
Slomberg, D.L."Role of Size and Shape on Blm Eradication for Nitric Oxide- releasing Silica," ACS Appl. Mater. Interfaces, 5(19):9322-9329, (2013).
Slots et al., "Antibiotics in periodontal therapy: advantages and disadvantages," J. Clin. Periodontol., 17(7 (Pt 2)):479-493, (1990).
Solleti et al., "Antimicrobial properties of liposomal azithromycin for Pseudomonas infections in cystic fibrosis patients," J Antibicrob Chemother, 70:784-796, (2015).
Soto et al., "Design Considerations for Silica-Particle-Doped Nitric-Oxide-Releasing Polyurethane Glucose Biosensor Membranes," ACS Sensors, 2(1):140-150, (2017).
Soto et al., "Functionalized Mesoporous Silica via an Aminosilane Surfactant Ion Exchange Reaction: Controlled Scaffold Design and Nitric Oxide Release," ACS Appl. Mater. Interfaces, 8(3):2220-2231, (2016).
Southerland et al., "Periodontitis and diabetes associations with measures of atherosclerosis and CHD," Atherosclerosis, 222(1):196-201, (2012).
Spellberg, B., et al., "The Epidemic of Antibiotic-Resistant Infections: a Call to Action for the Medical Community from the Infectious Diseases Society of America," Clin. Infect. Dis., 46:155-164, (2008).
Stasko and Schoenfisch, "Dendrimers as a Scaffold for Nitric Oxide Release," J. Am. Chem. Soc., 128(25):8265-8271, (2006).
Stasko et al., "Cytotoxicity of polypropylenimine dendrimer conjugates on cultured endothelial cells," Biomacromolecules, 8(12):3853-3859, (2007).
Stasko, N. A. et al., "S-Nitrosothiol-Modified Dendrimers as Nitric Oxide Delivery Vehicles," Biomacromolecules, 9(3):834-841, (2008).
Suchyta and Schoenfisch, "Controlled release of nitric oxide from liposomes," ACS Biomater. Sci. Eng., 3(9):2136-2143, (2017).
Sun et al., "Nitric Oxide-Releasing Dendrimers as Antibacterial Agents," Biomacromolecules, 13(10):3343-3354, (2012).
Tomalia et al., "A New Class of Polymers: Starburst-Dendritic," Polym. J, 17:117-132, (1985).
Valko, M. et al., "Metals, Toxicity and Oxidative Stress," Curr Med Chem., 12(10):1161-1208, (2005).
Van Strydnc et al., "Plaque inhibition of two commercially available chlorhexidine mouthrinses," J. Clin. Periodontol., 32(3)305-309, (2005).
Voit and Lederer, "Hyperbranched and highly branched polymer architectures--synthetic strategies and major characterization aspects," Chem. Rev., 109(11):5924-5973, (2009).
Wan, A., et al., "Characterization of folate-graft-chitosan as a scaffold for nitric oxide release," International Journal of Biological Macromolecules, Elsevier B.V. 43:415-421, (2008).
Wan, A., et al., "Effects of Molecular Weight and Degree of Acetylation on the Release of Nitric Oxide from Chitosan—Nitric Oxide Adducts," Journal of Applied Polymer Science, Wiley Periodicals, Inc., 117:2183-2188, (2010).
Wang et al., "Synthesis and applications of stimuli-responsive hyperbranched polymers," Prog. Polym. Sci., 64:114-153, (2017).
Wang et al., "Synthesis and gene delivery of poly(amido amine)s with different branched architecture,"Biomacromolecules, 11(2):489-495, (2010).
Wang et al., "Bioapplictions of hyperbranched polymers," Chemical Society Reviews, 44(12):4023-4071, (2015).
Wang et al., "Synthesis and evaluation of phenylalanine-modified hyperbranched poly (amido amine)s as promising gene carriers," Biomacromolecules, 11(1):241-251, (2009).
Wang et al., "The effect of a branched architecture on the antimicrobial activity of poly(sulfone amines) and poly(sulfone amine)/silver nanocomposites" J. Mater. Chem., 22:15227-15234, (2012).

(56) References Cited

OTHER PUBLICATIONS

Wang, J. And Xu, Tongwen, "Facile Construction of Multivalent Targeted Drug Delivery System from Boltorn® Series Hyperbranched Aliphatic Polyester an Folic Acid," Poly Adv Technol., 22:763-767, (2009).
Williams, D.L.H., "S-Nitrosation and the Reactions of S-Nitroso Compounds," Chem Soc Rev., 14(2):171-196, (1985).
Williams, D.L.H., "The Chemistry of S-Nitrosothiols," Acc Chem Res., 32(10):869-876, (1999).
Wink et al., "DNA deaminating ability and genotoxicity of nitric oxide and its progenitors," Science, 254(5034):1001-1003, (1991).
Wo et al., "Recent advances in thromboresistant and antimicrobial polymers for biomedical applications: just say yes to nitric oxide (NO)," Biomater. Sci., 4(8):1161-1183, (2016).
Wold et al., "Fabrication of Biodegradable Polymeric Nanofibers with Covalently Attached No Donors," ACS Appl. Mater. Interfaces, 4(6):3022-3030, (2012).
Worley et al., "Anti-Biofilm Efficacy of Dual-Action Nitric Oxide-Releasing Alkyl Chain Modified Poly(amidoamine) Dendrimers," Mol. Pharmaceutics, 12:1573-1583, (2015).
Worley et al., "Nitric Oxide-Releasing Quaternary Ammonium-Modified Poly(amidoamine) Dendrimers as Dual Action Antibacterial Agents," Bioconjugate Chem., 25(5):918-927, (2014).
Wu et al., "'Living' controlled in situ gelling systems: thiol-disulfide exchange method toward tailor-made biodegradable hydrogels," J. Am. Chem. Soc., 132(43):15140-15143, (2010).
Xiao, Y.L. et al., "Multifunctional Unimolecular Micelles for cancer-Targeted Drug Delivery and Positron Emission Tomography Imaging," Biomaterials, 33(11):3071-3082, (2012).
Xu et al., "Well-defined poly (2-hydroxyl-3-(2-hydroxyethylamino) propyl methacrylate) vectors with low toxicity and high gene transfection efficiency," Biomacromolecules, 11(6):1437-1442, (2010).
Yang et al., "S-Nitrosothiol-modified hyperbranched polyesters," Polym. Chem., 7(46):7161—7169, (2016).
Yapor, J.P. et al., "Biodegradable Citrate-Based Polyesters with S-Nitrosothiol Functional Groups for Nitric Oxide Release," J Mater Chem B., 3(48):9233-9241, (2015).
Zagar, E. and Zigon, M., "Aliphatic Hyperbranched Polyesters Based on 2,2-bis(methylol)propionic Acid—Determination of Structure, Solution and Bulk Properties," Prog Polymer Sci., 36(1):53-88, (2011).
Zambon, Joseph J., "Actinobacillus actinomycelemcomitans in hum periodontal disease," Journal of Clinical Periodontology, 12(1):1-20, (1985).
Zamboulis et al: "Polyglycerol Hyperbranched Polyesters: Synthesis, Properties and Pharmaceutical and Biomedical Applications," International Journal of Molecular Sciences, 20(24):6210, (2019).
Zeng, X.H. et al., "Endocytic Uptake and Intracellular Trafficking of Bis-MPA-Based Hyperbranched Copolymer Micelles in Breast Cancer Cells," Biomacromolecules, 13(11):3814- 3822, (2012).
Zhai, X. et al., "Amphiphilic Dendritic Molecules: Hyperbranched Polyesters with Alkyl-Terminated Branches," Macromolecules, 36(9):3101-3110, (2003).
Zhang et al., "Nitric oxide-releasing fumed silica particles: synthesis, characterization, and biomedical application," J. Am. Chem. Soc., 125(17):5015-5024, (2003).
Zhang et al., "A psyhical gel made from hyperbranched polymer gelator," Chem. Commun., 25:2587-2589, (2007).
Zhang et al., "Antibacterial cotton fabric grafted with silver nanoparticles and its excellent laundering durability," Carbohydr. Polym., 92(2):2088-2094, (2013).
Zhang et al., "Synthesis of an amino-terminated hyperbranched polymer and its application in reactive dyeing on cotton as a salt-free dyeing auxiliary," Color. Technol., 123(6):351-357, (2007).
Zhang et al., "The antimicrobial activity of the cotton fabric grafted with an amino-terminated hyperbranched polymer," Cellulose, 16:281-288, (2009).
Zhang, H. et al., "Hyperbranched Pyester Hydrogels with Control Adhesion Properties," Biomacromoleolcules, 14(5):1299-1310, (2013).
Zhang, X.F. et al., "Nitric Oxide Delivery by Core/shell Superparamagnetc Nanopartical Vehicles with Enhanced Biocompatibility," Langmuir., 28(35):12879-12885, (2012).
Zheng et al. "Hyperbranched polymers: Advances from synthesis to applications," Chemical Society Reviews, 44(12):4091-4130, (2015).
Zhong, Yong-Li, et al., "Scalable Synthesis of Diazeniumdiolates: Application to the Preparation of MK-8150," Organic letters, 21(11):4210-4214, (2019).
Zhou et al., "Water-soluble poly (ethylenimine)-based nitric oxide donors: preparation, characterization, and potential application in hemodialysis," Biomacromolecules, 7(9):2565-2574, (2006).
Zhu et al., "Influence of Branching Architecture on Polymer Properties," Journal of Polymer Science Part B: Polymer Physics, 49(18):1277-1286, (2011).
European Application No. 18775628.3, Extended European Search Report dated Sep. 28, 2020.
European Application No. 18812540.5, Communication pursuant to Rules 161(1) and 162 EPC, dated Jul. 8, 2020.
European Serch Report and Search Opinon dated Aug. 3, 2020 by the European Search Authority for EP Application No. 18736471.6 (8 pages).
European Search Report dated May 4, 2020 by the European Search Authority for EP Application No. 17859196.2 (32 pages).
Supplementary European Search Report dated Feb. 5, 2016 in EP Application No. 13829755.1.
WIPO Application No. PCT/IB2018/050051, PCT International Search Report and Written Opinion of the International Searching Authority dated Jun. 8, 2018.
WIPO Application No. PCT/IB2018/052144, PCT International Search Report and Written Opinion of the International Searching Authority dated Aug. 8, 2018.
WIPO Application No. PCT/US2013/055360, PCT International Search Report and Written Opinion of the International Searching Authority dated Dec. 23, 2013.
WIPO Application No. PCT/US2017/055371, PCT International Preliminary Report on Patentability dated Apr. 9, 2019.
WIPO Application No. PCT/US2017/055371, PCT International Search Report and Written Opinion of the International Searching Authority dated Dec. 28, 2017.
WIPO Application No. PCT/US2018/061061, PCT International Search Report and Written Opinion of the International Searching Authority dated Apr. 5, 2019.
WIPO Application No. PCT/US2019/068412, PCT International Search Report and Written Opinion of the International Searching Authority dated May 21, 2020.

* cited by examiner

NITRIC OXIDE-RELEASING CYCLODEXTRINS AS BIODEGRADABLE ANTIBACTERIAL SCAFFOLDS AND METHODS PERTAINING THERETO

CROSS-REFERENCE TO RELATED APPLICATIONS

This patent application is a continuation of International Application No. PCT/US2019/21051, filed Mar. 6, 2019, which claims the benefit of priority to U.S. Provisional Patent Application No. 62/639,119, filed Mar. 6, 2018. The foregoing applications are fully incorporated herein by reference for all purposes.

STATEMENT REGARDING FEDERALLY SPONSORED R&D

This invention was made with government support under Grant Number DE025207 awarded by The National Institutes of Health. The Government has certain rights in the invention.

BACKGROUND

Field

The presently disclosed subject matter relates generally to nitric oxide-releasing cyclodextrin units which are covalently modified with units that store and release nitric oxide in a controlled manner. Additionally, disclosed are methods of synthesis and use of the same as antibacterial agents.

Description of the Related Art

Bacterial infections pose a great challenge to human health in community and hospital settings. Several chronic infections, such as those associated with implanted devices, chronic wounds, and cystic fibrosis are frequently caused by biofilm-forming pathogens such as *Pseudomonas aeruginosa* and *Staphylococcus aureus*. Biofilms are cooperative communities of bacteria encapsulated by an exopolysaccharide (EPS) matrix protecting the bacteria from host immune response and antibiotics.

SUMMARY

Nitric oxide (NO) plays a variety of physiological roles as a signaling molecule and, as disclosed herein, can also play significant roles in treating or ameliorating pathophysiology, for example as a therapeutic agent. NO as a therapeutic has heretofore been underused, based at least in part on limited NO payloads of therapeutic compositions, NO release rates that are more rapid than desired, and the lack of targeted NO delivery. Provided herein are NO-releasing constructs, methods of producing such constructs, and methods of treating various pathophysiologies using such constructs that leverage the enhanced NO-release characteristics and harness the abundant potential of NO-releasing pharmacological compounds. In particular, provided herein are compounds that are highly efficacious as antimicrobials.

In several embodiments, provided herein are NO-releasing cyclodextrin compounds. In several embodiments, provided herein is a functionalized cyclodextrin represented by the following structure:

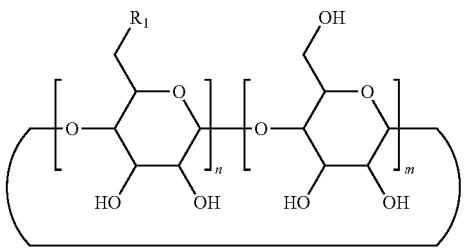
Formula III'

In several embodiments, n is an integer selected from 1 to 8. In several embodiments, m is an integer from 0 to 7. In several embodiments, each instance of $R_1$ is represented by $-X^1-((CH_2)_fX^2)_g-((CH_2)_qX^3)_r-(CH_2)_{h'}H$. In several embodiments, each of f', q, g, r, and h' is independently selected from an integer from 0 to 4. In several embodiments, each instance of $X^1$, $X^2$, or $X^3$ is independently selected from O, NH, and a nitric oxide donating substituent.

In several embodiments, at least one instance of $R^1$ is represented by one of the following:

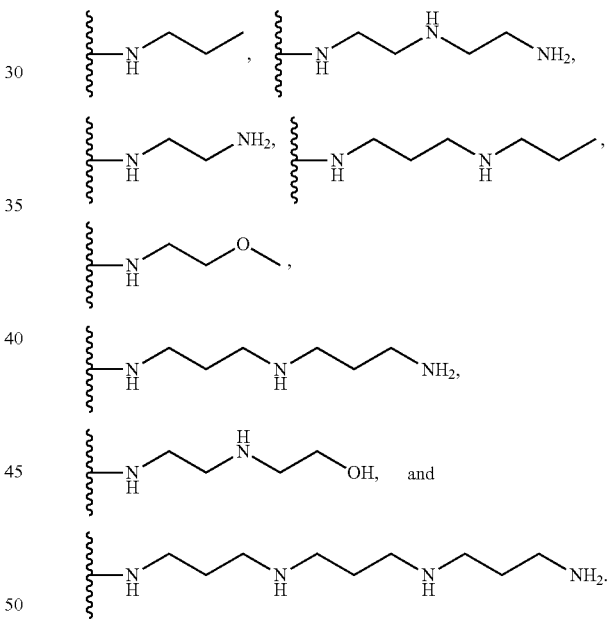

In several embodiments, at least one instance of $X^1$, $X^2$, or $X^3$ is represented by the following:

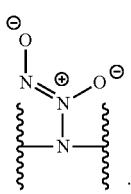

In several embodiments, the structure of Formula III' is further represented by the structure of Formula III:

Formula III
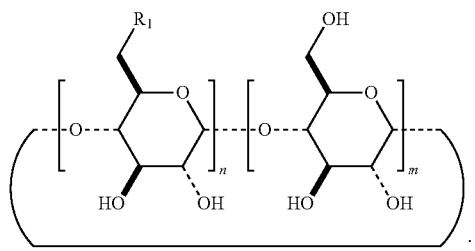
In several embodiments, at least one instance of $R^1$ is represented by one of the following:
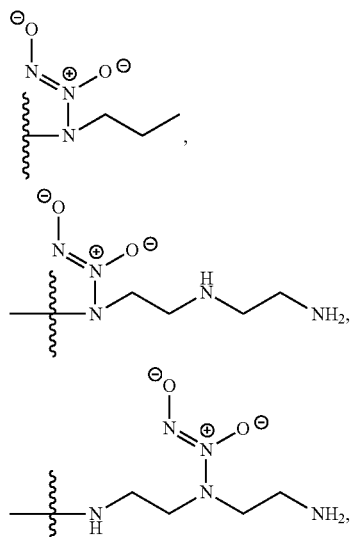
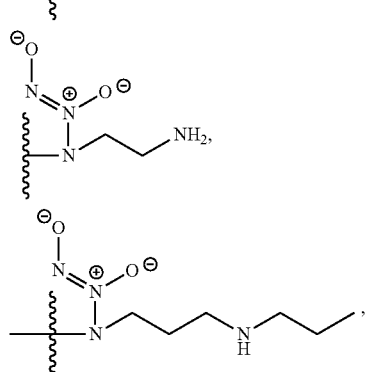
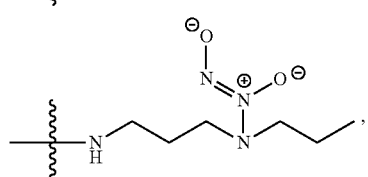
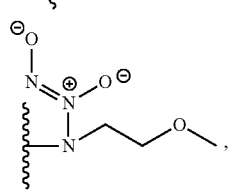
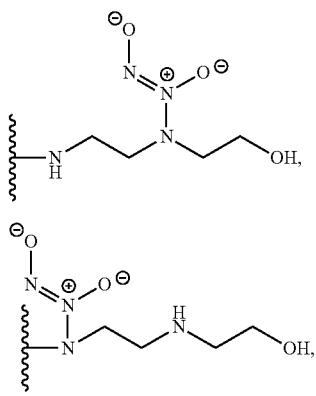
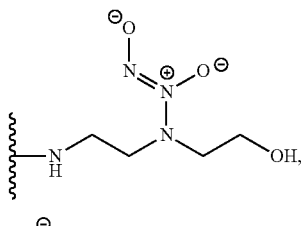
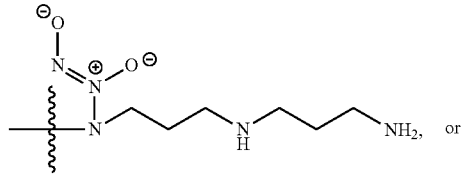
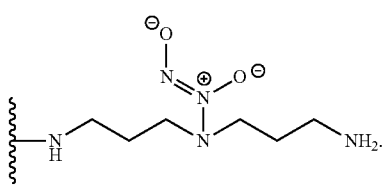
In several embodiments, at least one instance of $R^1$ is represented by one of the following:
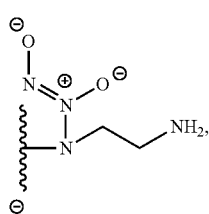
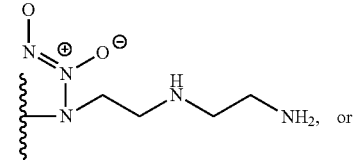
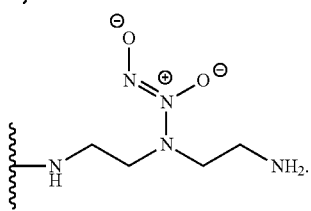

In several embodiments, n is an integer selected from 6, 7, and 8. In several embodiments, m is 0. In several embodiments, n is 1 and m is 6. In several embodiments, n is 7 and m is 0.

In several embodiments, the functionalized cyclodextrin has a total releasable nitric oxide storage of at least 0.5 µmol of NO per milligram of functionalized cyclodextrin. In several embodiments, the functionalized cyclodextrin has a total releasable nitric oxide storage in a range of about 0.5 µmol to 2.5 µmol of NO per milligram of functionalized cyclodextrin. In several embodiments, greater per milligram NO release is achieved, for example, at least about 2.5 µmol, about 3.0 µmol, about 3.5 µmol, about 4.0 µmol, about 4.5 mol, about 5 µmol or greater amounts of NO per milligram of functionalized cyclodextrin. In several embodiments, the functionalized cyclodextrin has a half-life for nitric oxide release in a range of between about 0.7-4.2 hours. In several embodiments, longer half-lives are achieved, such as for example, about 5 hours, about 6 hours, about 8 hours, about 10 hours, or any time between the listed times. In several embodiments, the functionalized cyclodextrin has a total NO release after 4 hours in a range of between about 0.1-4.0 µmol of NO per milligram of the functionalized cyclodextrin, including about 0.3-2.0 µmol of NO per milligram of the functionalized cyclodextrin, about 0.1-3.0 µmol of NO per milligram of the functionalized cyclodextrin, about 1.5-4 µmol of NO per milligram of the functionalized cyclodextrin, or, about 0.7-3.0 µmol of NO per milligram of the functionalized cyclodextrin (or any range therebetween, including endpoints).

Several embodiments pertain to a composition comprising the functionalized cyclodextrin and a pharmaceutically acceptable carrier. In several embodiments, the composition comprises a cyclodextrin that is not functionalized. In several embodiments, the composition comprises one or more guest drugs complexed with the functionalized cyclodextrin. In several embodiments, the one or more guest drugs comprise one or more drugs for the treatment of a cancer, a cardiovascular disease, a microbial infection, platelet aggregation and/or platelet adhesion, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, sexually transmitted diseases, or wound healing.

Several embodiments pertain to a method of delivering nitric oxide to a subject. In several embodiments, an effective amount of the functionalized cyclodextrin or the composition is administered to said subject.

Several embodiments pertain to a method of treating a disease state. In several embodiments, an effective amount of the functionalized cyclodextrin is administered to said subject to a subject in need thereof, wherein said disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases. In several embodiments, the disease state is a microbial infection.

Several embodiments pertain to a method of treating a disease state, comprising administering an effective amount of the functionalized cyclodextrin or the composition to said subject to a subject in need thereof, wherein said disease state is lung cancer.

Several embodiments pertain to use of the functionalized cyclodextrin or the composition of for delivering nitric oxide to a subject. Several embodiments pertain to use of the functionalized cyclodextrin or the composition in the preparation of a medicament for treating a subject in need. In several embodiments, the disease state is selected from the group consisting of one or more of: a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

Several embodiments pertain to a functionalized cyclodextrin comprising at least one ring unit of Formula I:

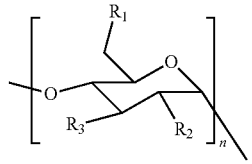

Formula I

In several embodiments, n is an integer selected from 1 to 8. In several embodiments, $R_1$, $R_2$, and $R_3$ are independently selected from the group consisting of —OH, —$CH_2CH_2OH$, —$CH_2CH(OH)CH_3$, —O—$((CH_2)_tO)_u$—H, —O—$((CH_2)_tO)_{u'}$—$(CH_2)_v$H, —O—$(C_{1-8}alkyl)$, —$C_2H_5$, —$C_8H_{17}$, —NH—$((CH_2)_cNH)_d$—H, —NH—$((CH_2)_cNH)_{d'}$—$(CH_2)_e$H, —$X^1$—$((CH_2)_fX^2)_g$—$(CH_2)_h$H, —$X^1$—$((CH_2)_fX^2)_g$—$((CH_2)_qX^3)_r$—$(CH_2)_h$H, —C(O)Me, —$C(O)C_3H_7$, —$C(O)C_4H_9$, —$CH_2COONa$, —$(CH_2)_4SO_3^-$, —$SO_3$—, —C(O)O—$((CH_2)_tO)_u$—H, —C(O)O—$((CH_2)_tO)_{u'}$—$(CH_2)_v$H, —C(O)O—$(C_{1-5}alkyl)$, —C(O)NH—$((CH_2)_cNH)_d$—H, —C(O)NH—$((CH_2)_cNH)_{d'}$—$(CH_2)_e$H, —$C(O)X^1$—$((CH_2)_fX^2)_g$—$(CH_2)_h$H, —$C(O)X^1$—$((CH_2)_fX^2)_g$—$((CH_2)_qX^3)_r$—$(CH_2)_h$—H, glycosyl, maltosyl, and glucoronate. In several embodiments, each instance of c, c', d, d', e, f, f', g, g', h, h', q, r, t, t', u, u', and v is independently selected from an integer from 0 to 10. In several embodiments, each instance of $X^1$, $X^2$, and $X^3$ is independently selected from O, S, NH, and a NO donating substituent. In several embodiments, at least one instance of $X^1$, $X^2$, and $X^3$ is a NO donating substituent.

In several embodiments, the NO donating substituent is selected from one of the following:

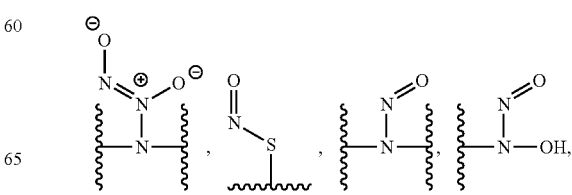

-continued

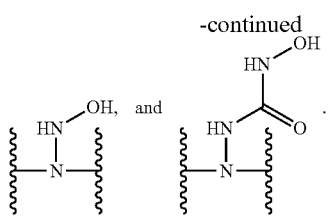

In several embodiments, at least one instance of $X^1$, $X^2$, and $X^3$ is represented by the following structure:

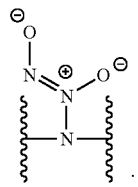

In several embodiments, provided is a functionalized cyclodextrin comprising at least one ring unit of Formula I:

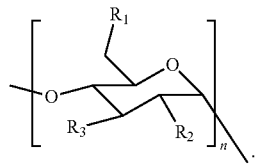

Formula I

In several embodiments, functionalized cyclodextrins as provided for herein are advantageous in that they provide for one or more of enhanced NO delivery to a target site, enriched NO delivery capacity, improved compound stability, and enhanced anti-microbial effects (e.g., activity and/or duration of NO delivery). In several embodiments, n is an integer selected from 1 to 8. In some embodiments, $R_1$, $R_2$, and $R_3$ are independently selected from the group consisting of —OH, —O—$((CH_2)_tO)_u$—H, —O—$((CH_2)_tO)_{u'}$—$(CH_2)_vH$, —O—$(C_{1-5}alkyl)$, —NH—$((CH_2)_cNH)_d$—H, —NH—$((CH_2)_cNH)_{d'}$—$(CH_2)_eH$, —$X^1$—$((CH_2)_fX^2)_g$—$(CH_2)_hH$, and —$X^1$—$((CH_2)_fX^2)_g$—$((CH_2)_qX^3)_r$—$(CH_2)_hH$. In some embodiments, c, c', d, d', e, f, f', g, g', h, h', q, r, t, t', u, u', and v, are independently selected from an integer from 0 to 10 (e.g., 0, 1, 2, 3, 4, 5, 6, 7, 8, 9, or 10). In some embodiments, d, d', g, g', r, u, and u' are independently selected from an integer from 0 to 4 (e.g., 0, 1, 2, 3, 4). In some embodiments, c, c', e, f, f', h, h', q, t, t', and v, are independently selected from an integer from 0 to 3 (e.g., 0, 1, 2, 3). In several embodiments, $X^1$, $X^2$, and $X^3$ are independently selected from O, S, or NH. In several embodiments, at least one of $X^1$, $X^2$, and $X^3$ is represented by the following functional unit:

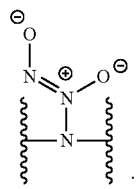

In several embodiments, $R^1$ is —$X^1$—$((CH_2)_fX^2)_g$—$((CH_2)_qX^3)_r$—$(CH_2)_hH$. In several embodiments, $R_2$ and $R_3$ are —OH.

In several embodiments, the functionalized cyclodextrin further comprises at least one glycopyranoside ring unit having the following structure:

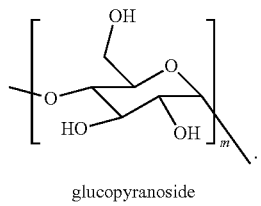

glucopyranoside

In several embodiments, m is an integer selected from 1 to 8. In several embodiments, n is 1 and m is 5, 6, or 7. In several embodiments, n is 6, 7, or 8. In several embodiments, n+m is equal to 10 where n is any integer from 0 to 10 and m is any integer from one to ten. For instance, where n+m is 7 and n is 3, then m is 4, etc.

In several embodiments, the functionalized cyclodextrin is selected from one of the following structures:

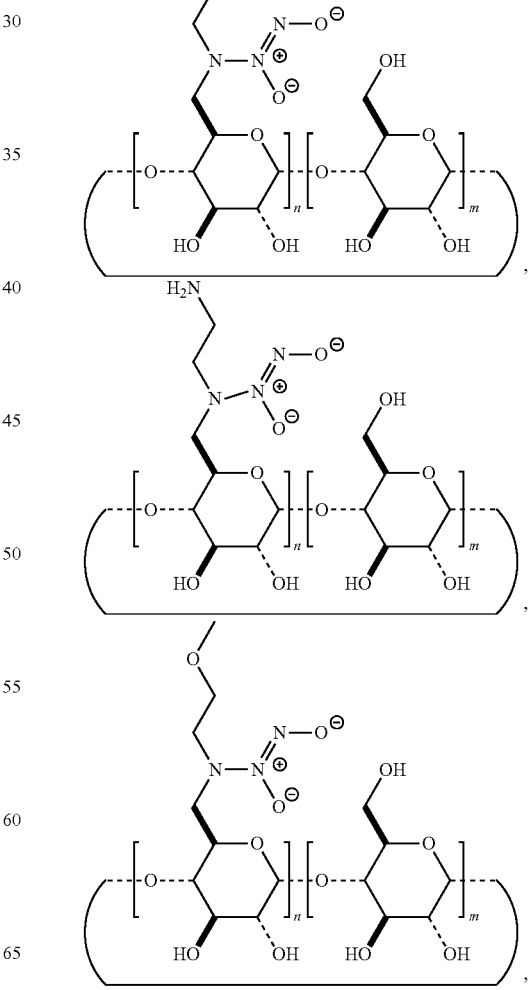

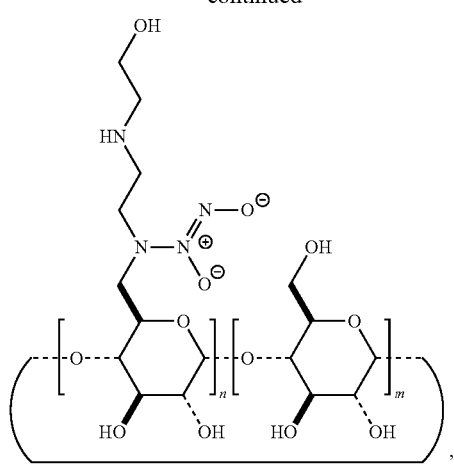
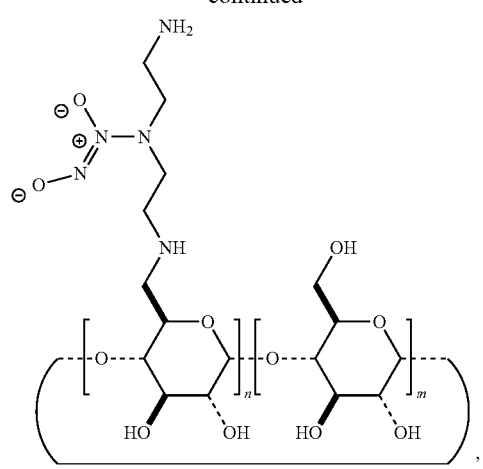
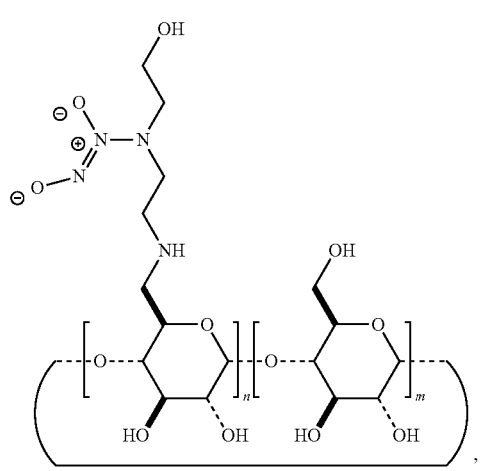
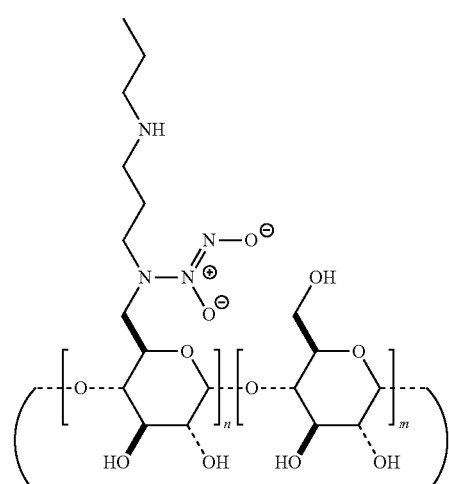
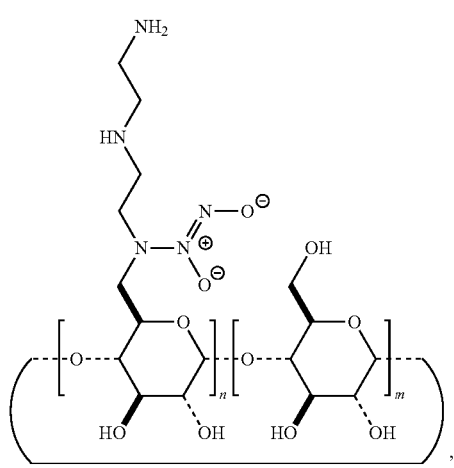
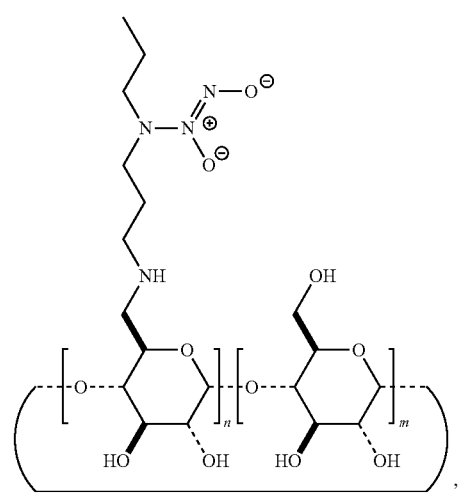

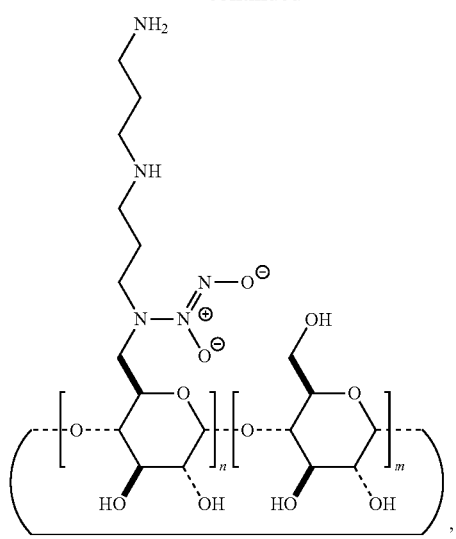
,
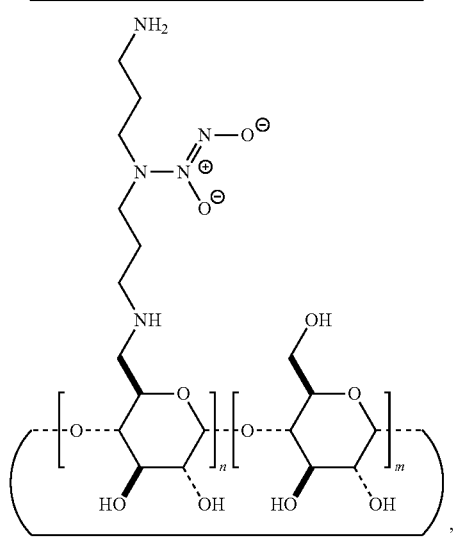
,
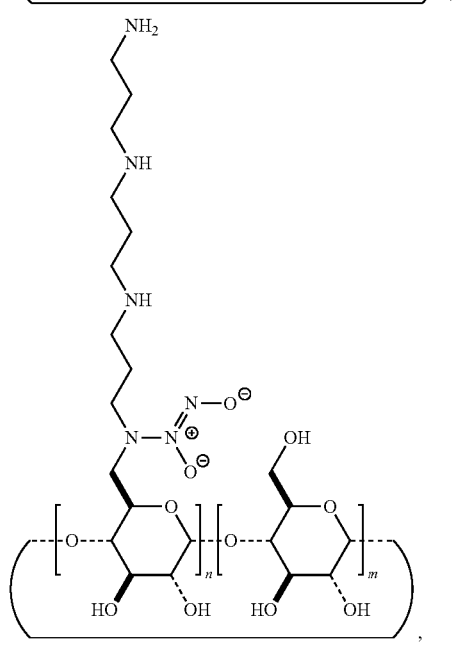
,
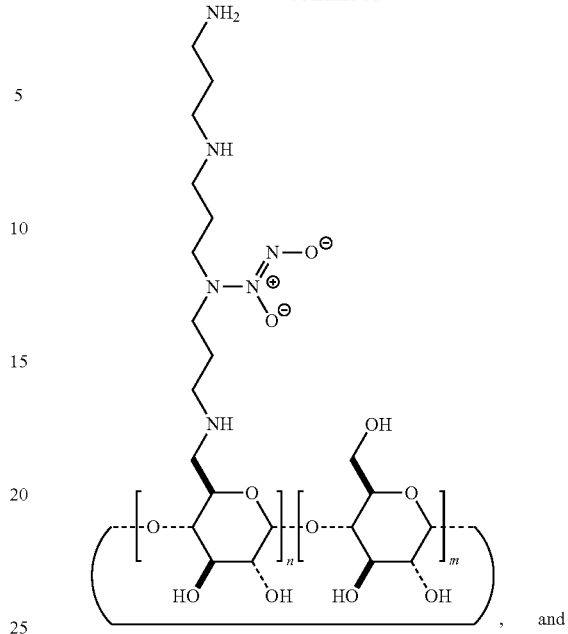
, and
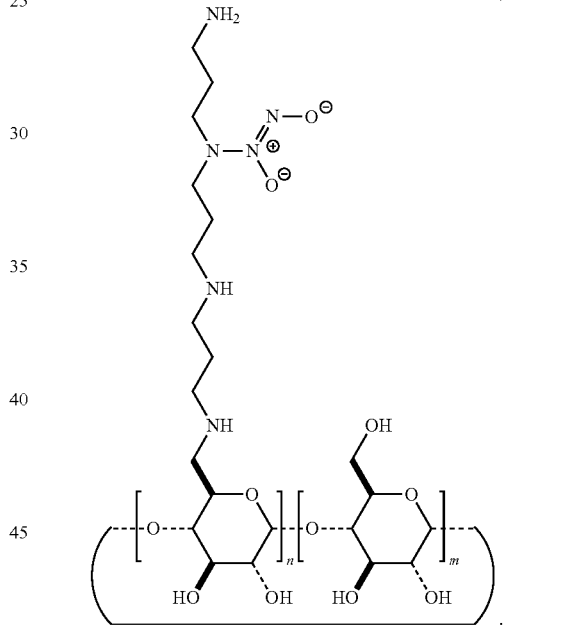
.
In several embodiments, a formulation is provided that comprises functionalized cyclodextrins, wherein the formulation is made up of a plurality of cyclodextrins having one or more of the structures above.
In several embodiments, provided is a functionalized cyclodextrin comprising at least one ring unit of Formula I:
Formula I
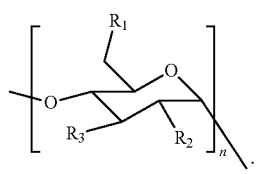

In several embodiments, n is an integer selected from 1 to 8. In several embodiments, $R_1$, $R_2$, and $R_3$ are independently selected from the group consisting of —OH, —O—$((CH_2)_tO)_u$—H, —O—$((CH_2)_tO)_{u'}$—$(CH_2)_vH$, —O—$(C_{1-5}alkyl)$, —NH—$((CH_2)_cNH)_d$—H, —NH—$((CH_2)_cNH)_{d'}$—$(CH_2)_eH$, —$X^1$—$((CH_2)_fX^2)_g$—$(CH_2)_hH$, and —$X^1$—$((CH_2)_fX^2)_{g'}$—$((CH_2)_qX^3)_r$—$(CH_2)_{h'}H$. In some embodiments, c, c', d, d', e, f, f', g, g', h, h', q, r, t, t', u, u', and v, are independently selected from an integer from 0 to 10 (e.g., 0, 1, 2, 3, 4, 5, 6, 7, 8, 9, or 10). In several embodiments, $X^1$, $X^2$, and $X^3$ are independently selected from O, S, or NH. In several embodiments, at least one of $X^1$, $X^2$, and $X^3$ is selected from the group consisting of

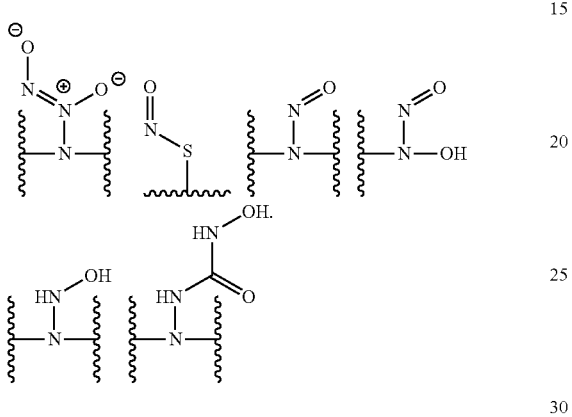

Depending on the embodiment, $X^1$, $X^2$, and $X^3$ can each have the same structure above, or in some embodiments, one or more of $X^1$, $X^2$, and $X^3$ have different structures.

In several embodiments, $R^1$ is —$X^1$—$((CH_2)_fX^2)_g$—$(CH_2)_hH$ and at least one of $X^1$ and $X^2$ is the following:

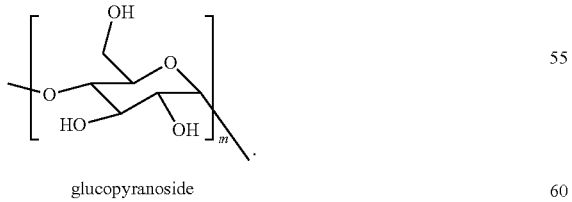

In several embodiments, $R_2$ and/or $R_3$ are —OH.

In several embodiments, the functionalized cyclodextrin comprises at least one glycopyranoside ring unit having the following structure:

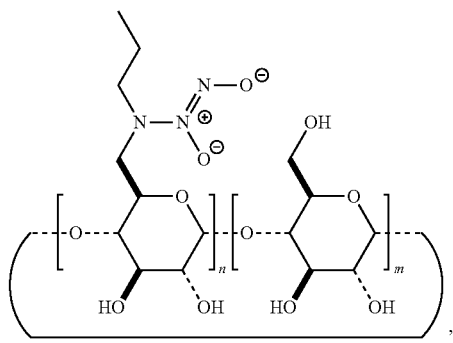

glucopyranoside

In several embodiments, m is an integer selected from 1 to 8. In several embodiments, n is 1 and m is 5, 6, or 7. In several embodiments, n is 6, 7, or 8.

In several embodiments, the functionalized cyclodextrin is selected from the group consisting of:

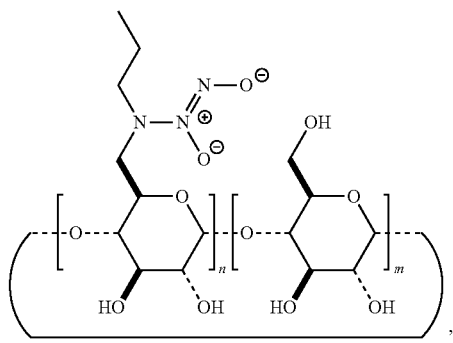

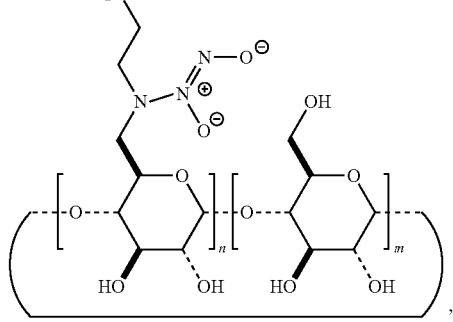

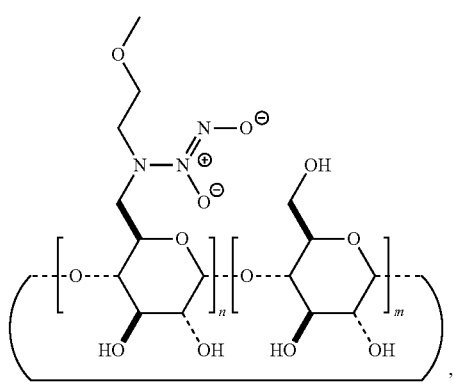

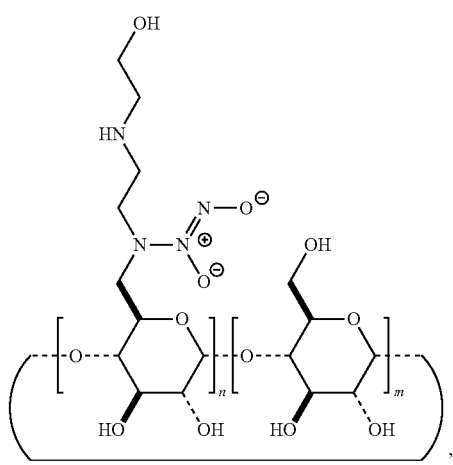

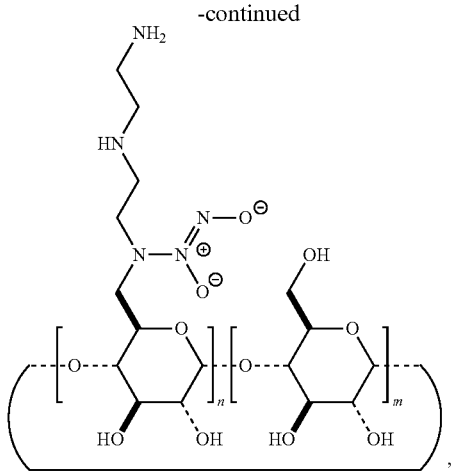

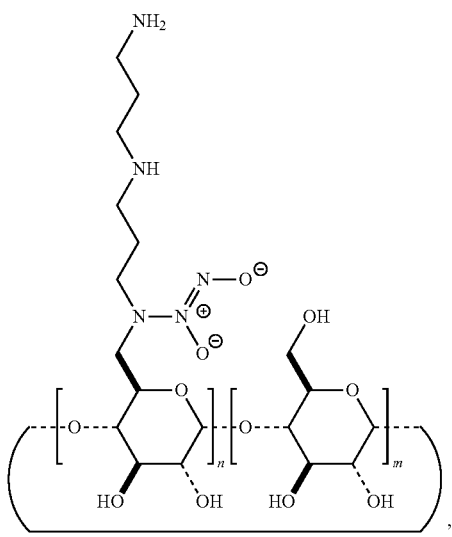
, and

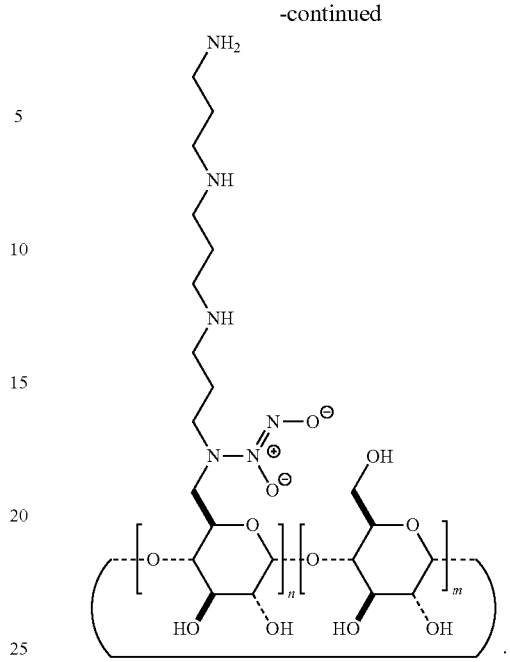

In several embodiments, combinations of such functionalized cyclodextrins are used in an anti-microbial formulation.

In several embodiments, provided is a functionalized cyclodextrin compound having the following formula:

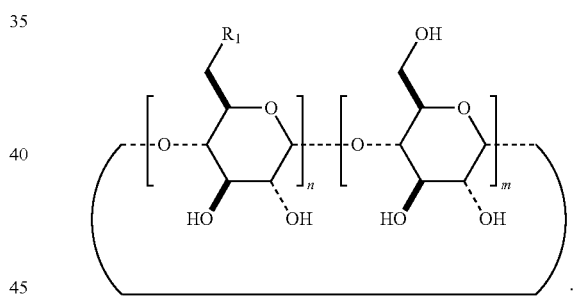

In several embodiments, n is an integer selected from 1 to 8. In several embodiments, m is an integer from 0 to 7. In several embodiments, $R_1$ is $-X^1-((CH_2)_f X^2)_{g'}$ $((CH_2)_q X^3)_r-(CH_2)_{h'}H$. In several embodiments, each of f', g' q, r, and h' is independently selected from an integer from 0 to 10. In several embodiments, $X^1$, $X^2$, and $X^3$ are independently selected from NH or

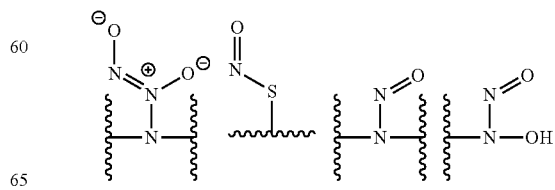

-continued

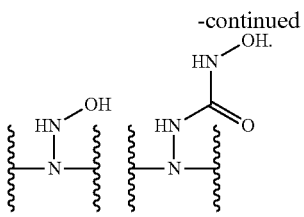

In several embodiments, the functionalized cyclodextrin has a total releasable nitric oxide storage of at least 0.5 μmol of NO per milligram of functionalized cyclodextrin. In a further embodiment, the functionalized cyclodextrin has a total releasable nitric oxide storage in a range of about 0.5 μmol to 2.5 μmol of NO per milligram of functionalized cyclodextrin. In another embodiment, the functionalized cyclodextrin has a total releasable nitric oxide storage in a range of about 1.0 μmol to 2.5 μmol of NO per milligram of functionalized cyclodextrin.

In several embodiments, the functionalized cyclodextrin has a half-life for nitric oxide release in a range of between about 0.1-24 hours. In a further embodiment, the functionalized cyclodextrin has a half-life for nitric oxide release in a range of between about 0.7-4.2 hours.

In several embodiments, the functionalized cyclodextrin has a total duration of NO release in a range of between about 1-60 hours.

In several embodiments, the functionalized cyclodextrin has a total NO release after 4 hours in a range of between about 0.3-2.0 μmol of NO per milligram of the functionalized cyclodextrin.

Several embodiments pertain to a method of delivering nitric oxide to a subject (e.g., use of NO-generating compounds). In several embodiments, the method comprises a step of administering an effective amount of a functionalized cyclodextrin as disclosed herein to the subject.

Several embodiments pertain to a method of treating a disease state. In several embodiments, the method comprises a step of administering an effective amount of a functionalized cyclodextrin as described herein to a subject in need of treatment. In several embodiments, the disease state is a cancer, a cardiovascular disease, a microbial infection, platelet aggregation and/or platelet adhesion caused by the exposure of blood to a medical device, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders (including cystic fibrosis), sexual dysfunctions, sexually transmitted diseases, or wound healing (e.g., from burns). Subject may be affected with more than one of such diseases simultaneously, in which case the method of administering a functionalized cyclodextrin, in several embodiments, is effective to treat multiple conditions. In several embodiments, said disease state is a microbial infection.

Several embodiments relate to a use of a functionalized cyclodextrin as disclosed herein for delivering nitric oxide to a subject. In several embodiments, the use provides involves the preparation of a medicament for treating a subject in need with a disease state selected from the group consisting of one or more of: a cancer, a cardiovascular disease, a microbial infection, platelet aggregation and/or platelet adhesion caused by the exposure of blood to a medical device, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, and/or sexually transmitted diseases. In one embodiment, there is provide a use of a functionalized cyclodextrin configured to release nitric oxide for use in treating microbial infection and/or reducing a microbial load.

In several embodiments, provided is a functionalized cyclodextrin comprising at least one ring unit of Formula I:

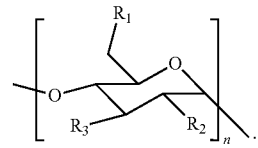

Formula I

In several embodiments, n is an integer selected from 1 to 8. In several embodiments, $R_1$, $R_2$, and $R_3$ are independently selected from the group consisting of —OH, —O—$((CH_2)_tO)_u$—H, —O—$((CH_2)_tO)_{u'}$—$(CH_2)_v$H, —O—$(C_{1-5}alkyl)$, —NH—$((CH_2)_c NH)_d$—H, —NH—$((CH_2)_c NH)_{d'}$—$(CH_2)_e$H, —$X^1$—$((CH_2)_f X^2)_g$—$(CH_2)_h$H, and —$X^1$—$((CH_2)_f X^2)_g$—$((CH_2)_q X^3)_r$—$(CH_2)_{h'}$H. In some embodiments, c, c', d, d', e, f, f', g, g', h, h', q, r, t, t', u, u', and v, are independently selected from an integer from 0 to 10 (e.g., 0, 1, 2, 3, 4, 5, 6, 7, 8, 9, or 10). In several embodiments, $X^1$, $X^2$, and $X^3$ are independently selected from O, S, or NH. In several embodiments, $R^2$ and $R^3$ are —OH. In several embodiments, $R^1$ is —$X^1$—$((CH_2)_f X^2)_{g'}$—$((CH_2)_q X^3)_r$—$(CH_2)_h$H. In several embodiments, where present, each of $X^1$, $X^2$, and $X^3$ is —NH.

In several embodiments, the functionalized cyclodextrin has chemical structure selected from the group consisting of:

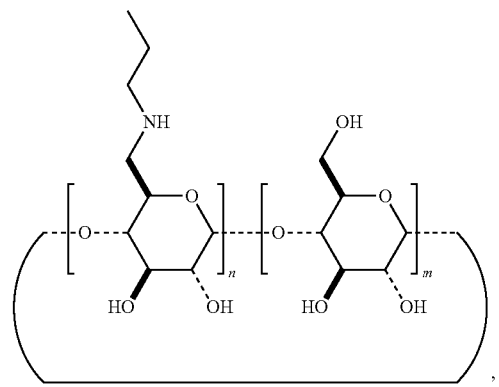

CD-PA

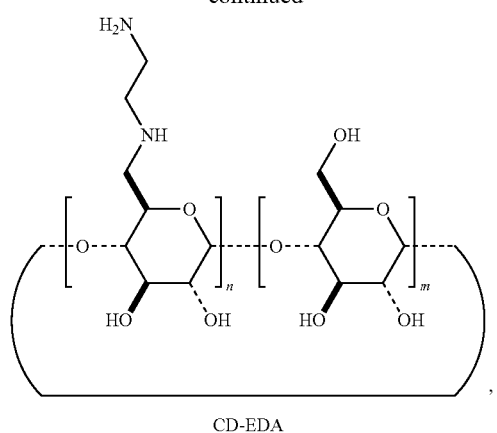

CD-EDA

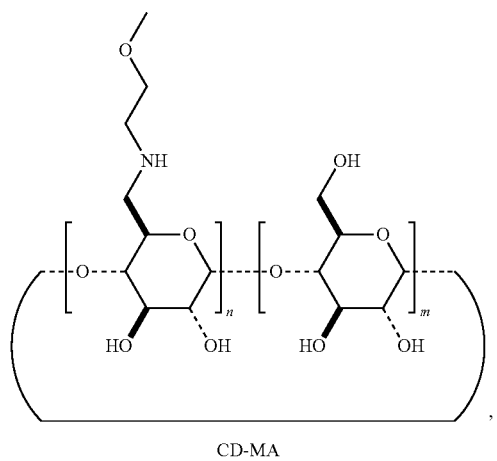

CD-MA

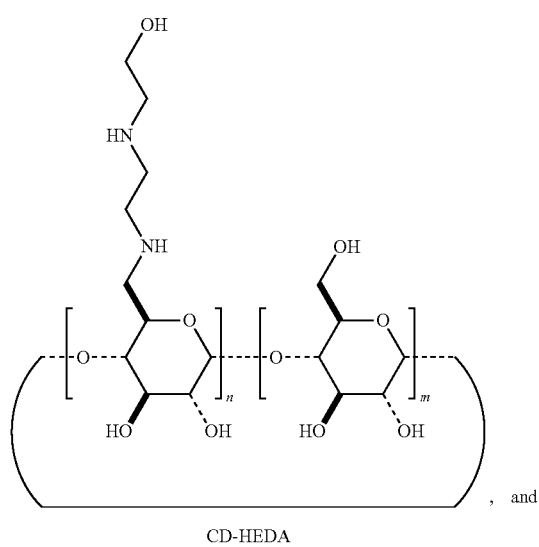

CD-HEDA, and

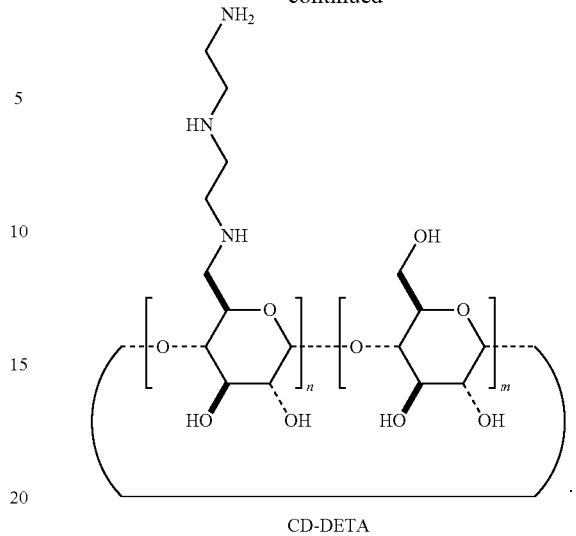

CD-DETA

In several embodiments, provided herein is a functionalized cyclodextrin represented by the following structure:

Formula III'

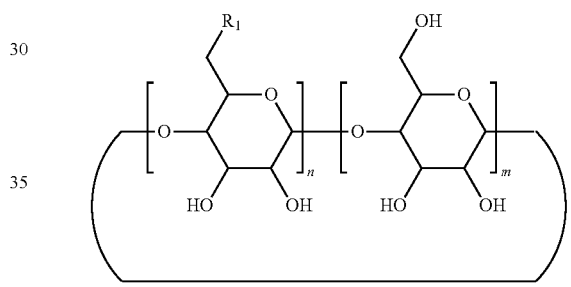

In several embodiments, n is an integer. In several embodiments, m is an integer. In several embodiments, each instance of $R_1$ is represented by $-X^1-((CH_2)_fX^2)_g-((CH_2)_qX^3)_r-(CH_2)_{h'}H$. In several embodiments, each of f, q, g, r, and h' is independently selected as an integer. In several embodiments, each instance of $X^1$, $X^2$, or $X^3$ is independently selected from O, NH, and a nitric oxide donating substituent. In several embodiments, the total releasable nitric oxide storage ranges from about 1.0 μmol to 2.5 μmol of NO per milligram of functionalized cyclodextrin. In several embodiments, the half-life for nitric oxide release ranges from about 0.1-24 hours. In several embodiments, the total duration of NO release ranges from about 1-60 hours.

In several embodiments, the functionalized cyclodextrin further comprises at least one guest drug, wherein the guest drug exerts therapeutic effects at a lower concentration when complexed with the functionalized cyclodextrin, as compared to the guest drug alone.

Several embodiments pertain to a method of delivering NO to a subject comprising, administering the functionalized cyclodextrin to the subject. In several embodiments, the administration route is via inhalation and the NO delivery treats a disease of the lungs. In several embodiments, the disease of the lungs is cystic fibrosis. In several embodiments, the disease of the lungs is lung cancer.

Several embodiments pertain to a functionalized cyclodextrin in the preparation of a medicament for the treatment of a disease or condition.

Several embodiments pertain to use of a functionalized cyclodextrin for the treatment of a disease or condition.

Several embodiments pertain to a method of treating the respiratory system. In several embodiments, a composition comprising functionalized cyclodextrin is administered to a lung via inhalation. In several embodiments, the functionalized cyclodextrin has a total releasable nitric oxide storage as disclosed elsewhere herein. In several embodiments, the functionalized cyclodextrin has a total releasable nitric oxide storage ranging from about 1.0 µmol to 2.5 µmol of NO per milligram of functionalized cyclodextrin. In several embodiments, the functionalized cyclodextrin has a half-life for nitric oxide release as disclosed elsewhere herein. In several embodiments, the functionalized cyclodextrin has a half-life for nitric oxide release ranges from about 0.1-24 hours. In several embodiments, the functionalized cyclodextrin has a total duration of NO release as disclosed elsewhere herein. In several embodiments, the functionalized cyclodextrin has a total duration of NO release ranges from about 1-60 hours. In several embodiments, the functionalized cyclodextrin has a total releasable nitric oxide storage of at least about 1.0 µmol per milligram of functionalized cyclodextrin. In several embodiments, the functionalized cyclodextrin has a half-life for nitric oxide release of at least 1 hour.

In several embodiments, provided herein is a functionalized cyclodextrin represented by the following structure:

Formula III'

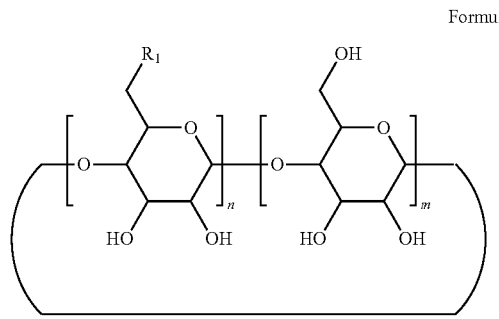

In several embodiments, n is an integer selected from 1 to 8. In several embodiments, m is an integer from 0 to 7. In several embodiments, each instance of $R_1$ is represented by $-X^1-((CH_2)_fX^2)_g((CH_2)_qX^3)_r-(CH_2)_{h'}H$. In several embodiments, each of f', q, g, r, and h' is independently selected from an integer from 0 to 4. In several embodiments, each instance of $X^1$, $X^2$, or $X^3$ is independently selected from O, NH, and a nitric oxide donating substituent.

In several embodiments, at least one instance of $R^1$ is represented by one of the following:

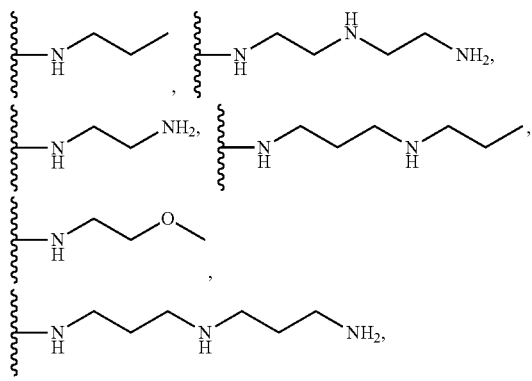

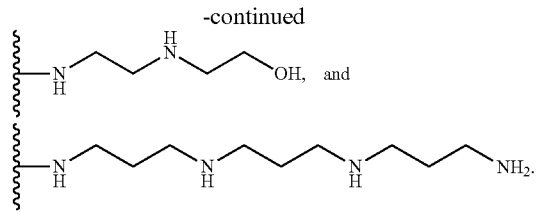

In several embodiments, at least one instance of $X^1$, $X^2$, or $X^3$ is represented by the following:

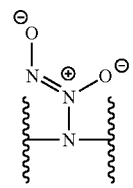

In several embodiments, the structure of Formula III' is further represented by the structure of Formula III:

Formula III

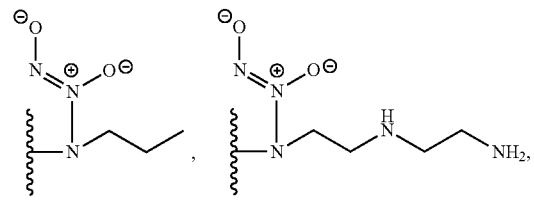

In several embodiments, at least one instance of $R^1$ is represented by one of the following:

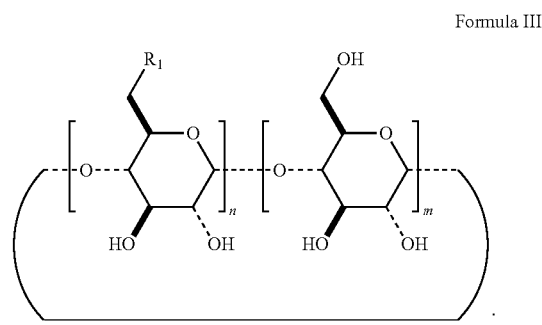

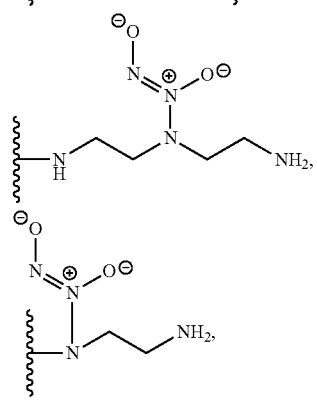

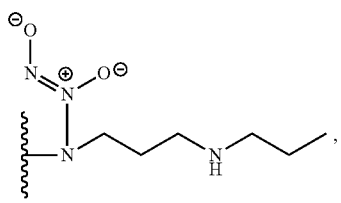

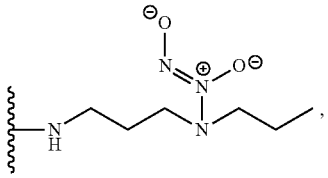

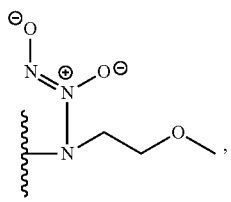

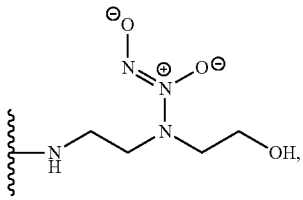

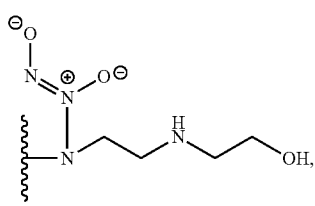

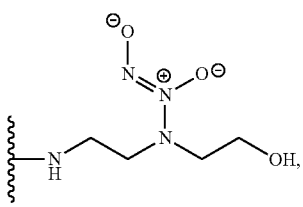

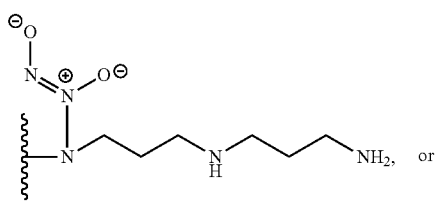

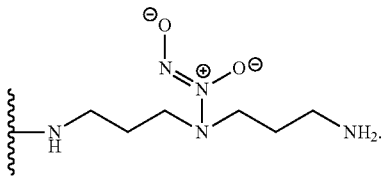

In several embodiments, n is an integer selected from 6, 7, and 8. In several embodiments, m is 0. In several embodiments, at least one instance of $R^1$ is represented by one of the following:

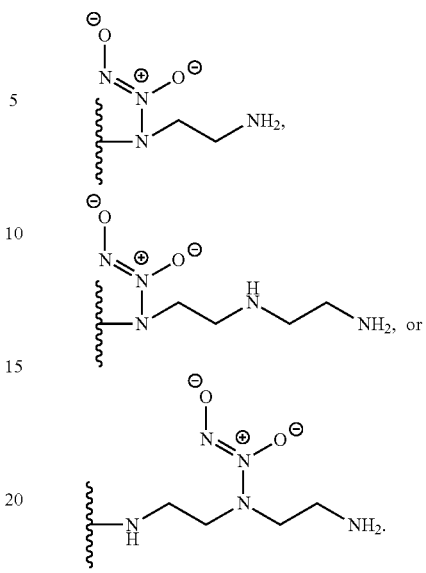

In several embodiments, n is 1 and m is 6. In several embodiments, n is 7 and m is 0.

In several embodiments, the functionalized cyclodextrin has a total releasable nitric oxide storage of at least 0.5 μmol of NO per milligram of functionalized cyclodextrin. In several embodiments, the functionalized cyclodextrin has a total releasable nitric oxide storage in a range of about 0.5 μmol to 2.5 μmol of NO per milligram of functionalized cyclodextrin. In several embodiments, the functionalized cyclodextrin has a half-life for nitric oxide release in a range of between about 0.7-4.2 hours. In several embodiments, the functionalized cyclodextrin has a total NO release after 4 hours in a range of between about 0.3-2.0 μmol of NO per milligram of the functionalized cyclodextrin.

In several embodiments, provided herein is a composition comprising the functionalized cyclodextrin and a pharmaceutically acceptable carrier. In several embodiments, the composition further comprises a cyclodextrin that is not functionalized. In several embodiments, the functionalized cyclodextrin or the composition further comprising one or more guest drugs complexed with the functionalized cyclodextrin. In several embodiments, the one or more guest drugs comprise one or more drugs for the treatment of a cancer, a cardiovascular disease, a microbial infection, platelet aggregation and/or platelet adhesion, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, sexually transmitted diseases, or wound healing.

In several embodiments, a method of delivering nitric oxide to a subject is provided. In several embodiments, an effective amount of the functionalized cyclodextrin is administered to said subject.

In several embodiments, a method of treating a disease state is provided. In several embodiments, an effective amount of the functionalized cyclodextrin or the composition is administered to a subject in need thereof. In several embodiments, said disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases. In several embodiments, said disease state is a microbial infection.

In several embodiments, method of treating a disease state is provided. In several embodiments, an effective amount of the functionalized cyclodextrin or the composition is administered to said subject to a subject in need thereof, wherein said disease state is lung cancer.

In several embodiments, a use of the functionalized cyclodextrin or the composition for delivering nitric oxide to a subject is provided. In several embodiments, provided is a use of the functionalized cyclodextrin or the composition in the preparation of a medicament for treating a subject in need with a disease state selected from the group consisting of one or more of: a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

Several embodiments pertain to a method of manufacturing a functionalized cyclodextrin. In several embodiments, the method comprises mixing a cyclodextrin with a functionalizing compound comprising a leaving group and a secondary amine to provide a cyclodextrin having a secondary amine. In several embodiments, the leaving group is one or more of —OTs, —OMs, —Cl, —Br, or —I. In several embodiments, the method further comprises exposing the cyclodextrin having a secondary amine with NO to afford an NO releasing functionalized cyclodextrin. In several embodiments, the method comprises mixing the cyclodextrin with a guest molecule to provide a host guest complex.

BRIEF DESCRIPTION OF THE DRAWINGS

In FIG. 1(a), the synthesis of secondary amine-modified CDs was carried out using the non-limiting examples of reagents and conditions as shown in (i)-(iv): (i) TsOCl, NaOH, $H_2O/CH_3CN$, at room temperature (r.t.); (ii) Primary amine ($RNH_2$), 75° C.; (iii) Bromine, $P(Ph)_3$, DMF, 80° C.; (iv) Primary amine ($RNH_2$), DMF, r.t. FIG. 1(b) Depicts a synthetic route with subsequent N-diazeniumdiolate formation (for CD-HEDA7/NO for example).

FIG. 2(a) Synthetic route of CD-HEDA7/NO. FIG. 2(b) $^1H$ NMR spectra of CD-HEDA7 (top line) and CD-HEDA7/NO (bottom line). FIG. 2(c) UV-Vis spectra of CD-HEDA7 (solid line) and CD-HEDA7/NO (dash line).

FIG. 12(a) CD-HEDA/NO, FIG. 12(b) CD-MA/NO, FIG. 12(c) CD-PA/NO, FIG. 12(d) CD-EDA/NO, and FIG. 12(e) CD-DETA/NO. NO-releasing materials are dash lines, and non-NO-releasing controls are solid lines.

FIG. 13(a) CD-HEDA7/NO (0.01 mg/mL), FIG. 13(b) CD-MA7/NO (0.02 mg/mL), FIG. 13(c) CD-PA7/NO (0.02 mg/mL), FIG. 13(d) CD-EDA7/NO (0.02 mg/mL), and FIG. 13(e) CD-DETA7/NO (0.01 mg/mL). NO-releasing materials are dash lines, and non-NO-releasing controls are solid lines.

FIG. 14(a) Proposed non-limiting mechanism for decomposition of N-diazeniumdiolate-modified CD derivatives. FIG. 14(b) Real-time plot of t[NO] vs time for NO-releasing CD derivatives. Solid line represents CD-PA/NO; dash line represents CD-MA7/NO; dot line represents CD-HEDA7/NO. FIG. 14(c) Proposed non-limiting structure for stabilization of N-diazeniumdiolate CD derivatives (according to several embodiments) by neighboring cationic ammonium groups.

FIG. 15(a) Real-time plot of t[NO] vs time for NO-releasing mono-substituted CD derivatives. Brown line represents CD-HEDA/NO; red line represents CD-MA/NO; black line represents CD-PA/NO; green line represents CD-EDA/NO; blue line represents CD-DETA/NO. FIG. 15(b) Real-time plot of t[NO] vs time for NO-releasing hepta-substituted CD derivatives. Brown line represents CD-HEDA7/NO; red line represents CD-MA7/NO; black line represents CD-PA7/NO; green line represents CD-EDA7/NO; blue line represents CD-DETA7/NO.

FIG. 16(a) CD-HEDA/NO, FIG. 16(b) CD-MA/NO, FIG. 16(c) CD-PA/NO, FIG. 16(d) CD-EDA/NO, and FIG. 16(e) CD-DETA/NO. NO-releasing CDs are red filled circles, and control CDs are black filled squares. Error bars represents standard deviation of the mean viability (CFU/mL). For all measurements, n=3 or more pooled experiments.

FIG. 17(a) Bright field; FIG. 17(b) DAF-2; FIG. 17(c) PI.

FIG. 20(a) CD-HEDA7/NO, FIG. 20(b) CD-MA7/NO, FIG. 20(c) CD-PA7/NO, FIG. 20(d) CD-EDA7/NO, and FIG. 20(e) CD-DETA7/NO. NO-releasing CDs are red (filled circles), and control CDs are black (filled squares). Error bars represents standard deviation of the mean viability (CFU/mL). For all measurements, n=3 or more pooled experiments.

FIG. 21(a) Mono-substituted CD derivatives; FIG. 21(b) Hepta-substituted CD derivatives. FIG. 21(c) shows bacterial viability data for DETA, DETA/NO, and DETA/NO mixed with CD. FIG. 21(d) shows data gathered using CD-DETA and CD-DETA/NO (CD-DETA functionalized with NO). FIG. 21(e) shows the cytotoxicity against mammalian cells.

FIG. 22(a) 2 mg/mL of Promethazine in PBS buffer; FIG. 22(b) 2 mg/mL of Promethazine with equivalent CD in PBS buffer.

FIG. 23(a) 1:0; FIG. 23(b) 1:0.25; FIG. 23(c) 1:0.5; FIG. 23(d) 1:0.75; FIG. 23(e) 1:1; FIG. 23(f) 1:1.5. Based on the turbidity of the complex solution, a good inclusive complex between promethazine and CD-DETA is formed with the molar ratio of 1:1.

FIG. 24(a) Illustration of promethazine and NO co-delivery for antibacterial activity. FIG. 24(b) Bactericidal efficacy of PM (circle), the complex of PM and CD-DETA (triangle) and the complex of PM and CD-DETA/NO (square) against Gram-negative *P. aeruginosa*. PM and CD derivatives were delivered in a molar ratio of 1:1. The X-axis is the concentration of PM in different systems. FIG. 24(c) Cell viability (%) of L929 mouse fibroblasts following exposure to PM, the complex of PM and CD-DETA, and the complex of PM and CD-DETA/NO at the MBC4h concentrations. Left-side bar was PM; middle bar was the complex of PM and CD-DETA; right-side bar was the complex of PM and CD-DETA/NO.

DETAILED DESCRIPTION

Figure 1A:
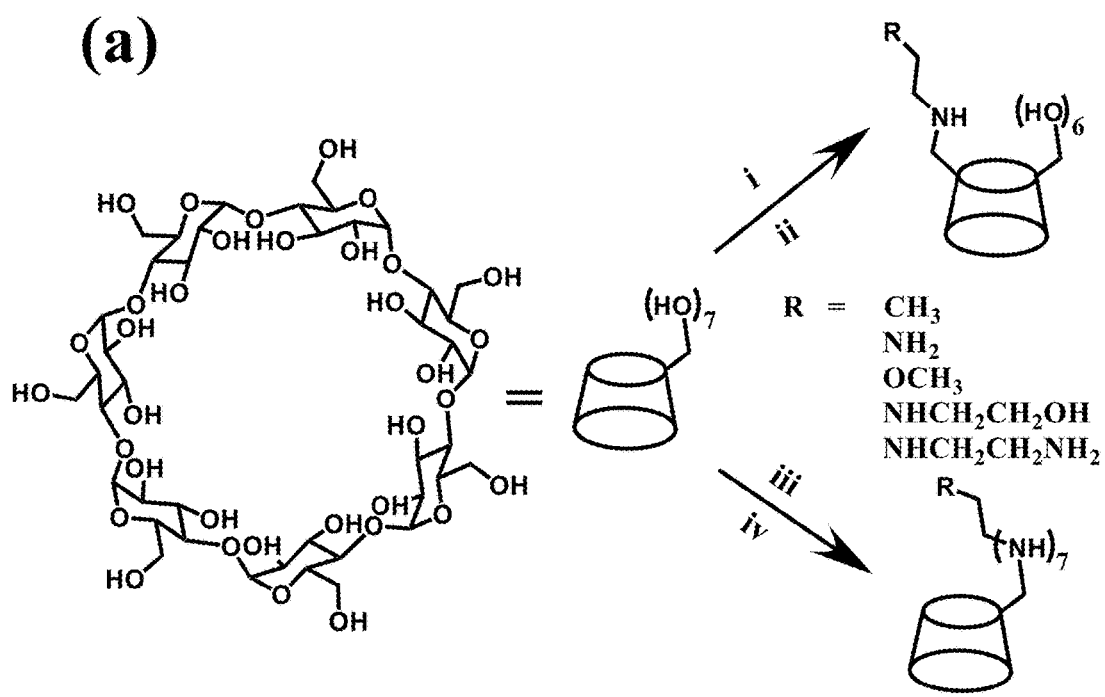
FIG. 1(a) and FIG. 1(b) are non-limiting schemes showing the synthesis of secondary amine- and N-diazeniumdiolate-functionalized CD derivatives.

Certain embodiments disclosed herein pertain to cyclodextrin (CD) derivatives with bactericidal and/or antimicrobial activity. In some embodiments, the cyclodextrin (CD) derivatives comprise NO binding moieties. In some embodiments, the cyclodextrin (CD) derivatives have controllable amounts of secondary-amines and diverse exterior terminal groups (e.g., hydroxyl, methyl, hydroxymethyl, primary amines, etc.). In some embodiments, the CD derivatives can be reacted with nitric oxide (NO) gas or some other NO donor to yield NO-donating CD derivatives. Nitric oxide (NO) is a broad-spectrum antibacterial agent capable of eradicating both bacteria and biofilms, primarily through the formation of reactive NO byproducts (e.g., peroxynitrite and dinitrogen trioxide) that cause oxidative and nitrosative damage to microbial DNA and/or membrane structures. Advantageously, the wide range of mechanisms by which NO exerts its antibacterial effects reduces the risk that bacteria will foster resistance.

In some embodiments, disclosed herein are methods for synthesizing CD scaffolds. In some embodiments, the CD scaffolds are reacted with and/or decorated with substituents to change one or more properties of the CD (e.g., enhance solubility, guest binding efficacy, NO binding, NO binding efficacy, etc.) affording CD derivatives. In some embodiments, where the CD derivative comprises NO binding moieties, the CD scaffolds can be reacted with and/or decorated with NO-binding moieties to afford NO-binding CD derivatives. In some embodiments, the CD derivatives are reacted with nitric oxide (NO) gas or some other NO donating agent to yield NO-donating CD derivatives. In some embodiments, the functionalization of CD derivatives with NO is performed under alkaline conditions. In some embodiments, the NO-donating CD derivatives are NO-releasing N-diazeniumdiolate NO donors. In some embodiments, by regulating one or more of the amount of secondary amines and the functional groups around the NO-donating moieties (e.g., N-diazeniumdiolate), a molecule encapsulated in the CD, the solubility of the CD, or other features, diverse NO-releasing CD derivatives with adjustable total NO storages and/or NO releasing half-lives can be realized. In some embodiments, the methods disclosed herein provide NO-releasing CD derivatives having NO storage capacities of between about 0.6 and about 2.4 µmol of NO/mg of CD nitric oxide donor compound, including, for example, about 0.6 to about 0.8 µmol/mg, 0.8 to about 1.0 µmol/mg, 1.0 to about 1.2 µmol/mg, 1.2 to about 1.5 µmol/mg, 1.5 to about 1.8 µmol/mg, 1.8 to about 2.0 µmol/mg, 2.0 to about 2.2 mol/mg, 2.2 to about 2.4 µmol/mg, and any capacity therebetween, including endpoints. In some embodiments, the methods disclosed herein provide NO-releasing CD derivatives having half-lives of NO release of between about 0.7 and about 4.2 hours. In some embodiments, the NO-releasing CD derivatives have half-lives of NO release (in hours) of equal to or at least about: 0.5, 0.7, 0.9, 1.0, 2.0, 2.5, 3.0, 3.5, 4.0, 4.2, 4.5, 5.0, 6.0, 10.0, or ranges including and/or spanning the aforementioned values. In some embodiments, the disclosed NO-releasing CD derivatives have bactericidal efficacy against Gram-negative *Pseudomonas aeruginosa*, among other bacteria (including, in several embodiments, drug-resistant bacteria). In some embodiments, the antibacterial efficacy of NO-releasing CD derivatives is dependent on the total NO storage and derivatives terminus. In some embodiments, NO-releasing materials containing a high density of NO donors or primary amines were effective antimicrobial agents. In some embodiments, the NO-releasing CD derivatives disclosed herein exhibit low and/or and substantially no cytotoxicity against mammalian cells (e.g., L929 mouse fibroblast cells in vitro). In several embodiments, this provides a targeted effect with minimal, reduced, or non-existent off-target effects.

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

As used herein, "and/or" refers to and encompasses any and all possible combinations of one or more of the associated listed items, as well as the lack of combinations when interpreted in the alternative ("or").

As used herein, the term "about," is given its plain and ordinary meaning and, when referring to a measurable value such as an amount of a compound or agent of the current subject matter, dose, time, temperature, and the like, is meant to encompass variations of ±20%, ±10%, ±5%, ±1%, ±0.5%, or even ±0.1% of the specified amount.

The term "effective amount," as used herein, refers to that amount of a functionalized CD that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, an improvement in a condition can be a reduction in infection. In some embodiments, an improvement can be reduction of bacterial load (e.g., bioburden) on a surface or in a subject. In some embodiments, reduction in the thickness, production or other characteristic of a mucus layer is an improvement. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, curing the illness, etc.

The terms "nitric oxide donor" or "NO donor" refer to species and/or molecules that donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action.

The term "nitric oxide releasing" refers to species that donate, release and/or directly or indirectly transfer any one (or two or more) of the three redox forms of nitrogen monoxide (NO+, NO—, NO) and/or methods of donating, releasing and/or directly or indirectly transferring any one (or two or more) of the three redox forms of nitrogen monoxide (NO+, NO—, NO). In some embodiments, the nitric oxide releasing is accomplished such that the biological activity of the nitrogen monoxide species is expressed at the intended site of action.

The term "microbial infection" as used herein refers to bacterial, fungal, viral, yeast infections, as well other microorganisms, and combinations thereof, including infection that involves one or more type of drug-resistant microorganism.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults and geriatric subjects.

As used herein, the terms "functionalized CD," "cyclodextrin derivatives," or "CD derivatives" refer to a CD molecule which contains one or more covalently modified repeat units. Such "functionalized CDs" or "cyclodextrin derivatives" may or may not have a nitric oxide donor moiety attached.

For the general chemical formulas provided herein, if no substituent is indicated, a person of ordinary skill in the art will appreciate that the substituent is hydrogen. A bond that is not connected to an atom, but is shown, indicates that the position of such substituent is variable. A jagged line, wavy line, two wavy lines drawn through a bond or at the end of a bond indicates that some additional structure is bonded to that position. For a great number of the additional monomers disclosed herein, but not explicitly shown in structures, it is understood by those having ordinary skill in the art of polymers, that these monomers can be added to change the physical properties of the resultant polymeric materials even where the elemental analysis would not indicate such a distinction could be expected. Such physical properties include, but are not limited to, solubility, charge, stability, cross-linking, secondary and tertiary structure, and the like. Moreover, if no stereochemistry is indicated for compounds having one or more chiral centers, all enantiomers and diasteromers are included. Similarly, for a recitation of aliphatic or alkyl groups, all structural isomers thereof also are included. Unless otherwise stated, groups shown as $A_1$ through $A_n$ and referred to herein as an alkyl group, in the general formulas provided herein are independently selected from alkyl or aliphatic groups, particularly alkyl having 20 or fewer carbon atoms, and even more typically lower alkyl having 10 or fewer atoms, such as methyl, ethyl, propyl, isopropyl, and butyl. The alkyl may be optionally substituted (e.g., substituted or not substituted, as disclosed elsewhere herein). The alkyl may be a substituted alkyl group, such as alkyl halide (e.g. —$CX_3$ where X is a halide, and combinations thereof, either in the chain or bonded thereto,), alcohols (i.e. aliphatic or alkyl hydroxyl, particularly lower alkyl hydroxyl) or other similarly substituted moieties such as amino-, amino acid-, aryl-, alkyl aryl-, alkyl ester-, ether-, keto-, nitro-, sulfhydryl-, sulfonyl-, sulfoxide modified-alkyl groups.

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (i.e., NONO).

Whenever a group is described as being "optionally substituted" (or as having "optional substituents") that group may be unsubstituted (e.g., comprising one or more —H moieties bonded to the group where substituents could otherwise be) or substituted with one or more of the indicated substituents. Likewise, when a group is described as being "unsubstituted or substituted" (or "substituted or unsubstituted") if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amine group, a di-substituted amine group, a mono-substituted amine (alkyl), a di-substituted amine(alkyl), a diamino-group, a polyamino, a diether-group, and a polyether-.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" or "$C_1$-$C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

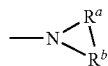

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by ⋯, followed by the number of carbon atoms, followed by a "*". For example,

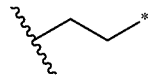 [SMILES: *CC*]

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group (e.g.,

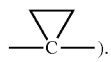

).

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "aryl" refers to a carbocyclic (all carbon) monocyclic or multicyclic (such as bicyclic) aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted. As used herein, "heteroaryl" refers to a monocyclic or multicyclic (such as bicyclic) aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "cycloalkyl(alkyl)" refer to an cycloalkyl group connected, as a substituent, via a lower alkylene group. The lower alkylene and cycloalkyl group of a cycloalkyl(alkyl) may be substituted or unsubstituted.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

As used herein, a "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—$SO_2$N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2$N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "nitro" group refers to an "—$NO_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The terms "amino" and "unsubstituted amino" as used herein refer to a —$NH_2$ group.

A "mono-substituted amine" group refers to a "—$NHR_A$" group in which $R_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The $R_A$ may be substituted or unsubstituted. A mono-substituted amine group can include, for example, a mono-alkylamine group, a mono-$C_1$-$C_6$ alkylamine group, a mono-arylamine group, a mono-$C_6$-$C_{10}$ arylamine group and the like. Examples of mono-substituted amine groups include, but are not limited to, —NH(methyl), —NH(phenyl) and the like.

A "di-substituted amine" group refers to a "—$NR_A R_B$" group in which $R_A$ and $R_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_A$ and $R_B$ can independently be substituted or unsubstituted. A di-substituted amine group can include, for example, a di-alkylamine group, a di-$C_1$-$C_6$ alkylamine group, a di-arylamine group, a di-$C_6$-$C_{10}$ arylamine group and the like. Examples of di-substituted amine groups include, but are not limited to, —N(methyl)$_2$, —N(phenyl)(methyl), —N(ethyl)(methyl) and the like.

As used herein, "mono-substituted amine(alkyl)" group refers to a mono-substituted amine as provided herein connected, as a substituent, via a lower alkylene group. A mono-substituted amine(alkyl) may be substituted or unsubstituted. A mono-substituted amine(alkyl) group can include, for example, a mono-alkylamine(alkyl) group, a mono-$C_1$-$C_6$ alkylamine($C_1$-$C_6$ alkyl) group, a mono-arylamine(alkyl group), a mono-$C_6$-$C_{10}$ arylamine($C_1$-$C_6$ alkyl) group and the like. Examples of mono-substituted amine(alkyl) groups include, but are not limited to, —$CH_2$NH(methyl), —$CH_2$NH(phenyl), —$CH_2CH_2$NH(methyl), —$CH_2CH_2$NH(phenyl) and the like.

As used herein, "di-substituted amine(alkyl)" group refers to a di-substituted amine as provided herein connected, as a substituent, via a lower alkylene group. A di-substituted amine(alkyl) may be substituted or unsubstituted. A di-substituted amine(alkyl) group can include, for example, a dialkylamine(alkyl) group, a di-$C_1$-$C_6$ alkylamine($C_1$-$C_6$ alkyl) group, a di-arylamine(alkyl) group, a di-$C_6$-$C_{10}$ arylamine($C_1$-$C_6$ alkyl) group and the like. Examples of di-substituted amine(alkyl) groups include, but are not limited to, —$CH_2$N(methyl)$_2$, —$CH_2$N(phenyl)(methyl), —$CH_2$N(ethyl)(methyl), —$CH_2CH_2$N(methyl)$_2$, —$CH_2CH_2$N(phenyl)(methyl), —$NCH_2CH_2$(ethyl)(methyl) and the like.

As used herein, the term "diamino-" denotes an a "—N($R_A$)$R_B$—N($R_C$)($R_D$)" group in which $R_A$, $R_C$, and $R_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "N" groups and can be (independently of $R_A$, $R_C$, and $R_D$) a substituted or unsubstituted alkylene group. $R_A$, $R_B$, $R_C$, and $R_D$ can independently further be substituted or unsubstituted.

As used herein, the term "polyamino" denotes a "—(N($R_A$)$R_B$—)$_n$—N($R_C$)($R_D$)". For illustration, the term polyamino can comprise —N($R_A$)alkylene-N($R_A$)alkylene-N($R_A$)alkylene-N($R_A$)alkylene-H. In some embodiments, the alkylene of the polyamino is as disclosed elsewhere herein. While this example has only 4 repeat units, the term "polyamino" may consist of 1, 2, 3, 4, 5, 6, 7, 8, 9, or 10 repeat units. $R_A$, $R_C$, and $R_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "N" groups and can be (independently of $R_A$, $R_C$, and $R_D$) a substituted or unsubstituted alkylene group. $R_A$, $R_C$, and $R_D$ can independently further be substituted or unsubstituted. As noted here, the polyamino comprises amine groups with intervening alkyl groups (where alkyl is as defined elsewhere herein).

As used herein, the term "diether-" denotes an a "—O$R_B$O—$R_A$" group in which $R_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_B$ connects the two "O" groups and can be a substituted or unsubstituted alkylene group. $R_A$ can independently further be substituted or unsubstituted.

As used herein, the term "polyether" denotes a repeating —(O$R_B$—)$_n$O$R_A$ group. For illustration, the term polyether can comprise —Oalkylene-Oalkylene-Oalkylene-Oalkylene-O$R_A$. In some embodiments, the alkyl of the polyether is as disclosed elsewhere herein. While this example has only 4 repeat units, the term "polyether" may consist of 1, 2, 3, 4, 5, 6, 7, 8, 9, or 10 repeat units. $R_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. $R_B$ can be a substituted or unsubstituted alkylene group. $R_A$ can independently further be substituted or unsubstituted. As noted here, the polyether comprises ether groups with intervening alkyl groups (where alkyl is as defined elsewhere herein and can be optionally substituted).

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

When a range of integers is given, the range includes any number falling within the range and the numbers defining ends of the range. For example, when the terms "integer from 1 to 20" is used, the integers included in the range are 1, 2, 3, 4, 5, 6, 7, 8, 9, 10, etc., up to and including 20.

As used herein, "pharmaceutically acceptable" refers to carriers, excipients, and/or stabilizers that are nontoxic to the cell or mammal being exposed thereto at the dosages and concentrations employed or that have an acceptable level of toxicity. A "pharmaceutically acceptable" "diluent," "excipient," and/or "carrier" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals. The term diluent, excipient, and/or "carrier" can refer to a diluent, adjuvant, excipient, or vehicle with which the pharmaceutical composition is administered. Such pharmaceutical diluent, excipient, and/or carriers can be sterile liquids, such as water and oils, including those of petroleum, animal, vegetable or synthetic origin. Water, saline solutions and aqueous dextrose and glycerol solutions can be employed as liquid diluents, excipients, and/or carriers, particularly for injectable solutions. Suitable pharmaceutical diluents and/or excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A non-limiting example of a physiologically acceptable carrier is an aqueous pH buffered solution. The physiologically acceptable carrier may also comprise one or more of the following: antioxidants, such as ascorbic acid, low molecular weight (less than about 10 residues) polypeptides, proteins, such as serum albumin, gelatin, immunoglobulins, hydrophilic polymers such as polyvinylpyrrolidone, amino acids, carbohydrates such as glucose, mannose, or dextrins, chelating agents such as EDTA, sugar alcohols such as mannitol or sorbitol, salt-forming counterions such as sodium, and nonionic surfactants such as TWEEN®, polyethylene glycol (PEG), and PLURONICS®. The composition, if desired, can also contain minor amounts of wetting, bulking, emulsifying agents, or pH buffering agents. These compositions can take the form of solutions, suspensions, emulsion, sustained release formulations and the like. The formulation should suit the mode of administration. In particular, those formulation components listed as approved inactive ingredients by the FDA may be included. For inhalable formulations, the list currently includes: citric acid, calcium carbonate, calcium chloride, carrageenan, cetylpyridinium chloride, chorobutanol, benzalkonium chloride, dichlorodifluoromethane, dichlorotetrafluoroethane, edetate disodium, ferric oxide yellow, fluorochlorohydrocarbons, fumaryl diketopiperazine, glycerin, gelatin, hydrochloric acid, hydrogenated soybean lecithin, Hypromellose, lactose, magnesium stearate, menthol, methyl parabon, nitric acid, norflurane, oleic acid, polysorbate 80, potassium chloride, propylene glycol saccharin, or silicon dioxide.

The term "consists essentially of" (and grammatical variants), shall be given its ordinary meaning and shall also mean that the composition or method referred to can contain additional components as long as the additional components do not materially alter the composition or method. The term "consists of" (and grammatical variants), shall be given its ordinary meaning and shall also mean that the composition or method referred to is closed to additional components. The term "comprising" (and grammatical variants), shall be given its ordinary meaning and shall also mean that the composition or method referred to is open to contain additional components.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible. Depending on the embodiment, certain compositions, formulations and related methods summarized above and set forth in further detail below describe certain actions taken by a practitioner; however, it should be understood that they can also include the instruction of those actions by another party. Thus, actions such as "administering an NO-releasing functionalized CD to a subject" also include "instructing the administration of an NO-releasing functionalized CD to a subject."

Nitric oxide, an endogenously produced diatomic free radical, is associated with numerous biological processes and physiological roles, including platelet aggregation and adhesion, vasodilation, wound repair, the immune response, and carcinogenesis. Deficiency of NO can lead to some degree of malfunction of NO-relevant physiological systems and has been linked to certain health disorders and disease, such as diabetes and cystic fibrosis. Low levels of exhaled NO are associated with impaired lung function in cystic fibrosis. Exogenous NO delivery may be an effective strategy for the resolution of biomedical therapies ranging from cardiovascular diseases to antibacterial and anticancer therapies. However, the difficulty in regulating gaseous NO for therapeutics warrants the use of assorted synthetic NO donors (e.g., N-diazeniumdiolates, S-nitrosothiols, metal nitrosyls, organic nitrates), in order to control NO delivery. N-diazeniumdiolates (NONOates) may be useful as NO donors because of their good stability and their capacity for proton-triggered NO delivery under physiological conditions. In some instances, high NO total is an important parameter to effectively evaluate storage capability of good scaffolds. Additionally, a high density of secondary amine groups imbues certain donors with a high NO storage capacity. However, fast NO release and high NO storage may result in undesired toxicity to mammalian cells. Additionally, the concentration of low molecular weight NO donors necessary to illicit a biological response often is harmful to mammalian cells and tissue.

Macromolecular-based NO-storage systems, including silica nanoparticles, liposomes, and metal organic frameworks have been developed to increase NO payloads without compromising cell/tissue viability. While possessing attractive (e.g., therapeutically relevant) NO pay-loads, the synthetic burden of these systems, limited water solubility, and/or restricted control over release kinetics represent a significant challenge in their further development for clinical use.

Therefore, challenges exist in preparing biocompatible NO-releasing materials with one or more of high NO storage, tailored NO release, biodegradability, high antimicrobicidal activity, low cytotoxicity, increased solubility, etc. Such challenges, among others, are addressed according to several embodiments disclosed herein. Several embodiments of the invention have one or more of the following advantages: efficient and unique synthesis routes and resultant chemical composition generated, in several embodiments, by contacting amine-containing chains with non-functionalized cyclodextrins. Controllable amounts of secondary-amines and diverse exterior terminal groups (e.g., hydroxyl, methyl, hydroxymethyl, and primary amine) can be provided. The NO storage and NO-release kinetics of the generated nitric-oxide releasing scaffolds can be tuned for a particular application. This tuning is achieved, in several embodiments, by altering the type and/or number of functionalized monomers of e.g., Formula I. In several embodiments, additional functionalization of the amines in the generated nitric-oxide releasing scaffolds, for example, by compounds with different compositions further enables the control over NO-release kinetics. Indeed, excellent NO storage was observed with the presently disclosed functionalized cyclodextrins. In some embodiments, the secondary amine group directly influences the stability of the N-diazeniumdiolate (or other NO carrier group), allowing for control over both NO storage and release kinetics. The antibacterial efficacy of NO-releasing materials is dependent on both NO payloads and associated release kinetics. Disclosed herein is the bactericidal efficacy of the functionalized cyclodextrins with respect to NO-release kinetics, total NO storage, and amine structure. In several embodiments, one or more of the disclosed cyclodextrins are antimicrobial but substantially non-toxic to mammalian cells.

Cyclodextrins (CDs), a family of naturally produced cyclic oligosaccharides, are composed of ($\alpha$-1,4)-linked $\alpha$-D-glucopyranose residues. CDs are of a doughnut-shaped, cyclic structure. CDs can possess a hydrophobic central cavity and hydrophilic exterior. Because some CDs have a lipophilic cavity and low cytotoxicity, enzyme-degradable CDs may be useful as agents to enhance aqueous solubility of poorly water-soluble compounds, further increasing their biocompatibility and stability against other peripheral stimulants (e.g., light, heat, oxygen, enzymes). CDs may have use in fields, including agrochemicals, fragrances, food additive, drug delivery, and gene delivery. In some embodiments, as disclosed elsewhere herein, the NO-releasing cyclodextrin compounds and/or functionalized cyclodextrins can be used to deliver NO to a subject in need of treatment. In some embodiments, by virtue of the CD guest site, the CD derivatives disclosed herein can also be used to bind a drug effective in treating the subject. In several embodiments, the NO-binding CD can deliver NO and a bound drug simultaneously to a patient in need thereof, resulting, in several embodiments, in synergy between the NO and the drug in treating the patient. Additionally, CDs may be useful as macrocyclic host molecules, which could recognize with hydrophobic guest molecules to construct supramolecular architectures of supramolecular devices (e.g., polyrotaxane, molecular shuttle), supramolecular assemblies (e.g., micelle, vesicle, tube, sheet, hydrogel), and supramolecular polymers.

Cyclodextrins can be used to fabricate supramolecular devices (e.g., polyrotaxane, molecular shuttle), assemblies (e.g., micelle, vesicle, tube, sheet, hydrogel), and polymers. These favorable properties make CDs intriguing as NO-release/drug delivery vehicles, though, prior to the present disclosure, a CD-based scaffold with tunable NO-release payloads and kinetics that could be applied clinically as a therapeutic remained elusive. Disclosed herein is the synthesis of NO carrying CD derivatives as NO-releasing biopolymers with variable NO payloads, biodegradability, solubility, highly tunable NO-release kinetics, large NO payloads for biopolymer, and the ability to co-deliver hydrophobic drugs (or guest drugs).

As shown below, there are three primary classes of CD structures: those having 6 glucopyranoside units (e.g., sugar units) in the cycle (α-cyclodextrins), those having 7 glucopyranoside units in the cycle (β-cyclodextrins), and those having 8 glucopyranoside units in the cycle (γ-cyclodextrins):

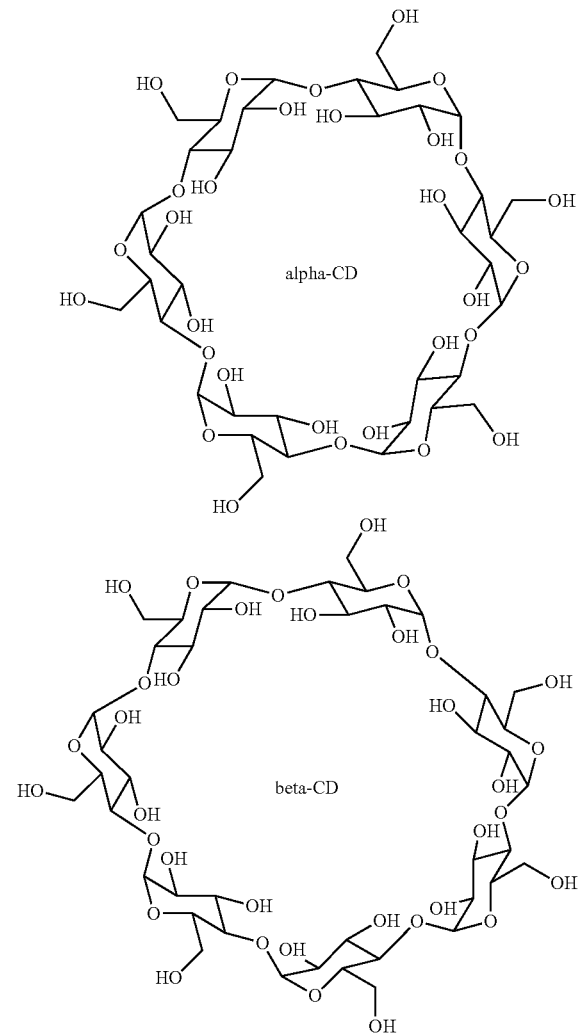

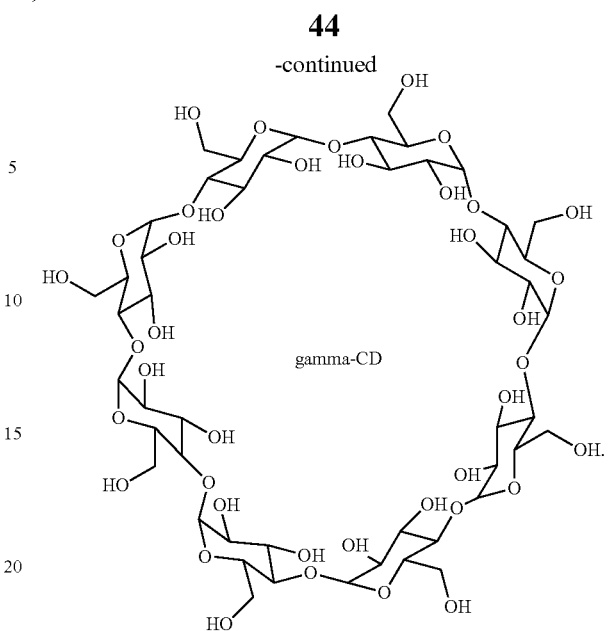

In some embodiments, the NO-donating CD derivatives disclosed herein comprise any one or more of α-cyclodextrins, β-cyclodextrins, and/or γ-cyclodextrins.

As disclosed herein, a cyclodextrin molecule can be depicted as one or more repeat units of glucopyranosides (having the following structure):

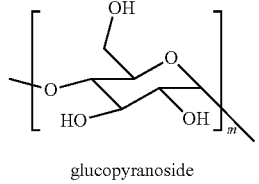

glucopyranoside wherein m is 6 (e.g., α-cyclodextrins), 7 (e.g., β-cyclodextrins), or 8 (e.g., γ-cyclodextrins). In some embodiments, m is an integer selected from 3, 4, 5, 6, 7, 8, 9, 10, or more. In some embodiments, mixtures of CDs with different m values can be employed simultaneously. Because the sugar units such as the glucopyranoside form part of the cyclic structure of a CD, they are referred to herein as ring units. In some embodiments, the CDs as disclosed herein can be depicted using any one or more of the following representations (illustrated for β-cyclodextrin):

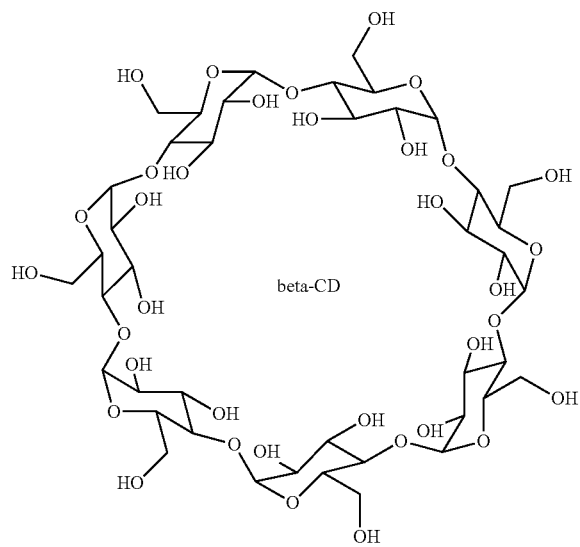

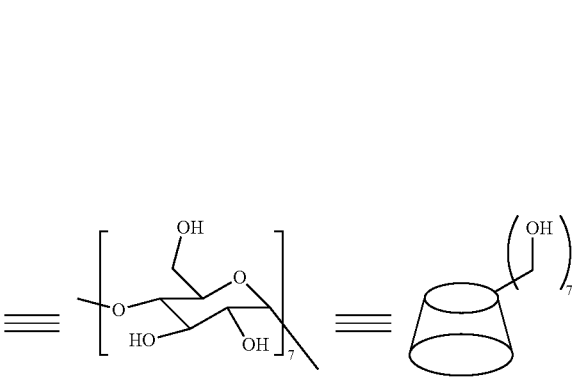

In several embodiments, the functionalized CDs may be optionally substituted (e.g., where a hydroxyl is replaced by and/or substituted with one or more optional substituents as disclosed elsewhere herein). In some embodiments, the functionalized CD comprises one or more ring units of Formula I:

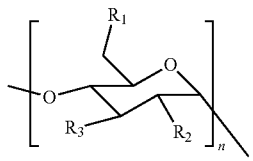

Formula I

In several embodiments, any one of $R_1$, $R_2$, and $R_3$ may independently be —O— or —NH— optionally substituted. In several embodiments, $R_1$, $R_2$, and $R_3$ may independently be —OH, $C_1$-$C_6$ alkoxy, polyamino, or polyether. In several embodiments, $R_1$, $R_2$, and $R_3$ may independently be —OH, $C_1$-$C_6$ alkoxy, polyamino having 1 to 7 repeat units with $C_1$-$C_6$ bridging alkylenes, or a polyether having 1 to 7 repeat units with $C_1$-$C_6$ bridging alkylenes. In some embodiments, $R_1$, $R_2$, and $R_3$ are independently selected from the group consisting of —OH, —O—$((CH_2)_tO)_u$—H, —O—$((CH_2)_tO)_{u'}$—$(CH_2)_v$H, —O—$(C_{1-5}$alkyl), —NH—$((CH_2)_c$NH$)_d$—H, —NH—$((CH_2)_c$NH$)_{d'}$—$(CH_2)_e$H, —$X^1$—$((CH_2)_fX^2)_g$—$(CH_2)_h$H, and —$X^1$—$((CH_2)_fX^2)_{g'}$—$((CH_2)_qX^3)_r$—$(CH_2)_h$H. In some embodiments, c, c', d, d', e, f, f', g, g', h, h', q, r, t, t', u, u', and v, are independently selected from an integer from 0 to 10 (e.g., 0, 1, 2, 3, 4, 5, 6, 7, 8, 9, or 10). In some embodiments, d, d', g, g', r, u, and u' are independently selected from an integer from 0 to 4 (e.g., 0, 1, 2, 3, 4). In some embodiments, c, c', e, f, f', h, h', q, t, t', and v, are independently selected from an integer from 0 to 3 (e.g., 0, 1, 2, 3). In some embodiments, $X^1$, $X^2$, and $X^3$ are independently selected from O, S, NH, or a NO releasing moiety. In some embodiments, each of $X^1$, $X^2$, and $X^3$ is NH or a NO releasing moiety. In some embodiments, n is an integer selected from 1 to 8 (e.g., 1, 2, 3, 4, 5, 6, 7, 8). In some embodiments, n is an integer selected from 5 to 8 (e.g., 5, 6, 7, 8).

In several embodiments, in addition to the variables described above, $R_1$, $R_2$, and $R_3$ may independently be any one of —OH, —$CH_2CH_2OH$, $CH_2CH(OH)CH_3$, —O—$((CH_2)_tO)_u$—H, —O—$((CH_2)_tO)_{u'}$—$(CH_2)_v$H, —O—$(C_{1-8}$alkyl), $C_2H_5$, $C_8H_{17}$—NH—$((CH_2)_c$NH$)_d$—H, —NH—$((CH_2)_c$NH$)_{d'}$—$(CH_2)_e$H, —C(O)Me, C(O)$C_3H_7$, C(O)$C_4H_9$, $CH_2$COONa, —$(CH_2)_4SO_3^-$, —$SO_3^-$ —$X^1$—$((CH_2)_fX^2)_g$—$(CH_2)_h$H, —$X^1$—$((CH_2)_fX^2)_g$—$((CH_2)_qX^3)_r$—$(CH_2)_h$H, glycosyl, maltosyl, and glucuronate (e.g. the sodium salt).

In several embodiments, $R_1$ may be —$OR_{1'}$, $R_2$ may be —$OR_{2'}$, and $R_3$ may be —$OR_{3'}$ as represented by Formula I'.

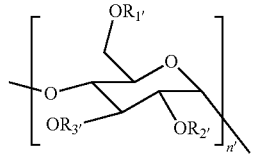

Formula I'

In several embodiments, each of $R_{1'}$, $R_{2'}$, or $R_{3'}$ may independently be —H (e.g., a hydrogen of a hydroxyl group) or an optionally substituted —O—. In several embodiments, $R_{1'}$, $R_{2'}$, and $R_{3'}$ may independently be $C_1$-$C_6$ alkyl, or a polyether. In several embodiments, the polyether includes 1 to 10 repeat units with $C_1$-$C_3$ bridging alkylenes and being terminated by —OH or $C_1$-$C_6$ alkyloxy. The aqueous solubility of CD can be enhanced even more by functionalizing one or more hydroxyl groups of the CD with, for example, a methoxy group, which disrupts the relatively strong intramolecular binding of CD molecule in their crystal state. In some embodiments, the CD comprises a mixture of Formula I and Formula I' ring units. In several embodiments, n+n' is equal to 10 where n is any integer from 0 to 10 and n' is any integer from one to ten. For instance, where n+n' is 7 and n is 3, then n' is 4. In some embodiments, a composition comprising functionalized CD comprises a mixture of structures functionalized with Formula I and/or Formula I' ring structures (or any other formulae disclosed herein) units in combination with CD that is not functionalized. In some embodiments, the composition does not include CD that is not functionalized.

In some embodiments, $R_1$, $R_2$, and $R_3$ as disclosed elsewhere herein or are selected from one or more of the following structures:

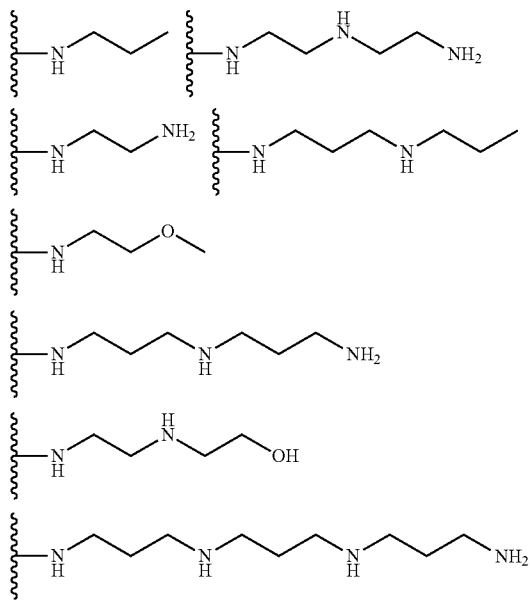

In some embodiments, any one or more of $R_1$, $R_2$, and $R_3$ can be functionalized with a nitric oxide to provide a CD nitric oxide donor compound (a nitric oxide releasing compound). In some embodiments, the CD compound is a nitric oxide releasing compound where any one of $X^1$, $X^2$, and $X^3$ comprises any one of the following nitric oxide releasing moieties:

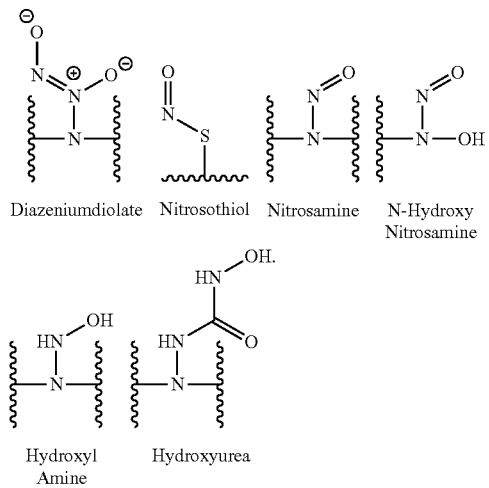

Diazeniumdiolate  Nitrosothiol  Nitrosamine  N-Hydroxy Nitrosamine

Hydroxyl Amine  Hydroxyurea where "⸾" indicates attachment to other atoms within $R_1$, $R_2$, and $R_3$ on the functionalized CD structure (e.g., any instance of —H, —CH$_2$—, etc. within $R_1$, $R_2$, and $R_3$).

In some embodiments, where the compound is a CD nitric oxide donor compound (e.g., a nitric oxide releasing compound), $R_1$, $R_2$, and $R_3$ can be independently selected from —OH and one or more of the following structures:

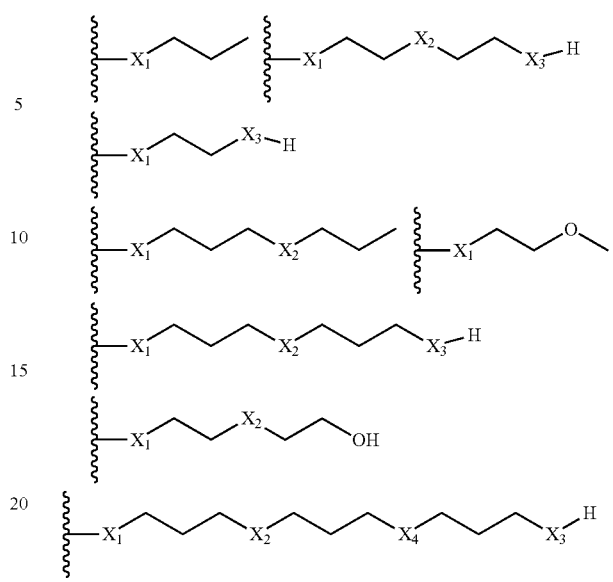

where $X^1$, $X^2$, and $X^3$ are as disclosed elsewhere herein and $X^4$ is selected from O, S, NH or a nitric oxide releasing moiety as disclosed elsewhere herein.

While in several areas throughout this disclosure variables (such as $R_1$, $X^1$, $X^2$, $X^3$ etc.) are specifically designated as having particular structures (e.g., —OH, O, S, NH, etc.), for brevity, in several other areas these variables are not defined and/or are defined as being "as disclosed elsewhere herein." In areas where variables are not defined or are defined as being "as disclosed elsewhere herein," etc., those variables may be of any structure by which they were defined elsewhere in this disclosure.

In some embodiments, the nitric oxide donor is selected from the group consisting of a diazeniumdiolate, nitrosothiol, a nitrosamine, a hydroxyl nitrosamine, a hydroxyl amine, a hydroxyurea, and a combination thereof.

In some embodiments, $R_1$, $R_2$, and $R_3$ are independently selected from the groups as disclosed elsewhere herein or

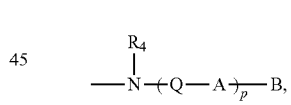

wherein
$R_4$ is, in each instance, hydrogen or $C_{1-5}$ alkyl;
Q is —(CR$_a$R$_b$)$_s$—;
wherein R$_a$ and R$_b$ are independently hydrogen or $C_{1-5}$ alkyl; and s is an integer from 2 to 6;
A is

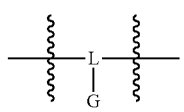

wherein, L is S, O, or N; and
G, in each instance, is hydrogen, is taken together with L to form a nitric oxide donor, or is absent;
p is an integer from 1 to 10;
B is selected from the group consisting of hydrogen, —Y—Z, and $C_{1-5}$ alkyl, wherein the $C_{1-5}$ alkyl is optionally substituted with amino, hydroxyl, nitrile, $CO_2H$, mono($C_{1-6}$)alkylamino-, di($C_{1-6}$)alkylamino-, —(CO)$NR_cR_d$ or —$NR_c$(CO)$R_d$, or B is absent;

wherein $R_c$ and $R_d$ are each independently selected from the group consisting of hydrogen and $C_{1-6}$ alkyl, wherein Y has a structure of:

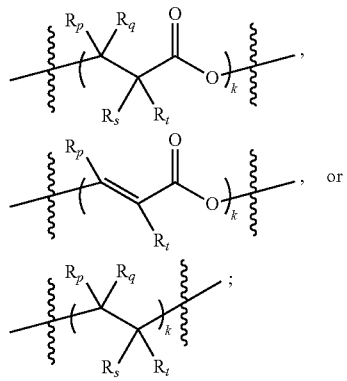

wherein $R_p$, $R_q$, $R_s$ and $R_t$, in each instance, are independently, hydrogen or hydroxyl; and k is an integer from 1 to 20; and Z has a structure of:

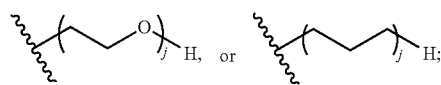

wherein j, in each instance, is an integer from 1 to 100.

In some embodiments, the nitric oxide donors (e.g., G taken together with L) can be depicted structurally as:

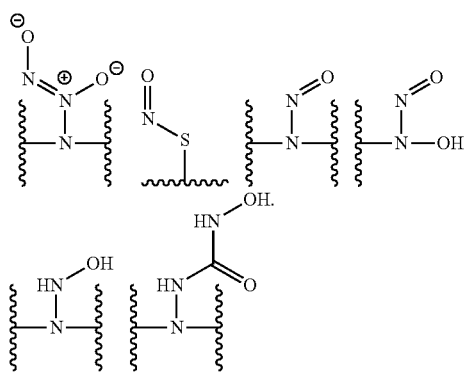

where " ⸹ ", here and as disclosed elsewhere herein, indicates attachment to adjacent atoms. In this case " ⸹ " indicates attachment to adjacent atoms of $R_1$, $R_2$, and $R_3$ on the functionalized CD structure (e.g., —H, —$CH_2$—, etc.).

In several embodiments, as noted elsewhere herein, the CD derivative may comprise one or more units of Formula I'. In several embodiments, the CD comprises rings of only Formula I'. In several embodiments, the CD comprises rings of Formula I and Formula I' (or other ring structures as disclosed herein). In several embodiments, the Formula I' rings may be selected from those show in Table A:

TABLE A

Potential CD Derivatives for use in some embodiments.

Formula I'

$$\left[ \begin{array}{c} OR_{1'} \\ O \\ R_{3'}O \quad OR_{2'} \end{array} \right]_n$$

n = 6, 7, or 8

| | | $R_{2'}$ | $R_{3'}$ | $R_{1'}$ |
|---|---|---|---|---|
| RM-CD | Randomly methylated | Me or H | Me or H | Me or H |
| DM-CD | 2,6-di-O-methy | Me | H | Me |
| TM-CD | per-2,3,6-tri-O-methyl | Me | Me | Me |
| DMA-CD | per-acetylated DM | Me | C(O)Me | Me |
| 2-HE-CD | 2-hydroxy-ethyl | $CH_2CH_2OH$ or H | H | H |
| 2-HP-CD | 2-hydroxy-propyl | $CH_2CH(OH)CH_3$ or H | H | H |
| 3-HP-CD | 3-hydroxy-propyl | H | $CH_2CH(OH)CH_3$ or H | H |
| 2,3-DHP-CD | 2,3-dihydroxy-propyl | $CH_2CH(OH)CH_3$ or H | $CH_2CH(OH)CH_3$ or H | H |
| $G_1$-CD | glycosyl | H | H | Glucosyl or H |
| $G_2$-CD | maltosyl | H | H | Maltosyl or H |
| GUG-CD | Glucuronyl-glucosyl | H | H | glucuronateNa |
| DE-CD | 2,6-di-O-ethyl | $C_2H_5$ | H | $C_2H_5$ |
| TE-CD | per-2,3-tri-O-ethyl | $C_2H_5$ | $C_2H_5$ | $C_2H_5$ |
| TA-CD | per-2,3,6-tri-O-acyl | $C(O)CH_3$ | $C(O)CH_3$ | $C(O)CH_3$ |
| TB-CD | per-2,3,6-tri-O-butanoyl | $C(O)C_3H_7$ | $C(O)C_3H_7$ | $C(O)C_3H_7$ |
| TV-CD | per-2,3,6-tri-O-valeryl | $C(O)C_4H_9$ | $C(O)C_4H_9$ | $C(O)C_4H_9$ |
| TO-CD | per-2,3,6-tri-O-octanoyl | $C_8H_{17}$ | $C_8H_{17}$ | $C_8H_{17}$ |
| CME-CD | O-carboxy-methyl-O-ethyl | H | H | $CH_2COONa$ |
| SBE-CD | sulfobutyl ether | $(CH_2)_4SO_3^-$ or H | $(CH_2)_4SO_3^-$ or H | $(CH_2)_4SO_3^-$ or H |
| SPE-CD | sulfopropyl ether | $(CH_2)_3SO_3^-$ or H | $(CH_2)_3SO_3^-$ or H | $(CH_2)_3SO_3^-$ or H |
| S-CD | sulfate | $SO_3^-$ or H | $SO_3^-$ or H | $SO_3^-$ or H |

In several embodiments, a NO donating group or other groups can be functionalized to a structure of Formula I' as shown in Table A by, for example, removing one or more H atoms or OH groups (e.g., such as $OR_{1'}$, $OR_{2'}$, or $OR_{3'}$ where $R_{1'}$, $R_{2'}$, or $R_{3'}$ are H) from a structure as shown in Table A and replacing it with one or more of —NH—(($CH_2$)$_c$NH)$_d$—H, —NH—(($CH_2$)$_c$NH)$_d$—($CH_2$)$_e$H, —$X^1$—(($CH_2$)$_f X^2$)$_g$—($CH_2$)$_h$H, and —$X^1$—(($CH_2$)$_f X^2$)$_{g'}$(($CH_2$)$_m X^3$)$_q$—($CH_2$)$_h$H, as disclosed elsewhere herein. In several embodiments, the H atom or OH group that is removed is one that is located on the glucopyranoside ring. In several embodiments, one or more ring units of the CD comprises one or more of glucopyranosides substituted with: 2,3-DHP ("2,3-dihydroxypropyl"), 2-HE ("2-hydroxyethyl"), 2-HP ("2-hydroxypropyl"), 3-HP ("3-hydroxypropyl"), CME ("O-carboxymethyl-O-ethyl"), DE ("2,6-di-O- ethyl"), DM ("2,6-di-O-methyl"), DMA ("acetylated DM"), G1 ("glycosyl"), G2 ("maltosyl"), GUG ("Glucuronyl-glucosyl"), RM ("randomly-methylated"), SBE ("sulfobutyl ether"), TA "2,3,6-tri-O-acyl (C2-C18)"), TB ("2,3,6-tri-O-butanoyl"), TE ("2,3,6-tri-O-ethyl"), TM ("2,3,6-tri-O-methyl"), TO ("2,3,6-tri-O-octanoyl"), TV ("2,3,6-tri-O-valeryl"). In several embodiments, as disclosed elsewhere herein, the CD can comprise a mixture of Formula I and Formula I' rings.

In some embodiments, the functionalized CD comprises one or more repeat units of Formula II:

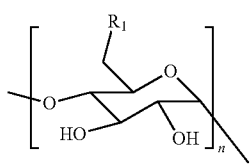

Formula II where $R_1$ is as disclosed elsewhere herein and $X^1$, $X^2$, and $X^3$ are as disclosed elsewhere herein. In some embodiments, the functionalized CD further comprises one or more glucopyranoside repeat units.

In some embodiments, the functionalized CD comprises:

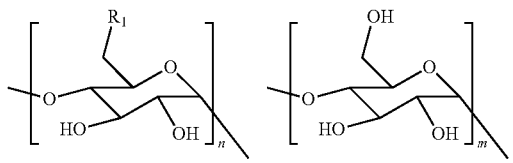

where n is an integer from 1 to 8 (e.g., 1, 2, 3, 4, 5, 6, 7, or 8) and m is 5, 6, or 7; and $R_1$ is selected from the group consisting of

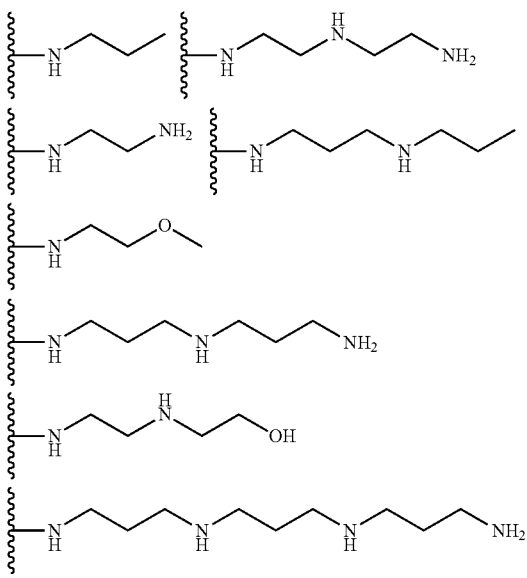

In some embodiments, the functionalized CD comprises:

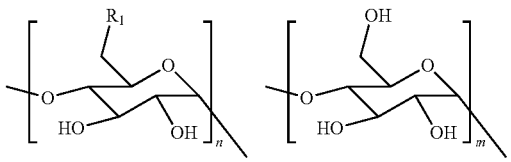

where $R_1$ and n are as disclosed elsewhere herein, m is an integer between 0 and 7, and $X^1$, $X^2$, and $X^3$ are independently selected from —NH or diazeniumdiolate.

In some embodiments, the functionalized CD comprises:

Formula III

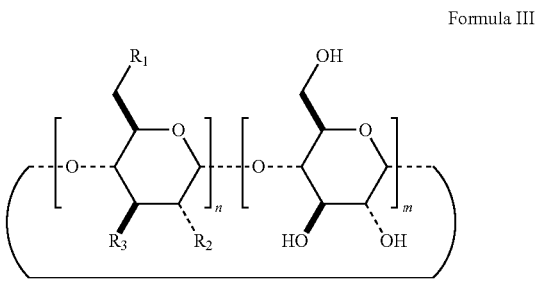

where $R_1$, $R_2$, $R_3$, n, and m are as disclosed elsewhere herein.

In some embodiments, the functionalized CD is selected from the group consisting of:

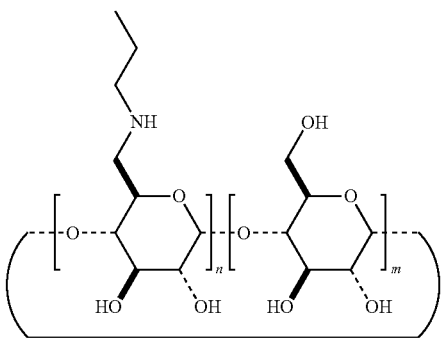

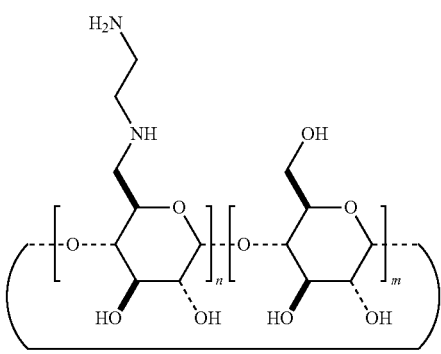

53
-continued
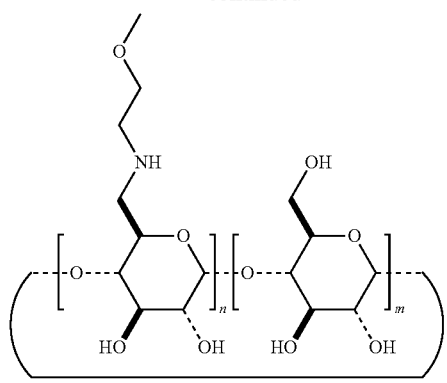
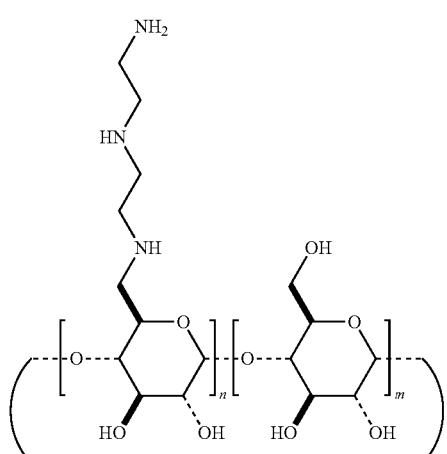
54
-continued
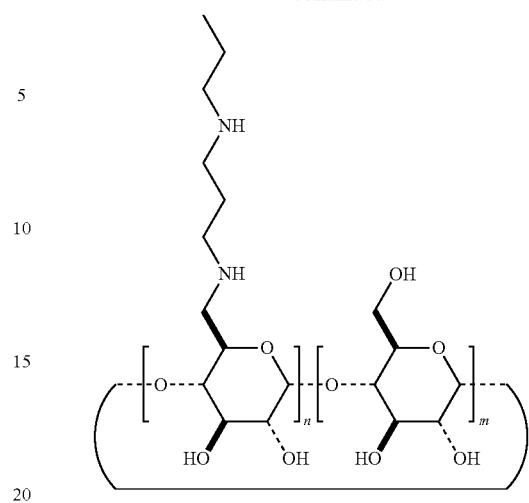
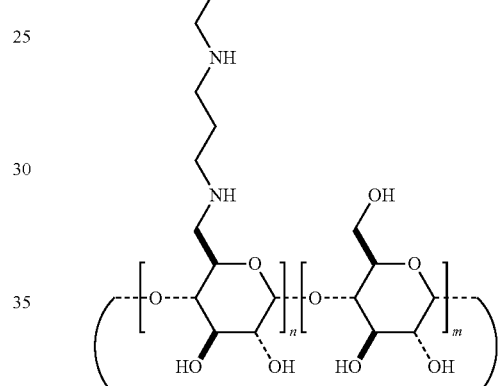
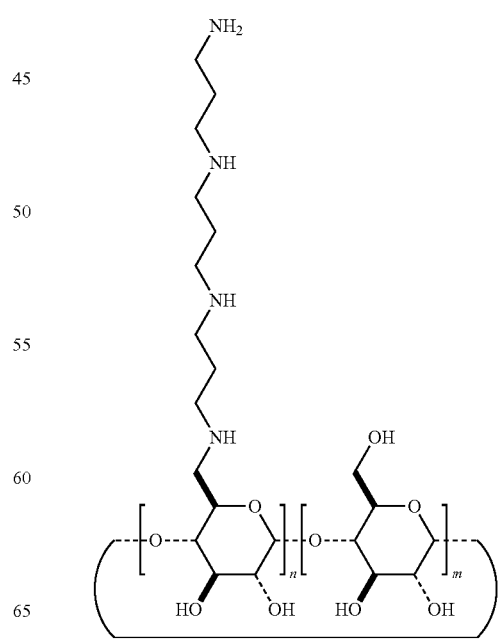

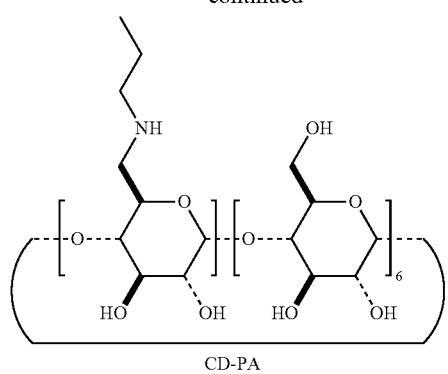
CD-PA
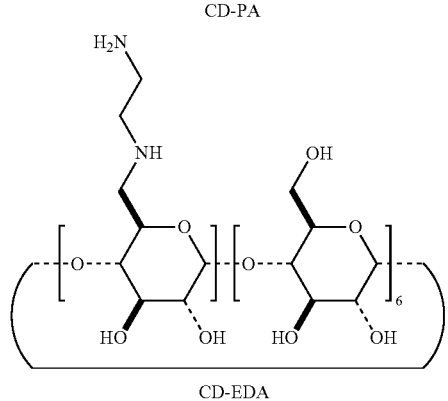
CD-EDA
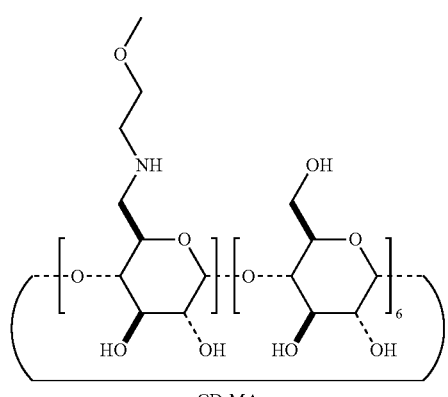
CD-MA
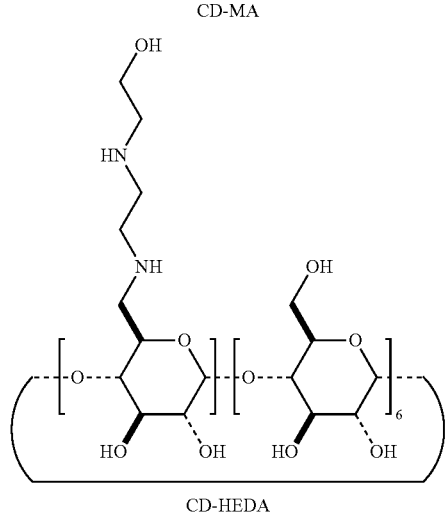
CD-HEDA
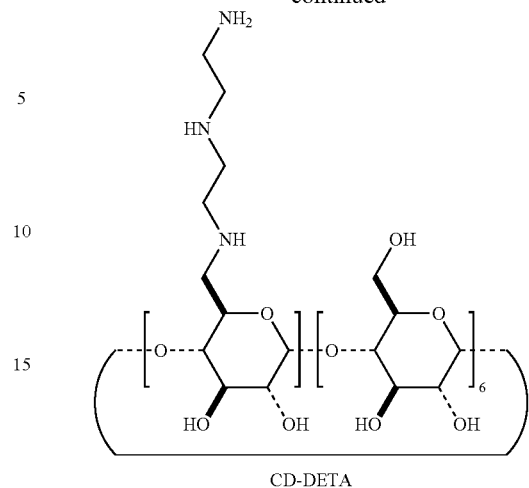
CD-DETA
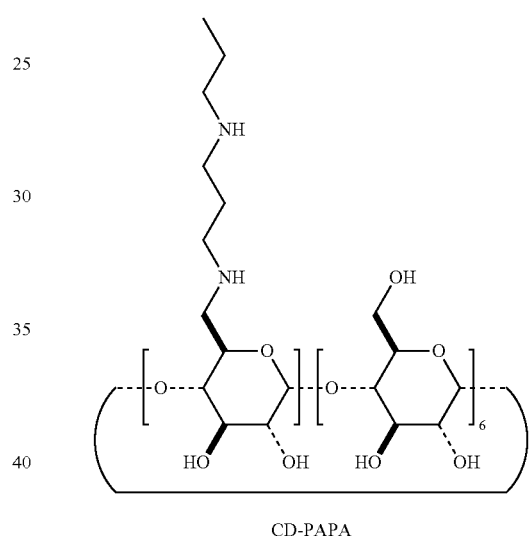
CD-PAPA
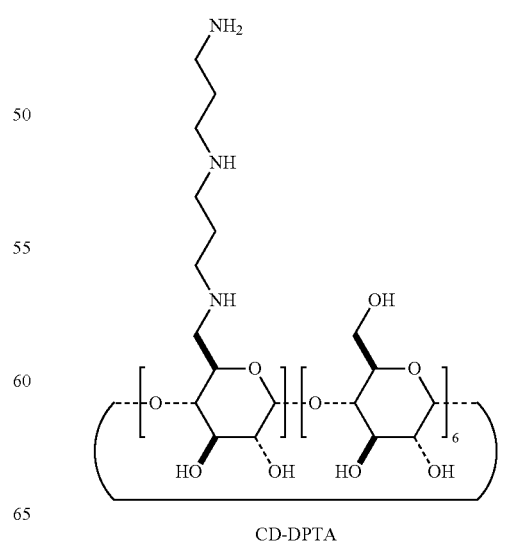
CD-DPTA -continued

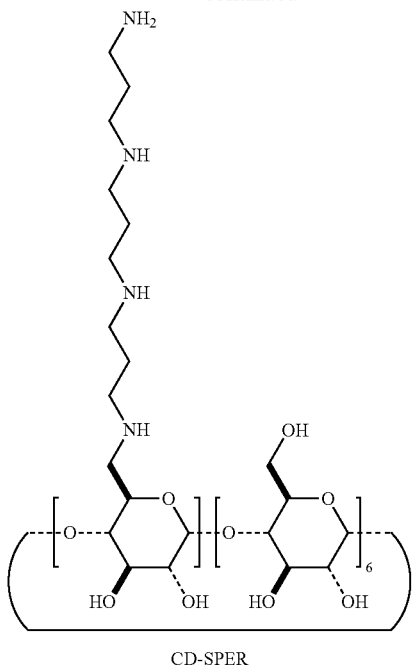

CD-SPER where n and m are as disclosed elsewhere herein.

In some embodiments, the functionalized CD comprises:

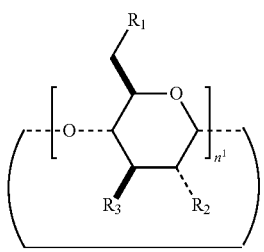

Formula Ia wherein $n^1$ is about 0.125 to 1 of the mole fraction of the monomers present and $R_1$, $R_2$ and $R_3$ are as disclosed elsewhere herein.

In some embodiments, the functionalized CD comprises:

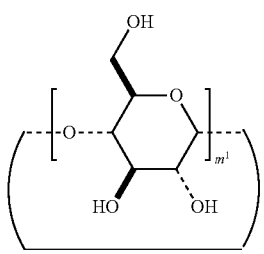

Formula Ib wherein $m^1$ is 0 to about 0.875 of the mole fraction of the monomers present.

In some embodiments, the functionalized CD comprises:

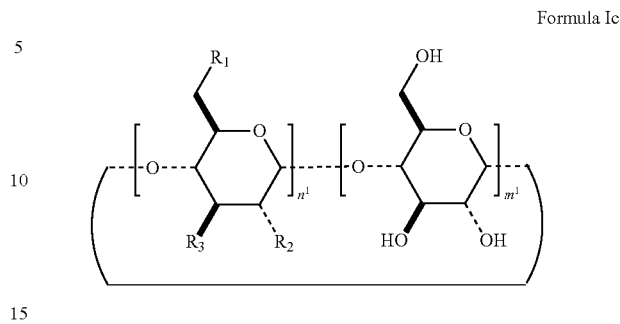

Formula Ic wherein $n^1$ is about 0.125 to 1 of the mole fraction of the monomers present;

wherein $m^1$ is 0 to about 0.875 of the mole fraction of the monomers present; and wherein $m^1$ and $n^1$ represent the mole fraction of each unit, the sum of $m^1$ and $n^1$ is 1, and $R_1$, $R_2$ and $R_3$ are as disclosed elsewhere herein.

In some embodiments, the nitric oxide releasing CD disclosed herein is selected from any one of CD-PA, CD-EDA, CD-MA, CD-HEDA, CD-DETA, CD-PAPA, CD-DPTA, and CD-SPER, wherein any one or more of the secondary amines is functionalized with a diazeniumdiolate group.

In some embodiments, the functionalized CD comprises a structure of Formula IV:

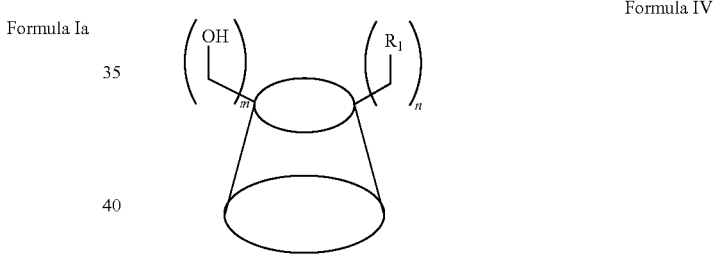

Formula IV where n, m, and $R_1$ are as disclosed elsewhere herein.

Figure 1B:
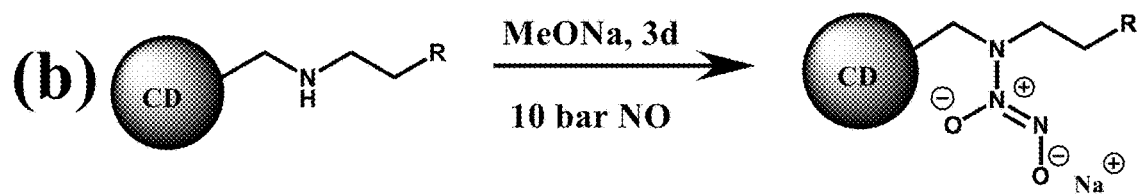

Because of lack of secondary-amine groups in their molecular backbones, CDs have heretofore not been functionalized N-diazeniumdiolate-type NO donors. In some embodiments, described herein are CDs functionalized to provide N-diazeniumdiolate NO donor CDs. In some embodiments, as shown in FIG. 1(a), the CDs are β-CD derivatives. In some embodiments, as shown in FIG. 1(a)-1(b), a series of CD derivatives with tunable amounts of secondary amines and diverse terminal groups are disclosed herein. In some embodiments, the resulting secondary amine-functionalized CD derivatives are reacted with NO gas to form N-diazeniumdiolate-modified CD derivatives, with controllable NO totals and tunable NO-release kinetics. The antibacterial ability and cytotoxicity against mammalian cells were evaluated in vitro against Gram-negative *Pseudomonas aeruginosa* and L929 mouse fibroblast, respectively.

As disclosed elsewhere herein, some embodiments pertain to methods of synthesizing CD derivatives (and still other embodiments, to their use as antibacterials). In some embodiments, the method includes functionalizing one or more repeat units of a CD with a leaving group as shown below to provide a CD molecule of Formula V:

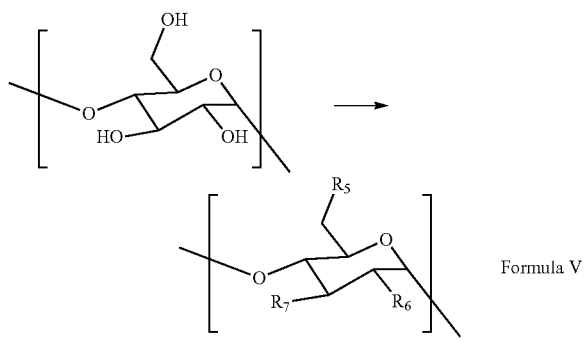

Formula V wherein $R_5$, $R_6$, and $R_7$ are independently selected from the group consisting of —OH, —OTs, —OMs, —Cl, —Br, and —I. In some embodiments, the method of preparing the functionalized CD comprises a step of reacting CD via one or more of the following reaction schemes:

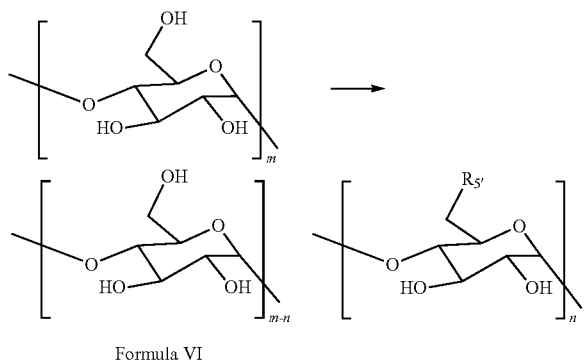

Formula VI

In several embodiments, $R_{5'}$ is OTs, halogen (e.g., —F, —Cl, —Br, —I), —C(O)H, —N$_3$.

In several embodiments, the —OTs functionalized CD is prepared by combining CD with p-toluenesulfonyl chloride in the presence of base (e.g., triethyl amine, pyridine, etc.).

In several embodiments, the halogen functionalized CD is prepared by combining CD with Cl$_2$, Br$_2$, I$_2$, a halogenating compound, etc., or by mixing the tosylated CD with Cl$_2$, Br$_2$, I$_2$, a halogenating compound, etc.

In several embodiments, the —C(O)H functionalized CD is prepared by mixing CD with Dess-Martin periodinane or by mixing the tosylated CD with collidine in dimethyl sulfoxide (DMSO). In several embodiments, the —C(O)H group reacted with an amine (e.g., H$_2$N—((CH$_2$)$_c$NH)$_d$—H, H$_2$N—((CH$_2$)$_c$NH)$_{d'}$—(CH$_2$)$_e$H, HX$^1$—((CH$_2$)$_f$X$^2$)$_g$—(CH$_2$)$_h$H, and HX$^1$—((CH$_2$)$_f$X$^2$)$_g$((CH$_2$)$_q$X$^3$)$_r$—(CH$_2$)$_h$H) to provide an imine that can be reduced (e.g., with H$_2$ and catalyst) to afford to afford a functionalized CD (e.g., functionalized with one or more of —NH—((CH$_2$)$_c$NH)$_d$—H, —NH—((CH$_2$)$_c$NH)$_{d'}$—(CH$_2$)$_e$H, —X$^1$—((CH$_2$)$_f$X$^2$)$_g$—(CH$_2$)$_h$H, and —X$^1$—((CH$_2$)$_f$X$^2$)$_{g'}$((CH$_2$)$_q$X$^3$)$_r$—(CH$_2$)$_h$H).

In several embodiments, the —C(O)H group can be further oxidized to a —C(O)OH group through reaction with for example Br$_2$ (e.g., at pH 6 for 5 days). In several embodiments, the —C(O)OH functionalized CD can be reacted with HO—((CH$_2$)$_t$O)$_u$—H, HO—((CH$_2$)$_t$O)$_{u'}$—(CH$_2$)$_v$H, HO—(C$_{1-5}$alkyl), H$_2$N—((CH$_2$)$_c$NH)$_d$—H, H$_2$N—((CH$_2$)$_c$NH)$_{d'}$—(CH$_2$)$_e$H, HX$^1$—((CH$_2$)$_f$X$^2$)$_g$—(CH$_2$)$_h$H, and HX$^1$—((CH$_2$)$_f$X$^2$)$_g$((CH$_2$)$_q$X$^3$)$_r$—(CH$_2$)$_h$H (e.g., in the presence of base, acid, or a coupling agent such as EDC, DCC, and the like) to afford an ester or amide. Thus, in several embodiments, $R_1$ of a functionalized CD could additionally comprise: —C(O)O—((CH$_2$)$_t$O)$_u$—H, —C(O)O—((CH$_2$)$_t$O)$_{u'}$—(CH$_2$)$_v$H, —C(O)O—(C$_{1-5}$alkyl), —C(O)NH—((CH$_2$)$_c$NH)$_d$—H, —C(O)NH—((CH$_2$)$_c$NH)$_{d'}$—(CH$_2$)$_e$H, —C(O)X$^1$—((CH$_2$)$_f$X$^2$)$_g$—(CH$_2$)$_h$H, and —C(O)X$^1$—((CH$_2$)$_f$X$^2$)$_g$((CH$_2$)$_q$X$^3$)$_r$—(CH$_2$)$_h$H.

In several embodiments, the N$_3$ functionalized CD is prepared by combining CD with NaN$_3$ in the presence of PPh$_3$ or by mixing the tosylated CD with NaN$_3$. In several embodiments, the —N$_3$ group can be converted (e.g., in the presence of triphenylphosphine and ammonia) to an amine. In some embodiments, using a Schiff base (e.g., HC(O) ((CH$_2$)$_t$O)$_{u'}$—(CH$_2$)$_v$H, HC(O)(C$_{1-5}$alkyl), HC(O)—((CH$_2$)$_f$X$^2$)$_g$—(CH$_2$)$_h$H, and HC(O)—((CH$_2$)$_f$X$^2$)$_{g'}$ ((CH$_2$)$_q$X$^3$)$_r$—(CH$_2$)$_h$H) structures where $R_1$ is —NHCH$_2$ ((CH$_2$)$_t$O)$_{u'}$—(CH$_2$)$_v$H, —NHCH$_2$(C$_{1-5}$alkyl), —NHCH$_2$ ((CH$_2$)$_f$X$^2$)$_g$—(CH$_2$)$_h$H, and —NHCH$_2$—((CH$_2$)$_f$X$^2$)$_{g'}$ ((CH$_2$)$_q$X$^3$)$_r$—(CH$_2$)$_h$H can be obtained (e.g., through reduction of the imine using H$_2$ and catalyst).

In some embodiments, the method includes a step of reacting a CD having at least one repeat unit having the structure of Formula V or Formula VI (where functionalized with a leaving group such as OTs or a halogen) with a nucleophile. In some embodiments, reaction with the nucleophile affords a CD with an NO binding substituent. In some embodiments, the nucleophile is one or more of HO—((CH$_2$)$_t$O)$_u$—H, HO—((CH$_2$)$_t$O)$_{u'}$—(CH$_2$)$_v$H, HO—(C$_{1-5}$alkyl), H$_2$N—((CH$_2$)$_c$NH)$_d$—H, H$_2$N—((CH$_2$)$_c$NH)$_{d'}$—(CH$_2$)$_e$H, HX$^1$—((CH$_2$)$_f$X$^2$)$_g$—(CH$_2$)$_h$H, and HX$^1$—((CH$_2$)$_f$X$^2$)$_g$((CH$_2$)$_q$X$^3$)$_r$—(CH$_2$)$_h$H. In some embodiments, the nucleophile is one or more of propylamine (PA), 2-methoxyethylamine (MA), ethylenediamine (EDA), diethylenetriamine (DETA), N-(2-Hydroxyethyl) ethylenediamine (HEDA), bis(3-aminopropyl)amine (DPTA), N-propyl-1,3-propanediamine (PAPA), and/or spermine (SPER) (as shown below). In some embodiments, c, c', d, d', e, f, f', g, g', h, h', q, r, t, t', u, u', and v are independently selected from an integer from 0 to 10. In some embodiments, and $X^1$, $X^2$, and $X^3$ are independently selected from O, S, NH, or a NO donating substituent. In some embodiments, the resultant compound is one having one or more repeat units of Formulas I or II as disclosed elsewhere herein.

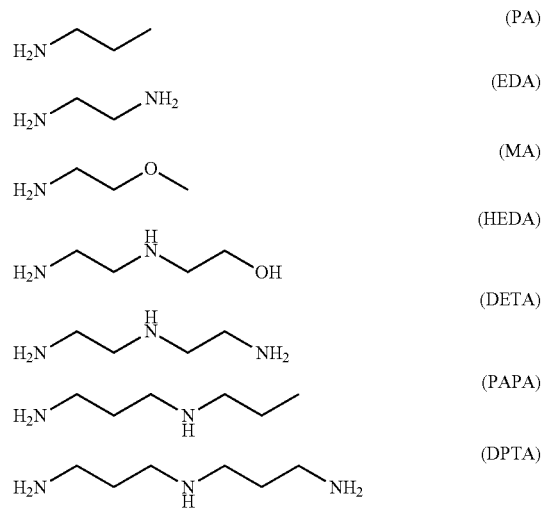

-continued

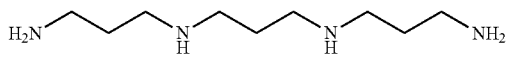

(SPER)

In some embodiments, the nitric oxide donor can be provided as a salt with a counter ion selected from the group consisting of alkali metal (e.g., sodium, potassium), alkaline earth metal (e.g., magnesium and calcium), ammonium and N—(alkyl)$_4$+ salts.

In some embodiments, the CD derivatives are reacted with nitric oxide (NO) gas or some other NO donating agent to yield NO-donating CD derivatives having one or more repeat units of Formula I or Formula II as disclosed elsewhere herein. In some embodiments, the functionalization of CD derivatives with NO is performed under alkaline conditions. In some embodiments, alkaline conditions include those having pH values of equal to or at least about: 7.5, 8.0, 9.0, 10.0, 12.0, or ranges including and/or spanning the aforementioned values.

In some embodiments, the CD nitric oxide donor compound has a total releasable nitric oxide storage in a range of 0.1-3.0 μmol of nitric oxide per milligram of the CD nitric oxide donor compound. In some embodiments, on a mol of NO per milligram of CD nitric oxide donor compound, the CD nitric oxide donor compound has a total releasable nitric oxide storage in mol of NO per milligram of CD nitric oxide donor compound of greater than or equal to about: 0.1, 0.15, 0.2, 0.5, 0.7, 0.8, 0.9, 1.0, 2.0, 3.0, 5.0, or ranges including and/or spanning the aforementioned values.

In several embodiments, the CD nitric oxide donor compound has a half-life for nitric oxide release in the range of 0.1-24 hours. In some embodiments, the half-life is in the range between about 0.25-18 hours, 0.5-13 hours, 1-8 hours, 2-6 hours, or 3-4 hours. In some embodiments, the half-life is in the range between about 0.7-4.2 hours, including about 0.7-1.7 hours or about 3.3-4.2 hours. In some embodiments, NO-release half-life of the CD nitric oxide donor compound is greater than or equal to about: 0.1 hours, 0.25 hours, 0.5 hours, 1 hour, 2 hours, 3 hours, 4 hours, 6 hours, 8 hours, 13 hours, 18 hours, 24 hours, or ranges including and/or spanning the aforementioned values.

In some embodiments, the total duration of NO release is in the range of 1-60 hours. In some embodiments, the total duration is in the range between about 2-50 hours, 3-40 hours, 4-30 hours, 5-20 hours, or 6-10 hours. In some embodiments, the total duration is greater than or equal to about: 1 hour, 2 hours, 3 hours, 4 hours, 5 hours, 6 hours, 10 hours, 20 hours, 30 hours, 40 hours, 50 hours, 60 hours, or ranges including and/or spanning the aforementioned values.

In several embodiments, upon exposure to 10 bar NO gas for a period of about 1 to 3 days, the percentage of secondary amines converted to N-diazeniumdiolates from a solution of a functionalized CD derivatives (e.g., the efficiency of conversion) is at least about: 5%, 10%, 20%, 40%, 50%, 75%, or ranges including and/or spanning the aforementioned values.

In several embodiments, a composition is provided. In several embodiments, the composition comprises a functionalized CD and one or more pharmaceutically acceptable carriers and/or excipients. In several embodiments, the composition comprises a functionalized CD. In several embodiments, the composition further comprises a non-functionalized CD. In several embodiments, the ratio of non-functionalized CD to functionalized CD in the composition is equal to or less than about: 1:99, 1:80, 1:50, 1:25, 1:10, 1:5, 1:2, 1:1, 1:2, 7:3, or ranges including and/or spanning the aforementioned values.

In several embodiments, the composition comprises a CD (e.g., a functionalized CD or non-functionalized CD) having a guest molecule. For example, in several embodiments, the CD nitric oxide donor compound can complex a guest molecule (e.g., that is bound within the pocket of the CD structure). In several embodiments, this CD NO donor inclusion complex comprises a guest drug. In some embodiments, the CD NO donor inclusion complex provides an antimicrobial effect from the NO in conjunction with a therapeutic effect via the complexed drug (e.g., the drug within the CD pore). In several embodiments, the drug and NO provide the same therapeutic effect (e.g., are both antimicrobial). In several embodiments, where the CD NO donor and the drug provide the same therapeutic effect, the CD NO donor and the drug act synergistically. In several embodiments, alternatively, the CD NO donor and drug can be directed toward different therapeutic effects (e.g., one is anti-microbial and the other is anti-inflammatory).

In several embodiments, the molar ratio between the drug and the CD can vary (e.g., drug in the composition and/or that is complexed in the functionalized CD and/or non-functionalized CD). In several embodiments, the molar ratio between the drug and the CD is equal to or at least about: 1:50, 1:20, 1:10, 1:5, 1:2, 1:1, 2:1, 5:1, 10:1, 20:1, 50:1 or ranges including and/or spanning the aforementioned values and ratios.

In several embodiments, a composition comprising the CD NO donor and the drug can be prepared in different ways. In several embodiments, the functionalized CD and drug are mixed together in solution (e.g., water, organic solvent, etc.). In several embodiments, due to the low solubility of most drugs in water, where water is used as a liquid mixing medium, the drug is partly or fully dissolved when complexed with the CD. In several embodiments, the solution is then dried and the solid recovered. In several embodiments, it is also possible to use a cosolvent (e.g. ethanol) which is miscible with water and that solubilizes the drug. In several embodiments, it is also possible to isolate the pure complex by using a two phase system: a lipophilic solvent wherein the drug is soluble, and water. In several embodiments, the CD dissolves in the water phase, the drug in the lipophilic phase. The complex CD-drug is formed at the interphase. If it is soluble in water, it is recovered from the water phase. In several embodiments, the functionalized CD can be activated by reaction with NO gas before or after complexation with the guest drug.

In several embodiments, the drug used in the complex, is selected from the following classes of compounds: non-steroidal anti-inflammatory and analgesic drugs, antibacterial (antibiotics), antiviral, steroids, antineoplastic, β-adrenergics (agonists and blockers), antihyperlipoproteinemic, bone resorption inhibitors. In several embodiments, mixtures of inclusion complexes having one or more drugs in an individual class and/or one or more drugs in a different classes can be prepared and administered to a patient in need of treatment.

In several embodiments, non-limiting examples of antibacterials (e.g., antibiotics) drugs that may be used include one or more of Metronidazolo, Ethambutol, Cycloserina, Cloxyquin, Negamycin, Nitroxoline, Mupirocin, Myxin, Novobiocin, Spectinomycin, Sulbactam, Tigemonam, Tubercidin, Nifurpirinol, Nifurprazine, Glyconiazide, Isoniazide, Opiniazide, Clofazamine, Meclocycline, Minocycline, Sancicline, Tetracicline, Oxytetracycline, Chlortetracycline, Demeclocycline, Methacycline, Doxicycline, Clomocycline, Cinoxacin, Rolitetraciclyne, Pipaciclyne, Guamecycline, Lymecyclinem, Apiciclyne, Nalidixic acid, Cyprofloxacin, Enoxacin, Florosaxin, Pipemidic acid, Difloxacin, Perfloxacin, Enrofloxacin Nadifloxacin, Grepafloxacin, Lomefloxacin, Sparfloxacin, Clinafloxacin, Tosufloxacin, Trovafloxacin, Ofloxacin, Flumequine, Pazufloxacin, Rufloxacin, Norfloxacin, Cefroxadine, Cephradine, Cefaclor, Cefadroxil, Cefprozil Cefatrizine, Cefpiramide, Cephalexin, Cephaloglycin, Loracarbef, Pivcephalexin, Cephamandole, Moxalactam, Cefclidin, Cefepime, Cefuzopran, Ceftibuten, Cefpodoxime Proxetil, Cefotaxime, Cefcapene Pivoxil, Cefodizime, Ceftiofur, Ceftriaxone, Cefditoren, Cefinenoxime, Cefteram, Cefuzonam, Cefdinir, Cefetamet, Cefixime, Cefpirome, Ceftazidine, Cefminox, Cephalosporin, Cefotiam, Ceforamide, Cefazolin, Ceftizoxime, Cefazedone, Cefonicid, Ceftezole, Cephacetrile, Cephapirin, Fenbenicillin, Hetacillin, Quinacillin, Pivampicillin, Aspoxicillin, Meziocillin, Amoxicillin, Ampicillin, Epicillin, Phenethamate Cyclacillin, Amdinocillin, Penicillin N, Apalcillin, Bacampicillin, Sultamicillin, Talampicillin, Lenampicillin, Benzyl penicillic acid, Carbenecillin, Carindacillin, Clometocillin, Cloxacillin, Dicloxacillin, Floxacillin, Metampicillin, Methicillin, Oxacillin, Penicillin O, Penicillin V, Pheneticillin, Piperacillin, Propicillin, Sulbenicillin, Ticarcillin, Meropenem, Panipenem, Imipenem, Aztreonam, Carumonan, Sulfabenzamide, Sulfacetamide, Sulfachloropyridazine, Sulfacytine, Sulfadiazine, 4'-(Methylsulfamoyl) sulfanilanilide, Sulfadicramide, Sulfadoxine, Sulfamethoxine, Sulfaethidolo, Sulfaguanole, Sulfalene, Sulfamerazine, Sulfameter, Sulfamethazine, Sulfamethizolo, Sulfamethonide, Sulfamethoxazole, Sulfamethoxypyridazine, Sulfamethylthiazole, Sulfametrole, Sulfamoxolo, Sulfanilamide, N 4-Sulfanilyl sulfanilamide, Sulfanilyurea, N-Sulfanil-3,4-xylamide, Sulfaperine, Sulfaphenazole, Sulfaproxyline, Sulfapyrazine, Sulfapyridine, 4-Sulfanilamido salicylic acid, Sulfasomizole, Sulfasymazine, Sulfathiazole, Sulfathiourea, Sulfisomidine, Sulfisoxazole, Acetyl sulfamethoxypyrazine, Sulfaguanidine, Mafenide, Succisulfone, p-Sulfanylbenzylamine, Dapsone, Acediasulfone, Thiazolsulfone, 2-p-Sulfanilylanilino-ethanol, Benzylsulfamide, p-Aminosalicylic acid, p-Aminosalicylic acid hydrazide, Phenyl aminosalicylate, 4-4'-sulfinyldianiline, Clindamycin, Lincomycin, Josamycin, Midecamycins, Rokitamycin, Spiramycins, Mikamycin B, Rosaramycin, Azithromycin, Clarithromycin, Erytromycin, Dirithromycin, Amikacin, Arbekacin, Dibekacin, Tobramycin, Dihydrostreptomycin, Streptomycin, Deoxydihydrostreptomycin, Trospectomycin, Spectinomycin, Micronomicin, Netilmicin, Apramycin, Sisomicin, Neomycin, Paromomycin, $R_1$ bostamycin, $R_1$ fampin, $R_1$ fapentine. Sulfachrysoidine, Sulfamidochrysoidine, and/or Salazosulfadimidine.

In several embodiments, non-limiting examples of non-steroidal anti-inflammatory and analgesic drugs that may be used include one or more of Aspirin, Salicylic acid, Mesalamine, Acetylsalicylsalicylic acid, Paracetamol, Etodolac, Pirazolac, Tolmetin, Bromefenac, Fenbufen, Mofezolac, Diclofenac, Pemedolac, Sulindac, Ketorolac, Indomethacin, Suprofen, Ketoprofen, Tiaprofenic acid, Fenoprofen, Indoprofen, Carprofen, Naproxen, Loxoprofen, Ibuprofen, Pranoprofen, Bermoprofen, CS-670, Zaltoprofen, Tenoxicani, Piroxicam, Meloxicam, Tenidap, Aceclofenac, Acemetacin, 5-amino-acetylsalicylic acid, Alclofenac, Alminoprofen, Amfenac, Bendazac, α-bisabolol, Bromosaligenin, Bucloxic acid, Butibufen, Cinmetacin, Clidanac, Clopirac, Diflunisal, Ditazol, Enfenamic acid, Etofenamate, Felbinac, Fenclozic acid, Fendosal, Fentiazac, Fepradinol, Flufenamic acid, Flunixin, Flunoxaprofen, Flurbiprofen, Glucametacin, Glycol salicylate, Ibuproxam, Isofezolac, Isoxepac, Isoxicam, Lornoxicam, Meclofenamic acid, Mefenamic acid, Metiazinic acid, Niflunic acid, Oxaceprol, Oxaprozin, Oxyphenbutazone, Parsalmide, Perisoxal, Olsalazine, Pirprofen, Protizinic acid, Salacetamide, Salicilamide O-acetic acid, Salsalate, Suxibuzone, Tiaramide, Tinoridine, Tolfenamic acid, Tropesin, Xenbucin, Ximoprofen, Zomepirac, and/or Tomoxiprol.

In several embodiments, non-limiting examples of antiviral drugs that may be used include one or more of Acyclovir, Amantadine, Cidofovir, Cytarabine, Didanosine, Dideoxyadenosine, Edoxuridine, Famciclovir, Floxuridine, Ganciclovir, Idoxuridine, Indanavir, Lamivudine, Kethoxal, MADU, Penciclovir, $R_1$ bavirin, Sorivudine, Stavudine, Trifluridine, Valacyclovir, Vidarabine, Xenazoic acid, Zaltacitabine, and/or Zidovudine.

In several embodiments, non-limiting examples of anti-tumor drugs that may be used include one or more of Antacitabine, Anthramycin, Azacitidine, 6-Azauridine, Carubicin, Chlorambucil, Chlorozotocin, Cytarabine, Daunomicin, Defosfamide, Denopterin, Doxifluridine, Doxorubicin (DOX), Droloxifene, Edatrexate, Eflornithine, Enocitabine, Epirubicin, Epitiostanol, Etanidazole, Etoposide, Fenretinide, Fludarabine, Fluorouracil, Gemcitabine, Hexestrol, Idarubicin, Lonidamine, Melphalan, 6-mercaptopurine, Methotrexate, Mitoxantrone, Mycophenolic acid, Pentostatin, Pirarubicin, Piritexim, Podophyllic acid, Puromycin, Retinoic acid, Roquinimex, Streptonigrin, Teniposide, Tenuazonic acid, Thiamiprine, Thioguanine, Tomudex, Topotecan, Trimetrexate, Tubercidin, Ubenimex, and/or Zorubicin.

In several embodiments, non-limiting examples of steroid drugs that may be used include one or more of Budesonide, Hydrocortisone, Aclomethasone, Algestone, Beclomethasone, Betamethasone, Chlorprednisone, Clobetasol, Clobetasone, Clocortolone, Cloprednol, Cortisone, Corticosterone, Deflazacort, Desonide, Desoximethasone, Dexamethasone, Diflorasone, Diflucortolone, Difluprednate, Fluazacort, Flucoronide, Flumethasone, Flunisolide, Fluocinolone acetonide, Flucinonide, Fluocortin butyl, Fluocortolone, Fluorometholone, Fluperolone acetate, Fluprednilene acetate, Fluprednisolone, Flurandrenolide, Formocortal, Halcinonide, Halobetasol propionate, Halomatasone, Halopredone acetate, Hydrocortamate, Loteprednol etabonate, Medrysone, Meprednisone, Methylprednisolone, Mometasone furoate, Paramethasone, Prednicarbate, Prednisone, Prednisolone 21-diethylaminoacetate, Prednisolone sodium phosphate, Prednival, Prednylidene, $R_1$ mexolone, Triamcinolone, Triamcinolone acetonide, 21-Acetoxypregnenolone, Cortivazol, Amcinonide, Fluticasone propionate, Mazipredone, Tixocortol, Triamcinolone hexacetonide, Ursodeoxycholic acid, Chenodeoxycholic, Mytatrienediol, Ethynil Estradiol, Estradiol, and/or Mestranol.

In several embodiments, non-limiting examples of adrenergic drugs that may be used include one or more of Albuterol, Bambuterol, Bitoterol, Carbuterol, Clenbuterol, Chlorprenalina, Dioxethedrine, Ephedrine, Epinephrine, Etafredine, Ethyinorepinephrine, Fenoterol, Isoetharine, Isoprotenerol, Mabuterol, Metaproterenol, Pirbuterol, Salmeterol, Soterenol, Terbutalina, Tuloterol, Procaterol, Bufetalol, Acebutolol, Alprenolol, Arotinolol, Atenolol, Betaxolol, Bevantolo, Bucumolol, bufuiralol, Bunitrolol, Bupranolol, Carazolol, Carteolol, Celiprolol, Epanolol, Indenolol, Mepindolol, Metoprolol, Nadolol, Nifenalol, Penbutolol, Pindolol, Pronethalol, Propanolol, Sotalol, Timolol, Toliprolol, Butofilol, Cervedilol, Cetamolol, Dilevalol, Esmolol, Labetalol, Metipranolol, Moprolol, Nebivolol, Oxprenolol, Practolol, Sulfinalol, Tertatolol, Tilisolol, Xibenolol, Eprozinol, Etophylline, Exoprenaline, Propoxyphilline, Reproterol, $R_1$ miterol, 1-Teobrominacetic acid, Tetroquinol, and/or Nadoxolol.

In several embodiments, non-limiting examples of antihyperlipoproteinemic drugs that may be used include one or more of Atovarstatin, Cilastatin, Dermostatin A, Dermostatin B, Fluvastatin, Lovastatin, Mevastatin, Nystatin A 1, Pentostatin, Pepstatin, and/or Sinvastatin.

In several embodiments, non-limiting examples of bone resorption inhibitor drugs that may be used include one or more of Alendronic acid, Butedronic acid, Etidronic acid, Oxidronic acid, Pamidronic acid, and/or $R_1$ sedronic acid.

In several embodiments, the guest molecule is a drug for treating respiratory disorders and/or is a drug that acts in the respiratory tract. In several embodiments, the CD nitric oxide donor compounds and the guest molecule work in conjunction in the respiratory tract to achieve synergistic results. In some embodiments, the guest molecule is selected from one or more of beclomethasone, budesonide, formoterol, epinephrine (adrenaline), ipratropium bromide, and/or salbutamol (albuterol), or combinations thereof.

Beclometasone dipropionate, also spelled beclomethasone dipropionate and sold under the brand name Qvar among others, is a steroid medication. Beclometasone is mainly a glucocorticoid. Budesonide (BUD), sold under the brand name Pulmicort among others, is a medication of the corticosteroid type. Budesonide/formoterol, sold under the brand name Symbicort among others, is a combination medication used in the management of asthma or chronic obstructive pulmonary disease (COPD). It contains budesonide, a steroid and formoterol, a long-acting β2-agonist (LABA). Epinephrine, also known as adrenalin or adrenaline, is a medication and hormone. As a medication, it is used to treat a number of conditions, including anaphylaxis, cardiac arrest, and superficial bleeding. Inhaled epinephrine may be used to improve the symptoms of croup. It may also be used for asthma when other treatments are not effective. Ipratropium bromide, sold under the trade name Atrovent among others, is a medication which opens up the medium and large airways in the lungs. It is used to treat the symptoms of chronic obstructive pulmonary disease and asthma. Salbutamol, also known as albuterol and marketed as Ventolin among other names, is a medication that opens up the medium and large airways in the lungs. It is used to treat asthma including asthma attacks, exercise-induced bronchoconstriction, and chronic obstructive pulmonary disease (COPD). It may also be used to treat high blood potassium levels. In several embodiments, the host and guest may be provided is available as an inhaler, pill, nasal spray, and rectal forms. In several embodiments, the host and respiratory drug guest may be provided as an composition for inhalation, as a cream, pill, and/or nasal spray.

In several embodiments, the inclusion complexes, when paired with one or more non-steroidal anti-inflammatories, analgesic drugs, or steroids, can be used to treat pain or inflammation. In several embodiments, the inclusion complexes, when paired with antibacterial (antibiotics) or antivirals, can be used to treat infection. In several embodiments, the inclusion complexes, when paired with antineoplastic agents, can be used to treat cancer (e.g., lung cancer, including but not limited to, non-small cell lung cancer, (NSCLC) and small cell lung cancer). Additional embodiments provided for herein include treatment or prevention of the following non-limiting examples of cancers including, but not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, glioblastoma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, pancreatic cancer, bowel cancer, lymphoma, melanoma, ocular cancer, ovarian cancer, pancreatic cancer, prostate cancer, pituitary cancer, uterine cancer, and vaginal cancer. In several embodiments, the inclusion complexes, when paired with β-adrenergics agonists and blockers, can be used to relax muscles of the airways, which widen the airways and result in easier breathing while treating underlying infections. In several embodiments, the inclusion complexes, when paired with antihyperlipoproteinemics, can be used to reduce lipoprotein levels while treating underlying infections. In several embodiments, the inclusion complexes, when paired with bone resorption inhibitors, can be used to reduce bone resorption while treating underlying infections.

Also provided herein are methods for delivering nitric oxide to a subject (e.g., a patient), comprising administering an effective amount of any of the CD nitric oxide donor compounds disclosed herein to the subject. Methods of treating a disease state are also provided for herein, the methods comprising, in several embodiments administering an effective amount of any of the CD nitric oxide donor compounds disclosed herein to a subject in need of treatment, wherein the disease state is selected from one or more of a cancer, a cardiovascular disease, a microbial infection, platelet aggregation and platelet adhesion caused by the exposure of blood to a medical device, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, and sexually transmitted diseases. In several embodiments, the disease state is a microbial infection. In several embodiments, the disease state is cystic fibrosis.

In several embodiments, there is provided a method of treating a microbial infection comprising, contacting a surface contaminated with a plurality of microbes with a CD nitric oxide donor compound, the CD nitric oxide donor compound comprising an amine-containing group covalently bound to at least a repeat unit of the CD, wherein the amine-containing group comprises an nitric oxide donor, wherein the nitric oxide donor generates nitric oxide and induces damage to the membrane and/or DNA of the microbes, thereby reducing the number of viable microbes and treating the infection. In some embodiments, the microbes comprises one or more of viruses, gram positive bacteria, gram negative bacteria, drug resistant bacteria, molds, yeasts, fungi, and combinations thereof.

Cystic fibrosis-related bacterial infections include, but are not limited to *Stenotrophomonis, Mybacterium avium* intracellulaire and *M. abcessus, Burkhoderia cepacia* and *Pseudomonas aeruginosa (P. aeruginosa)* infections. In some embodiments, the disclosed NO-releasing CD compounds can be used to treat infection by one or more of *Stenotrophomonis, Mybacterium avium* intracellulaire and *M. abcessus, Burkhoderia cepacia* and/or *Pseudomonas aeruginosa* (*P. aeruginosa*). In some embodiments, the disclosed NO-releasing CD compounds are mucolytic. In some embodiments, as disclosed elsewhere herein, the disclosed NO-releasing CD compounds are both mucolytic and antimicrobial and provide enhanced treatment efficacy for CF.

In several embodiments, the compositions disclosed herein do not comprise polyglucosamine and/or polyglucosamine-based NO releasing agents. In several embodiments, the compositions disclosed herein do not comprise chitosan and/or chitosan-based NO releasing agents. In several embodiments, the compositions disclosed herein do not comprise mesoporous silica and/or mesoporous silica-based NO releasing agents. In several embodiments, the compositions disclosed herein do not comprise polyaminoglycosides and/or polyaminoglycosides NO releasing agents. In several embodiments, the compositions disclosed herein do not comprise hyperbranched structures and/or hyperbranched NO releasing agents. In several embodiments, the compositions disclosed herein do not comprise carboxymethylcellulose and/or carboxymethylcellulose based NO releasing agents. In several embodiments, the compositions disclosed herein do not comprise hyaluronic acid and/or hyaluronic acid based NO releasing agents. In several embodiments, the compositions disclosed herein do not comprise hydroxyethylcellulose and/or hydroxyethylcellulose based NO releasing agents. In several embodiments, the compositions disclosed herein do not comprise NO releasing agents, saccharides, oligosaccharides, or polysaccharides that are not cyclodextrins.

In some aspects, the subject matter described herein is directed to the following non-limiting embodiments:

1. A functionalized cyclodextrin represented by the following structure:

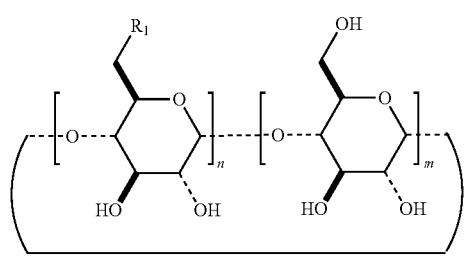

Formula III wherein n is an integer selected from 1 to 8;

m is an integer from 0 to 7;

each instance of $R_1$ is represented by $-X^1-((CH_2)_{f'}X^2)_g-((CH_2)_q X^3)_r-(CH_2)_{h'}H$;

wherein each of f', q, g, r, and h' is independently selected from an integer from 0 to 4; and each instance of $X^1$, $X^2$, or $X^3$ is independently selected from O, NH, and a nitric oxide donating substituent.

2. The functionalized cyclodextrin of embodiment 1, wherein at least one instance of $R_1$ is represented by one of the following:

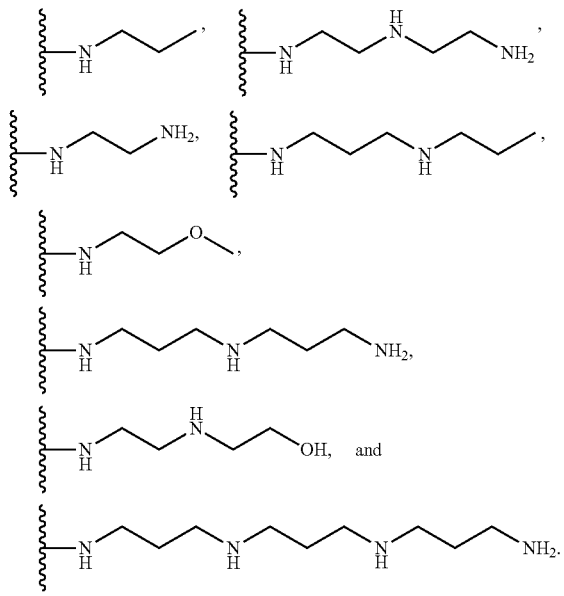

3. The functionalized cyclodextrin of embodiments 1 or 2, wherein at least one instance of $X^1$, $X^2$, or $X^3$ is represented by the following:

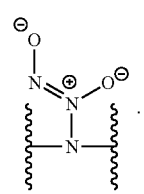 [SMILES: *N(*)/[N+]([O-])=N/[O-]]

4. The functionalized cyclodextrin of any one of embodiments 1-3, wherein at least one instance of $R_1$ is represented by one of the following:

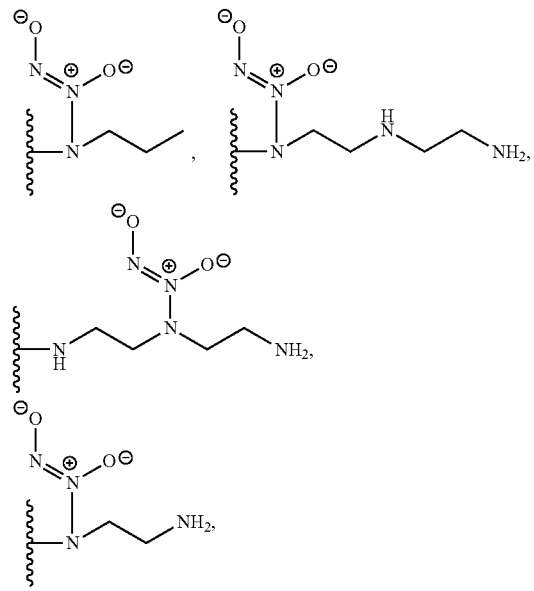

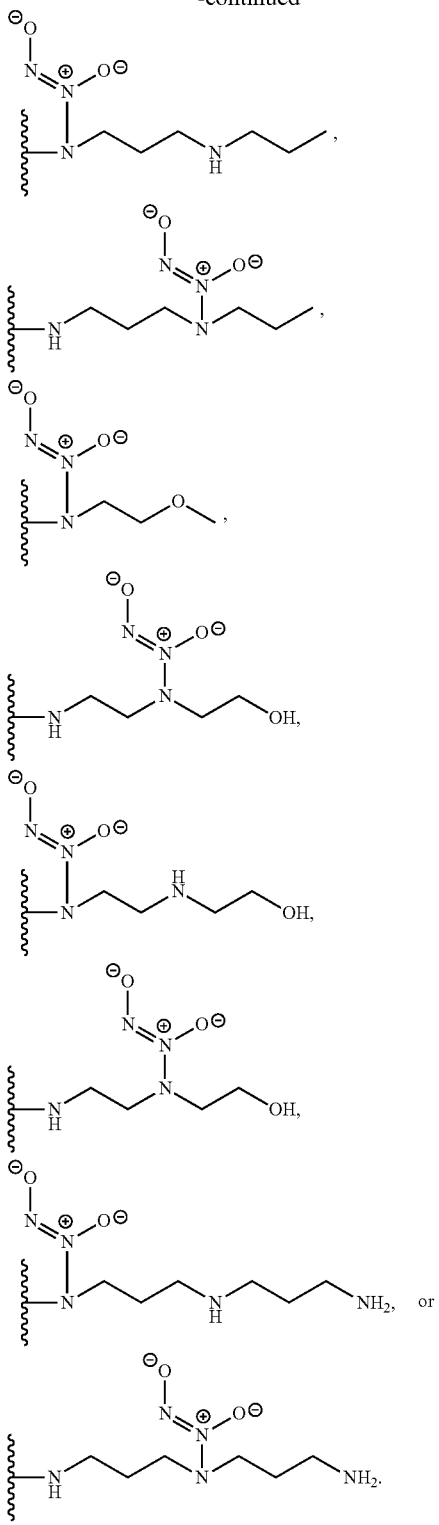

5. The functionalized cyclodextrin of any one of embodiments 1-4, wherein n is an integer selected from 6, 7, and 8.

6. The functionalized cyclodextrin of any one of embodiments 1-5, wherein m is 0.

7. The functionalized cyclodextrin of any one of embodiments 1-6, in particular, embodiment 3, wherein at least one instance of R¹ is represented by one of the following:

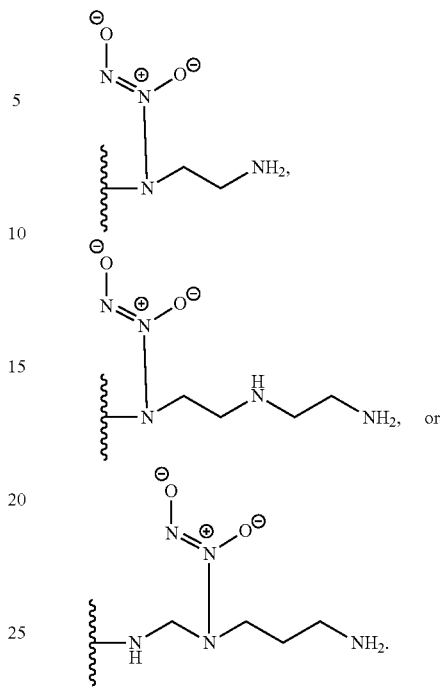

8. The functionalized cyclodextrin of any one of embodiments 1-7, wherein n is 1 and m is 6.

9. The functionalized cyclodextrin of any one of embodiments 1-7, wherein n is 7 and m is 0.

10. The functionalized cyclodextrin of any one of embodiments 1-9, wherein said functionalized cyclodextrin has a total releasable nitric oxide storage of at least 0.5 μmol of NO per milligram of functionalized cyclodextrin.

11. The functionalized cyclodextrin of any one of embodiments 1-10, wherein said functionalized cyclodextrin has a total releasable nitric oxide storage in a range of about 0.5 μmol to 2.5 μmol of NO per milligram of functionalized cyclodextrin.

12. The functionalized cyclodextrin of any one of embodiments 1-11, wherein said functionalized cyclodextrin has a half-life for nitric oxide release in a range of between about 0.7-4.2 hours.

13. The functionalized cyclodextrin of any one of embodiments 1-11, wherein said functionalized cyclodextrin has a half-life for nitric oxide release over about 1 hour.

14. The functionalized cyclodextrin of any one of embodiments 1-13, wherein said functionalized cyclodextrin has a total NO release after 4 hours in a range of between about 0.3-2.0 μmol of NO per milligram of the functionalized cyclodextrin.

15. A composition comprising the functionalized cyclodextrin of any one of embodiments 1-14 and a pharmaceutically acceptable carrier.

16. The composition of embodiment 15, further comprising cyclodextrin that is not functionalized.

17. The functionalized cyclodextrin of any one of embodiments 1-14, or the composition of embodiment 15 or embodiment 16, further comprising one or more guest drugs complexed with the functionalized cyclodextrin.

18. The composition of any one of embodiments 15-17, in particular, embodiment 17, wherein the one or more guest drugs comprise one or more drugs for the treatment of a cancer, a cardiovascular disease, a microbial infection, platelet aggregation and/or platelet adhesion, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, sexually transmitted diseases, or wound healing.

19. A method of delivering nitric oxide to a subject, comprising:
administering an effective amount of the functionalized cyclodextrin of any one of embodiments 1-18, in particular, any one of embodiments 1-10, to said subject.

20. A method of treating a disease state, comprising:
administering an effective amount of the functionalized cyclodextrin of any one of embodiments 1-18, in particular, any one of embodiments 1-10, to a subject in need thereof, wherein said disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

21. The method of embodiment 20, wherein said disease state is a microbial infection.

22. A method of treating a disease state, comprising:
administering an effective amount of the functionalized cyclodextrin of any one of embodiments 1-14 or the composition of any one of embodiments 15-18 to said subject to a subject in need thereof, wherein said disease state is lung cancer.

23. Use of the functionalized cyclodextrin of any one of embodiments 1-14 or the composition of any one of embodiments 15-18 for delivering nitric oxide to a subject.

24. Use of the functionalized cyclodextrin of any one of embodiments 1-14 or the composition of any one of embodiments 15-18 to said subject in the preparation of a medicament for treating a subject in need with a disease state selected from the group consisting of one or more of: a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

25. A functionalized cyclodextrin comprising:
at least one ring unit of Formula I:

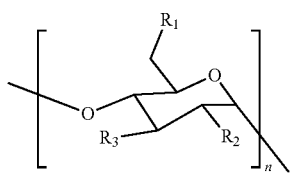

Formula I wherein
n is an integer selected from 1 to 8;
$R_1$, $R_2$, and $R_3$ are independently selected from the group consisting of —OH, —CH$_2$CH$_2$OH, —CH$_2$CH(OH) CH$_3$, —O—((CH$_2$)$_t$O)$_u$—H, —O—((CH$_2$)$_t$O)$_{u'}$—(CH$_2$)$_v$H, —O—(C$_{1-5}$alkyl), —C$_2$H$_5$, —C$_8$H$_{17}$, —NH—((CH$_2$)$_c$NH)$_d$—H, —NH—((CH$_2$)$_c$NH)$_{d'}$—(CH$_2$)$_e$H, —X$^1$—((CH$_2$)$_f$X$^2$)$_g$—(CH$_2$)$_h$H, —X$^1$—((CH$_2$)$_f$X$^2$)$_g$—((CH$_2$)$_q$X$^3$)$_r$—(CH$_2$)$_h$H, —C(O)Me, —C(O)C$_3$H$_7$, —C(O)C$_4$H$_9$, —CH$_2$COONa, —(CH$_2$)$_4$SO$_3$—, —SO$_3$—, —C(O)O—((CH$_2$)$_t$O)$_u$—H, —C(O)O—((CH$_2$)$_t$O)$_{u'}$—(CH$_2$)$_v$H, —C(O)O—(C$_{1-5}$alkyl), —C(O)NH—((CH$_2$)$_c$NH)$_d$—H, —C(O)NH—((CH$_2$)$_c$NH)$_{d'}$—(CH$_2$)$_e$H, —C(O)X$^1$—((CH$_2$)$_f$X$^2$)$_g$—(CH$_2$)$_h$H, —C(O)X$^1$—((CH$_2$)$_f$X$^2$)$_g$—((CH$_2$)$_q$X$^3$)$_r$—(CH$_2$)$_h$—H, glycosyl, maltosyl, and glucuronate;
wherein
each instance of c, c', d, d', e, f, f', g, g', h, h', q, r, t, t', u, u', and v is independently selected from an integer from 0 to 10;
each instance of X$^1$, X$^2$, and X$^3$ is independently selected from O, S, NH, and a NO donating substituent; and
at least one instance of X$^1$, X$^2$, and X$^3$ is a NO donating substituent.

26. The functionalized cyclodextrin of embodiment 25, wherein the NO donating substituent is selected from one of the following:

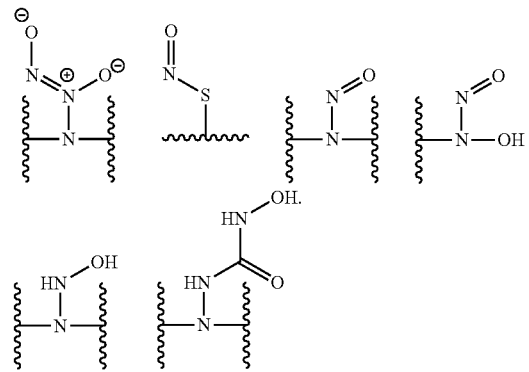

27. The functionalized cyclodextrin of embodiment 25 or 26, wherein;
at least one instance of X$^1$, X$^2$, and X$^3$ is represented by the following structure:

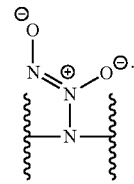

28. A functionalized cyclodextrin comprising:
at least one ring unit of Formula I:

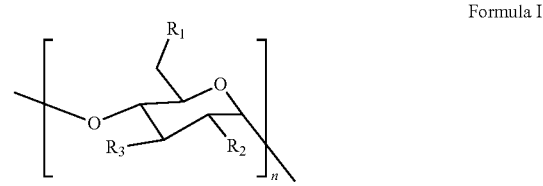

Formula I wherein n is an integer selected from 1 to 8;

$R_1$, $R_2$, and $R_3$ are independently selected from the group consisting of —OH, —O—$((CH_2)_tO)_u$—H, —O—$((CH_2)_tO)_{u'}$—$(CH_2)_v$H, —O—$(C_{1-5}$alkyl), —NH—$((CH_2)_cNH)_d$—H, —NH—$((CH_2)_cNH)_{d'}$—$(CH_2)_e$H, —$X^1$—$((CH_2)_fX^2)_g$—$(CH_2)_h$H, and —$X^1$—$((CH_2)_fX^2)_g$—$((CH_2)_qX^3)_r$—$(CH_2)_h$H;

wherein each of c, c', d, d', e, f, f', g, g', h, h', q, r, t, t', u, u', and v is independently selected from an integer from 0 to 10;

$X^1$, $X^2$, and $X^3$ are independently selected from O, S, or NH; and at least one of $X^1$, $X^2$, and $X^3$ is represented by the following structure:

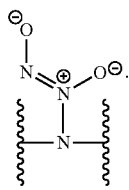

29. The functionalized cyclodextrin of any one of embodiments 25-28, wherein $R^1$ is —$X^1$—$((CH_2)_fX^2)_g$—$((CH_2)_qX^3)_r$—$(CH_2)_h$H.

30. The functionalized cyclodextrin of any one of embodiments 25-29, in particular, embodiments 28 or 29, wherein $R_2$ and $R_3$ are —OH.

31. The functionalized cyclodextrin of any one of embodiments 25-30, in particular, any one of embodiments 28-30, further comprising at least one glycopyranoside ring unit having the following structure:

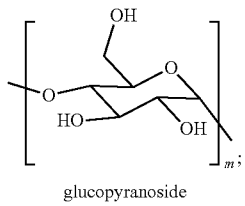
glucopyranoside wherein m is an integer selected from 1 to 8.

32. The functionalized cyclodextrin of any one of embodiments 25-31, wherein n is 1 and m is 5, 6, or 7.

33. The functionalized cyclodextrin of any one of embodiments 25-31, in particular, any one of embodiments 28-31, wherein n is 6, 7, or 8.

34. The functionalized cyclodextrin of any one of embodiments 25-33, in particular, embodiment 28, selected from the group consisting of:

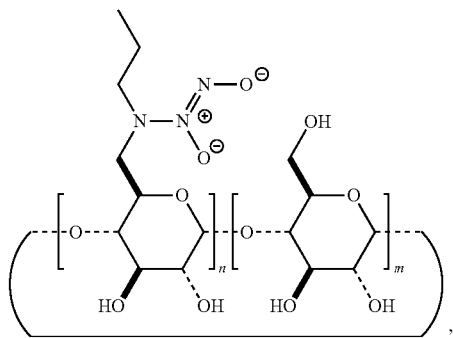
,

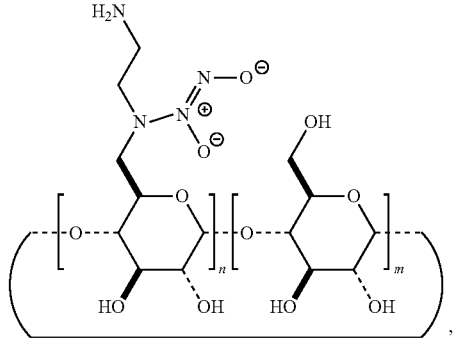
,

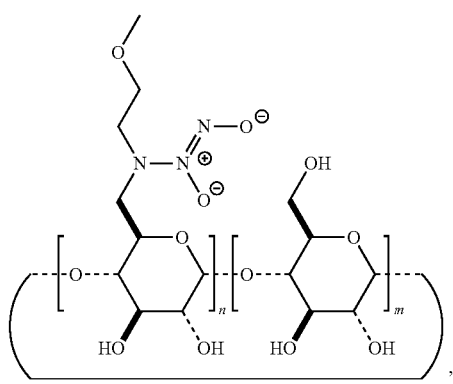
,

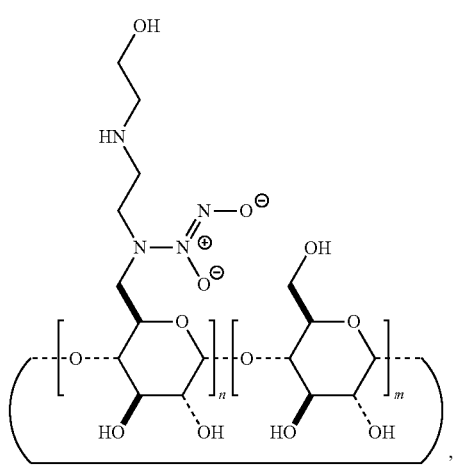
,

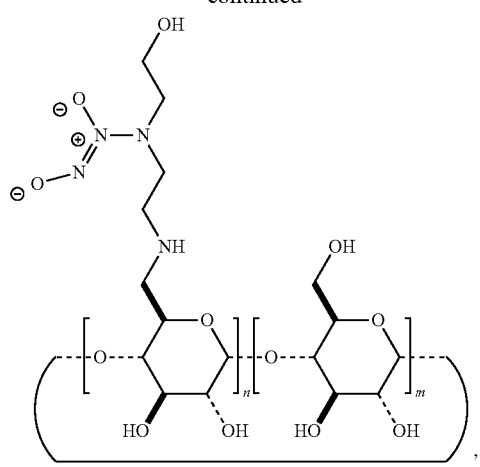
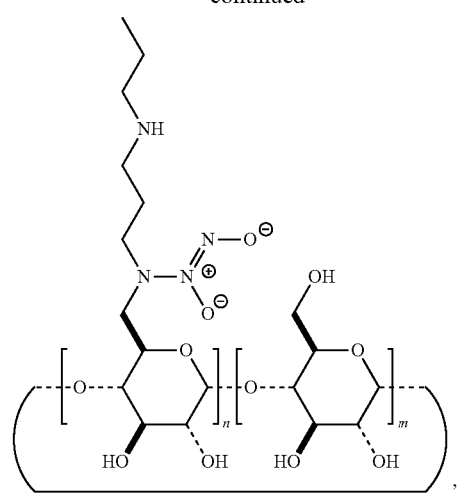
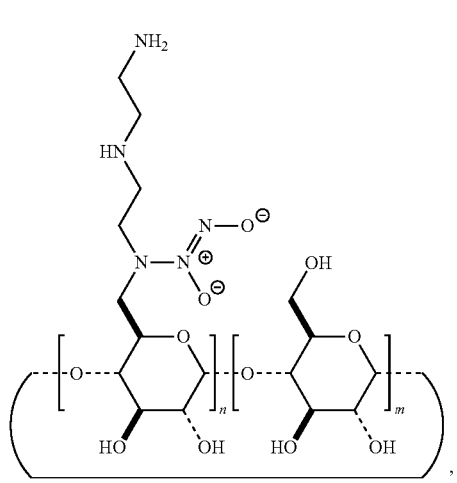
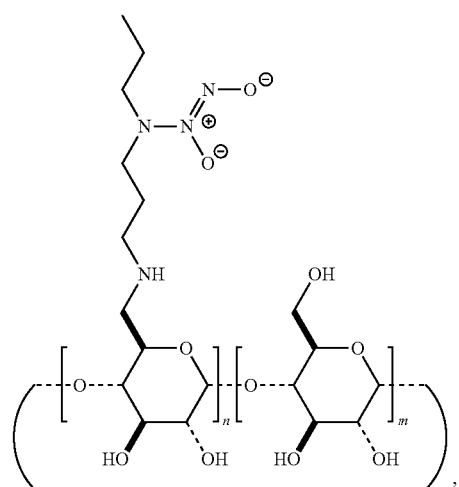
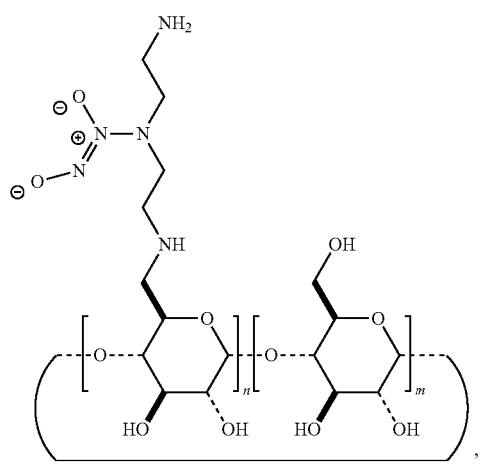
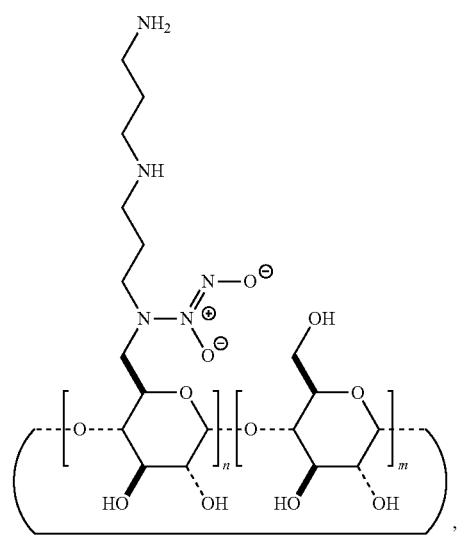

77
-continued
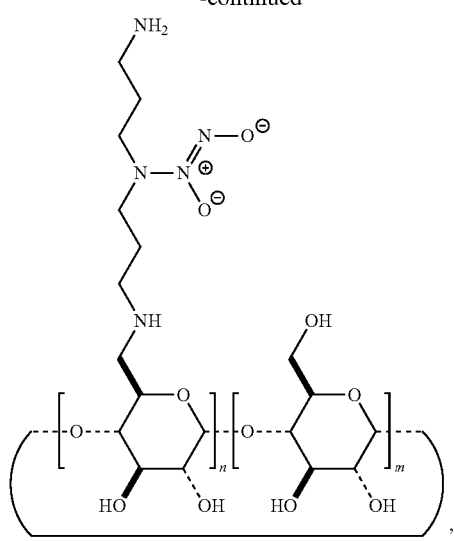
,
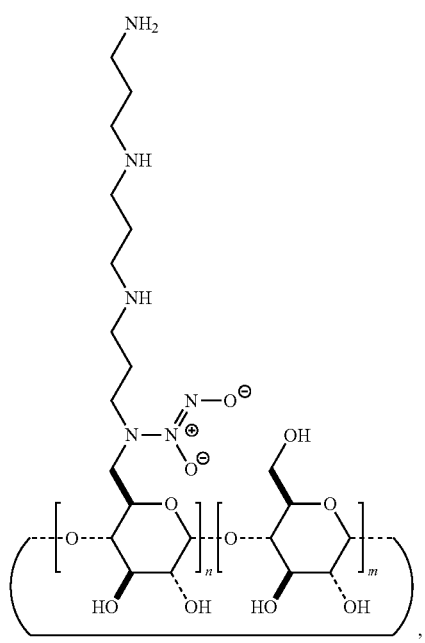
,
78
-continued
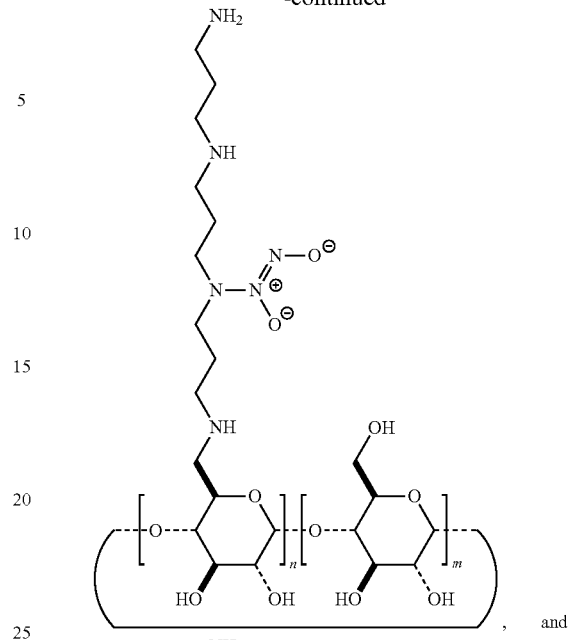
, and
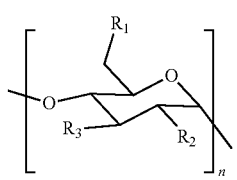
.
35. A functionalized cyclodextrin comprising:
at least one ring unit of Formula I:
Formula I
wherein
n is an integer selected from 1 to 8;
$R_1$, $R_2$, and $R_3$ are independently selected from the group consisting of —OH, —O—$((CH_2)_tO)_u$—H, —O—

$((CH_2)_tO)_{u'}$—$(CH_2)_vH$, —O—$(C_{1\text{-}5}\text{alkyl})$, —NH—$((CH_2)_c\text{NH})_{d'}$—H, —NH—$((CH_2)_c\text{NH})_{d'}$—$(CH_2)_eH$, —$X^1$—$((CH_2)_fX^2)_g$—$(CH_2)_hH$, and —$X^1$—$((CH_2)_fX^2)_g$—$((CH_2)_qX^3)_r$—$(CH_2)_hH$;

wherein
  each of c, c', d, d', e, f, f', g, g', h, h', q, r, t, t', u, u', and v is independently selected from an integer from 0 to 10;
  $X^1$, $X^2$, and $X^3$ are independently selected from O, S, or NH; and
  at least one of $X^1$, $X^2$, and $X^3$ is selected from the group consisting of

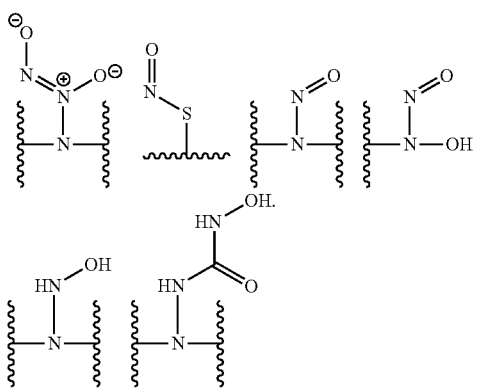

36. The functionalized cyclodextrin of embodiment 35, wherein $R^1$ is —$X^1$—$((CH_2)_fX^2)_g$—$((CH_2)_qX^3)_r$—$(CH_2)_hH$ and at least one of $X^1$, $X^2$, and $X^3$ is the following:

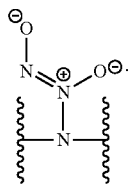

37. The functionalized cyclodextrin of any one of embodiments 35 or 36, wherein $R_2$ and $R_3$ are —OH.

38. The functionalized cyclodextrin of any one of embodiment 35-37, further comprising at least one glycopyranoside ring unit having the following structure:

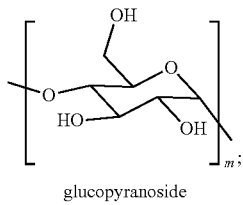

glucopyranoside wherein m is an integer selected from 1 to 8.

39. The functionalized cyclodextrin of any one of embodiments 35-38, wherein n is 1 and m is 5, 6, or 7.

40. The functionalized cyclodextrin of any one of embodiments 35-38, wherein n is 6, 7, or 8.

41. The functionalized cyclodextrin of any one of embodiments 35-40, selected from the group consisting of:

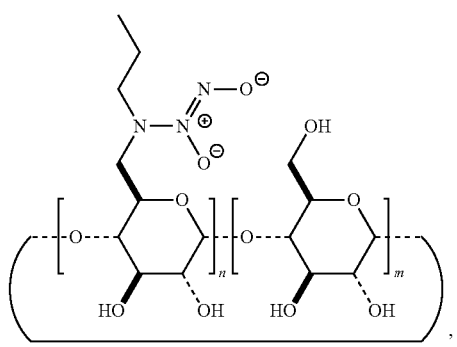

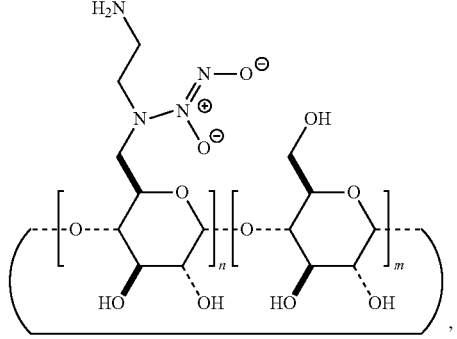

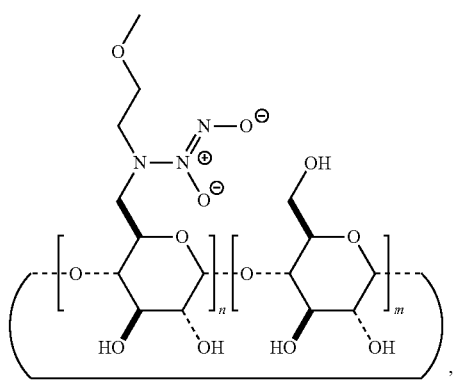

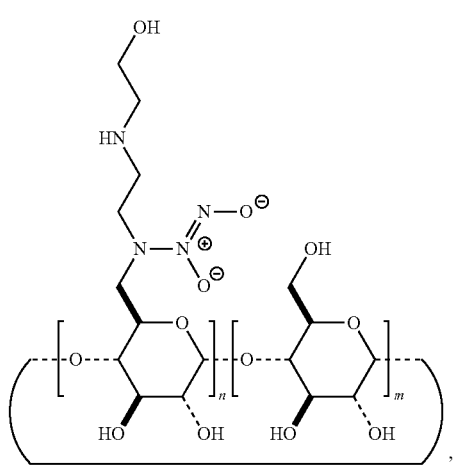

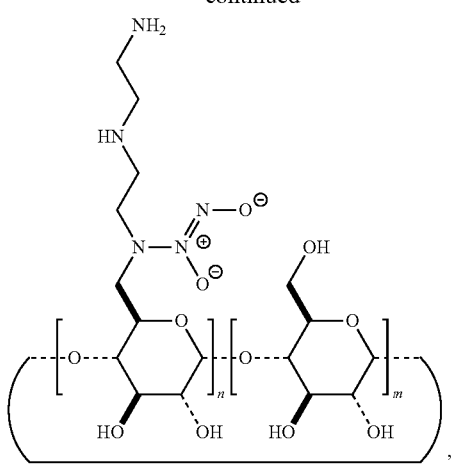
,
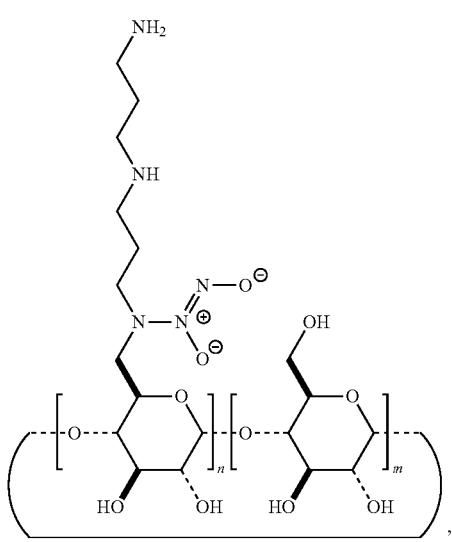
, and
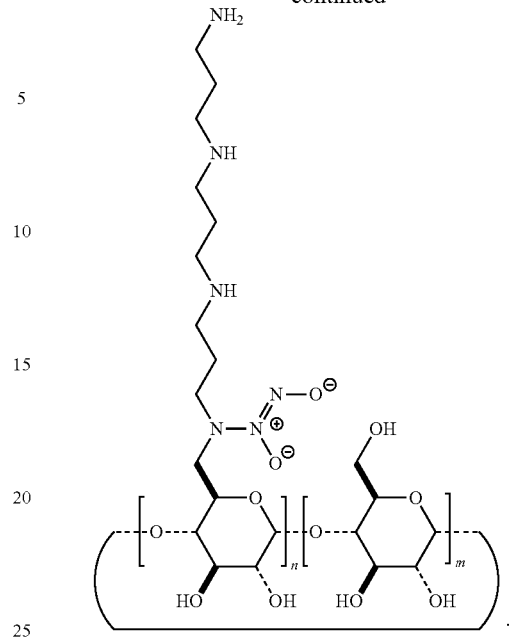
.
42. A functionalized cyclodextrin comprising:
wherein
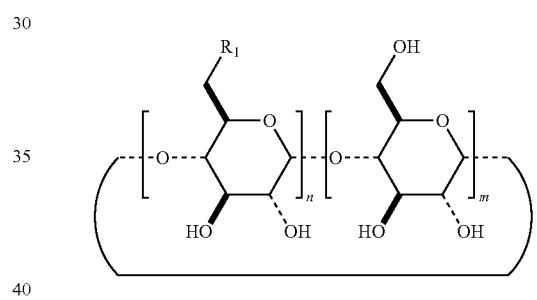
n is an integer selected from 1 to 8;
m is an integer from 0 to 7;
$R_1$ is $-X^1-((CH_2)_{f'}X^2)_{g'}((CH_2)_qX^3)_r-(CH_2)_{h'}H$;
wherein
each of f', g', q, r, and h' is independently selected from an integer from 0 to 10; and
$X^1$, $X^2$, and $X^3$ are independently selected from NH or
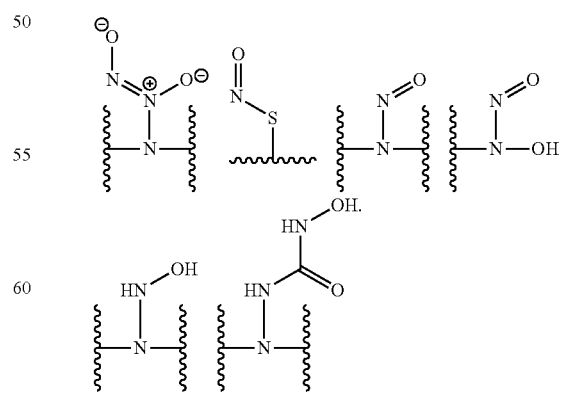
43. A method of delivering nitric oxide to a subject, comprising:

administering an effective amount of said functionalized cyclodextrin of any one of embodiments 25 to 42, to said subject.

44. A method of treating a disease state, comprising: administering an effective amount of said functionalized cyclodextrin of any one of embodiments 25 to 42, to a subject in need thereof, wherein said disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

45. The method of embodiment 44, wherein said disease state is a microbial infection.

46. Use of the functionalized cyclodextrin of any one of embodiments 25 to 42, for delivering nitric oxide to a subject.

47. Use of the functionalized cyclodextrin of any one of embodiments 25 to 42, in the preparation of a medicament for treating a subject in need with a disease state selected from the group consisting of one or more of: a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

48. A functionalized cyclodextrin comprising:
at least one ring unit of Formula I:

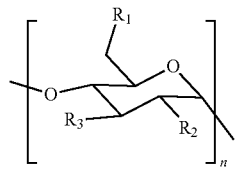

Formula I wherein
n is an integer selected from 1 to 8;
$R_1$, $R_2$, and $R_3$ are independently selected from the group consisting of —OH, —O—$((CH_2)_tO)_u$—H, —O—$((CH_2)_tO)_{u'}$—$(CH_2)_vH$, —O—$(C_{1-5}alkyl)$, —NH—$((CH_2)_cNH)_d$—H, —NH—$((CH_2)_cNH)_{d'}$—$(CH_2)_eH$, —$X^1$—$((CH_2)_fX^2)_g$—$(CH_2)_hH$, and —$X^1$—$((CH_2)_{f'}X^2)_{g'}((CH_2)_qX^3)_{r'}$—$(CH_2)_{h'}H$;
wherein
each of c, c', d, d', e, f, f', g, g', h, h', q, r, t, t', u, u', and v is independently selected from an integer from 0 to 10; and
$X^1$, $X^2$, and $X^3$ are independently selected from O, S, or NH.

49. The functionalized cyclodextrin of embodiment 48, wherein $R^2$ and $R^3$ are —OH.

50. The functionalized cyclodextrin of embodiments 48 or 49, wherein $R^1$ is —$X^1$—$((CH_2)_fX^2)_g((CH_2)_qX^3)_{r}$—$(CH_2)_hH$ and, where present, each of $X^1$, $X^2$, and $X^3$ is —NH.

51. The functionalized cyclodextrin of any one of embodiments 48-50, in particular, embodiment 48, having a chemical formula selected from the group consisting of:

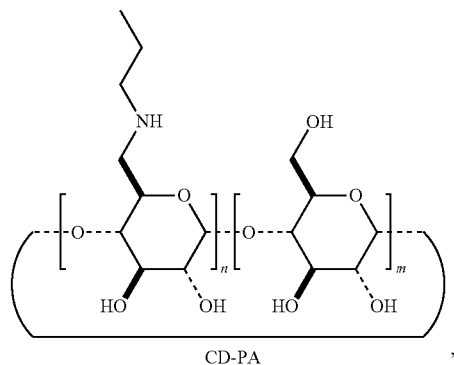

CD-PA,

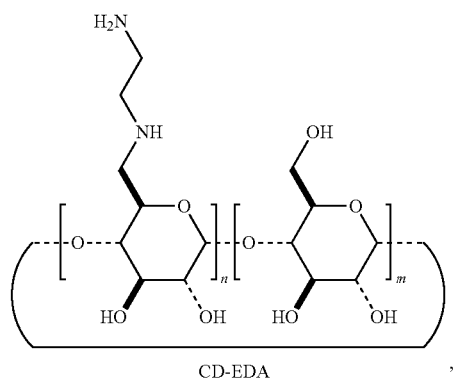

CD-EDA,

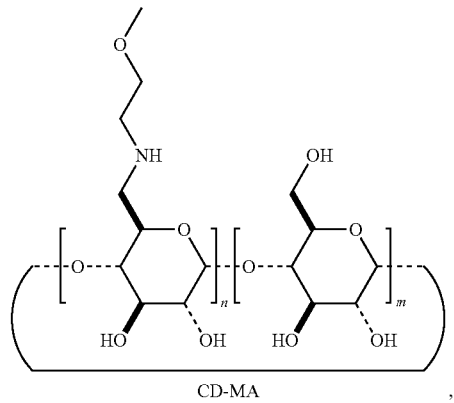

CD-MA,

-continued

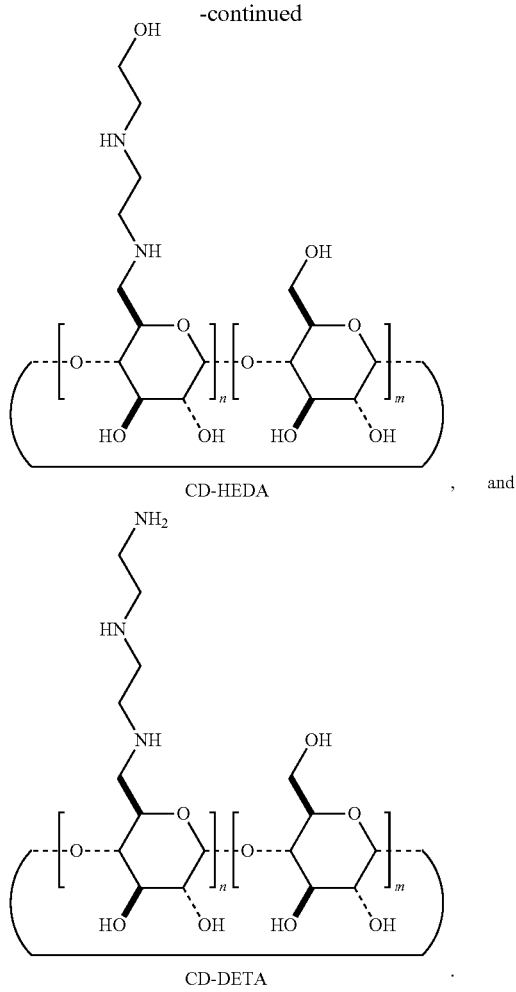

52. The functionalized cyclodextrin of any one of embodiments 25-42 or 48-51, in particular, any one of embodiments 25-42, wherein said functionalized cyclodextrin has a total releasable nitric oxide storage of at least 0.5 μmol of NO per milligram of functionalized cyclodextrin.

53. The functionalized cyclodextrin of any one of embodiments 25-42 or 48-52, wherein said functionalized cyclodextrin has a total releasable nitric oxide storage in a range of about 0.5 μmol to 2.5 μmol of NO per milligram of functionalized cyclodextrin.

54. The functionalized cyclodextrin of any one of embodiments 25-42 or 48-53, wherein said functionalized cyclodextrin has a total releasable nitric oxide storage in a range of about 1.0 μmol to 2.5 μmol of NO per milligram of functionalized cyclodextrin.

55. The functionalized cyclodextrin of any one of embodiments 25-42 or 48-54, in particular, any one of embodiments 25 to 42, wherein said functionalized cyclodextrin has a half-life for nitric oxide release in a range of between about 0.1-24 hours.

56. The functionalized cyclodextrin of any one of embodiments 25-42 or 48-55, wherein said functionalized cyclodextrin has a half-life for nitric oxide release in a range of between about 0.7-4.2 hours.

57. The functionalized cyclodextrin of any one of embodiments 25-42 or 48-56, in particular, any one of embodiments 25 to 42, wherein said functionalized cyclodextrin has a total duration of NO release in a range of between about 1-60 hours.

58. The functionalized cyclodextrin of any one of embodiments 25-42 or 48-57, in particular, any one of embodiments 25 to 42, wherein said functionalized cyclodextrin has a total NO release after 4 hours in a range of between about 0.3-2.0 μmol of NO per milligram of the functionalized cyclodextrin.

59. A functionalized cyclodextrin represented by the following structure:

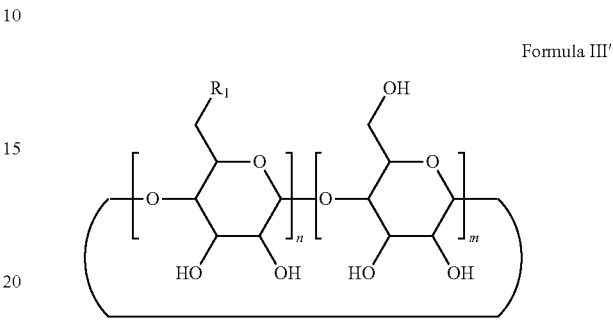

Formula III' wherein
n is an integer;
m is an integer;
each instance of $R_1$ is represented by $-X^1-((CH_2)_f X^2)_g-((CH_2)_q X^3)_r-(CH_2)_{h'}H$;
each of f', q, g, r, and h' is independently selected as an integer;
each instance of $X^1$, $X^2$, or $X^3$ is independently selected from O, NH, and a nitric oxide donating substituent,
the total releasable nitric oxide storage ranges from about 1.0 μmol to 2.5 μmol of NO per milligram of functionalized cyclodextrin,
the half-life for nitric oxide release ranges from about 0.1-24 hours, and
the total duration of NO release ranges from about 1-60 hours.

60. The functionalized cyclodextrin of embodiment 59, further comprising at least one guest drug, wherein the guest drug exerts therapeutic effects at a lower concentration when complexed with the functionalized cyclodextrin, as compared to the guest drug alone.

61. A method of delivering NO to a subject comprising, administering the functionalized cyclodextrin of embodiment 59 or 60 to the subject.

62. The method of embodiment 61, wherein the administration route is via inhalation and the NO delivery treats a disease of the lungs.

63. The method of embodiment 61 or 62, wherein the disease of the lungs is cystic fibrosis.

64. The method of any one of embodiments 61-63, wherein the disease of the lungs is lung cancer.

65. Use of the functionalized cyclodextrin of embodiment 59 or 60, in the preparation of a medicament for the treatment of a disease or condition.

66. Use of the functionalized cyclodextrin of embodiment 59 or 60, for the treatment of a disease or condition.

67. A method of treating the respiratory system, comprising:
administering to a lung via inhalation, a composition comprising functionalized cyclodextrin;
wherein functionalized cyclodextrin has a total releasable nitric oxide storage ranging from about 1.0 μmol to 2.5 μmol of NO per milligram of functionalized cyclodextrin, wherein the half-life for nitric oxide release ranges from about 0.1-24 hours, and wherein the total duration of NO release ranges from about 1-60 hours.

68. A method of treating the respiratory system, comprising:
administering to a lung via inhalation, a composition comprising functionalized cyclodextrin;
wherein functionalized cyclodextrin has a total releasable nitric oxide storage of at least about 1.0 µmol per milligram of functionalized cyclodextrin; and
wherein the half-life for nitric oxide release is at least 1 hour.

69. A functionalized cyclodextrin represented by the following structure:

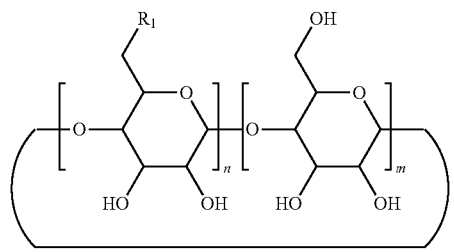

Formula III' wherein
n is an integer selected from 1 to 8;
m is an integer from 0 to 7;
each instance of $R_1$ is represented by $-X^1-((CH_2)_fX^2)_g((CH_2)_qX^3)_r-(CH_2)_{h'}H$;
wherein
each of f', q, g, r, and h' is independently selected from an integer from 0 to 4; and
each instance of $X^1$, $X^2$, or $X^3$ is independently selected from O, NH, and a nitric oxide donating substituent.

70. The functionalized cyclodextrin of embodiment 69, wherein at least one instance of $R^1$ is represented by one of the following:

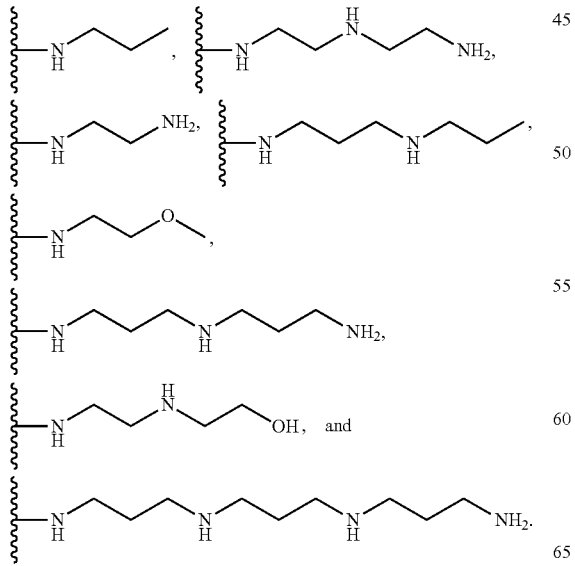

71. The functionalized cyclodextrin of embodiment 69 or 70, wherein at least one instance of $X^1$, $X^2$, or $X^3$ is represented by the following:

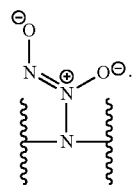

72. The functionalized cyclodextrin of any one of embodiments 69-71, wherein the structure of Formula III' is further represented by the structure of Formula III:

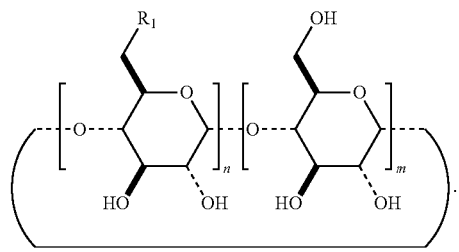

Formula III

73. The functionalized cyclodextrin of any one of embodiments 69-72, wherein at least one instance of $R^1$ is represented by one of the following:

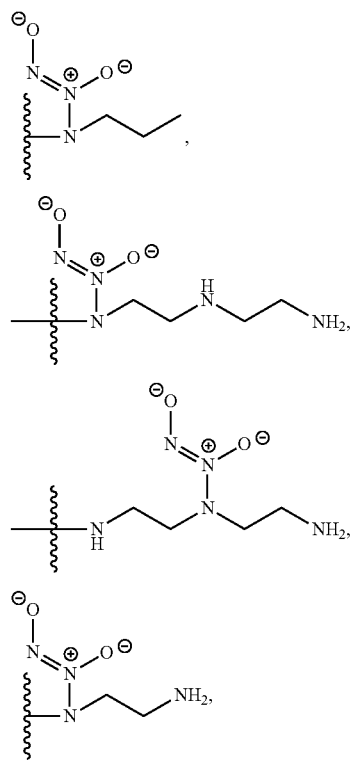

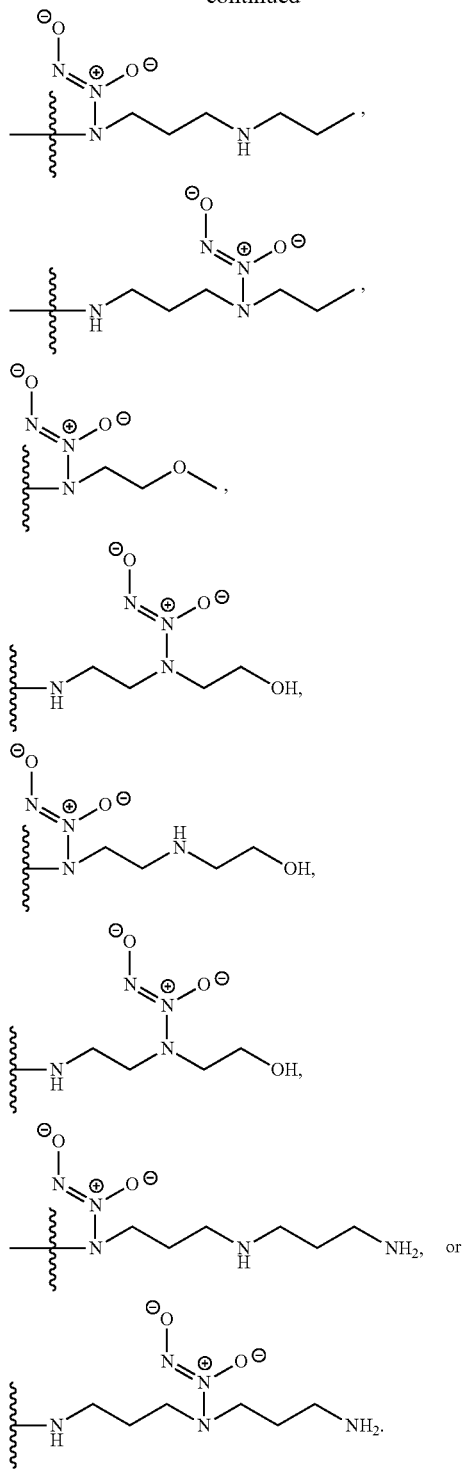

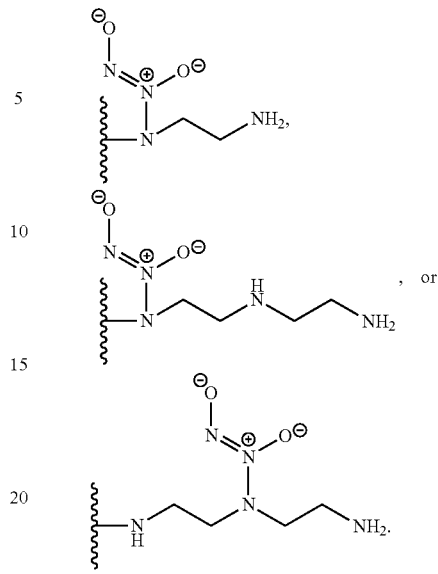

74. The functionalized cyclodextrin of any one of embodiments 69-73, wherein n is an integer selected from 6, 7, and 8.

75. The functionalized cyclodextrin of any one of embodiments 69-74, wherein m is 0.

76. The functionalized cyclodextrin of any one of embodiments 69-75, wherein at least one instance of $R^1$ is represented by one of the following:

77. The functionalized cyclodextrin of any one of embodiments 69-76, wherein n is 1 and m is 6.

78. The functionalized cyclodextrin of any one of embodiments 69-76, wherein n is 7 and m is 0.

79. The functionalized cyclodextrin of any one of embodiments 69-78, wherein said functionalized cyclodextrin has a total releasable nitric oxide storage of at least 0.5 μmol of NO per milligram of functionalized cyclodextrin.

80. The functionalized cyclodextrin of any one of embodiments 69-79, wherein said functionalized cyclodextrin has a total releasable nitric oxide storage in a range of about 0.5 μmol to 2.5 μmol of NO per milligram of functionalized cyclodextrin.

81. The functionalized cyclodextrin of any one of embodiments 69-80, wherein said functionalized cyclodextrin has a half-life for nitric oxide release in a range of between about 0.7-4.2 hours.

82. The functionalized cyclodextrin of any one of embodiments 69-81, wherein said functionalized cyclodextrin has a total NO release after 4 hours in a range of between about 0.3-2.0 μmol of NO per milligram of the functionalized cyclodextrin.

83. A composition comprising the functionalized cyclodextrin of any one of embodiments 69-82 and a pharmaceutically acceptable carrier.

84. The composition of embodiment 83, further comprising a cyclodextrin that is not functionalized.

85. The functionalized cyclodextrin of embodiments any one of 69-82 or the composition of embodiment 83 or embodiment 84 further comprising one or more guest drugs complexed with the functionalized cyclodextrin.

86. The functionalized cyclodextrin or composition of any one of embodiments 69-85, in particular, embodiment 85, wherein the one or more guest drugs comprise one or more drugs for the treatment of a cancer, a cardiovascular disease, a microbial infection, platelet aggregation and/or platelet adhesion, pathological conditions resulting from abnormal cell proliferation, transplantation rejections, autoimmune diseases, inflammation, vascular diseases, scar tissue, wound contraction, restenosis, pain, fever, gastrointestinal disorders, respiratory disorders, sexual dysfunctions, sexually transmitted diseases, or wound healing. 87. A method of delivering nitric oxide to a subject, comprising:

administering an effective amount of the functionalized cyclodextrin of any one of embodiments 69 to 82 or the composition of embodiment 83 or embodiment 84 to said subject.

88. A method of treating a disease state, comprising: administering an effective amount of the functionalized cyclodextrin of any one of embodiments 69-82 or the composition of embodiment 83 or embodiment 84 to a subject in need thereof, wherein said disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

89. The method of embodiment 88, wherein said disease state is a microbial infection.

90. A method of treating a disease state, comprising: administering an effective amount of the functionalized cyclodextrin of any one of embodiments 69 to 82 or the composition of embodiments 83 or 84 to said subject to a subject in need thereof, wherein said disease state is lung cancer.

91. Use of the functionalized cyclodextrin of any one of embodiments 69 to 82 or the composition of embodiment 83 or 84 for delivering nitric oxide to a subject.

92. Use of the functionalized cyclodextrin of any one of embodiments 69 to 82 or the composition of embodiment 83 or 84 to said subject in the preparation of a medicament for treating a subject in need with a disease state selected from the group consisting of one or more of: a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

93. A method of manufacturing a functionalized cyclodextrin comprising:
mixing a cyclodextrin with a functionalizing compound comprising a leaving group and a secondary amine to provide a cyclodextrin having a secondary amine.

94. The method of embodiment 93, wherein the leaving group is one or more of —OTs, —OMs, —Cl, —Br, or —I.

95. The method of embodiments 93 or 94, further comprising exposing the cyclodextrin having a secondary amine with NO to afford an NO releasing functionalized cyclodextrin.

96. The method of any one of embodiments 93 to 95, comprising mixing the cyclodextrin with a guest molecule to provide a host guest complex.

The following examples are offered by way of illustration and not by way of limitation.

EXAMPLES

Example 1

1.1 Materials and Instruments

β-Cyclodextrin (CD), p-toluenesufonyl chloride, sodium hydroxide, bromine, triphenylphosphine, propylamine (PfreportA), 2-methoxyethylamine (MA), ethylenediamine (EDA), diethylenetriamine (DETA), N-(2-Hydroxyethyl) ethylenediamine (HEDA), propidium iodide (PI), fetal bovine serum (FBS), Dulbecco's modified Eagle's medium (DMEM), phenazine methosulfate (PMS), trypsin, 3-(4,5-dimethylthiazol-2-yl)-5-(3-carboxymethoxyphenyl)-2-(4-sulfophenyl)-2H-tetrazolium inner salt (MTS), Dulbecco's phosphate buffered saline (DPBS), and penicillin streptomycin (PS) were purchased from Sigma-Aldrich and used without further purification. Sodium methoxide (5.4 M solution in methanol) was purchased from Acros Organics. Nitric oxide (NO) gas (99.5%) was purchased from Praxair. A Millipore Milli-Q UV Gradient A-10 System was used to purify distilled water to a final resistivity of 18.2 MΩ·cm and a total organic content of ≤6 ppb. *Pseudomonas aeruginosa* (*P. aeruginosa*; ATCC #19143) was obtained from the American Type Culture Collection. 4,5-Diaminofluorescein diacetate (DAF-2 DA) was purchased from Calbiochem. Tryptic soy agar (TSA) and Tryptic soy broth (TSB) were purchased from Becton, Dickinson, and Company. L929 mouse fibroblasts (ATCC #CCL-1) were obtained from the University of North Carolina Tissue Culture Facility. All other materials are obtained from commercial sources and used without further purification.

$^1$H nuclear magnetic resonance ($^1$H NMR) spectra were recorded on a Bruker (400 MHz) spectrometer. Mass spectrometry (MS) was performed on a Thermo Scientific LTQ FT Ultra mass spectrometer in positive ion mode. UV-Vis absorption spectra were measured on a PerkinElmer Lambda 40 Spectrophotometer.

1.2 Synthesis of Secondary Amine-Modified CD Derivates 1.2.1 Synthesis of Secondary Amine-Modified Mono-Substituted CD Derivatives:

Scheme S1. Synthesis route of secondary amine-modified mono-substituted CD derivatives.

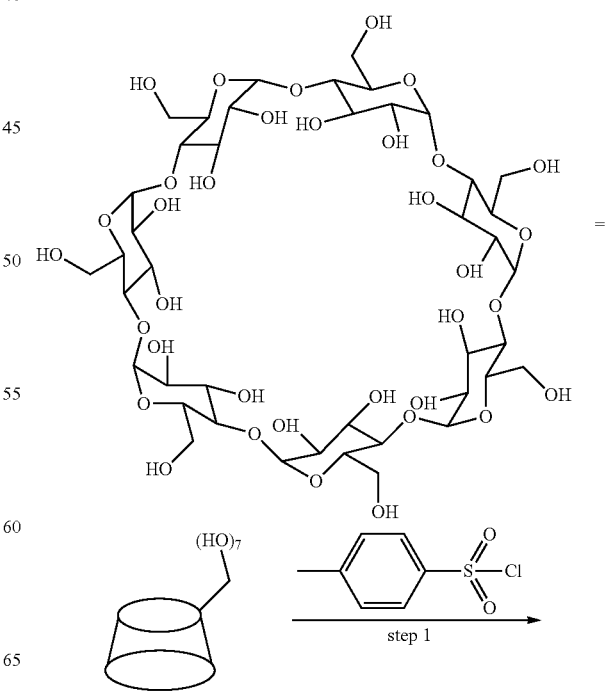

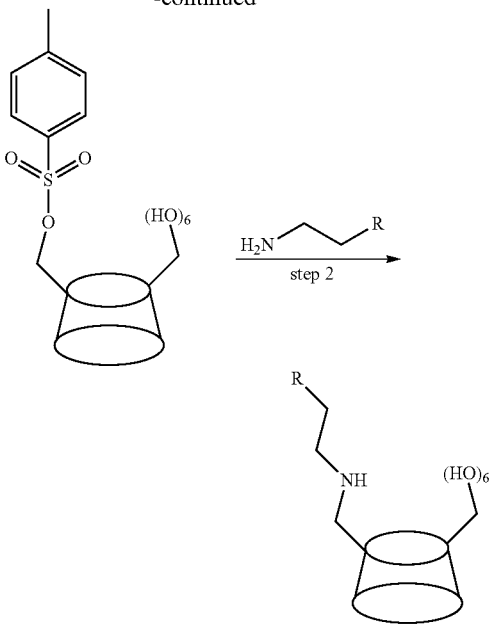

R = CH₃
NH₂
OCH₃
NHCH₂CH₂OH
NHCH₂CH₂NH₂

As shown in FIG. 1a (and Scheme S1), β-CD was modified with secondary amines with tunable percentages of secondary amines. Briefly, β-CD was reacted with tosyl chloride under basic conditions to yield mono-6-tosyl-β-cyclodextrin (CD-OTs), a mono-substituted intermediate.

Mono-6-(p-toluenesulfonyl)-6-deoxy-cyclodextrin (CD-OTs) was synthesized based on the reported literature. Briefly, (β-Cyclodextrin (50 g, 44.1 mmol) was dissolved in 300 mL of deionized water and then immersed in the 0 OC ice bath. Sodium hydroxide (5.475 g, 137 mmol) was added until complete dissolution of CDs. p-Toluenesulfonyl chloride (8.4 g, 44.1 mmol) dissolved in 30 mL of CH₃CN was added dropwise into the mixture, followed by reacting 3 hours at room temperature. The pH value of the crude product solution was adjusted to around 9.0, followed by putting in the 4° C. fridge overnight. The precipitate was filtered and dried under vacuum for 3 days. The final product of CD-OTs was collected as white solid powder (9.836 g, 7.63 mmol, Yield: 17.3%). ¹H NMR (400 MHz, DMSO, δ, ppm): 7.72~7.78 (2H, aromatic protons), 7.41~7.47 (2H, aromatic protons), 5.60~5.86 (14H, OH-2,3), 4.75~4.90 (7H, H-1), 4.15~4.60 (6H, OH-6), 3.45~3.75 (28H, H-3, 5, 6), 3.12~3.42 (14H, H-2,4, overlap with HOD), 2.41~2.45 (3H, —CH₃ attached to the aromatic ring).

Tosyl groups were further substituted with primary amines (e.g., N-(2-Hydroxyethyl)ethylenediamine (HEDA), propylamine (PA), 2-methoxyethylamine (MA), ethylenediamine (EDA), and diethylenetriamine (DETA)) to form secondary amine-modified mono-substituted β-CD derivatives. CD-OTs (1.475 g, 1.14 mmol) was added into the single-neck round-bottom flask, followed by addition of 10 mL of primary amine (PA, MA, EDA, DETA, HEDA) until completely dissolution of the CD-OTs. The mixture was heated to 75° C. for 1~3 days, depending on the primary amines functional moiety. The crude products were precipitated in cold acetone for 3 times and dried under vacuum at room temperature for 3 days. The final products of mono-substituted CD derivatives (CD-R, R=PA, MA, EDA, DETA, HEDA) were obtained as white solid powders.

These mono-substituted CD derivatives were named as CD-HEDA, CD-PA, CD-MA, CD-EDA, and CD-DETA, respectively, based on the primary amines employed in the reaction.

CD-HEDA (3 Days Reaction):

Product: 1.264 g, 1.04 mmol, Yield: 90.5%. Molecular weight: 1221.12 g/mol; MS m/z: 1221.46 for [M+]. ¹H NMR (400 MHz, D₂O, δ, ppm): 4.92~5.08 (7H, H-1), 3.71~4.00 (21H, H-3, 5, 6), 3.62~3.70 (2H, —CH₂OH), 3.30~3.62 (14H, H-2, 4), 2.57~3.05 (13H, H-6 and methylene groups of —NHCH₂CH₂NHCH₂—).

CD-PA (3 Days Reaction):

Product: 1.167 g, 0.99 mmol, Yield: 86.7%. Molecular weight: 1176.08 g/mol; MS m/z: 1176.44 for [M+]. ¹H NMR (400 MHz, D₂O, δ, ppm): 4.92~5.07 (7H, H-1), 3.70~3.93 (21H, H-3, 5, 6), 3.30~3.62 (14H, H-2, 4), 2.51~3.20 (9H, H-6 and methylene group in —NHCH2-), 1.37~1.55 (2H, methylene group adjacent to terminal methyl group), 0.74~0.90 (3H, terminal methyl group). Note: Owing to the low boiling point of PA, 10 mL of DMF was used as cosolvent to avoid liquid flooding.

CD-MA (3 Days Reaction):

Product: 1.230 g, 1.03 mmol, Yield: 90.2%. Molecular weight: 1192.08 g/mol; MS m/z: 1192.44 for [M+]. ¹H NMR (400 MHz, D₂O, δ, ppm): 4.92~5.05 (7H, H-1), 3.70~3.95 (21H, H-3, 5, 6), 3.30~3.62 (16H, —CH₂O— and H-2, 4), 3.25~3.30 (3H, —OCH₃), 2.55~3.10 (9H, H-6 and methylene group of CD-NHCH₂—).

CD-EDA (1 Day Reaction):

Product: 0.905 g, 0.77 mmol, Yield: 67.2%. Molecular weight: 1177.07 g/mol; MS m/z: 1177.43 for [M+]. ¹H NMR (400 MHz, D₂O, δ, ppm): 4.90~5.05 (7H, H-1), 3.70~3.93 (21H, H-3, 5, 6), 3.30~3.62 (14H, H-2, 4), 2.55~2.95 (11H, H-6 and methylene groups of —NH₂CH₂CH₂NH₂).

CD-DETA (2 Days Reaction):

Product: 1.195 g, 0.98 mmol, Yield: 85.6%. Molecular weight: 1220.14 g/mol; MS m/z: 1220.48 for [M+]. ¹H NMR (400 MHz, D₂O, δ, ppm): 4.92~5.05 (7H, H-1), 3.70~3.95 (21H, H-3, 5, 6), 3.30~3.62 (14H, H-2, 4), 2.55~3.05 (15H, H-6 and methylene groups of —NHCH₂CH₂NHCH₂CH₂NH₂).

Secondary hydroxyl groups of β-CD were totally converted into bromo groups to generate another intermediate heptakis-6-bromo-6-deoxyl-β-cyclodextrin (CD-Br7). Followed by displacement with primary amines, secondary amine-modified hepta-substituted β-CD derivatives were synthesized, which were classified as CD-HEDA7, CD-PA7, CD-MA7, CD-EDA7, and CD-DETA7, respectively.

1.2.2 Synthesis of Secondary Amine-Modified Hepta-Substituted CD Derivatives:

Scheme S2. Synthesis route of secondary amine-modified hepta-substituted CD derivatives.

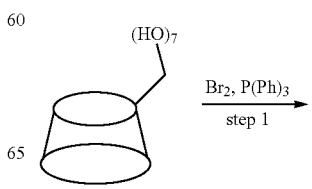

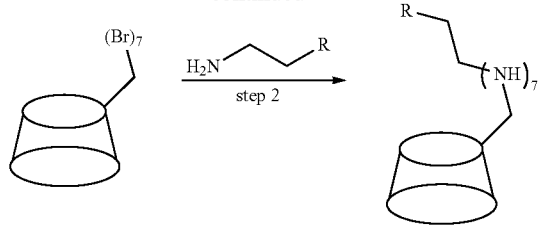

R = CH₃
NH₂
OCH₃
NHCH₂CH₂OH
NHCH₂CH₂NH₂

β-Cyclodextrin (4.320 g, 3.81 mmol) and triphenylphosphine (21 g, 80 mmol) was dissolved in 80 mL of dimethylformamide (DMF). Bromine (4 mL) was then added into the mixture. The solution was stirred at 80° C. for 15 hours. It was then concentrated to half the volume by nitrogen flow overnight. Afterwards, the pH was adjusted to 9~10, by addition of 5.4 M sodium methoxide in methanol. The mixture was stirred at room temperature for 30 minutes, followed by precipitation in 1.5 L of iced water. The precipitate was filtered and dried under vacuum at room temperature for 3 days. The final product of heptakis-6-bromo-6-deoxy-cyclodextrin (CD-Br7) was gained as brown solid powder (3.184 g, 2.02 mmol, Yield: 53.1%). $^1$H NMR (400 MHz, DMSO, δ, ppm): 5.75~6.10 (14H, OH-2, 3), 4.88~5.05 (7H, H-1), 3.9~4.07 (7H, H-5), 3.77~3.87 (7H, H-3), 3.57~3.75 (14H, H-2, 6), 3.25~3.45 (14H, H-4, 6, overlap with HOD).

The resulting secondary amine-modified hepta-substituted CD derivatives were synthesized. Briefly, CD-Br7 (1.050 g, 0.67 mmol) and 4 mL of DMF were added into the single-neck round-bottom flask. After complete dissolution, 4 mL of primary amine (PA, MA, EDA, DETA, HEDA) was added, reacting at room temperature for 2 days. The crude product was precipitated in cold acetone for 3 times and dried under vacuum at room temperature for 3 days. The final products of hepta-substituted CD derivatives (CD-R7, R=PA, MA, EDA, DETA, HEDA) were obtained as yellow solid powders.

CD-HEDA7:
Product: 0.728 g, 0.42 mmol, Yield: 62.8%. Molecular weight: 1737.93 g/mol; MS m/z: 869.49 for [M+]/2. $^1$H NMR (400 MHz, D₂O, δ, ppm): 4.89~5.20 (7H, H-1), 3.75~4.10 (14H, H-3, 5), 3.60~3.73 (14H, —CH₂OH), 3.30~3.60 (14H, H-2, 4), 2.40~3.13 (56H, H-6 and methylene groups in —NHCH₂CH₂NHCH₂—).

CD-PA7:
Product: 0.730 g, 0.51 mmol, Yield: 77.0%. Molecular weight: 1422.65 g/mol; MS m/z: 1422.85 for [M+] and 711.90 for [M+]/2. $^1$H NMR (400 MHz, D₂O, δ, ppm): 4.97~5.15 (7H, H-1), 3.80~4.10 (14H, H-3, 5), 3.35~3.65 (14H, H-2, 4), 2.31~3.15 (28H, H-6 and methylene group in —NHCH₂—), 1.46~1.65 (14H, methylene group adjacent to terminal methyl group), 0.74~1.00 (21H, terminal methyl group).

CD-MA7:
Product: 0.637 g, 0.42 mmol, Yield: 62.3%. Molecular weight: 1534.64 g/mol; MS m/z: 767.89 for [M+]/2. $^1$H NMR (400 MHz, D₂O, δ, ppm): 4.95~5.13 (7H, H-1), 3.70~4.10 (14H, H-3, 5), 3.32~3.65 (28H, —CH₂O— and H-2, 4), 3.23~3.32 (21H, —OCH₃), 2.60~3.15 (28H, H-6 and methylene group of CD-NHCH₂—).

CD-EDA7:
Product: 0.653 g, 0.46 mmol, Yield: 68.6%. Molecular weight: 1429.57 g/mol; MS m/z: 1429.78 for [M+], 714.86 for [M+]/2, and 477.26 for [M+]/3. $^1$H NMR (400 MHz, D₂O, δ, ppm): 4.85~5.20 (7H, H-1), 3.75~4.05 (14H, H-3, 5), 3.30~3.65 (14H, H-2, 4), 2.35~3.15 (42H, H-6 and methylene groups in —NHCH₂CH₂NH₂).

CD-DETA7:
Product: 0.836 g, 0.48 mmol, Yield: 72.4%. Molecular weight: 1731.04 g/mol; MS m/z: 1524.86 for [M+] and 762.93 for [M+]/2. $^1$H NMR (400 MHz, D₂O, δ, ppm): 4.85~5.15 (7H, H-1), 3.70~4.15 (14H, H-3, 5), 3.30~3.65 (14H, H-2, 4), 2.40~3.15 (54H, H-6 and methylene groups in —NHCH₂CH₂NHCH₂CH₂NH₂). [Note: according to the NMR and MS result, it was confirmed that some crosslink occurred in the synthesis of CD-DETA7. The possible structure was in scheme S3. However, the crosslink had no effect on the dissolution property in water.]

Scheme S3. Possible molecular structure of crosslinked CD-HEDA7.

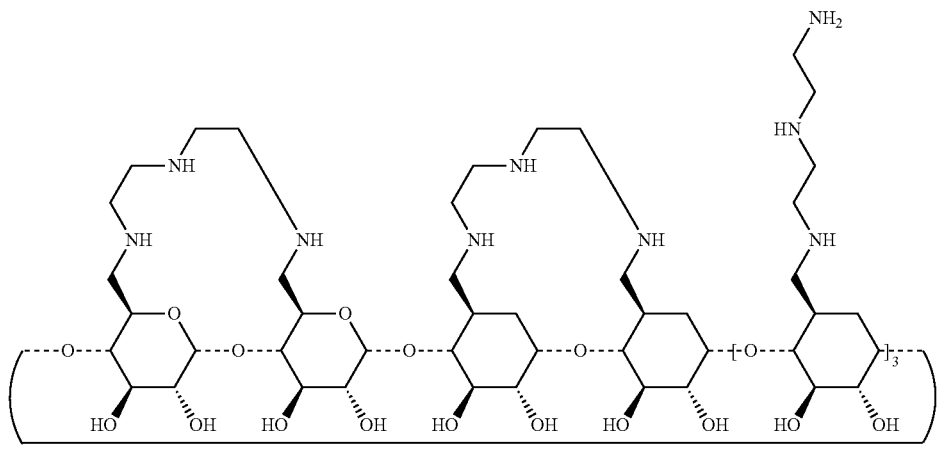

Example 2

1.3 Synthesis of N-Diazeniumdiolate-Modified CD Derivatives

The resulting secondary amine-modified CD derivatives were reacted with NO gas (10 bar) under strong alkaline conditions to yield the N-diazeniumdiolates (FIG. 1b). N-diazeniumdiolate-functionalized CD derivatives (CD-NONOates) were characterized by 1H NMR and UV-Vis spectroscopy.

To synthesize N-diazeniumdiolate-modified CD derivatives, mono-substituted or hepta-substituted CD derivatives were added into tunable ratios of $H_2O$ and anhydrous methanol (MeOH) (total volume 1.5 mL) depending on the terminal functional groups. The ratios were shown as follows: 1:1 $H_2O$:MeOH (CD-HEDA), 1:1 $H_2O$:MeOH (CD-PA), 1:1 $H_2O$:MeOH (CD-MA), 1:1 $H_2O$:MeOH (CD-EDA), 1:1 $H_2O$:MeOH (CD-DETA), 1:1 $H_2O$:MeOH (CD-HEDA7), 100% MeOH (CD-PA7), 2:8 $H_2O$:MeOH (CD-MA7), 1:1 $H_2O$:MeOH (CD-EDA7), 1:1 $H_2O$:MeOH (CD-DETA7). In the following step, 1 equiv of sodium methoxide in methanol (with respect to the molar amount of secondary amine in CD derivatives) was added into the mixture, followed by vortex to gain homogeneous solutions.

The CD derivatives solutions were placed in a stainless steel pressure vessel with strong magnetic stirring. The vessel was purged rapidly with argon three times to a pressure of 7 bar, followed by three longer argon purge cycles (10 minutes) to remove the residual oxygen in from the solutions. The vessel was then pressurized to 10 bar of NO gas, which was maintained for 3 days. The solutions were purged with argon at three times short durations, followed by three times longer purges (10 minutes) to remove unreacted NO gas. The solutions were precipitated in 15 mL of acetone once, followed by centrifugation to remove the solvent. The final product was dried in a vacuum drying oven at room temperature for 2 hours. The resulting NO-releasing CD derivatives were parafilmed and stored at −20° C. for future use.

Figure 2A:
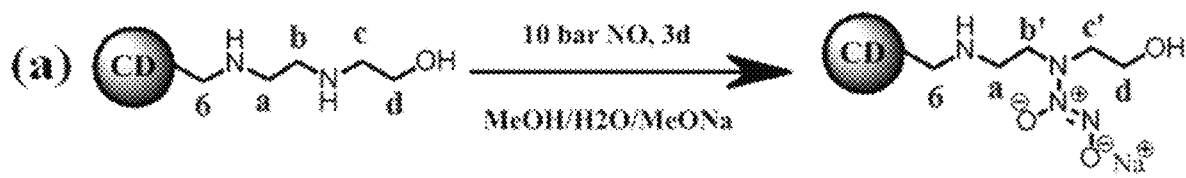
FIGS. 2(a)-(c) depict characterization data of NO donor CD-HEDA7/NO.
Figure 2B:
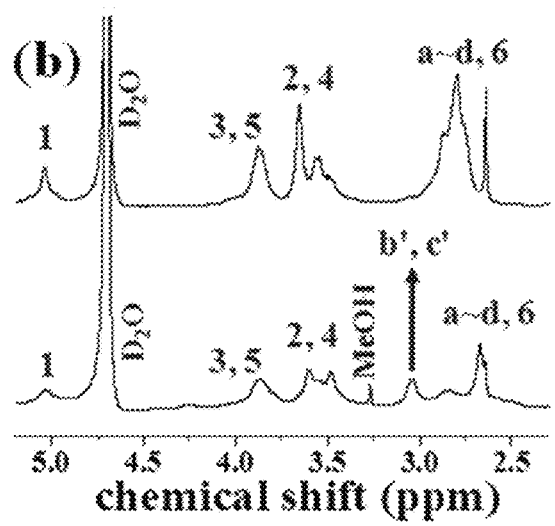
Figure 2C:
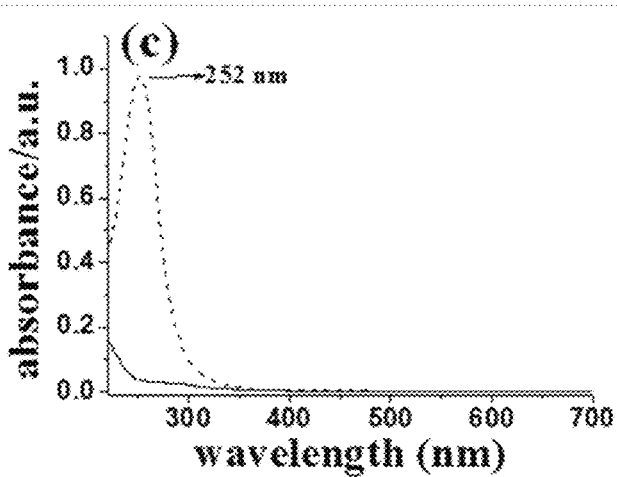
Figure 3:
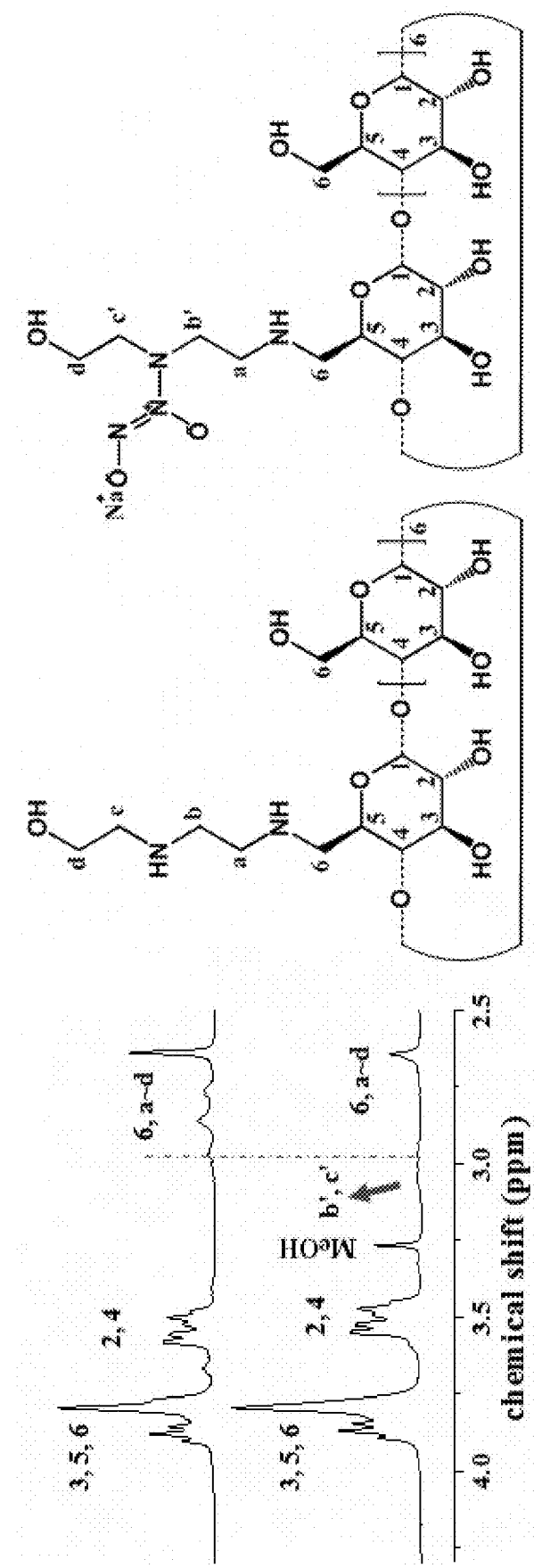
FIG. 3 shows characterization data and the structure of a non-limiting embodiment of a CD derivative. (Left) NMR spectra of CD-HEDA (top line) and CD-HEDA/NO (bottom line); (Middle) Molecular structure of CD-HEDA; ($R_1$ ght) Molecular structure of CD-HEDA/NO. Newly-appeared peaks of b' and c' assigned to the methylene groups adjacent to N-diazeniumdiolates demonstrated the successful synthesis of CD-HEDA/NO. The high chemical shift of these methylene groups was due to the hydrogen bonding between the terminal hydroxyl group and N-diazeniumdiolate.
Figure 4:
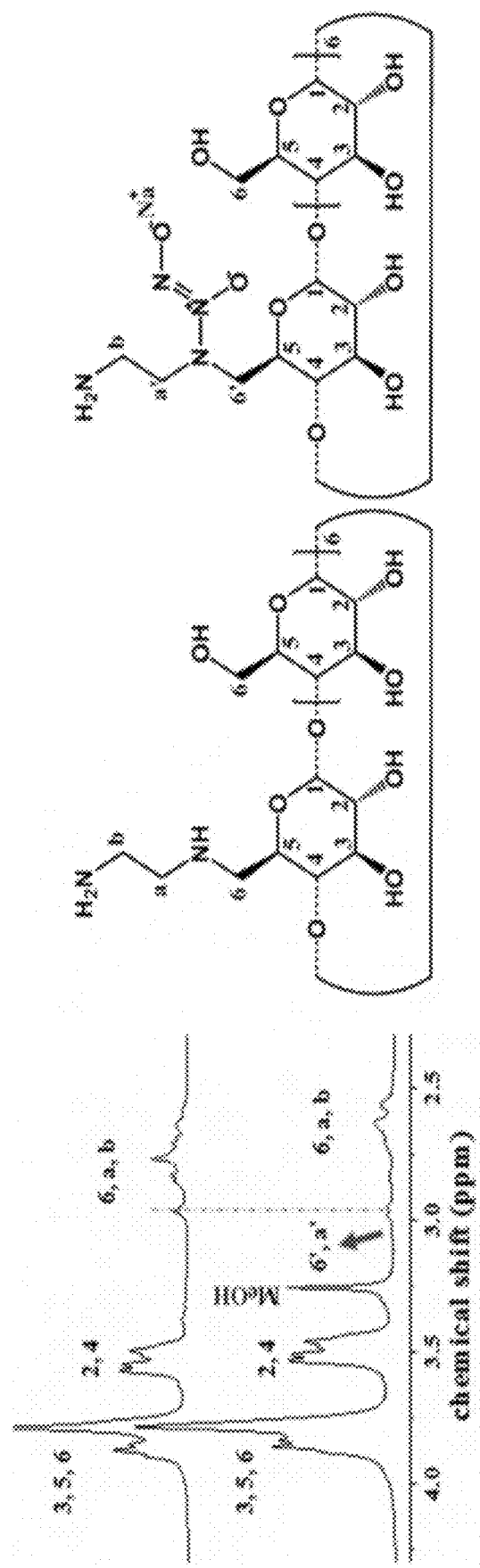
FIG. 4 shows characterization data and the structure of a non-limiting embodiment of a CD derivative. (Left) NMR spectra of CD-EDA (top line) and CD-EDA/NO (bottom line); (Middle) Molecular structure of CD-EDA; ($R_1$ ght) Molecular structure of CD-EDA/NO. Newly-appeared peaks of 6' and a' assigned to the methylene groups adjacent to N-diazeniumdiolates demonstrated the successful synthesis of CD-EDA/NO. The high chemical shift of these methylene groups was due to the hydrogen bonding between the terminal primary amine group and N-diazeniumdiolate.
Figure 5:
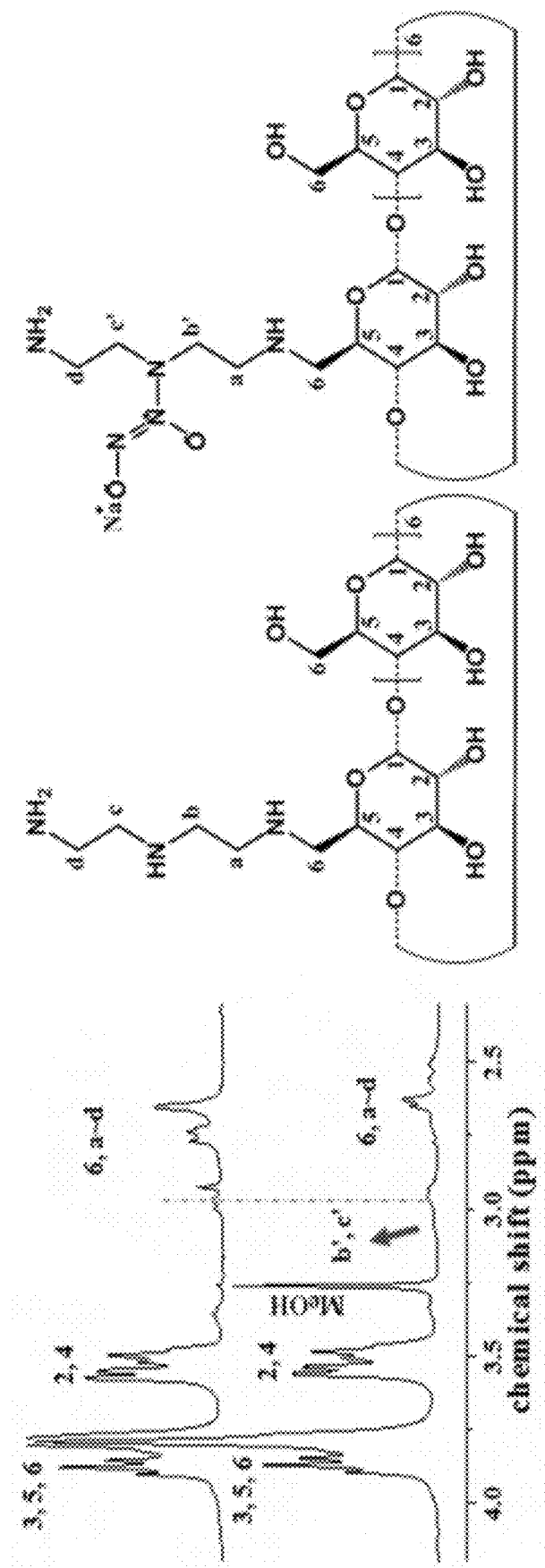
FIG. 5 shows characterization data and the structure of a non-limiting embodiment of a CD derivative. (Left) NMR spectra of CD-DETA (top line) and CD-DETA/NO (bottom line); (Middle) Molecular structure of CD-DETA; ($R_1$ ght) Molecular structure of CD-DETA/NO. Newly-appeared peaks of b' and c' assigned to the methylene groups adjacent to N-diazeniumdiolates demonstrated the successful synthesis of CD-DETA/NO. The high chemical shift of these methylene groups was due to the hydrogen bonding between the terminal primary amine group and N-diazeniumdiolate.
Figure 6:
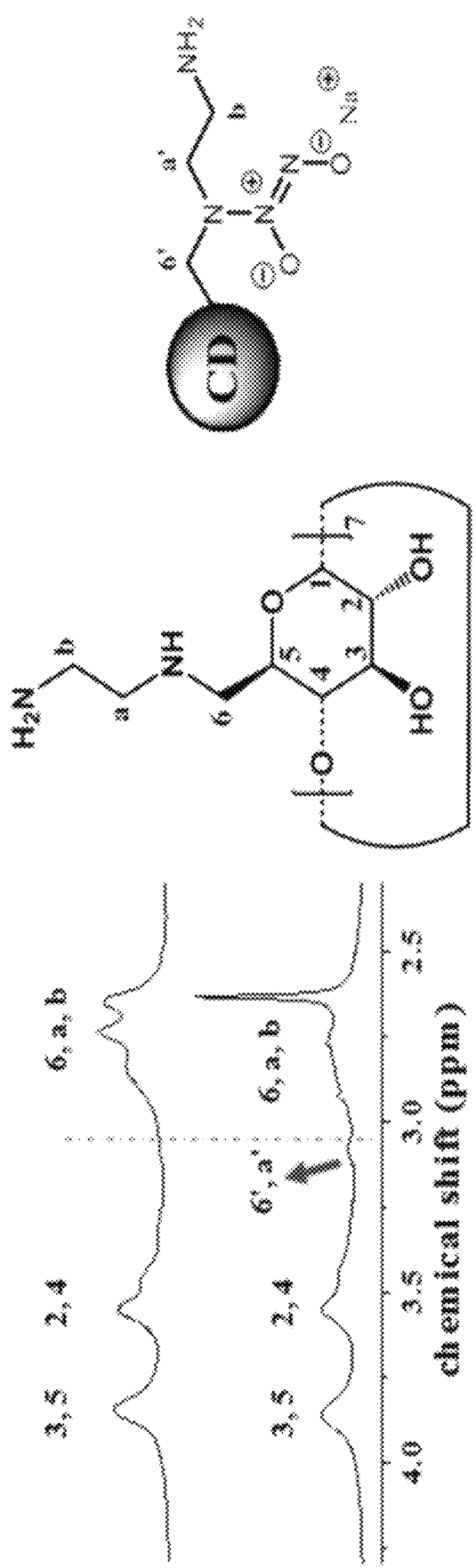
FIG. 6 shows characterization data and the structure of a non-limiting embodiment of a CD derivative. (Left) NMR spectra of CD-EDA7 (top line) and CD-EDA7/NO (bottom line); (Middle) Molecular structure of CD-EDA7; ($R_1$ ght) Molecular structure of CD-EDA7/NO. Newly-appeared peaks of 6' and a' assigned to the methylene groups adjacent to N-diazeniumdiolates demonstrated the successful synthesis of CD-EDA7/NO. The high chemical shift of these methylene groups was due to the hydrogen bonding between the terminal primary amine group and N-diazeniumdiolate.
Figure 7:
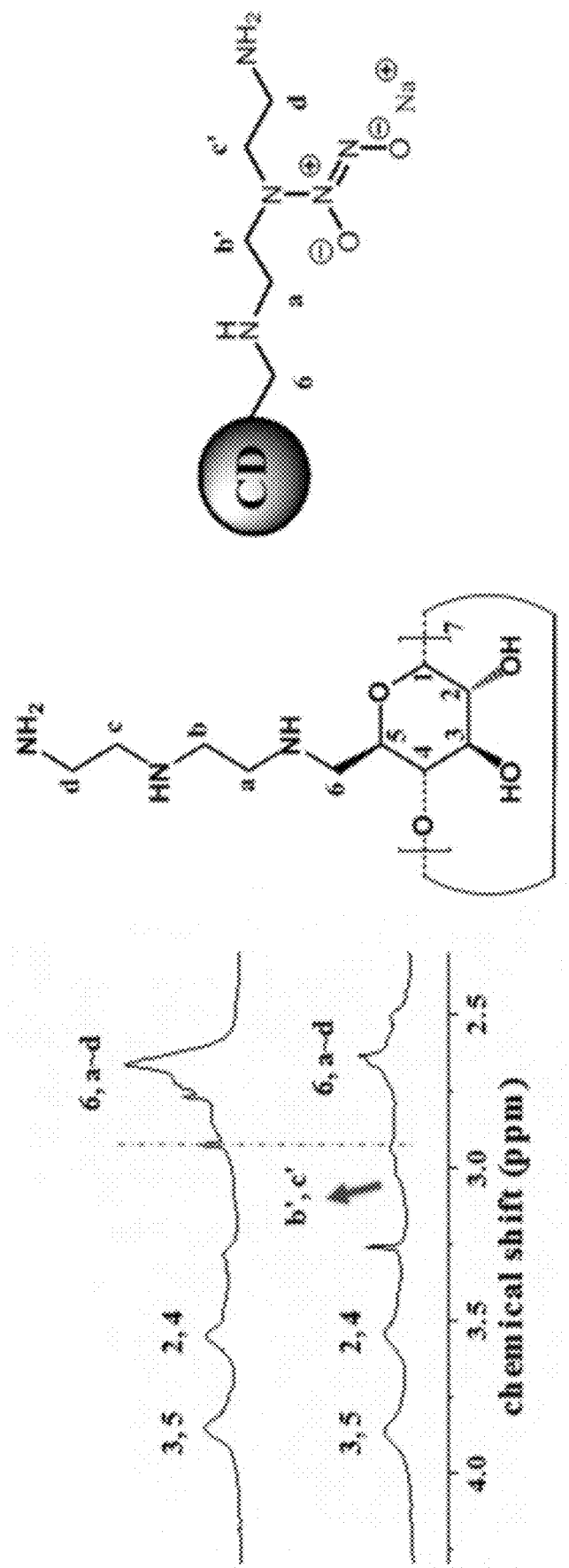
FIG. 7 shows characterization data and the structure of a non-limiting embodiment of a CD derivative. (Left) NMR spectra of CD-DETA7 (top line) and CD-DETA7/NO (bottom line); (Middle) Molecular structure of CD-DETA7; ($R_1$ ght) Molecular structure of CD-DETA7/NO. Newly-appeared peaks of b' and c' assigned to the methylene groups adjacent to N-diazeniumdiolates demonstrated the successful synthesis of CD-DETA7/NO. The high chemical shift of these methylene groups was due to the hydrogen bonding between the terminal primary amine group and N-diazeniumdiolate.
Figure 8:
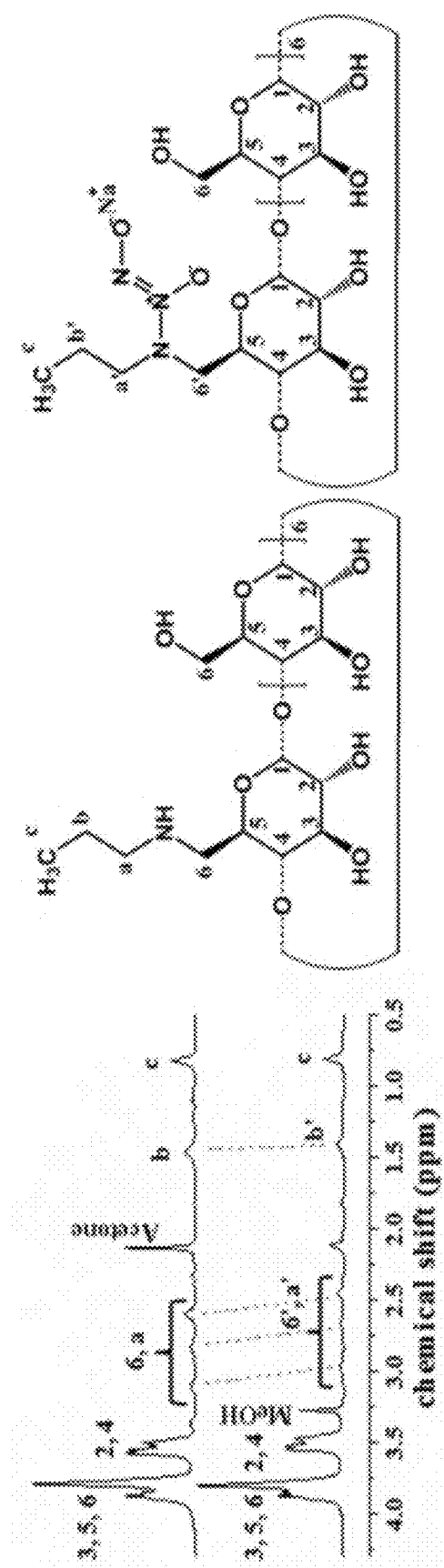
FIG. 8 shows characterization data and the structure of a non-limiting embodiment of a CD derivative. (Left) NMR spectra of CD-PA (top line) and CD-PA/NO (bottom line); (Middle) Molecular structure of CD-PA; ($R_1$ ght) Molecular structure of CD-PA/NO. Down-shifted peaks of 6', a' and b' assigned to the methylene groups around the N-diazeniumdiolate demonstrated the successful synthesis of CD-PA/NO. Since the terminal groups are methyl groups, they could not form the hydrogen bonding with the N-diazeniumdiolates, leading to down-shifted peaks.
Figure 9:
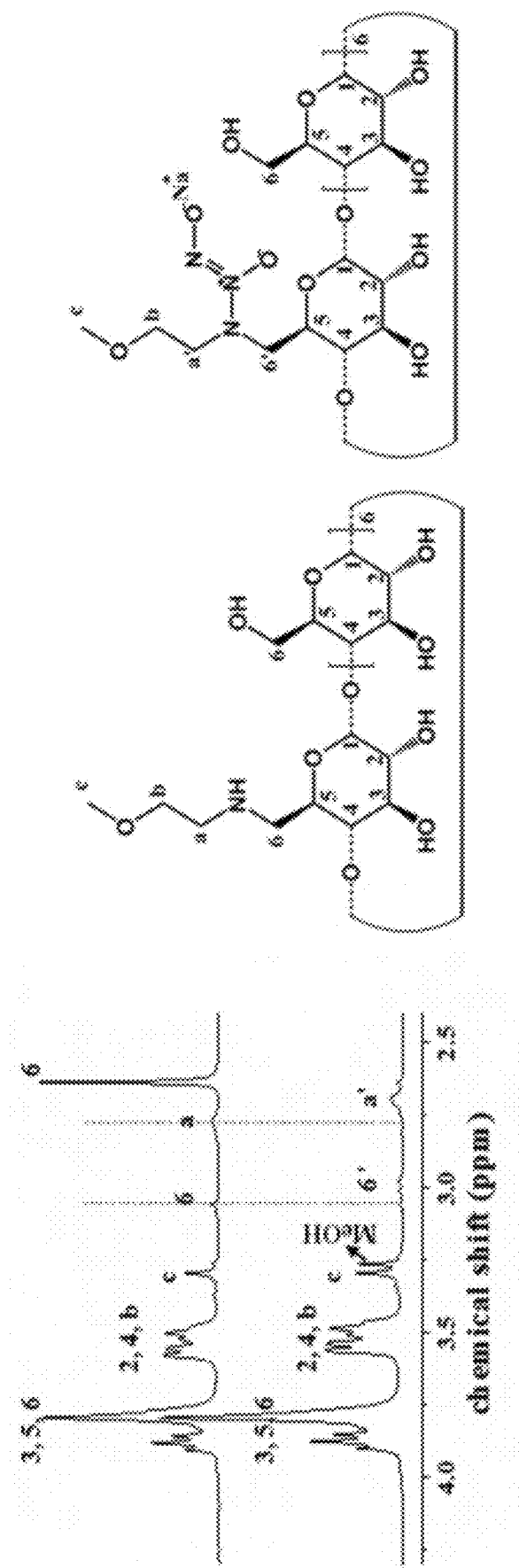
FIG. 9 shows characterization data and the structure of a non-limiting embodiment of a CD derivative. (Left) NMR spectra of CD-MA (top line) and CD-MA/NO (bottom line); (Middle) Molecular structure of CD-MA; ($R_1$ ght) Molecular structure of CD-MA/NO. Down-shifted peaks of 6' and a' assigned to the methylene groups around the N-diazeniumdiolate demonstrated the successful synthesis of CD-MA/NO. Since the terminal groups are hydroxymethyl groups, they could not form the hydrogen bonding with the N-diazeniumdiolates, leading to down-shifted peaks.
Figure 10:
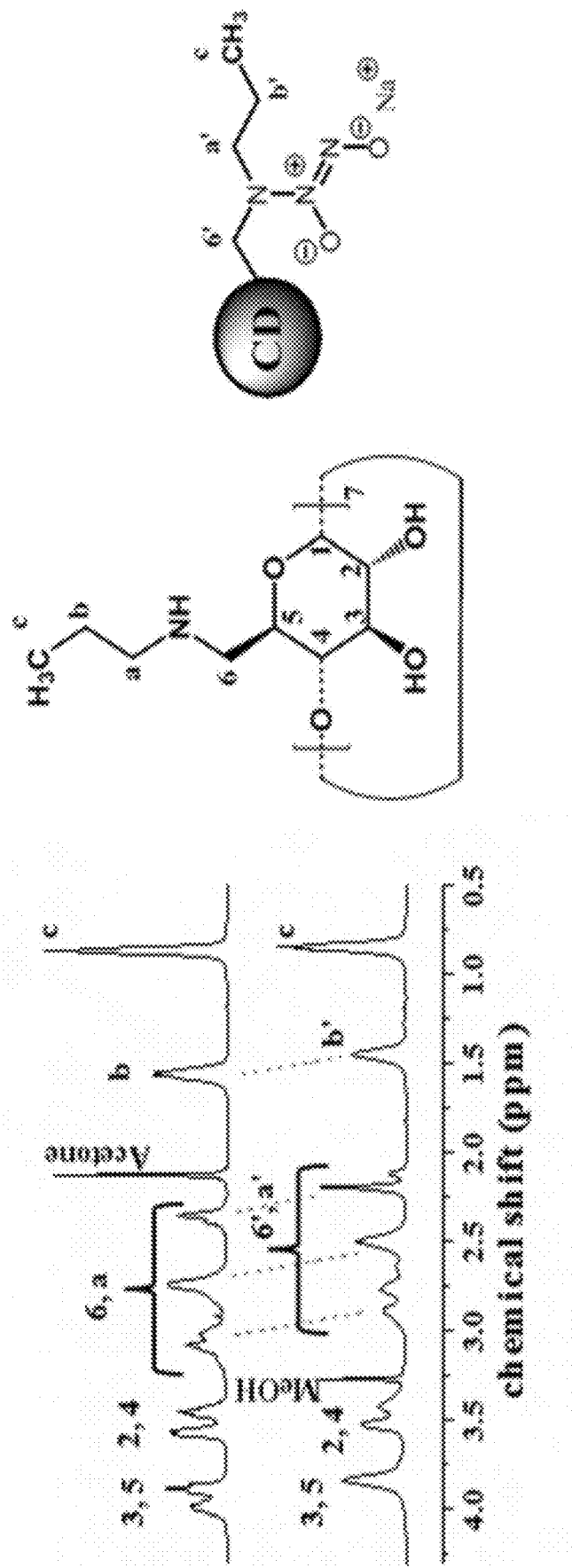
FIG. 10 shows characterization data and the structure of a non-limiting embodiment of a CD derivative. (Left) NMR spectra of CD-PA7 (top line) and CD-PA7/NO (bottom line); (Middle) Molecular structure of CD-PA7; ($R_1$ ght) Molecular structure of CD-PA7/NO. Down-shifted peaks of 6', a' and b' assigned to the methylene groups around the N-diazeniumdiolate demonstrated the successful synthesis of CD-PA7/NO. Since the terminal groups are methyl groups, they could not form the hydrogen bonding with the N-diazeniumdiolates, leading to down-shifted peaks.
Figure 11:
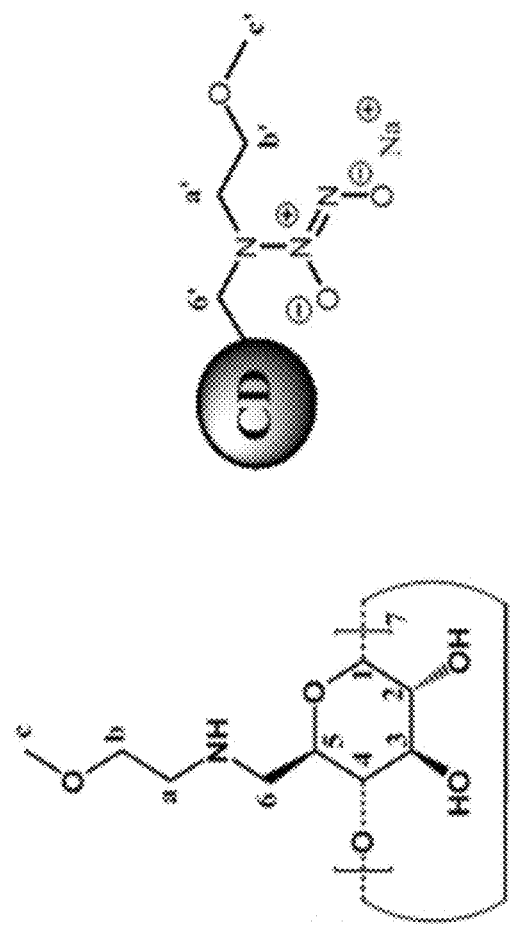
FIG. 11 shows characterization data and the structure of a non-limiting embodiment of a CD derivative. (Left) NMR spectra of CD-MA7 (top line) and CD-MA7/NO (bottom line); (Middle) Molecular structure of CD-MA7; ($R_1$ ght) Molecular structure of CD-MA7/NO. Down-shifted peaks of 6' and a' assigned to the methylene groups around the N-diazeniumdiolate demonstrated the successful synthesis of CD-MA7/NO. Since the terminal groups are hydroxymethyl groups, they could not form the hydrogen bonding with the N-diazeniumdiolates, leading to down-shifted peaks.
Figure 11:
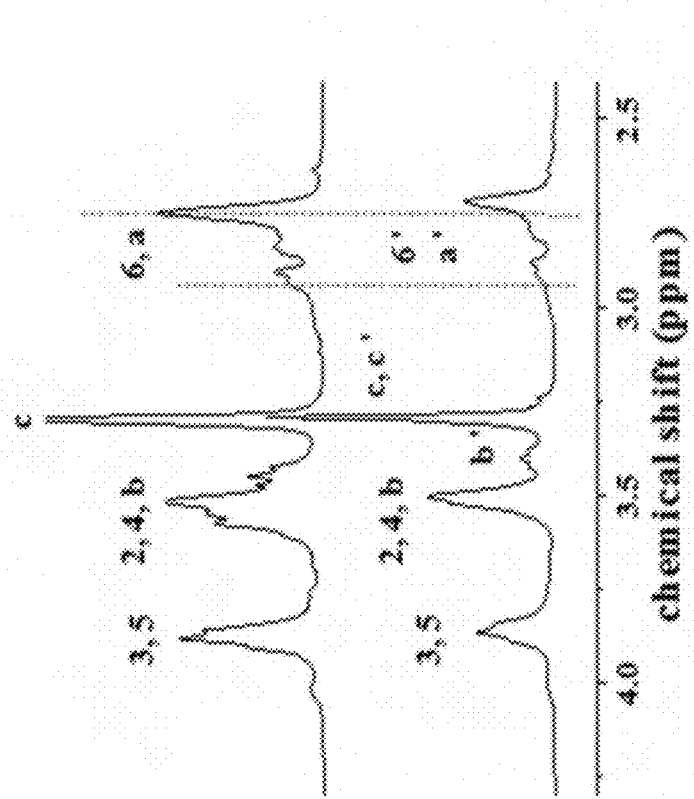
Figure 12A:
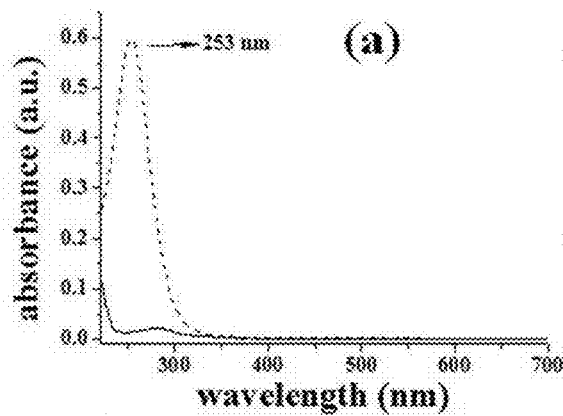
FIGS. 12(a)-(e) show UV-Vis spectra of mono-substituted NO-releasing CD derivatives, which were measured in 0.1 M NaOH at a concentration of 0.05 mg/mL.
Figure 12B:
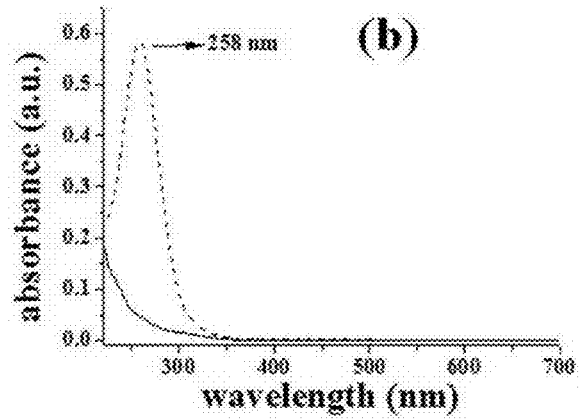
Figure 12C:
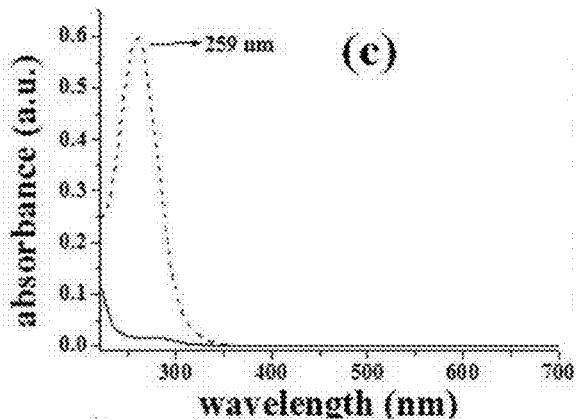
Figure 12D:
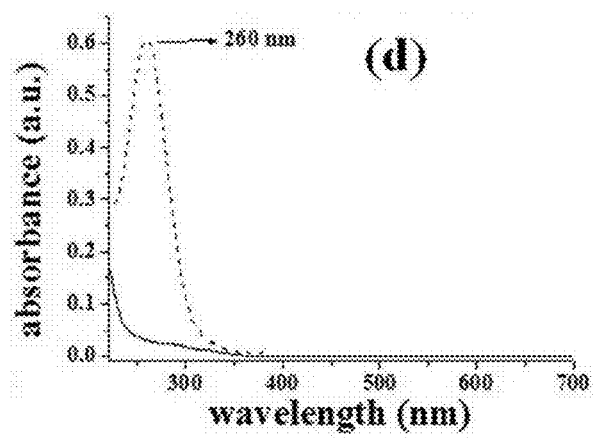
Figure 12E:
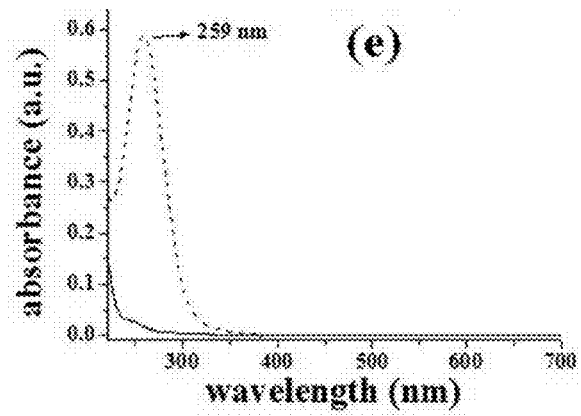
Figure 13A:
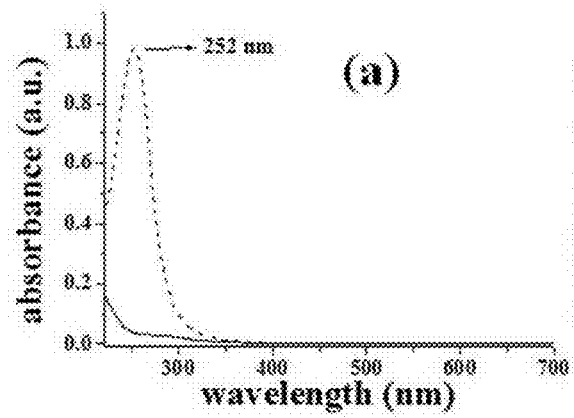
FIGS. 13(a)-(e) show UV-Vis spectra of hepta-substituted NO-releasing CD derivatives, which were measured in 0.1 M NaOH.
Figure 13B:
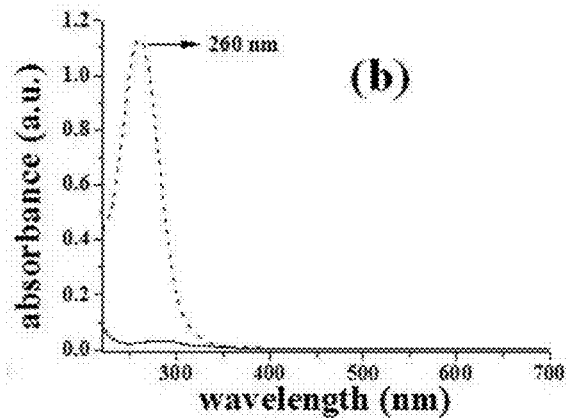
Figure 13C:
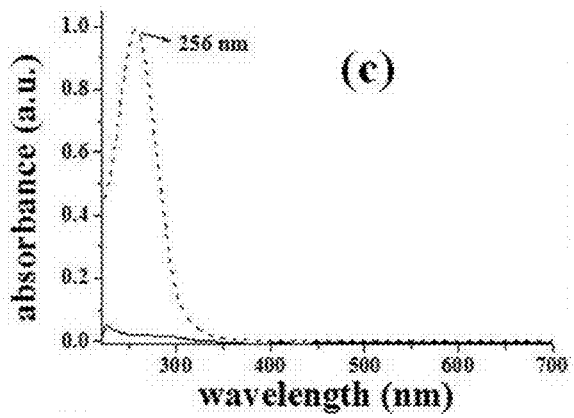
Figure 13D:
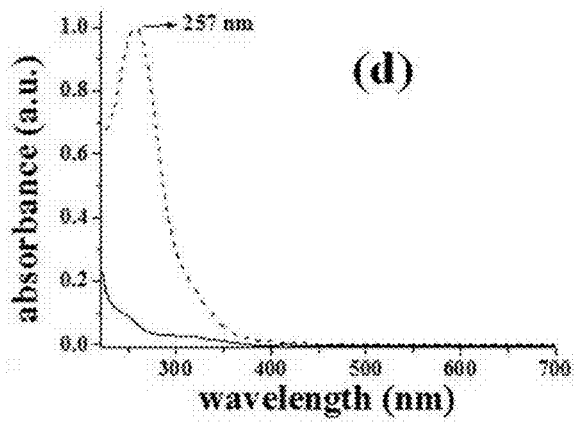
Figure 13E:
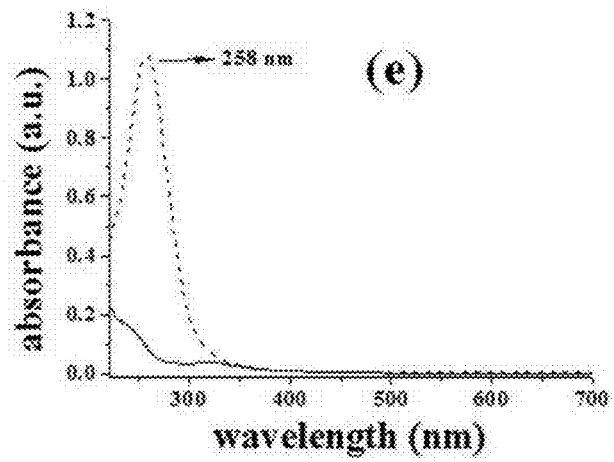

The representative synthesis and sequent characterization of CD-HEDA7/NO were shown in FIG. 2a. 1H NMR provided primary evidence for the successful introduction of N-diazeniumdiolates in CD-HEDA7 backbone (FIG. 2b). Of note, only one —NH— group may be sufficiently facile to react with NO, resulting from steric hindrance (FIG. 2a). Proton NMR indicated evidence for N-diazeniumdiolate NO donor-modification on the CD-HEDA7 backbone (FIG. 2b). Through diazeniumdiolation, the proton signals in the range of 2.72~3.05 ppm corresponding to methylene groups bound to secondary amines are shifted to downfield (2.90~3.11 ppm), owing to formation of hydrogen bonds between the terminal hydroxyl groups and N-diazeniumdiolate groups. Similar downfield shifts were also observed in the 1H NMR spectra of other hydroxyl- or primary amine-terminated CD-NONOates, such as CD-HEDA/NO, CD-EDA/NO, CD-DETA/NO, CD-EDA7/NO and CD-DETA7/NO (FIGS. 3-7). Of note, in the 1H NMR spectra of methyl- or hydroxymethyl-terminated CD-NONOates (CD-MA/NO, CD-MA7/NP, CD-PA/NO and CD-PA7/NO), it was found that chemical shifts of methylene groups around the N-diazeniumdiolates were moved to upfield after the formation of N-diazeniumdiolates (FIGS. 8-11). This may have been attributed to the absence of formation of hydrogen bonds. UV-Vis spectra provided further evidence for the formation of CD-NONOates. FIG. 1c depicts the UV-Vis spectra of CD-HEDA7 and CD-HEDA7/NO. A strong absorption peak (around ~252 nm) typically assigned to the N-diazeniumdiolate structure appeared in the UV-Vis spectrum, indicating the formation of CD-HEDA7/NO. The same strong absorption peaks (around ~255 nm) were also observed in all other CD-NONOates (FIGS. 12 and 13). Additionally, the broad absorption peak around 330~360 nm assigned to carcinogenic N-nitrosamine species was not detected, suggesting that these CD derivatives did not form N-nitrosamines during the N-diazeniudiolation synthesis. During the N-diazeniumdiolation step, in several embodiments, NO first reacts with a secondary amine to yield a nitrosamine radical anion intermediate; subsequently, this intermediate reacts with another molecule of NO to form the N-diazeniumdiolate. High pressures (e.g., about 10 bar or more) of NO drive the reaction to the desired N-diazeniumdiolate product.

1.4 Characterization of NO Storage and Release

The real-time NO release was monitored by using a Sievers NOA 280i chemiluminescence NO analyzer (NOA, Boulder, Colo.). Prior to analysis, the NO analyzer was calibrated with air passed through a NO zero filter (0 ppm of NO) and 25.87 ppm of standard NO gas. In a typical measurement, 1 mg of N-diazeniumdiolate-modified CD derivatives were added into a sample vessel with 30 mL of deoxygenated PBS (pH 7.4, 37° C.) to initiate NO release. The vessel was purged with nitrogen at a flow rate of 80 mL/min to carry the liberated NO gas to the NOA analyzer. Additional nitrogen flow was supplied to the vessel to match the collection rate of instrument (200 mL/min). NO analysis was terminated when NO level was reduced to below 10 ppb NO/mg CD derivatives. Chemiluminescence data for the NO-releasing CD derivatives were listed as follows: 1) total amount of NO storage (t[NO], mol NO/mg of secondary amine-functionalized CD derivatives); 2) the half-life of NO release ($t_{1/2}$, hour); 3) the maximum flux of NO release ([NO]max, ppb/mg of secondary amine-functionalized CD derivatives); 4) amount of NO released over 4 hours ($t_{4h}$ [NO], mol NO/mg of secondary amine-functionalized CD derivatives), 5) conversion efficiency of secondary amine to N-diazeniumdiolate (%).

Figure 14A:
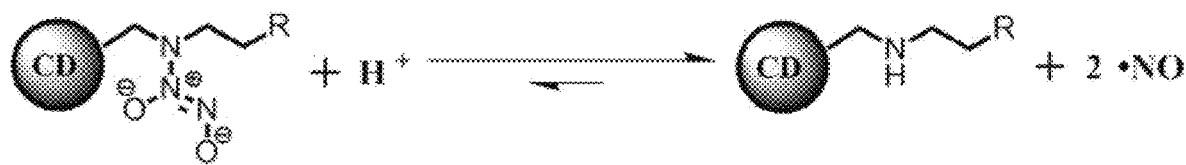
FIGS. 14(a)-(c) depicts characterization of the dissociation of NO-releasing CD derivatives.
Figure 14B:
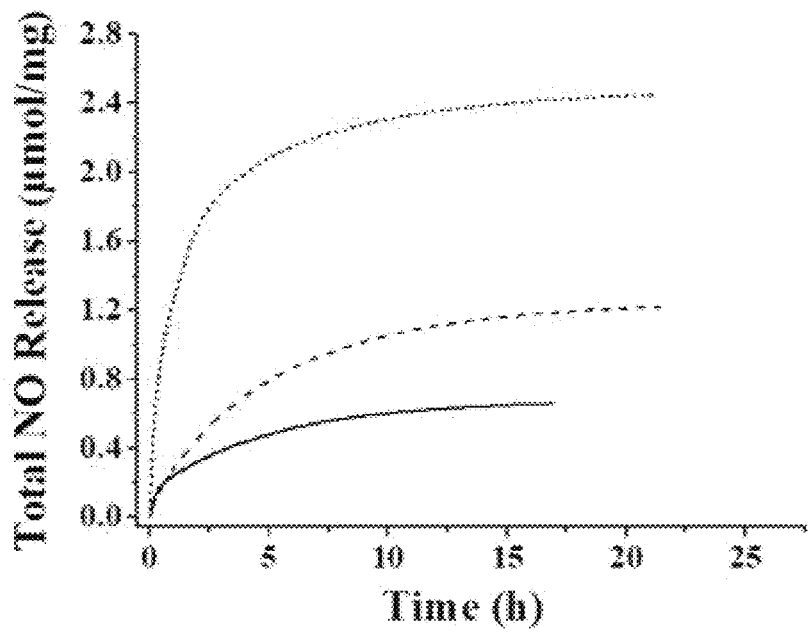
Figure 14:
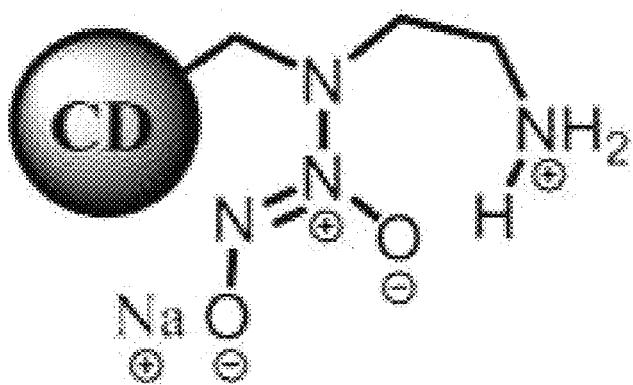

N-diazeniumdiolates NO scaffolds are pH-triggered NO-release donors. FIG. 14a displays the dissociation of N-diazeniumdiolate-functionalized CD derivatives. Reacting with proton in the physiological condition (e.g., 37° C., pH 7.4), 1 mole of N-diazeniumdiolate regenerates 1 mole of the parent secondary amine compounds and two moles of NO radicals. The real-time detection of NO was performed by using a chemiluminescence-based nitric oxide analyzer (NOA). The total NO storage and dissociation kinetics of water-soluble CD-NONOates were measured in physiological condition (pH 7.40, 37° C.). As shown in FIG. 14a, the degradation of the N-diazeniumdiolate upon protonation yields two moles of NO and the parent secondary amine. In several embodiments, degradation is pH-dependent, and results in more rapid release at lower pH. The resulting NO-release parameters (e.g., total NO storage, half-life of NO release, maximum flux, and conversion efficiency) are provided in Table 1. In Table 1 (Nitric oxide-releasing properties for CD-NONOates in PBS (pH 7.4) at 37° C.), (a)-(c) are as follows: (a) The molecular structure segment of N-diazeniumdiolate in the backbone; (b) NO payload; (c) NO released over 4 h (mol) per milligram of N-diazeniumdiolate-modified CD derivatives. Each parameter was analyzed in replicate (n≥3); (c) The theoretical maximum NO payloads were obtained by assuming that 1 mole secondary amine forms two moles of NO. Conversion efficiency was calculated by dividing the NOA data by the theoretical maximum NO payloads. Representative real-time NO release profiles of N-diazeniumdiolates CD derivatives are shown in FIGS. 14b and 15. In general, CD derivatives exhibited high and tunable NO storage capabilities (e.g., total NO storage from ~0.6 µmol/mg to ~2.4 µmol/mg) and adjustable NO-release kinetics (e.g., NO-release half-lives spanning about 0.7 h to about 4.2 h), by controlling the amount of secondary amines and exterior chemical modifications. In some embodiments, these characteristics can be further tuned to yield, for example total NO storage ranging from about 1.0 µmol/mg to about 5.0 µmol/mg, including about 1.5 µmol/mg, about 2.0 µmol/mg, about 2.5 µmol/mg, about 3.0 µmol/mg, about 3.5 µmol/mg, about 4.0 µmol/mg, about 4.5 µmol/mg, or about 5.0 mol/mg, including any amount of NO storage between those listed values. Additionally, in several embodiments the NO-release half-life can be tuned to about 2 hours to about 8 hours, including about 2.5 hours, about 3 hours, about 3.5 hours, about 4 hours, about 4.5 hours, about 5 hours, about 6 hours, about 7 hours, or about 8 hours, or any time between those listed. Further calculation reveals that conversion efficiencies of secondary amines in CD derivatives to N-diazeniumdiolates varied from 12% to 41%. Without being restricted to any particular mechanism, the high conversion efficiency may be attributed to the distance between the NO donor precursors (e.g., secondary amines) and the oligosaccharide ring, leading to less sterically hindered formation of N-diazeniumdiolates. Lower efficiencies may have been due to proximity to the CD saccharide backbone.

Figure 15A:
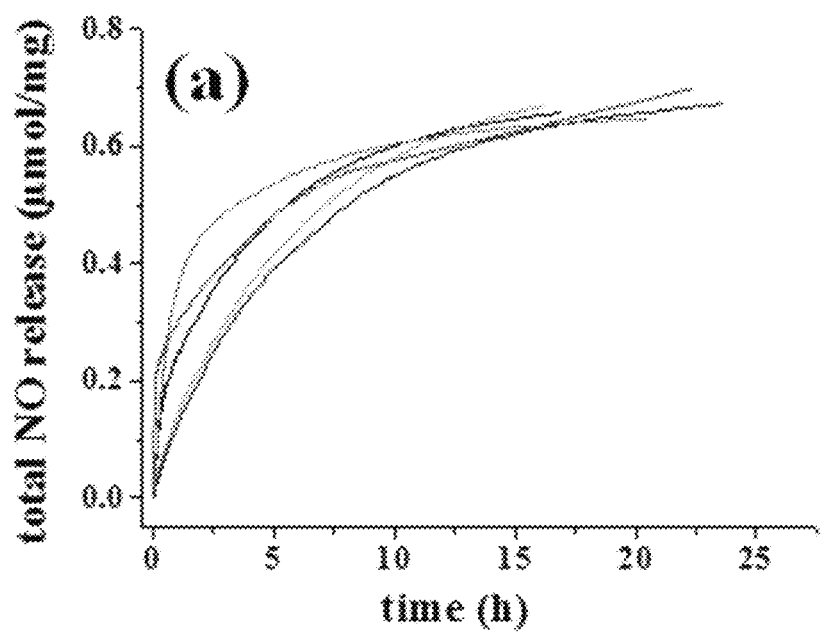
FIGS. 15(a)-(b) depict real time NO release measured by a chemiluminescence-based nitric oxide analyzer.
Figure 15B:
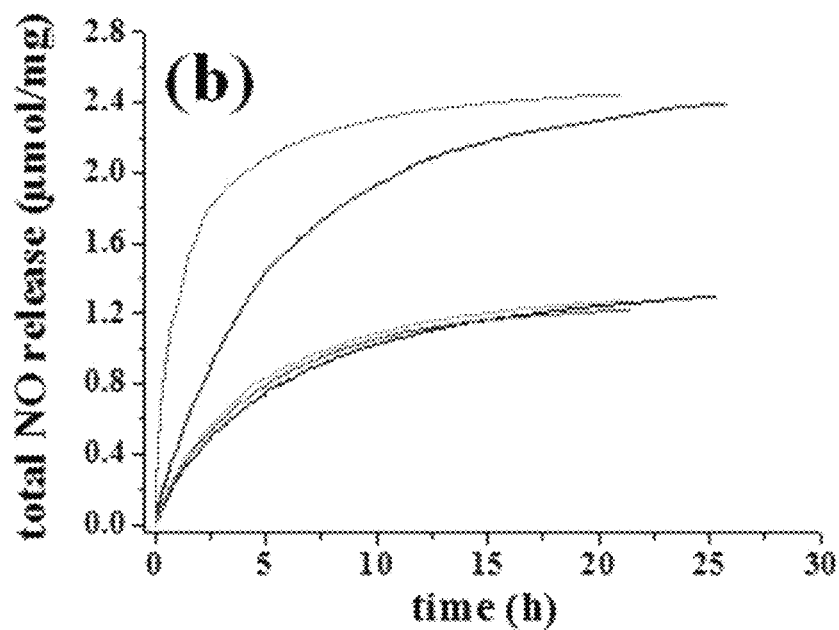
Figure 16A:
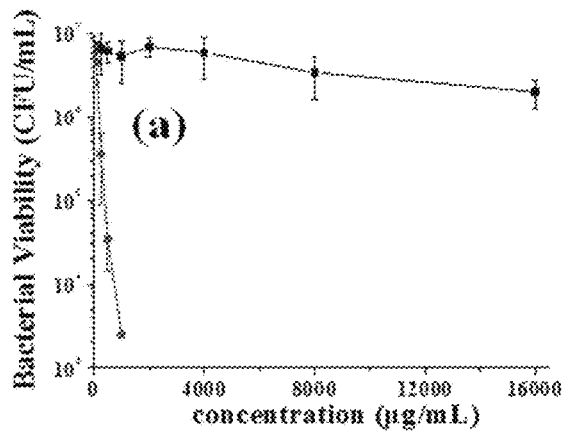
FIGS. 16(a)-(e) depict bactericidal efficacy of mono-substituted NO-releasing CD derivatives against *P. aeruginosa* over 4 hours' incubation.
Figure 16B:
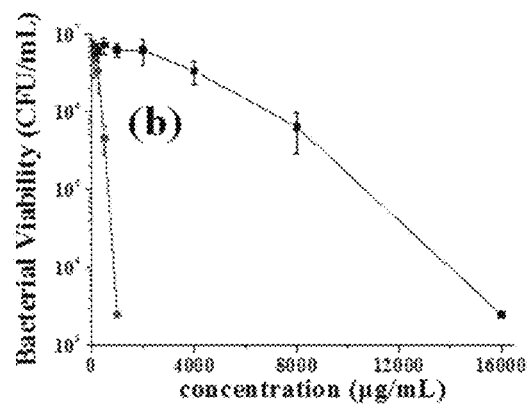
Figure 16C:
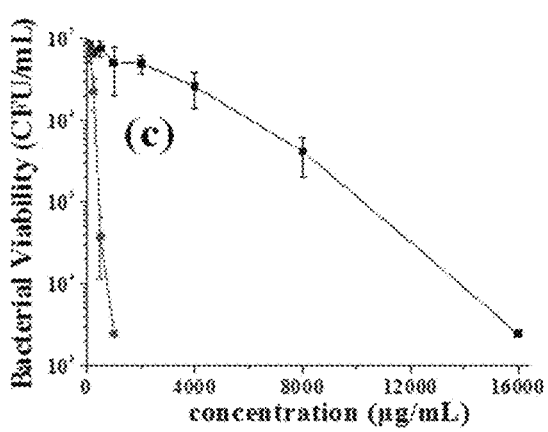
Figure 16D:
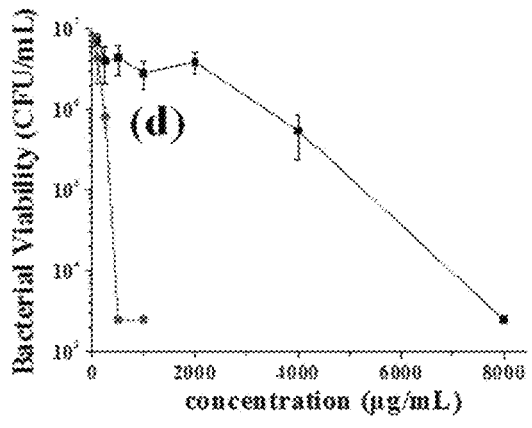
Figure 16E:
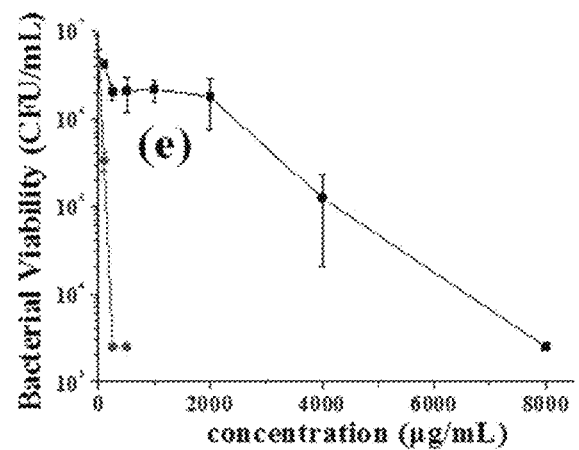

Further inspection was performed to discover the differences among the real-time NO releases of mono-substituted CD-NONOates (FIG. 15a). Total NO storage for all the mono-substituted CD-NONOates was found to be around ~0.6 µmol/mg. The NO-release kinetics of these CD-NONOates could be varied depending on the identity of the polyamine NO donor precursor. The NO release kinetics of these CD-NONOates can be adjusted by exterior chemical modifications (including adding additional NO binding moieties to each CD molecule), according to several embodiments. The half-lives of NO release for CD-HEDA/NO, CD-MA/NO and CD-PA/NO were 0.71 h, 1.46 h and 1.73 h, respectively. Such NO release kinetics are attributed to the diverse hydrophilicity of different functionalities (HEDA>MA>PA), facilitating water uptake quickly for the N-diazeniumdiolates decomposition. In some embodiments, N-diazeniumdiolates can be stabilized by the adjacent cationic ammonium groups, resulting in extended NO release (see, e.g., FIG. 14c). To demonstrate, EDA and DETA were selected to synthesize primary amine terminated CD derivatives (CD-EDA and CD-DETA) scaffolds. It was hypothesized that N-diazeniumdiolate NO donors can be stabilized by the cationic protonated amine groups as depicted in FIG. 14c, leading to extended NO release kinetics. It was found that, as according to several embodiments disclosed herein, primary amine-terminated CD-NONOates had long half-life times of 3.36 h (CD-EDA/NO) and 4.22 h (CD-DETA/NO). Thus, in several embodiments, where long half-lives are desired, stabilized CD-NONOates can be employed and where short half-lives are required, non-stabilized structures (e.g., those without primary amine terminations) can be employed. Both primary amine-terminated CD-NONOates led to significantly longer NO release (3.36 and 4.22 h NO-release half-lives for

TABLE 1

Nitric oxide-releasing properties for CD-NONOates in PBS (pH 7.4) at 37° C.

| Scaffold | Molecular Structure[a] | t[NO][b] µmol/mg | $t_{1/2}$ (h) | $t_{4h}$[NO][e] µmol/mg | Conv. Efficiency[d] (%) |
|---|---|---|---|---|---|
| CD-HEDA/NO | [structure] | 0.60 ± 0.05 | 0.71 ± 0.05 | 0.48 ± 0.03 | 36 ± 2 |
| CD-MA/NO | [structure] | 0.58 ± 0.04 | 1.46 ± 0.18 | 0.43 ± 0.03 | 35 ± 3 |
| CD-PA/NO | [structure] | 0.61 ± 0.05 | 1.73 ± 0.24 | 0.43 ± 0.04 | 36 ± 2 |
| CD-EDA/NO | [structure] | 0.57 ± 0.07 | 3.36 ± 0.33 | 0.32 ± 0.03 | 34 ± 4 |
| CD-DETA/NO | [structure] | 0.68 ± 0.07 | 4.22 ± 0.35 | 0.33 ± 0.04 | 41 ± 2 |

TABLE 1-continued

Nitric oxide-releasing properties for CD-NONOates in PBS (pH 7.4) at 37° C.

| Scaffold | Molecular Structure[a] | t[NO][b] μmol/mg | $t_{1/2}$ (h) | $t_{4h}$[NO][c] μmol/mg | Conv. Efficiency[d] (%) |
|---|---|---|---|---|---|
| CD-HEDA7/NO | -N(H)-CH₂CH₂-N(N₂O₂Na)-CH₂CH₂-OH | 2.44 ± 0.19 | 0.88 ± 0.06 | 1.99 ± 0.19 | 15 ± 1 |
| CD-MA7/NO | -N(N₂O₂Na)-CH₂CH₂-OCH₃ | 1.13 ± 0.15 | 3.15 ± 0.41 | 0.65 ± 0.05 | 12 ± 1 |
| CD-PA7/NO | -N(N₂O₂Na)-CH₂CH₂-CH₃ | 1.26 ± 0.05 | 3.79 ± 0.33 | 0.66 ± 0.06 | 13 ± 2 |
| CD-EDA7/NO | -N(N₂O₂Na)-CH₂CH₂-NH₂ | 1.24 ± 0.06 | 3.20 ± 0.30 | 0.64 ± 0.08 | 13 ± 1 |
| CD-DETA7/NO | -N(H)-CH₂CH₂-N(N₂O₂Na)-CH₂CH₂-NH₂ | 2.39 ± 0.19 | 3.39 ± 0.31 | 1.15 ± 0.12 | 15 ± 1 |

(a) Total NO storage;
(b) NO released over 4 h (μmol) per milligram of N-diazeniumdiolates CD derivatives. Each parameter was analyzed with multiple replicates (n ≥ 3).

CD-EDA/NO and CD-DETA/NO, respectively), relative to the alkyl substituted systems.

Whether CD derivatives with higher percentage of secondary amines increase NO storage was tested. In the design for this study, hepta-substituted CD derivatives were synthesized and used as new NO donor scaffolds, increasing the amount of secondary amines seven-fold compared to mono-substituted CD derivatives. Their representative real-time NO-release profiles were shown in FIG. 15b. It was found that, hepta-CD derivatives exhibited higher NO storage capabilities (Table 1). Their total NO storages for hepta-substituted CD-R7/NO (R=MA, PA, and EDA) are ~1.13 μmol/mg, ~1.26 μmol/mg, and ~1.24 μmol/mg, respectively, increasing by almost two times than that of mono-substituted CD-NONOates. In particular, CDs with seven longer molecular chains (e.g., DETA and HEDA) exhibited four times increase in NO storage, owing to the lessened steric hindrance. Although the percentage of secondary amine increased seven-fold, the increase of total NO storage was less than seven times, owing to the steric hindrance and repulsion interaction among negatively-charged N-diazeniumdiolates. Nevertheless, these biopolymers represent a notable advancement in NO loading on a sugar-like biopolymer that are, according to embodiments disclosed herein, amenable for delivering therapeutic levels of NO in a water-soluble and non-toxic form.

Example 3

1.5 Bactericidal Assays Against Planktonic *P. aeruginosa*

Nitric oxide may be an efficient antibacterial agent. The antibacterial activity of the NO-releasing CD derivatives was evaluated against Gram-negative *P. aeruginosa*, a model pathogen associated with serious medical infections (e.g., traumatic burns, cystic fibrosis). *Pseudomonas aeruginosa* is a Gram-negative pathogen. Bacterial viability assays were performed under static conditions. Minimum bactericidal concentrations over 4 hours exposure (MBC4h) were used to quantify their bactericidal activity, being required to eliminate bacteria viability by 3 logs (e.g., 99.9% killing). The total NO amount delivered by NO-releasing CD derivatives over this period was also calculated to quantitatively evaluate the required NO dose to achieve bactericidal activity.

1.6 Confocal Laser Scanning Microscope

*P. aeruginosa* was grown as in the above-mentioned methods and diluted to $10^7$ CFU/mL in sterile PBS containing 10 μM of DAF-2 DA and 30 μM of PI. Aliquots of bacteria solution (3 mL) were incubated in a glass bottom confocal dish for 45 minutes at 37° C. A Zeiss 510 Meta inverted confocal laser scanning microscope (Carl Zeiss, Thornwood, N.Y.) with a 488 nm Ar excitation laser (30.0 mW, 2.0% intensity) and a BP 505-530 nm filter was used to record DAF-2 (green) fluorescence images. A 543 nm HeNe excitation laser (1.0 mW, 25.0% intensity) with a BP 560-615 nm filter was used to obtain PI (red) fluorescence images. Both bright field and fluorescence images were collected using an N.A. 1.2 Capochromat water immersion lens with a 40× objective. Either CD-PA/NO or CD-EDA/NO was added into the bacteria solution to achieve a final concentration of 300 μg/mL. Images were collected every 15 minutes to temporally observe intracellular NO concentrations and bacterial cell death.

1.7 In-Vitro Cytotoxicity

L929 mouse fibroblasts were cultured in DMEM supplemented with 10% v/v fetal bovine serum (FBS) and 1 wt % penicillin/streptomycin, and incubated in 5% v/v $CO_2$ under humidified conditions at 37° C. After reaching confluency (80%), the cells were trypsinized, seeded onto tissue-culture treated polystyrene 96-well plates at a density of $1\times10^4$ cells/mL, and incubated at 37° C. for 24 hours. The supernatant was then aspirated and replaced with 100 μL of fresh growth medium containing various concentrations of both unmodified control and NO-releasing CD derivatives to each well. After incubation at 37° C. for 4 hours, the supernatant was aspirated and 100 μL of a mixture of DMEM/MTS/PMS (105/20/1, v/v/v) was added to each well. The absorbance of the resulting colored solutions over 3 hours incubation was quantified by using a ThermoScientific Multiskan EX plate reader (Waltham, Mass.) at 490 nm. The mixture of DMEM/MTS/PMS and untreated cells were used as a blank and control, respectively. Cell viability was calculated according to the following formula:

$$\text{Cell viability}(\%) = \frac{\text{Absorbance}_{490} - \text{Absorbance}_{blank}}{\text{Absorbance}_{control} - \text{Absorbance}_{blank}} \times 100\%$$

Both MBC4h and required NO doses are provided in Table 2.

The TSA bacterial stock of *P. aeruginosa* colony was cultured in 3 mL of TSB overnight (around 16 hours) at 37° C. A 1000 μL aliquot of the resulting suspension was added into 15 mL of fresh TSB and incubated at 37° C. for another 2 hours, to achieve a concentration of $10^8$ colony forming units per mL (CFU/mL, confirmed by the OD600). The bacteria was collected by centrifugation, resuspended in sterile PBS, and diluted to $10^6$ CFU/mL. The antibacterial efficacy of both non-NO-releasing and NO-releasing CD derivatives against *P. aeruginosa* was evaluated under static condition over 4 hours at 37° C. Blanks (untreated cells) were incubated in each experiment to ensure the bacteria remained viable at $10^6$ CFU/mL over 4 hour assay. 100 μL aliquots of blank, control or NO-releasing CD derivatives treated bacteria suspensions were shifted, diluted 10-fold in sterile $H_2O$ and plated on TSA plates using an Eddy Jet spiral plater (IUL; Farmingdale, N.Y.), followed by incubation overnight at 37° C. Bacterial viability was evaluated via total colony count on the TSA plates by using a Flash & Go colony counter (IUL; Farmingdale, N.Y.). Minimum bactericidal concentrations (MBC4h) were designated as the minimum concentration of NO-releasing CD-derivatives over 4 hours exposure that resulted in a 3-log reduction of bacterial viability compared to the blank. Of note, the limit of detection for this selected plate counting method is $2.5\times10^3$ CFU/mL.

The antibacterial ability of both control and NO-releasing mono-substituted CD derivatives was first tested to evaluate the effects of terminal groups on the bactericidal process. At equivalent concentrations, control mono-substituted CD derivatives did not result in a notable reduction in bacterial viability (without NO donor), indicating NO works as an antibacterial agent (FIG. 16). The bactericidal NO dose listed in Table 2 revealed that primary amine-terminated CD-NONOates required less NO dose to eliminate *P. aeruginosa*, compared to methyl-, hydroxyl-, or hydroxymethyl-terminated CD-NONOates. The methyl-, hydroxyl-, and methoxyl-terminated CD-NONOates took 2-4 times more NO to achieve similar action. It was hypothesized that the increased antibacterial capability of primary amine-terminated NO-releasing CD derivatives was ascribed to fast association between positively-charged primary amine groups and negatively-charged cellular membrane of *P. aeruginosa* and the resulting highly efficient NO delivery. In this regard, the bactericidal action of mono-substituted CD-NONOates, according to some embodiments, is related to the types of exterior modifications a particular CD has.

TABLE 2

Minimum bactericidal concentration (MBC) and NO doses of NO-releasing CD derivatives required for 3-log reduction in planktonic *P. aeruginosa* viability

| | *P. aeruginosa* | | | *P. aeruginosa* | |
| --- | --- | --- | --- | --- | --- |
| Mono-Substituted CD Derivatives | $MBC_{4h}$ (μg/mL) | NO dose (μmol/mL) | Hepta-Substituted CD Derivatives | $MBC_{4h}$ (μg/mL) | NO dose (μmol/mL) |
| CD-HEDA/NO | 1000 | 0.48 | CD-HEDA7/NO | 250 | 0.50 |
| CD-PA/NO | 1000 | 0.43 | CD-PA7/NO | 500 | 0.33 |
| CD-MA/NO | 1000 | 0.43 | CD-MA7/NO | 500 | 0.33 |
| CD-EDA/NO | 500 | 0.16 | CD-EDA7/NO | 250 | 0.16 |
| CD-DETA/NO | 250 | 0.08 | CD-DETA7/NO | 100 | 0.11 |

Figure 17A:
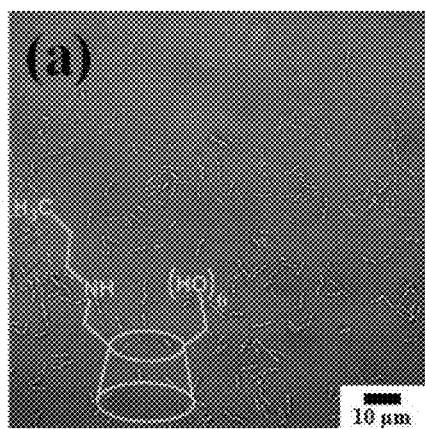
FIGS. 17(a)-(c) depict CLSM images of *P. aeruginosa* cells exposed to 300 μg/mL CD-PA/NO for 2 hours. DAF-2 green fluorescence indicated the intracellular NO delivery, while cellular membrane destruction (cell death) was indicated by the appearance of PI red fluorescence.
Figure 17B:
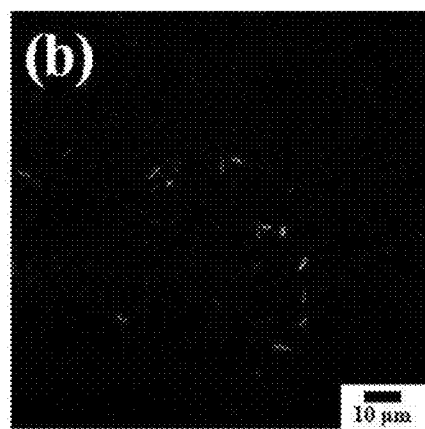
Figure 17C:
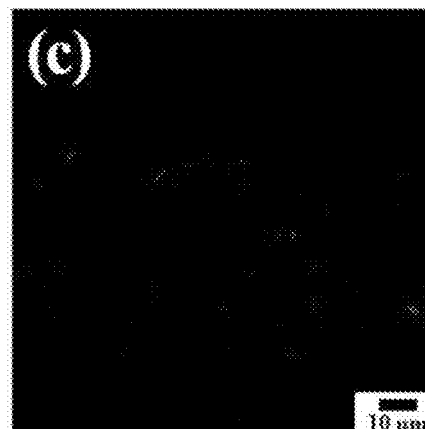
Figure 17D:
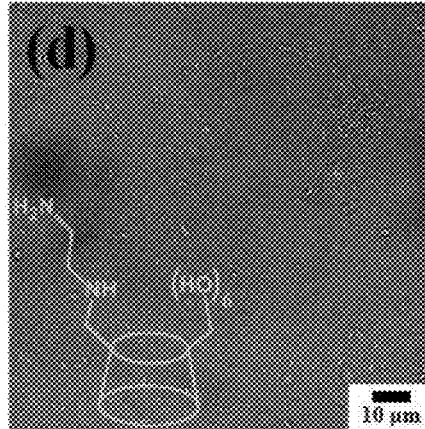
FIG. 17(d) Bright field.
Figure 17E:
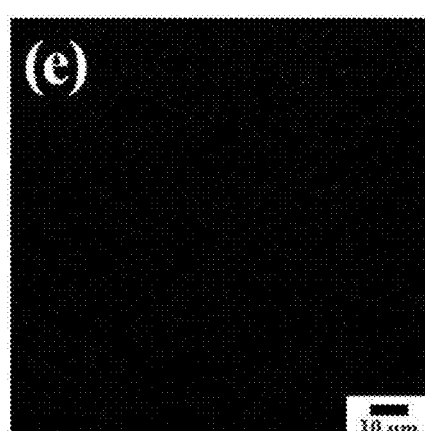
FIG. 17(e) DAF-2; (f) PI.
Figure 17F:
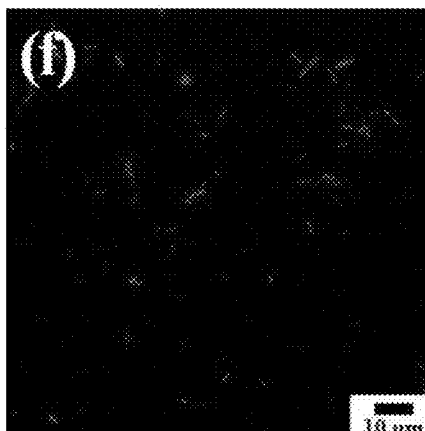
FIGS. 17(d-f) CLSM images of *P. aeruginosa* cells exposed to 300 μg/mL CD-EDA/NO.
Figure 18:
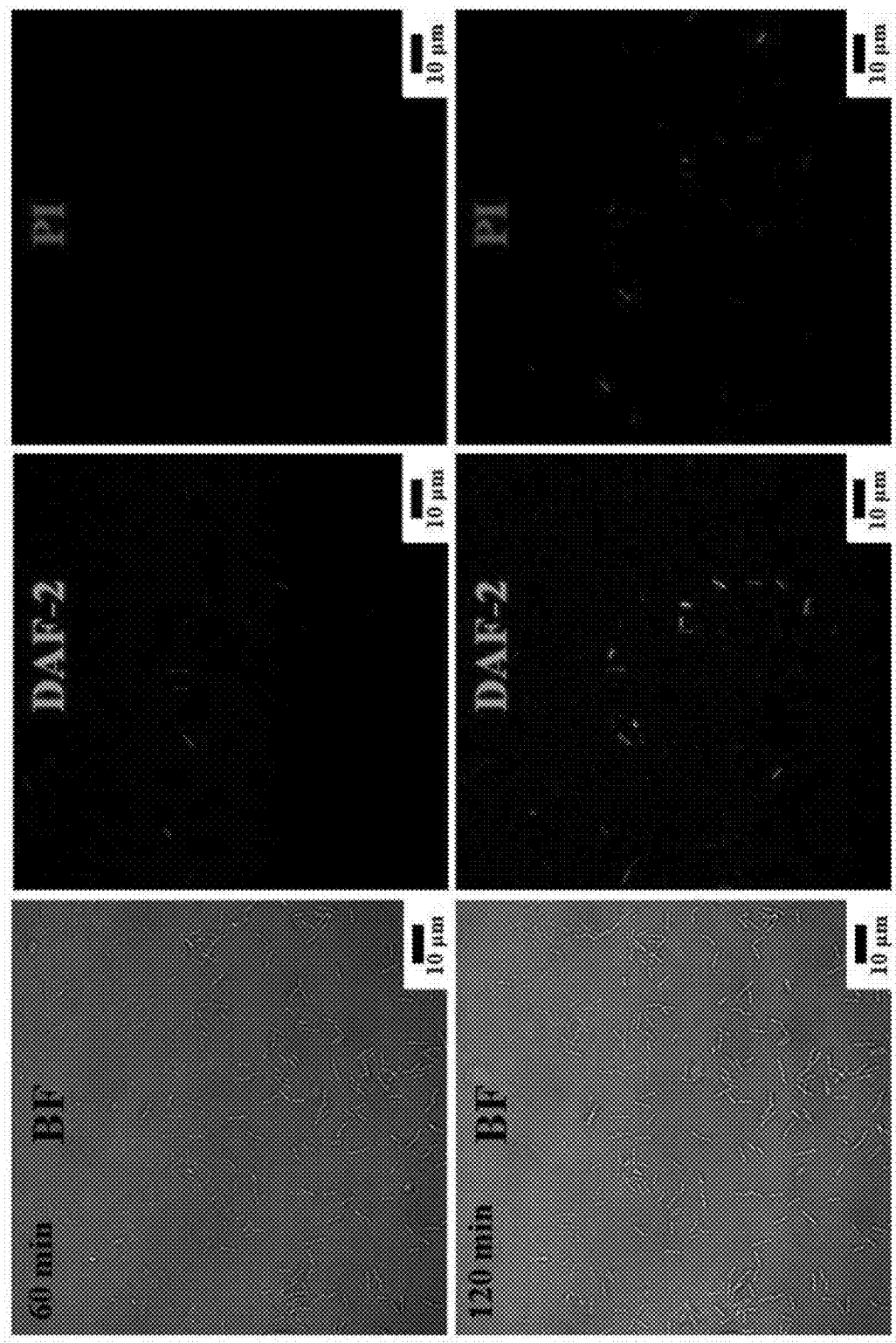
FIG. 18 depicts bright field, intracellular DAF-2 (green) and PI (red) fluorescence images of *P. aeruginosa* exposed to 300 μg/mL CD-PA/NO. DAF-2 green fluorescence indicates the appearance of NO in the cells, while PI red fluorescence indicates the cellular membrane destruction (cell death). The top images were taken at 60 minutes, and the bottom images were taken at 120 minutes.
Figure 19:
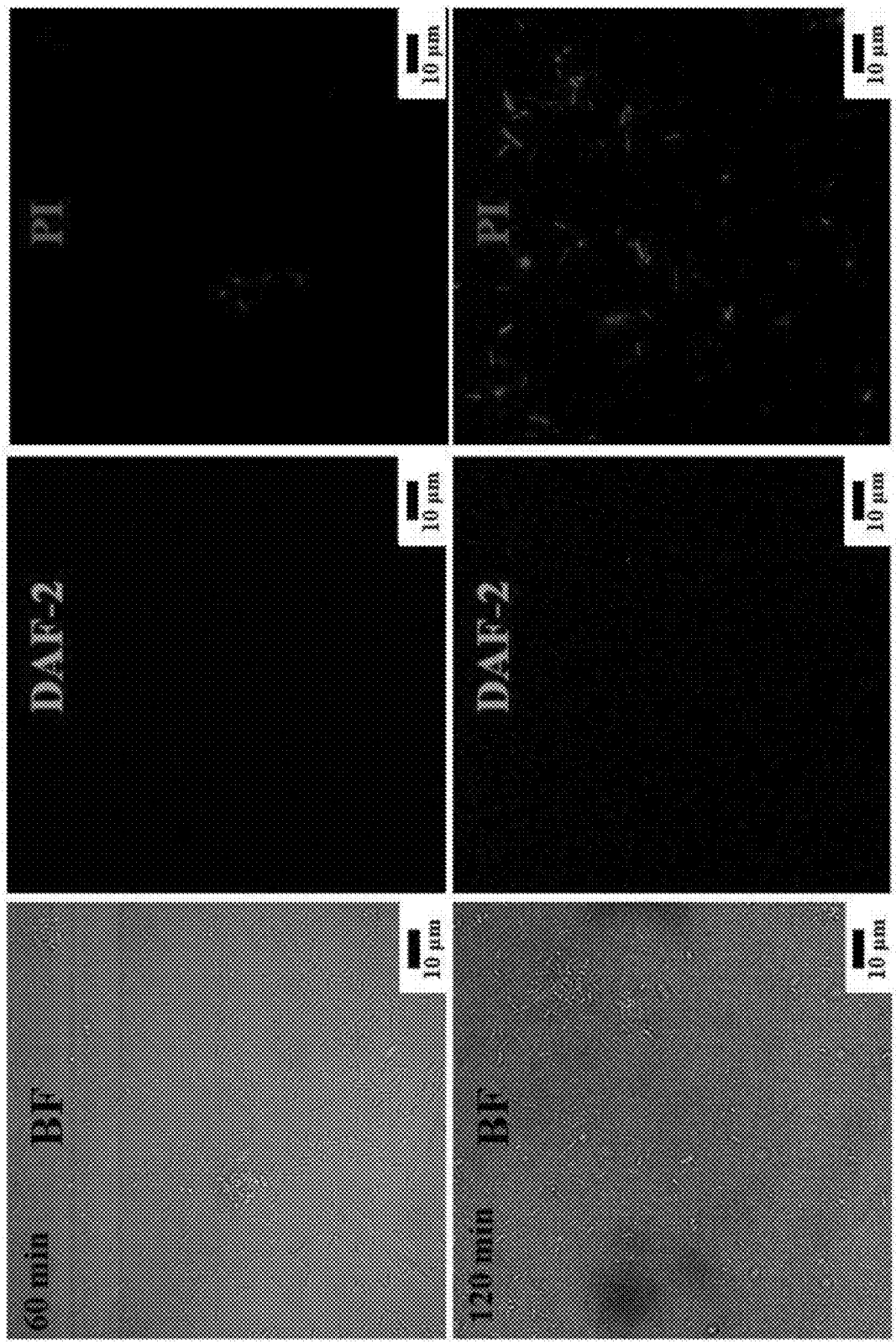
FIG. 19 depicts bright field, intracellular DAF-2 (green) and PI (red) fluorescence images of *P. aeruginosa* exposed to 300 μg/mL CD-EDA/NO. DAF-2 green fluorescence indicates the appearance of NO in the cells, while PI red fluorescence indicates the cellular membrane destruction (cell death). The top images were taken at 60 minutes, and the bottom images were taken at 120 minutes.
Figure 20A:
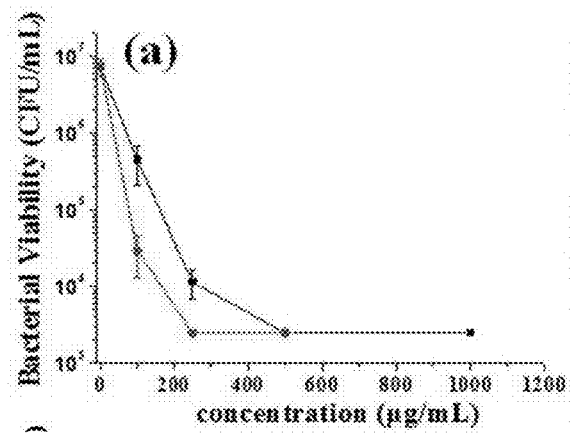
FIGS. 20(a)-(e) depict the bactericidal efficacy of hepta-substituted NO-releasing CD derivatives against *P. aeruginosa* over 4 hours' incubation.
Figure 20B:
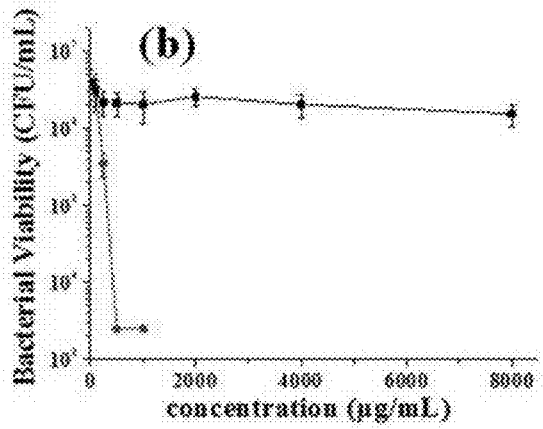
Figure 20C:
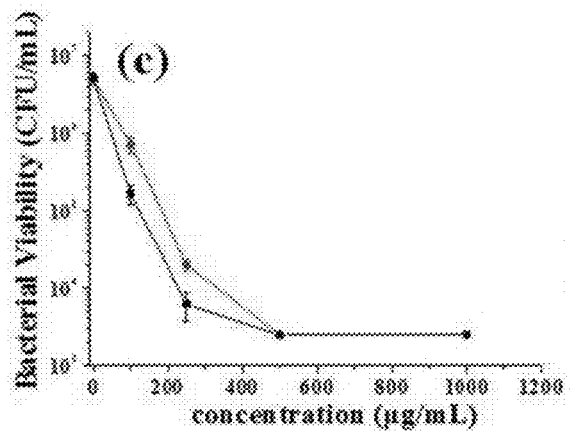
Figure 20D:
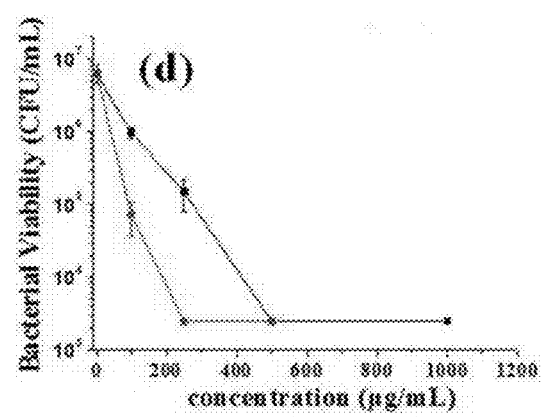
Figure 20E:
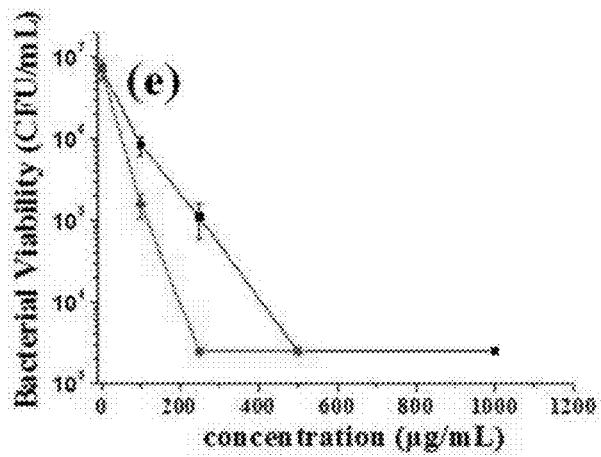

To further confirm the increased antibacterial activity of primary amine terminated mono-substituted CD-NONOates resulted from the fast interaction with bacteria membranes, confocal laser scanning microscopy (CLSM) was utilized to study the association activity of CD-EDA/NO and CD-PA/NO with *P. aeruginosa*. NO-responsive fluorescent probe 4,5-diaminofluorescein diacetate (DAF-2 DA) and nucleic acid-sensitive fluorescent dye propidium iodide (PI) were dispersed inside and outside *P. aeruginosa* cells, respectively. Prior to exposure to NO-releasing CD-NONOates, no autofluorescence was observed from either DAF-2 or PI. Upon exposure, progressively increased green DAF-2 fluorescence (FIGS. 17b and 18) was observed if *P. aeruginosa* loaded with DAF-2 was exposed to 300 μg/mL of CD-PA/NO, indicating CD-PA/NO permeated into the bacterial membranes and a high concentration of NO accumulated inside the bacterial membranes. Of note, green fluorescence was not observed when *P. aeruginosa* loaded with DAF-2 was exposed to 300 μg/mL of CD-EDA/NO (FIGS. 17e and 19). In this case, intracellular NO accumulation was no longer measurable owing to cellular membrane damage. Red PI fluorescence indicative of cell death was not observed in CD-PA/NO at 1 hour (FIG. 18), but observed in CD-EDA/NO (FIG. 19). Additionally, red PI fluorescence were both observed over 2 hours incubation (FIGS. 17c and 17f), with greater intensity in CD-EDA/NO. These data indicated that the cellular damage rate of CD-PA/NO is slower than that of CD-EDA/NO, indirectly manifesting that CD-EDA/NO exhibited a fast association with *P. aeruginosa*.

Table 2 also revealed that hepta-substituted CD-NONOates exhibited greater antibacterial capability than mono-substituted CD-NONOates with the same terminal functions, attributed to the increased NO storage. Although hepta-substituted CD-NONOates had lower MBCs, the NO doses required to kill *P. aeruginosa* were similar with that of mono-substituted CD-NONOates when overall mass of the biopolymer was taken into account. In addition, inspection of the bactericidal efficacy curves (FIG. 20) revealed that control hepta-substituted CDs with PA, HEDA, EDA and DETA possessed enhanced antibacterial ability compared with mono-substituted CDs. As in several embodiments, this is due to the increased percentages of modified alkyl- or amine groups in molecular backbones. The greater density of alkyl and/or amine functional groups may lead to faster membrane intercalation and cell membrane damage, respectively. These results may be similar to that observed with alkyl chains modified dendrimers or other primary amine-terminated antibacterial agents, attributing this effect to fast membrane interaction and cell membrane damage.

Figure 21A:
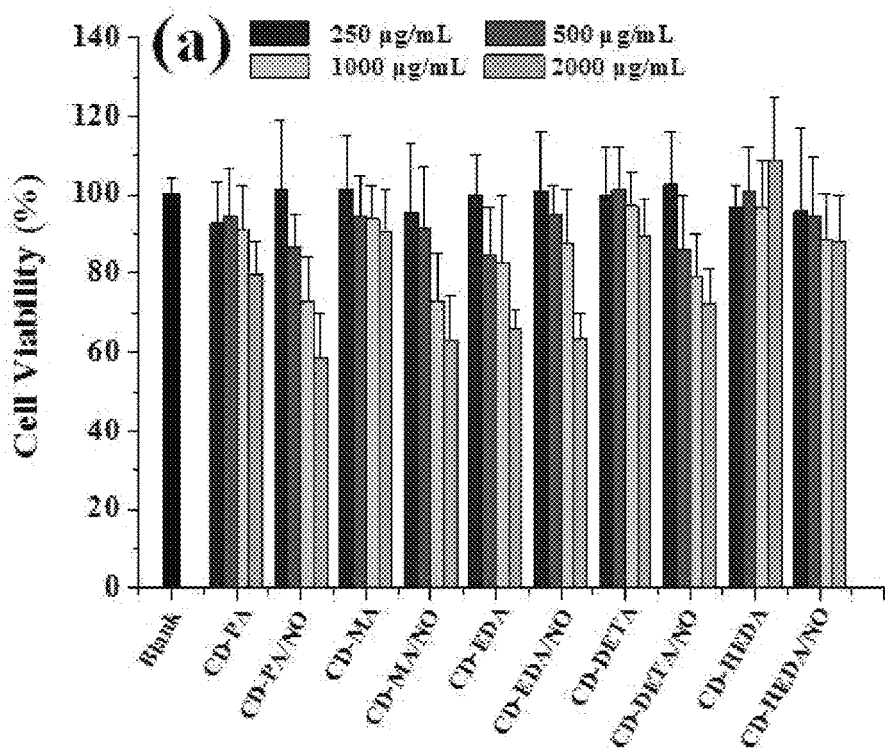
FIGS. 21(a)-(e) depict in vitro cytotoxicity. Cell viability (%) of L929 mouse fibroblasts exposure to blank, control and NO-releasing CD derivatives at various concentrations over 4 hours. Each value represents the mean standard deviation of at least three determinations.
Figure 21B:
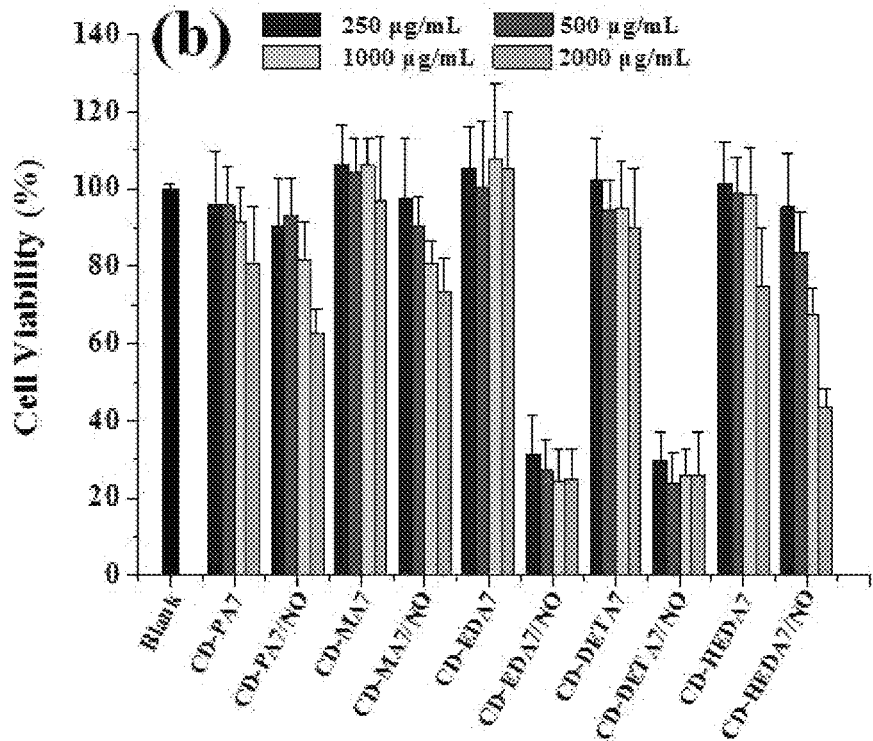

Despite effective bactericidal capability, the applicability of new antibacterial agents is also determined by their toxicity to mammalian cells. With respect to therapeutic potential, toxicity to mammalian cells is an important factor in the development of any new antibacterial agent. The cytotoxicity of CD-NONOates was evaluated by exposing mouse fibroblast cells to various concentrations (0~2000 µg/mL) of both control and NO-releasing CD derivatives over a 4 hour exposure. Both control and mono-substituted CD-NONOates exhibited a non-toxic nature (above 50% cell viability) against mouse fibroblast cells even up to 2000 µg/mL (FIG. 21a), regardless of their terminated functional moiety. While hepta-substituted CD derivatives are non-toxic, the cytotoxicity of hepta-substituted CD-NONOates was found to be related to their terminal functional groups (FIG. 21b). Both CD-PA7/NO and CD-MA7/NO were tolerable to the mouse fibroblasts even at 2000 µg/mL (63% and 73% cell viability for CD-PA7/NO and CD-MA7/NO, respectively). Cell viabilities of CD-EDA7/NO or CD-DETA7/NO were lower at all tested concentrations. The behavior is in part related to the effective delivery of NO induced by the fast cellular uptake of positively charged macromolecular systems. This behavior was also ascribed to the large amounts of terminal primary amines groups. Cytotoxicity can be diminished by introducing numerous hydroxyl groups so hydroxyl-terminated CD-HEDA7/NO with similar high NO total exhibited non-toxicity at the concentrations below 1000 µg/mL. In summary, the non-toxic nature of NO-releasing CD derivatives and their antibacterial efficacy against *P. aeruginosa* suggests that these NO-releasing CD derivatives may be utilized as new antimicrobial agents for applications including wound healing and respiratory disease (e.g., cystic fibrosis).

Example 4

Additional testing was done to determine the antibacterial efficacy and toxicity of DETA, DETA/NO (DETA functionalized with NO), and DETA/NO mixed with CD (at ratios of 1:1 or 1:2) as compared to CD-DETA or CD-DETA/NO (CD-DETA functionalized with NO). The same conditions as disclosed above for antibacterial testing and cytotoxicity was used.

Figure 21C:
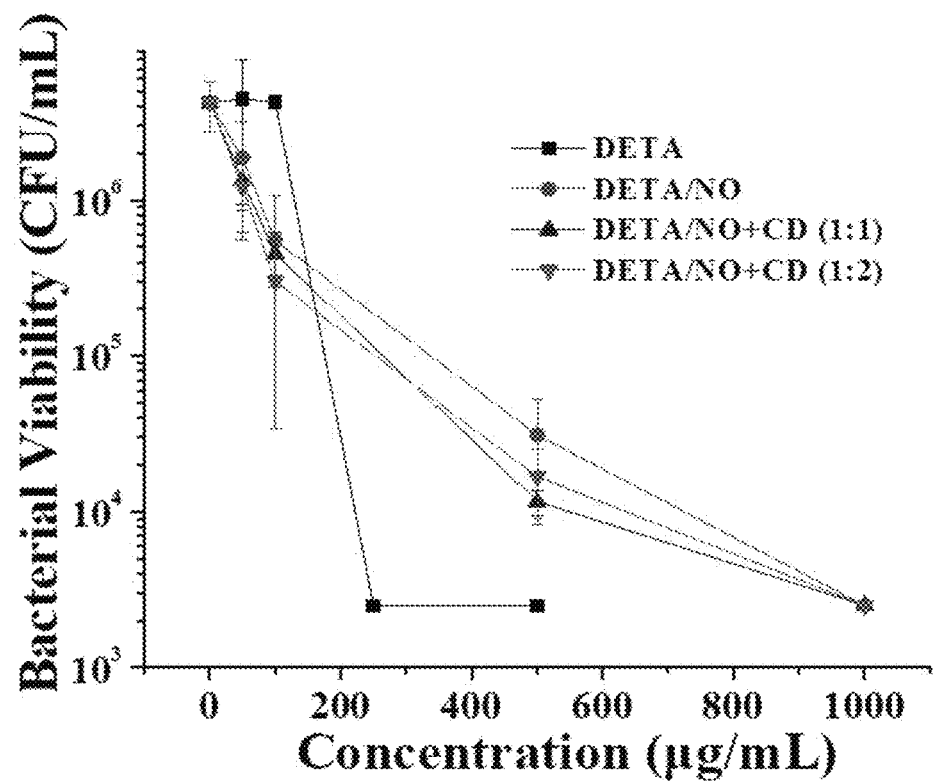
Figure 21D:
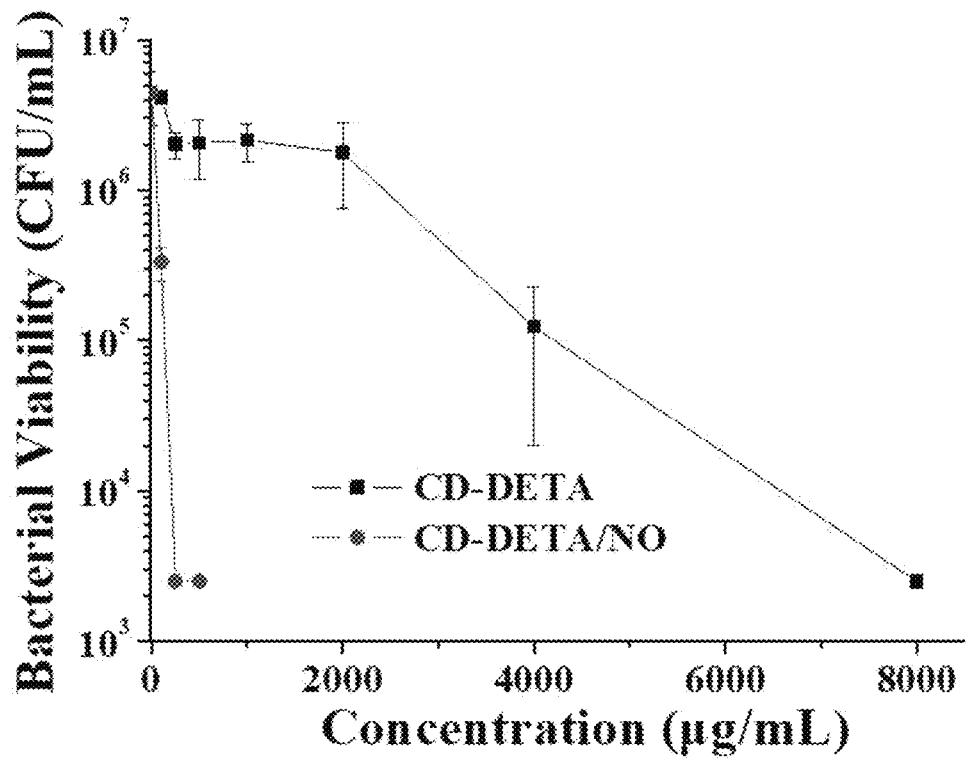

FIG. 21c shows bacterial viability data for DETA, DETA/NO, and DETA/NO mixed with CD (at ratios of 1:1 or 1:2). These data indicate that, as anticipated, DETA alone is highly antimicrobial, and that mixtures of DETA with NO, and various ratios of CD, while also effective antimicrobials, require greater concentrations to achieve the same effect. FIG. 21d shows data gathered using CD-DETA and CD-DETA/NO (CD-DETA functionalized with NO). These data show a substantial increase in the antimicrobial effects of the CD-DETA/NO functionalized molecule as compared to CD-DETA alone. The concentration of CD-DETA/NO required to achieve a reduction of bacterial cell viability to the 103-104 range was over 4-fold less than that of CD-DETA. Advantageously, in several embodiments, functionalized NO-releasing CDs can achieve desired degrees of antimicrobial activity at lower concentrations (thereby reducing risks of side effects) than non-NO releasing compounds. On a molar basis CD-DETA/NO was much more effective as an antimicrobial agent than even DETA. For instance, CD-DETA/NO has a molecular weight that is about 10 times that of DETA, yet their MBC4h values were similar at similar concentrations. The minimum bactericidal concentrations of the samples are shown in Table 3.

TABLE 3

| | CD-DETA | CD-DETA/NO | DETA | DETA/NO | DETA/NO + CD (1:1) | DETA/NO + CD (1:2) |
|---|---|---|---|---|---|---|
| *P. Aeruginosa* $MBC_{4h}$ (µg/mL) | 8000 | 250 | 250 | 1000 | 1000 | 1000 |

Figure 21E:
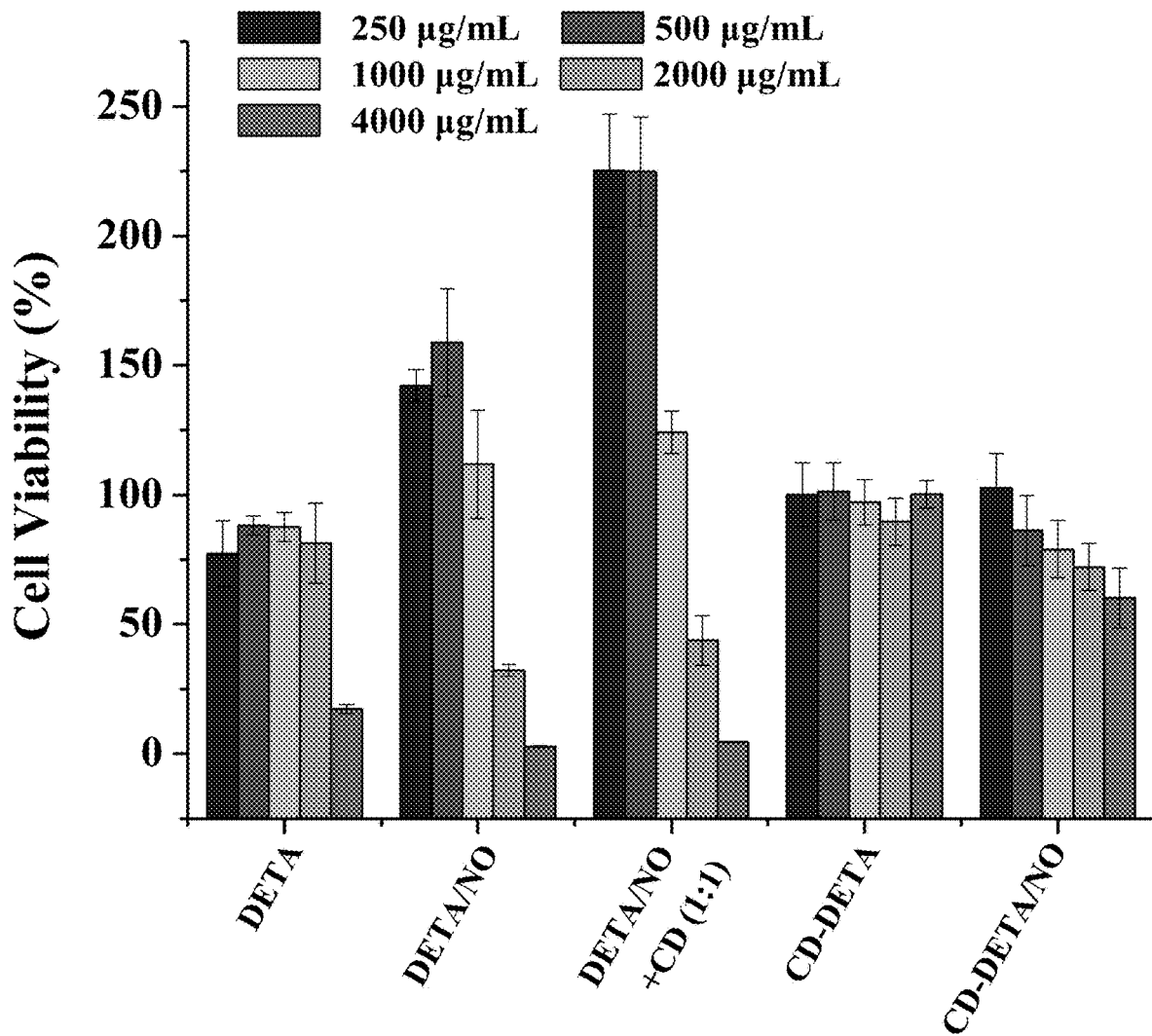

FIG. 21e shows the cytotoxicity against mammalian cells. From the data, it seemed that the DETA/NO was somewhat favorable for cell proliferation. This was attributed to the presence of NO, which is proliferative at low concentrations and cytotoxic at high concentrations. For bacteria, the addition of NO is more bactericidal at low concentrations and less so at high concentrations. Coupling the DETA to CD makes the combo less cytotoxic and less bactericidal than DETA. Adding the NO to the CD-DETA results in a highly bactericidal compound with similar cytotoxicity to the unloaded CD-DETA. This data also shows that the cytotoxicity of polyamines can be reduced by coupling to CD.

Surprisingly, it was also found that adding CD, even just to solution, seems to augment the proliferative effect of loading NO. The addition of "loose" CD appears protective to mammalian cells and damaging to bacteria. Of note, not all compositions were soluble enough to gather data. For example, the mixture of DETA/NO with CD could only be carried out at a molar ratio of 1:1 because unmodified CD had low water solubility. DETA/NO is more favorable for the cells proliferation. Low concentration of DETA/NO in accompany with CD is also favorable for cell proliferation. CD-DETA and CD-DETA/NO are non-toxic, up to (at least) 4 mg/mL. DETA is toxic when the concentration is increased to 4 mg/mL.

Biocompatible N-diazeniumdiolate modified cyclodextrin derivatives with controllable NO storage and tunable NO kinetics were reported in this study. The utility of NO-releasing CD derivatives as new antibacterial agents was demonstrated via the systematic study of total NO storage and exterior terminal functions. In general, NO-releasing CD derivatives with high NO storage exhibit increased bactericidal ability at the same terminal groups. Primary amine-terminated NO-releasing CD derivatives also display enhanced antibacterial activity at similar NO totals. Most of these new NO-releasing CD derivatives are nontoxic against mammalian cells at the bactericidal doses.

A series of secondary amine-modified cyclodextrin (CD) derivatives were synthesized with diverse exterior terminal groups (i.e., hydroxyl, methyl, methoxyl, and primary amine). Subsequent reaction with nitric oxide (NO) gas under alkaline conditions yielded N-diazeniumdiolate-modified CD derivatives. Adjustable NO payloads (e.g., about 0.6-2.4 µmol/mg) and release half-lives (e.g., about 0.7-4.2 h) were achieved by regulating both the amount of secondary amine precursors and the functional groups around the NO donor. The bactericidal action of these NO-releasing cyclodextrin derivatives was evaluated against *Pseudomonas aeruginosa*, a Gram-negative pathogen with antibacterial activity proving dependent on both the NO payload and exterior modification. Materials containing a high density of NO donors or primary amines exhibited the greatest ability to eradicate *P. aeruginosa*. Of the materials prepared, only the primary amine-terminated hepta-substituted CD derivatives exhibited toxicity against mammalian L929 mouse fibroblast cells.

Example 5

Figure 22A:
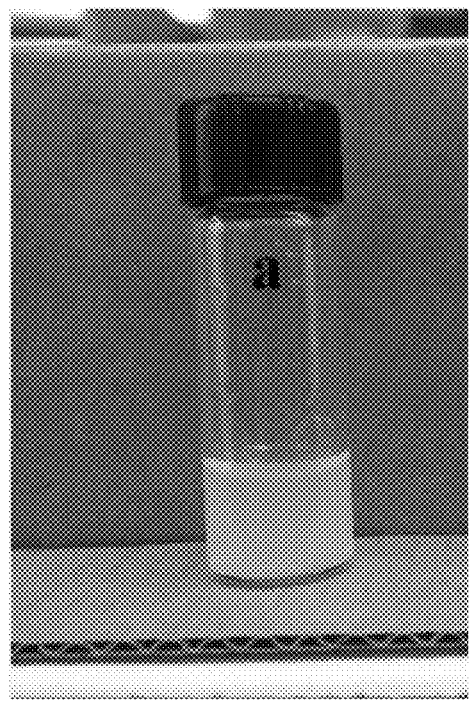
FIGS. 22(a)-(b). Dissolution ability of promethazine/cyclodextrins inclusion complex.
Figure 22B:
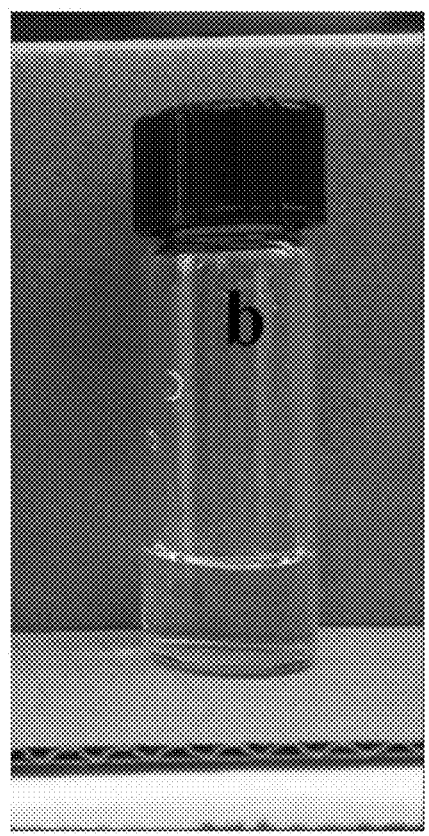
Figure 23A:
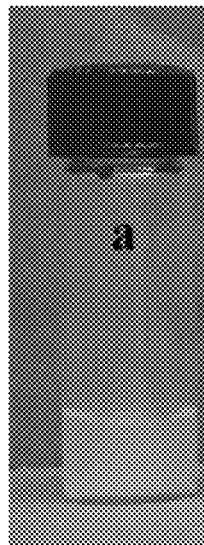
FIGS. 23(a)-(f). Dissolution ability of promethazine/CD-DETA inclusive complex under different molar ratios. The concentration of promethazine in PBS buffer is constant as 2 mg/mL. Molar ratio of promethazine versus CD-DETA.
Figure 23B:
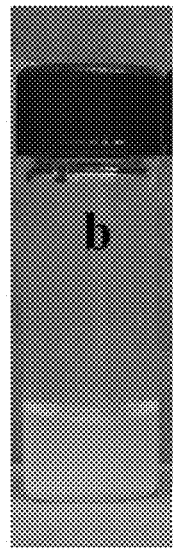
Figure 23C:
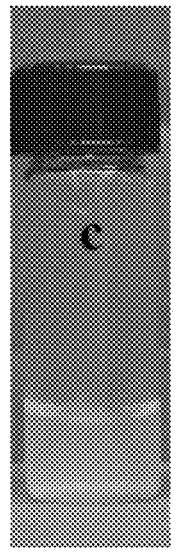
Figure 23D:
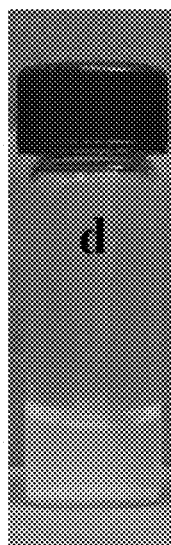
Figure 23E:
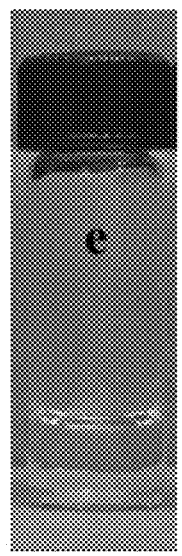
Figure 23F:
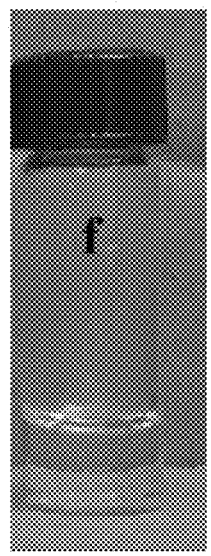
Figure 24A:
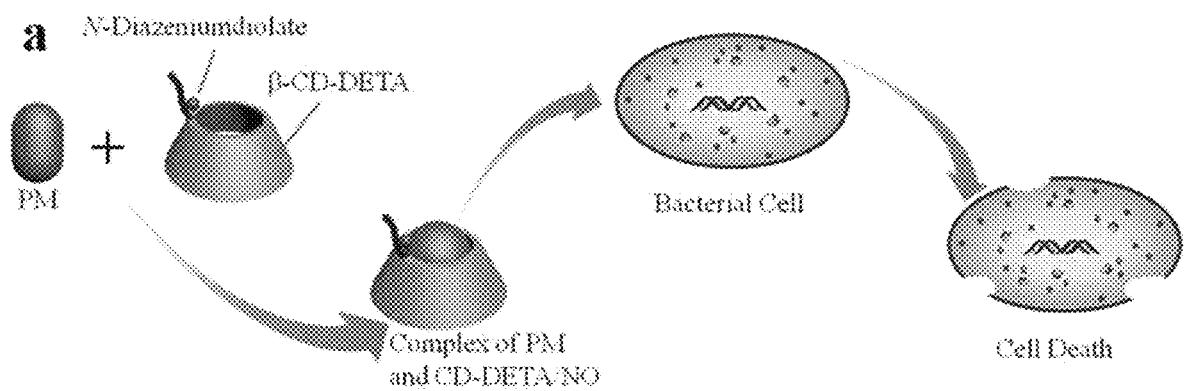
FIGS. 24(a)-(c) depicts schematics and data using CD as a host molecule or as an antimicrobial alone.
Figure 24B:
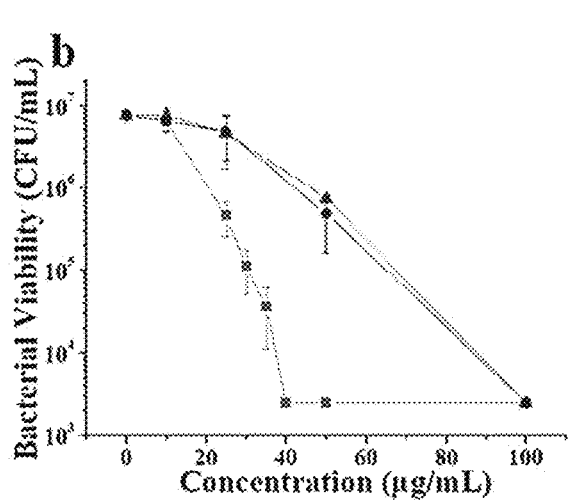
Figure 24C:
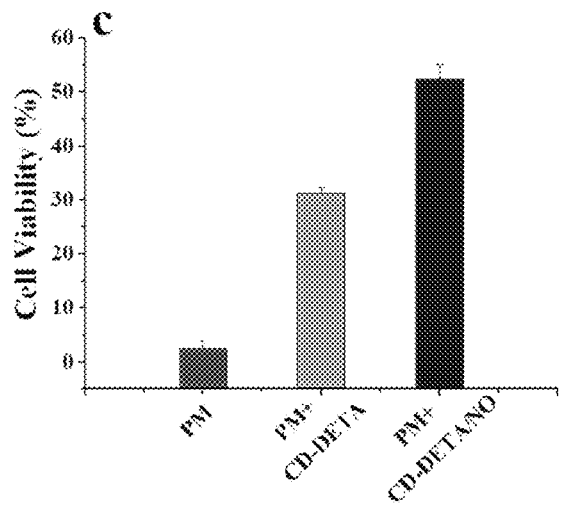
Figure 24D:
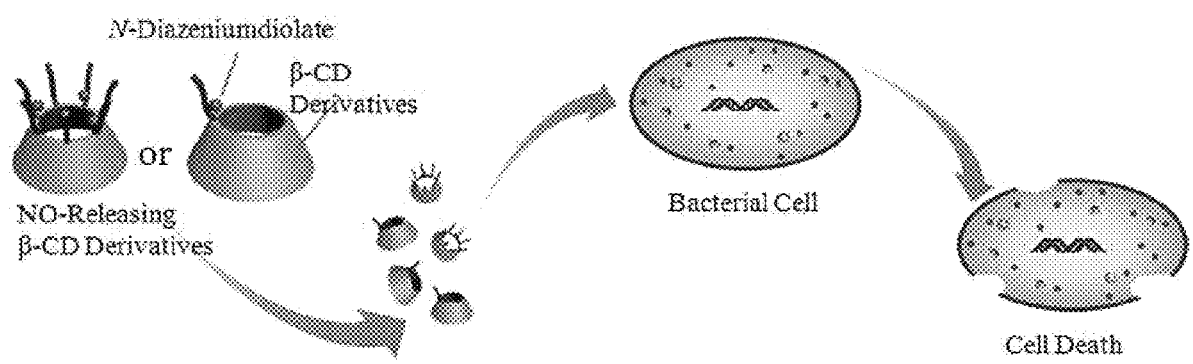
FIG. 24(*d*) is an illustration of NO delivery for antibacterial activity.

Apart from exterior modifications to facilitate NO delivery, the interior cavity of cyclodextrin derivatives may be employed as a carrier of hydrophobic drugs. According to several embodiments, delivery of NO with a drug is effective in decreasing the required therapeutic concentration of the drug alone. With this in mind, the ability of CD-NONOates to deliver both NO and a hydrophobic drug was investigated. As a proof-of-concept, promethazine (PM) was selected as a model hydrophobic drug. PM is a neuroleptic mediation used as an antiemetic and remedy for motion sickness. It has also been used off-label as an antibacterial agent. CD may be used as an effective carrier for PM, with both enhanced water-solubility and tolerability (FIG. 22). The antibacterial actions of PM, the complex of PM and CD-DETA, and the complex of PM and CD-DETA/NO was investigated against *P. aeruginosa*. As shown in Table 4 and FIG. 24*b*, the MBC4h for PM was 100 g/mL, even when encapsulated within CD-DETA. The use of CD-DETA/NO to co-deliver NO and PM resulted in significant synergistic activity against *P. aeruginosa*, decreasing the MBC4h of PM from 100 to 40 µg/mL. As CD-DETA forms an inclusive complex with PM at a molar ratio of 1:1 (FIG. 23), the corresponding concentration of CD-DETA/NO was 162 g/mL. Bacterial degradation of CD-DETA likely promotes the release of encapsulated PM initiating antibacterial action, in a similar manner to CD-capping silver nanoparticles. Of note, the MBC4h values of CD-DETA and CD-DETA/NO were 8 mg/mL and 250 µg/mL, respectively. Comparing these data, the combined delivery of NO and PM decreases the required MBC of each drug, with potential benefits for drug tolerability and avoiding/reducing potential adverse side-effects clinically. The cytotoxicity of PM, the complex of PM and CD-DETA, and the complex of PM and CD-DETA/NO was evaluated by exposing L929 mouse fibroblast cells to the respective MBC4h (bacteria eradication) concentrations. As shown in FIG. 24*c*, the PM at 100 µg/mL was toxic to the vast majority of the mouse fibroblast cells. In contrast, the cell viability was 31% when using CD-DETA to deliver the PM, as a result of both the lower concentration of PM and its isolation to within the CD derivative. The co-delivery of NO and PM (via CD-DETA/NO) resulted in the least cell toxicity (viability of 52%), unequivocally demonstrating the enhanced effects of co-delivery with NO.

TABLE 4

MBC4 h for NO-releasing CD-DETA and PM against planktonic *P. aeruginosa*.[a]

|  | PM MBC$_{4\,h}$ (µg/mL) | Corresponding carrier concentration (µg/mL) |
|---|---|---|
| PM | 100 | — |
| PM/CD-DETA complex | 100 | 380 |
| PM/CD-DETA/NO complex | 40 | 162 |

[a]Results of n ≥ 3 pooled experiments.

Herein, the synthesis of N-diazeniumdiolate-modified cyclodextrin derivatives with tunable NO pay-loads and NO-release kinetics based on the NO donor pre-cursor structure and modification extent is reported. CD derivatives modified fully with N-diazeniumdiolate precursors resulted in significant NO payloads and bactericidal action against *P. aeruginosa*, regardless of terminal group modification. The antibacterial activity of primary amine-terminated CD derivatives proved greater than any other terminal group functionalization of equivalent NO payload, and was attributed in part to their positive charge and ensuing ability to facilitate greater bacterial association with the negatively charged bacteria. Many CD-NONOates are nontoxic against L929 mouse fibroblast cells at their bactericidal doses. The combined action of NO and promethazine via PM/CD-DETA/NO demonstrates the potential of co-delivering NO with another drug from the same complex. The NO donor-modified CD was capable of delivering promethazine, a hydrophobic drug, thus demonstrating potential as a dual-drug releasing therapeutic.

Example 6

Additional studies were carried out to investigate NO-release properties from β-cyclodextrin under conditions consistent with healthy tissue (pH 7.4) and those of tumor microenvironments (pH 5.4). These studies also evaluated the role of NO-release properties on anticancer action using A549 lung cancer cells with two modifications to vary release kinetics (mono- and hepta-substitution to vary NO totals). This study also evaluated the efficacy of a combined therapeutic (a nitric oxide releasing CD with DOX) as compared to each therapeutic agent individually. This study demonstrates that an effective, targeted, dual-action lung cancer therapeutic can be prepared via encapsulation of doxorubicin within NO-releasing β-cyclodextrin.

Figure 25:
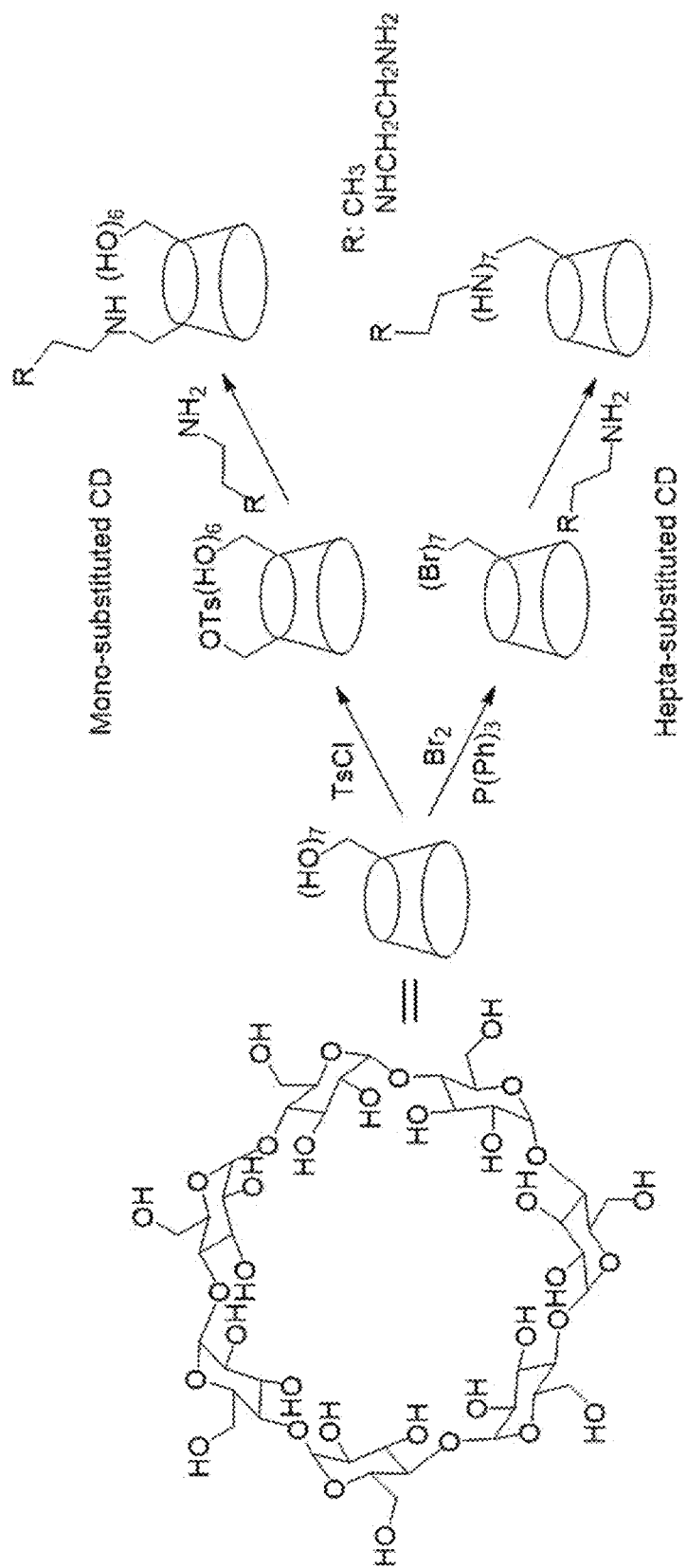
FIG. 25 shows non-limiting schemes showing the synthesis of functionalized CD derivatives. In several embodiments, the synthesis of secondary amine-modified CDs can be carried out using the exemplary reagents and conditions as shown in (e.g., TsOCl, a primary amine (R(CH$_2$)$_2$NH$_2$) or Bromine, P(Ph)$_3$, and a primary amine).
Figure 26A:
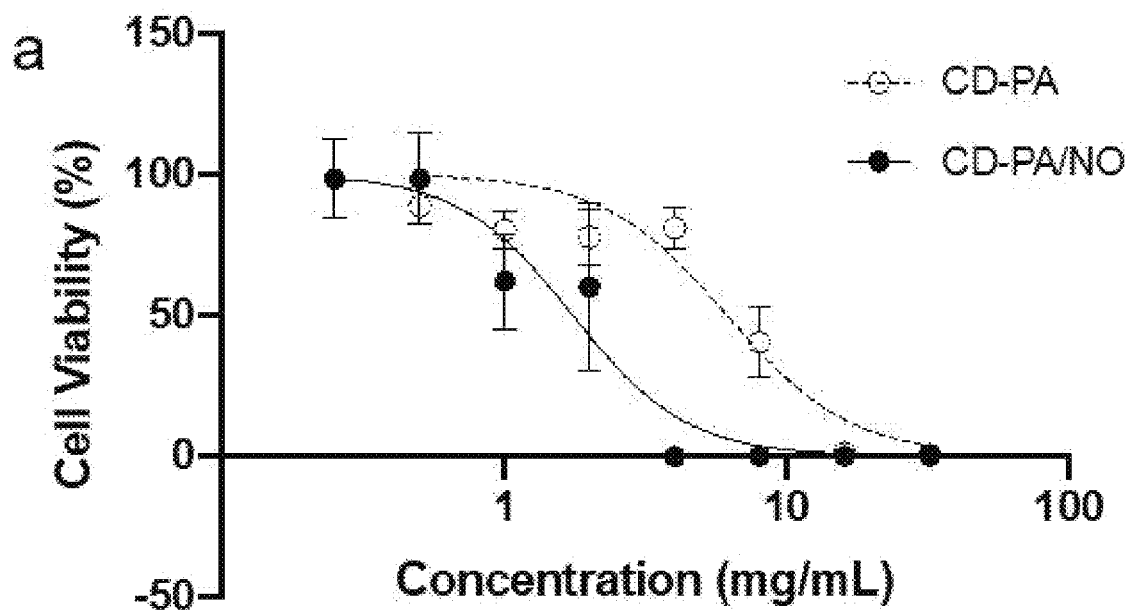
FIGS. 26(*a*)-(*d*) show the dose response for cell viability after CD treatment using various functionalized CDs where FIG. 26(*a*) is for CD-PA and CD-PA/NO, FIG. 26(*b*) is for CD-DETA and CD-DETA/NO, FIG. 26(*c*) is for CD-PA7 and CD-PA7/NO, and FIG. 26(*d*) is for CD-DETA7 and CD-DETA7/NO.
Figure 26B:
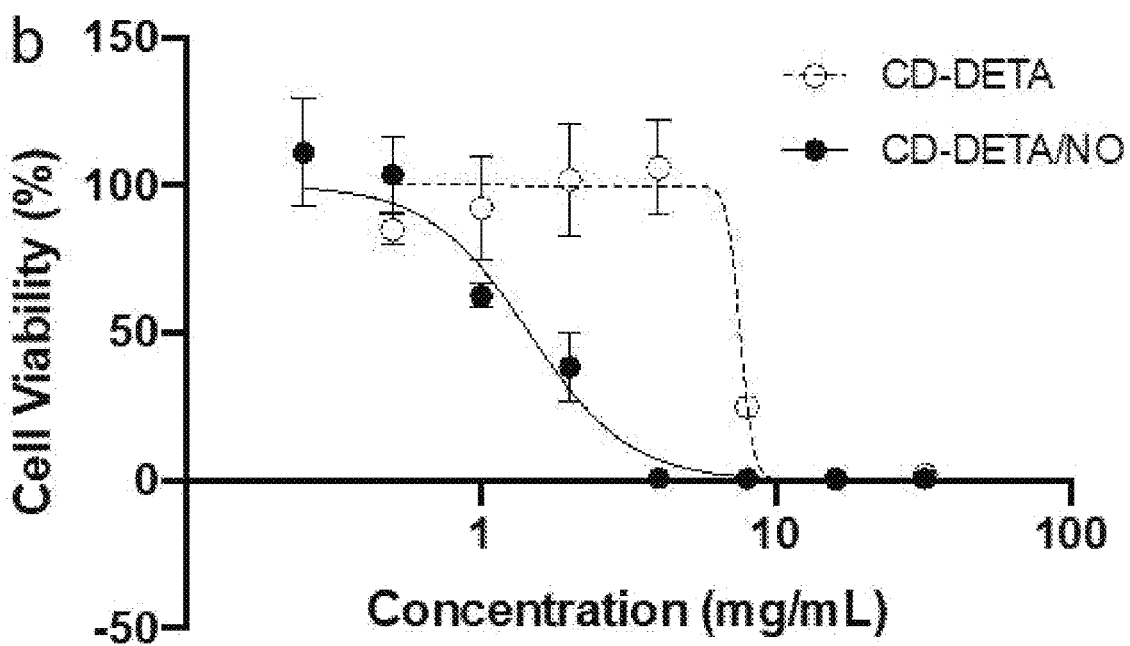
Figure 26C:
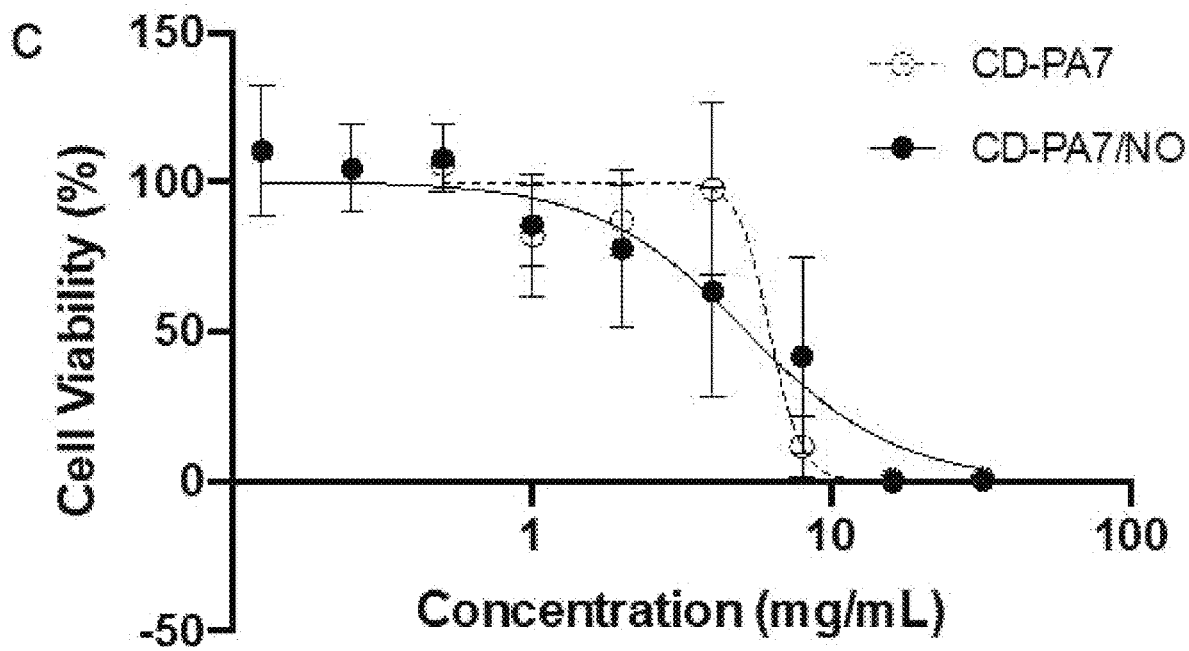
Figure 26D:
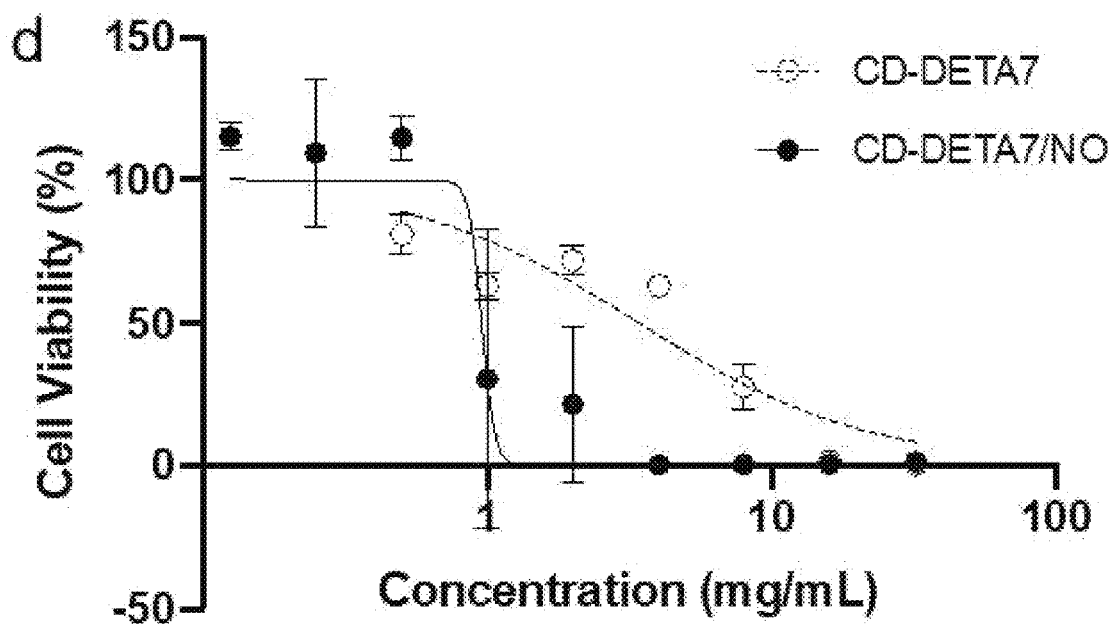

The synthesis of NO-releasing CDs is shown in FIG. 25. Several different functionalized CDs were prepared as shown in Table 5 and using techniques as described elsewhere herein.

TABLE 5

| pH | Modification | $[NO]_t$ (µmol mg$^{-1}$) | $[NO]_{max}$ (ppb mg$^{-1}$) | $t_{1/2}$ (min) | $t_d$ (h) |
|---|---|---|---|---|---|
| 5.4 | CD-PA | 0.56 ± 0.09 | 25100 ± 5700 | 2.3 ± 0.3 | 5.0 ± 0.8 |
|  | CD-PA7 | 1.30 ± 0.05 | 10500 ± 1300 | 25.6 ± 1.0 | 15.6 ± 0.3 |
|  | CD-DETA | 0.74 ± 0.04 | 32000 ± 2500 | 2.6 ± 0.3 | 14.6 ± 0.8 |
|  | CD-DETA7 | 2.37 ± 0.17 | 48500 ± 6200 | 5.7 ± 0.8 | 35.8 ± 2.7 |

TABLE 5-continued

| pH | Modification | [NO]$_t$ (μmol mg$^{-1}$) | [NO]$_{max}$ (ppb mg$^{-1}$) | t$_{1/2}$ (min) | t$_d$ (h) |
|---|---|---|---|---|---|
| 7.4 | CD-PA | 0.60 ± 0.07 | 2100 ± 300 | 128 ± 19 | 17.0 ± 1.0 |
| | CD-PA7 | 1.22 | 1600 | 219 | 39.9 |
| | CD-DETA | 0.68 ± 0.03 | 900 ± 100 | 205 ± 7 | 20.2 ± 0.6 |
| | CD-DETA7 | 2.66 | 2600 | 205 | 32.7 |

As shown in Table 5, NO-releasing cyclodextrins exhibit slow, sustained NO release under physiological conditions consistent with healthy tissue (pH 7.4). Release shifts to that of a burst release profile under conditions mimicking a tumor microenvironment (pH 5.4), suggesting targeted release of NO. All modifications (PA, DETA, and DETA7) except for PA7 have t$_{1/2}$ under 10 min.

Figure 27:
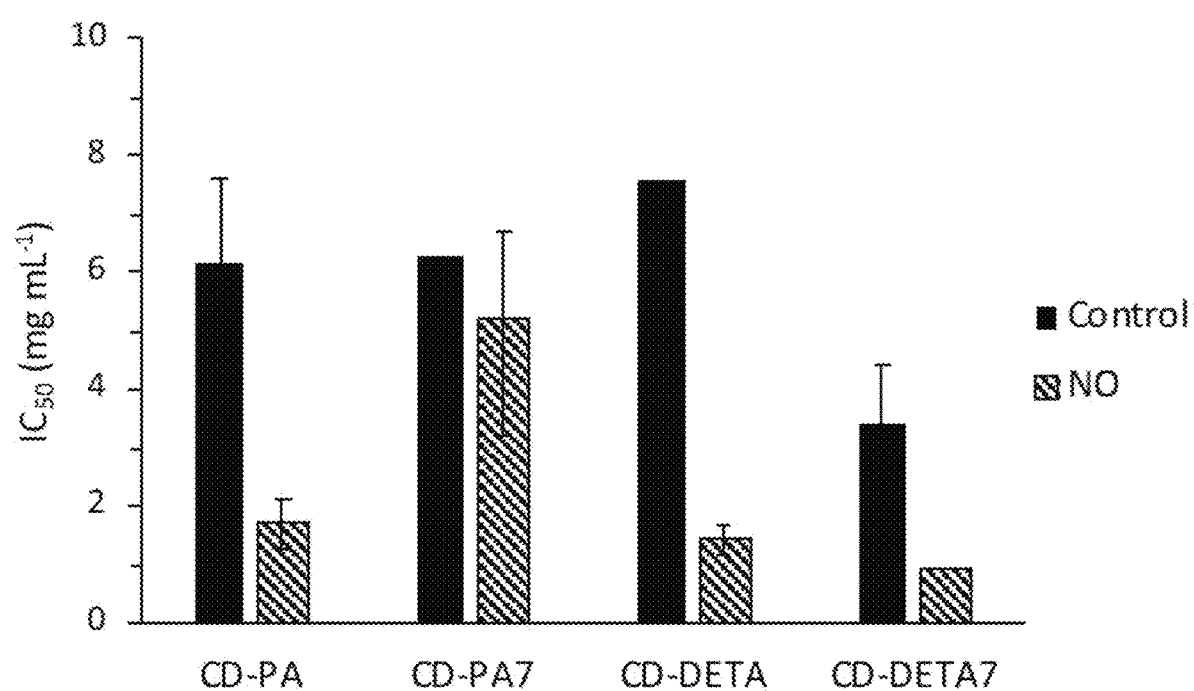
FIG. 27 depicts data showing the anticancer action of NO-releasing CD derivatives against A549 human lung carcinoma cells using a 24 h MTS assay.

Anticancer potential was evaluated against A549 human lung carcinoma cells using an MTS assay. FIG. 26 shows the dose response for CD treatment. All cell work performed in RPMI media and materials corrected for pH using 0.1 M HCl. FIG. 27 shows the anticancer action of NO-releasing CD against A549 human lung carcinoma cells using a 24 h MTS assay. Table 6 provides data for that study:

TABLE 6

NO dose from CD-PA, CD-PA7, CD-DETA, and CD-DETA7

| Modification | NO dose (μmol mL$^{-1}$) |
|---|---|
| CD-PA | 0.97 ± 0.16 |
| CD-PA7 | 6.77 ± 0.26 |
| CD-DETA | 1.07 ± 0.06 |
| CD-DETA7 | 2.21 ± 0.14 |

The error represents 95% confidence interval for IC50. It was found that the addition of NO decreases the IC50 for A549 cells for CD-PA, CD-DETA, and CD-DETA7. This data supports the necessity of a high initial NO flux for enhanced anticancer action. The CD-DETA7 control scaffold showed some cytotoxicity it was shown that it reduced L929 viability to ~20% at about 0.25 mg/mL. CD-DETA7 also required higher NO doses. CD-DETA showed large differences in IC50 for NO vs. control, was not cytotoxic (>60% viability) to L929 up to 2 mg/mL. CD-DETA also showed large differences in release kinetics between pH 5.4 and 7.4, and had higher starting NO totals than CD-PA. For these reasons, CD-DETA was chosen as a model for DOX encapsulation.

Figure 28:
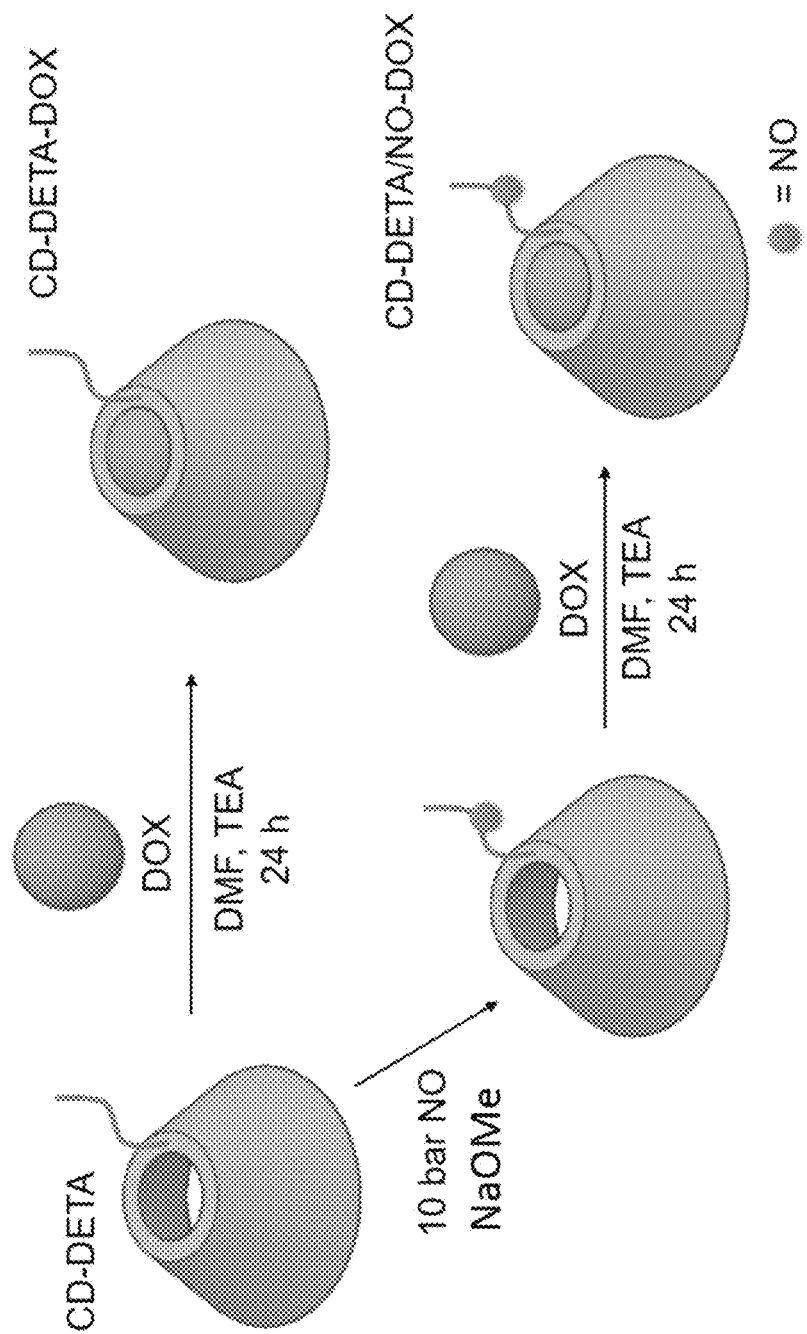
FIG. 28 shows a non-limiting example of a model of CD complexing doxorubicin.

FIG. 28 shows a model of CD complexing doxorubicin. As shown, DOX can be bound by a functionalized CD by exposing the functionalized CD to the guest molecule (e.g., DOX) in the presence of appropriate solvents (dimethylformamide (DMF) and trimethylamine (TEA)). Alternatively, as shown, the functionalized CD can be bound with NO prior to complexation with the guest molecule.

Figure 29A:
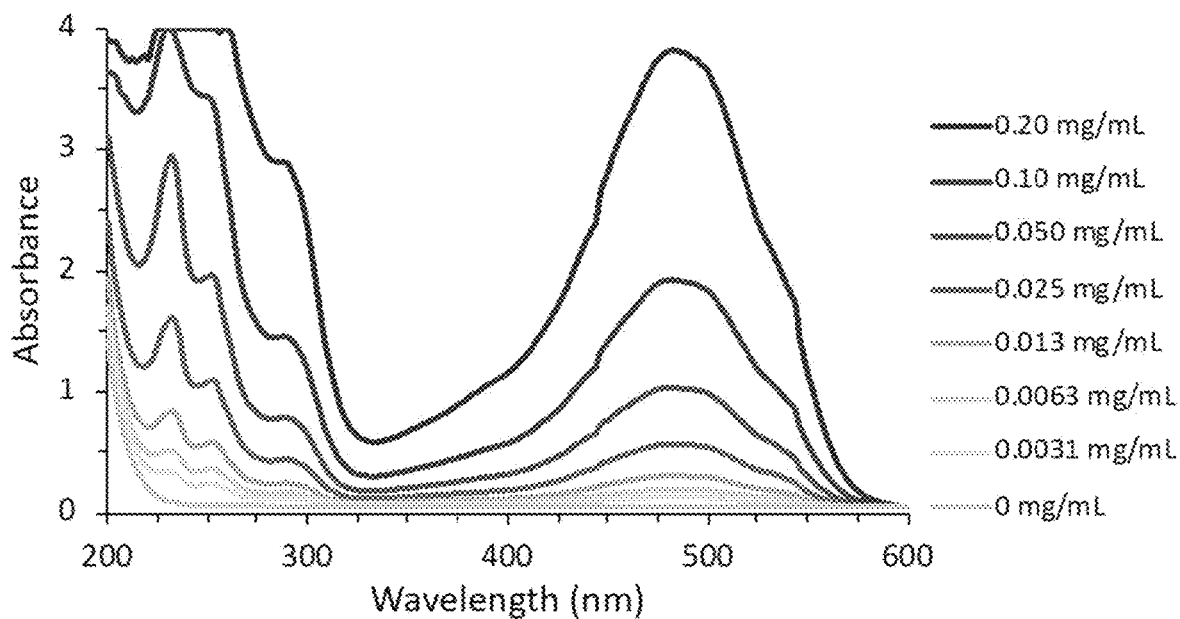
FIGS. 29(*a*)-(*b*) show UV/Vis data for DOX (dissolved in acetate buffer (pH 5.4, 10 mM)) where FIG. 29(*a*) is DOX at various concentrations and FIG. 29(*b*) shows a concentration calibration curve for DOX.
Figure 29B:
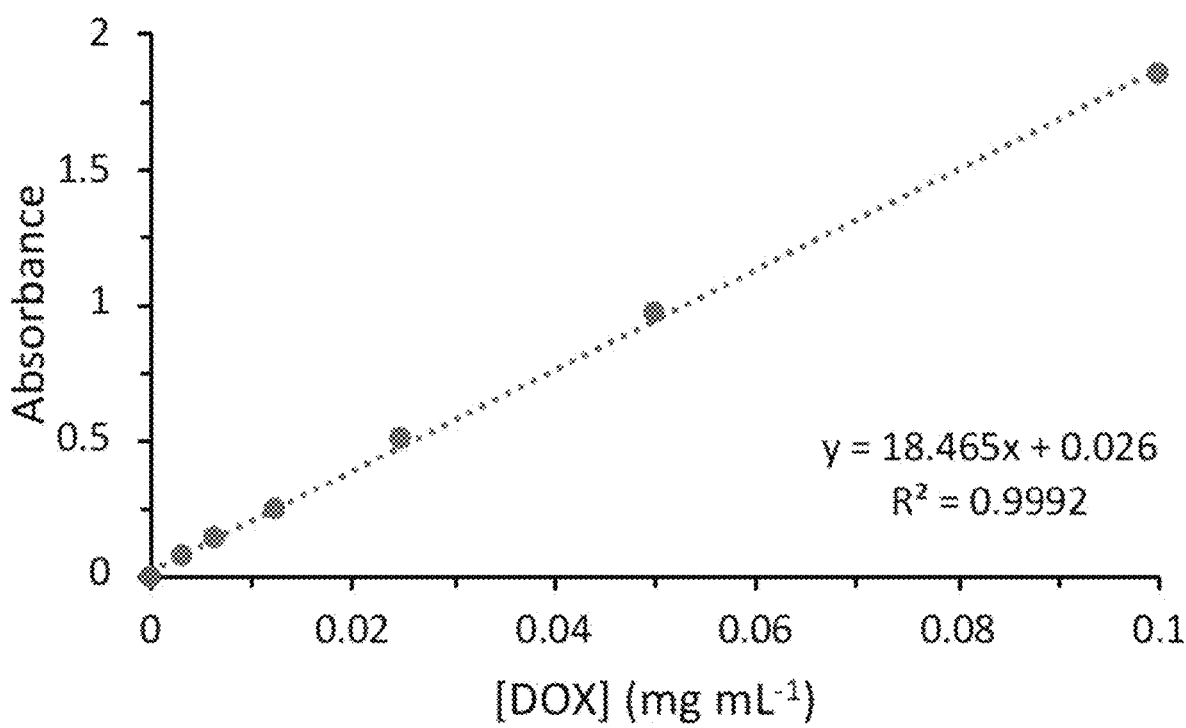
Figure 30A:
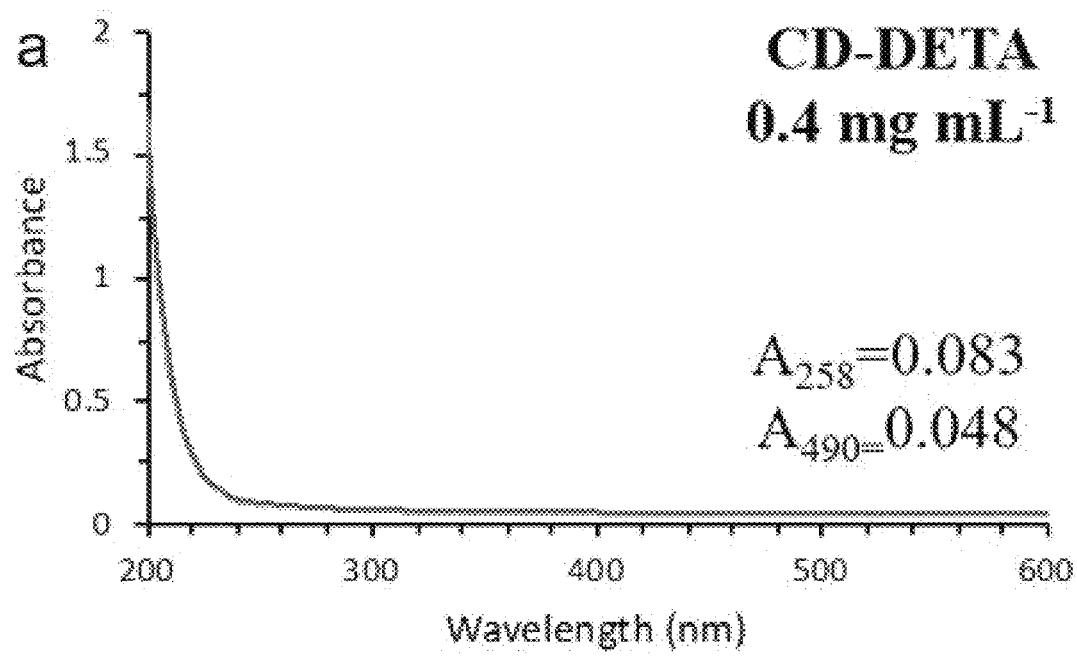
FIGS. 30(*a*)-(*d*) show characterization various functionalized-CD compounds using UV/Vis, where (a) is CD-DETA, (b) is CD-DETA-DOX, (c) is CD-DETA/NO, and (d) is CD-DETA/NO-DOX.
Figure 30B:
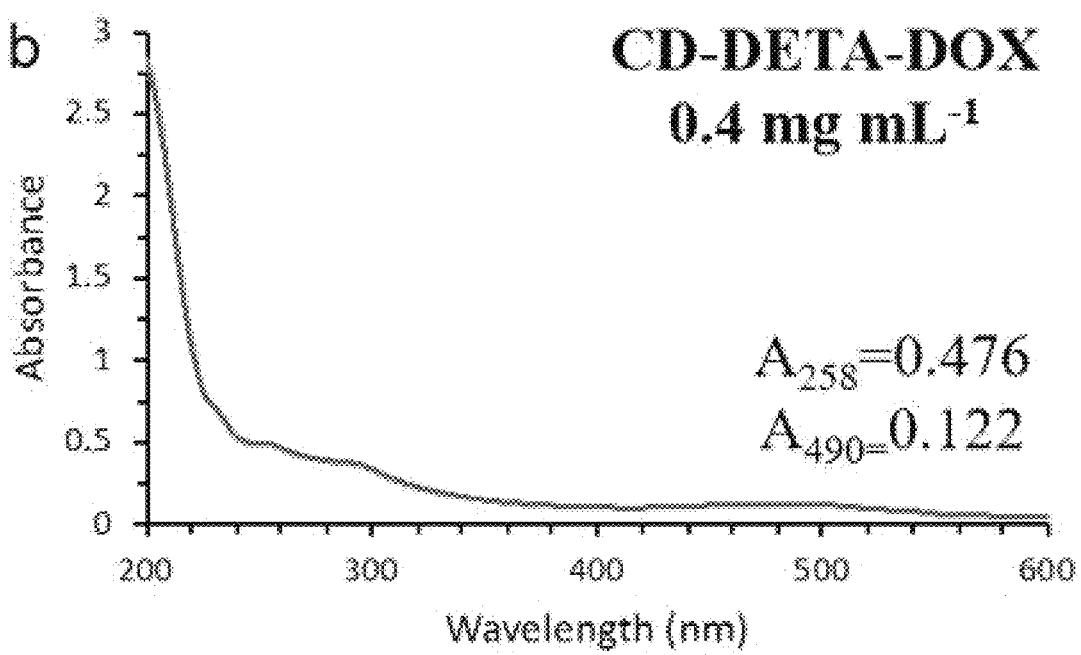
Figure 30C:
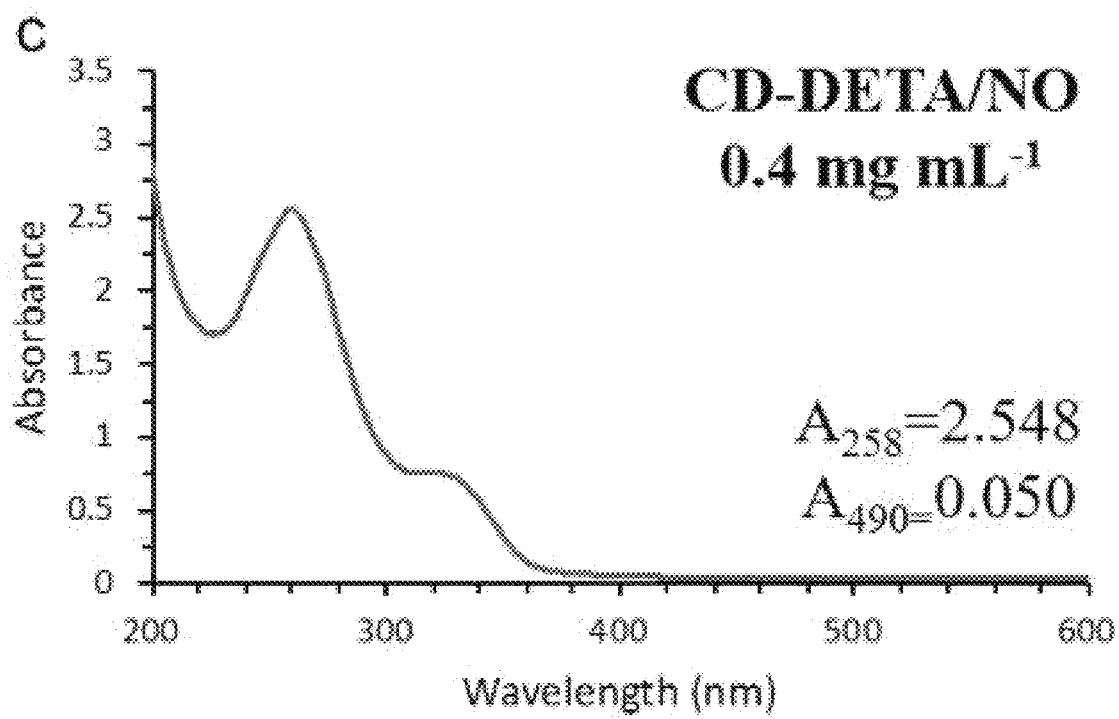
Figure 30D:
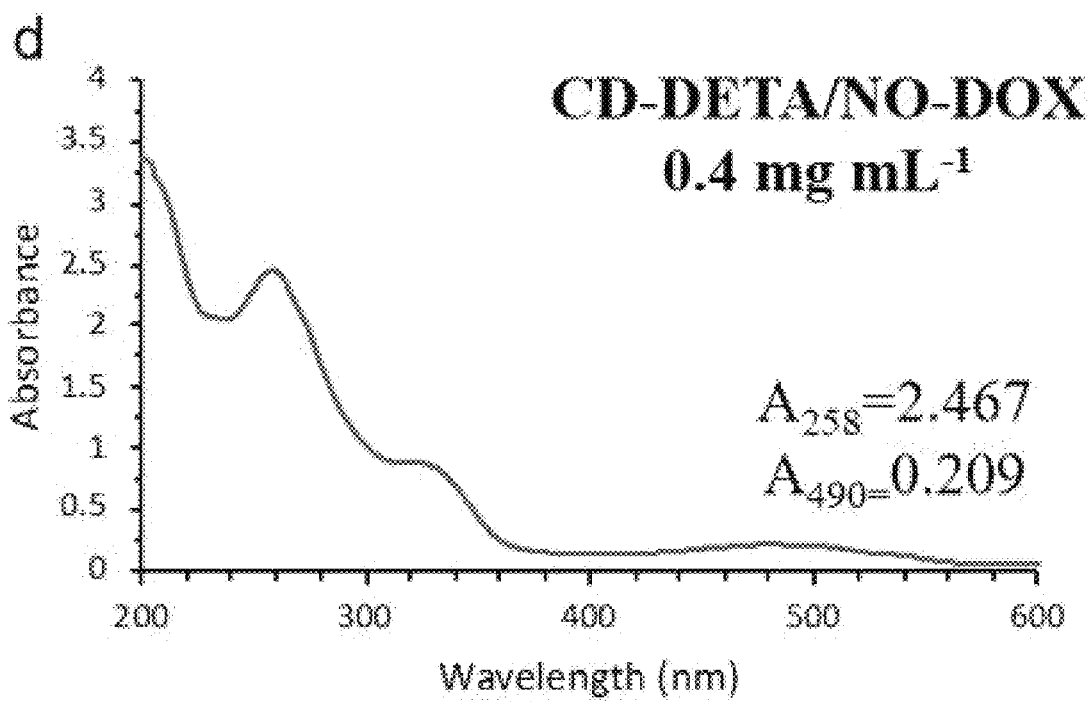

FIGS. 29a and 29b show DOX (dissolved in acetate buffer (pH 5.4, 10 mM)) at various concentrations and an absorbance curve measured at λmax=490 nm, respectively. UV-Vis data show that this technique is suitable for analysis of DOX release, as the LOD is lower than expected values will be. LDR likely extends lower, currently limited by lowest calibration point tested. The limit of detection range (LDR) was 0.0031-0.10 mg mL$^{-1}$. The limit of detection (LOD) and limit of quantification (LOQ) for DOX are shown below:

$$LOD = \frac{3s}{m} = 9.4 \times 10^{-6} \text{ mgmL}^{-1}$$

$$LOQ = \frac{10s}{m} = 3.1 \times 10^{-5} \text{ mgmL}^{-1}$$

Figure 31A:
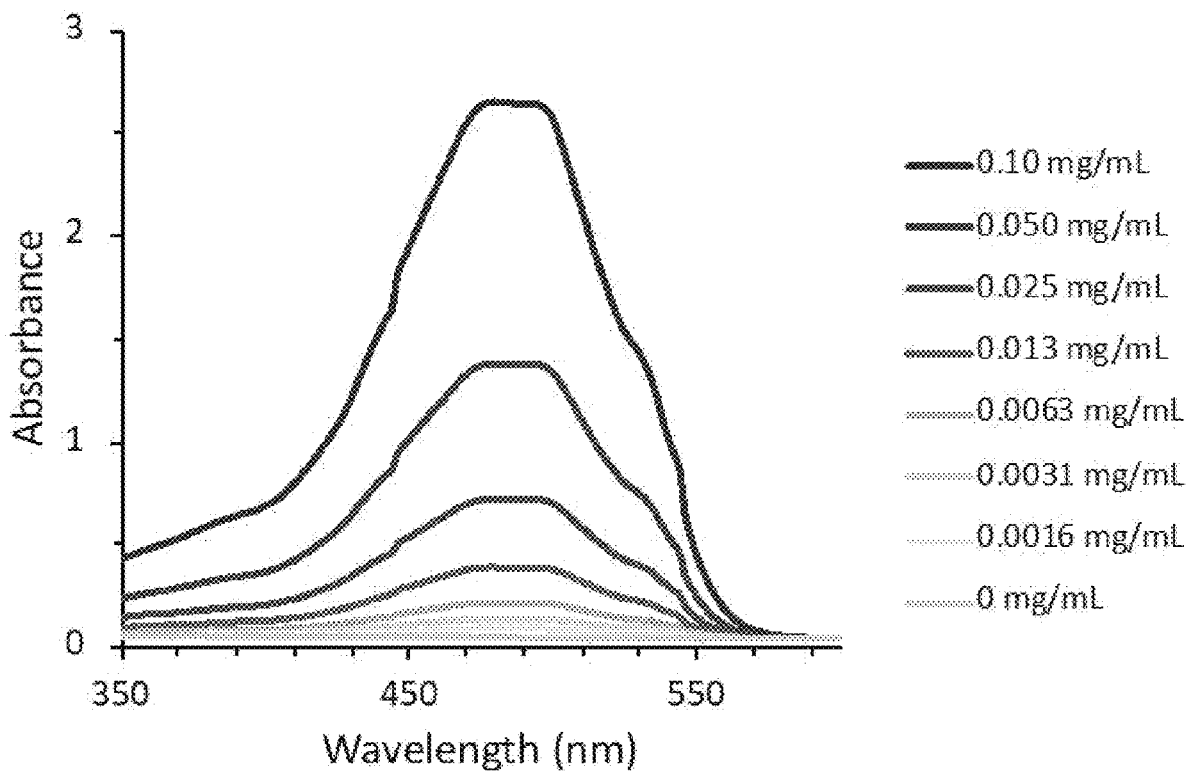
FIGS. 31(*a*)-(*b*) show UV/Vis data for DOX (in 3:7 acetonitrile:water (pH 3.0)) where FIG. 31(*a*) is DOX at various concentrations and FIG. 31(*b*) shows a concentration calibration curve for DOX.
Figure 31B:
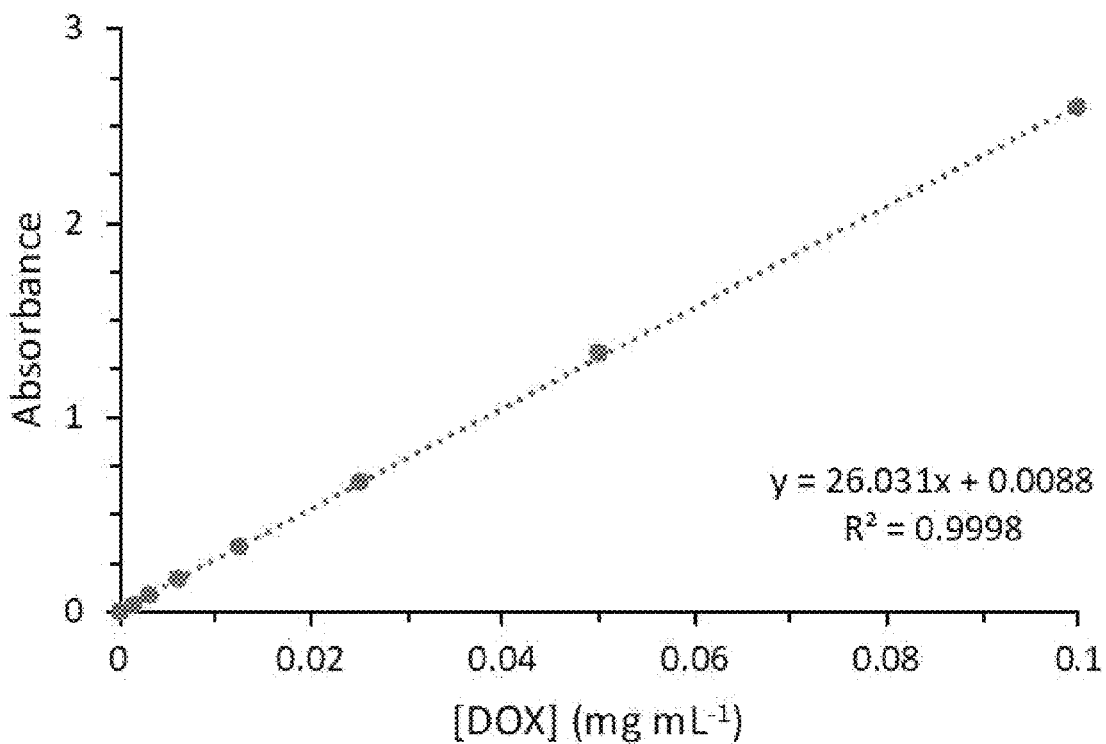

FIGS. 30a-d show characterization of encapsulated DOX. Samples were dissolved in acetate buffer (pH 5.4, 10 mM) and analyzed immediately. CD-DETA does not exhibit any characteristic peaks. CD-DETA-DOX exhibits peak at 490 nm. CD-DETA/NO exhibits strong peak at 258 nm, but also at 326 nm. CD-DETA/NO-DOX exhibits peaks at both 258 nm and 490 nm (also at 326 nm). FIGS. 31a-b shows the protocol for determining encapsulation efficiency determination for DOX. CD-DETA-DOX and CD-DETA/NO-DOX were dissolved at 1 mg mL$^{-1}$ in 3:7 acetonitrile:water, with pH adjusted to 3.0 using 0.1M phosphoric acid. Samples were incubated at 37° C. for 24 h. Standards prepared in 3:7 acetonitrile:water (pH 3.0). Absorbance measured at λmax=490 nm. LDR was 0.0016-0.10 mg mL$^{-1}$. LOD and LOQ were as follows:

$$LOD = \frac{3s}{m} = 3.1 \times 10^{-5} \text{ mgmL}^{-1}$$

$$LOQ = \frac{10s}{m} = 1.0 \times 10^{-4} \text{ mgmL}^{-1}$$

This protocol gave similar linear responses as in pH 5.4 acetate buffer and allowed for calculation of encapsulation efficiency. DOX was released quickly at low pH, allowing for totals to be calculated. Drug loading content (DLC) and drug loading efficiency DLE was calculated as follows:

$$DLC \text{ (wt \%)} = \frac{\text{(weight of loaded drug)}}{\text{(weight of drug loaded CD)}} \times 100$$

$$DLE \text{ (wt \%)} = \frac{\text{(weight of loaded drug)}}{\text{(weight of feeding drug)}} \times 100$$

The loading content and efficiency is shown below in Table 7:

TABLE 7

| | DLC (wt %) | DLE (wt %) |
|---|---|---|
| CD-DETA-DOX | 0.71 | 7.9 |
| CD-DETA/NO-DOX | 1.62 | 17.8 |

Figure 32A:
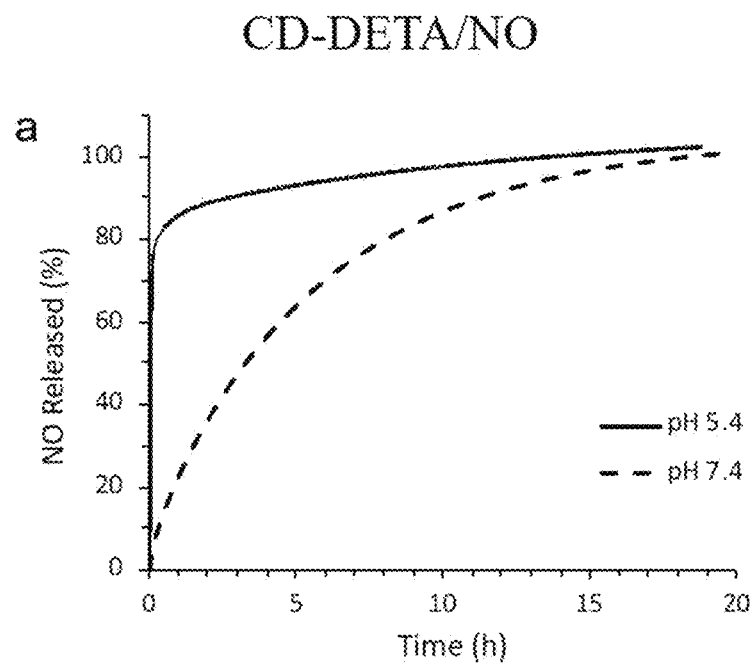
FIGS. 32(*a*)-(*b*) show NO release profiles of CD-DETA/NO (FIG. 32(*a*)) and CD-DETA/NO-DOX (FIG. 32(*b*)).
Figure 32B:
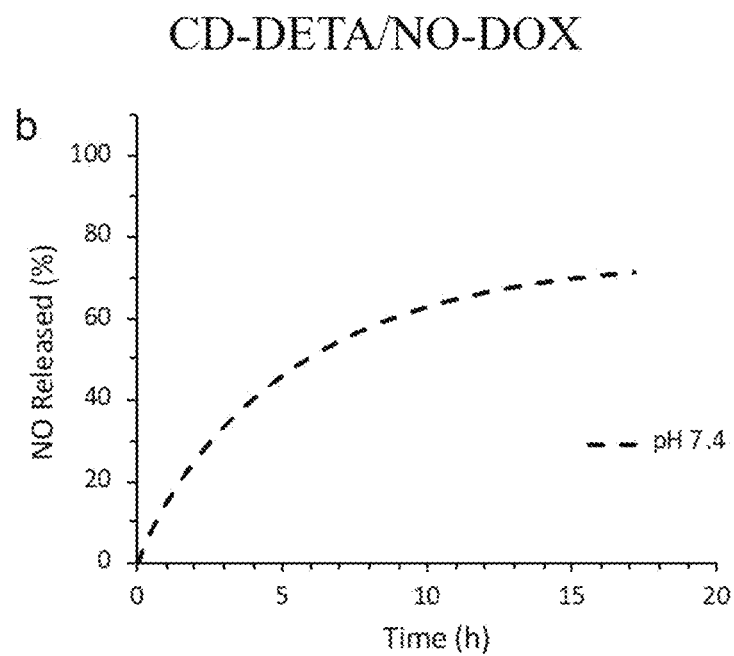

FIG. 32 shows NO release profiles of DOX from CD-DETA. Some NO is lost during the DOX encapsulation protocol (~30%), but release kinetics at pH 7.4 are maintained (as shown). The [NO]t for CD-DETA/NO-DOX is ~0.5 μmol mg$^{-1}$.

Example 7: In Vitro Testing of CD-DETA/NO-DOX

This is a prophetic example. Additional studies are carried out to determine whether the release profile of DOX from CD-DETA-DOX and from CD-DETA/NO-DOX is different. First DOX is encapsulated in CD-DETA and CD-DETA/NO inside dialysis tubing. Aliquots are taken from external solution at 2 h intervals for 24 h and analyzed via UV-Vis. Analysis is performed at both pH 5.4 and 7.4 (n=3) for CD-DETA-DOX and CD-DETA/NO-DOX. It is found that at the pH of healthy tissue (7.4) 95% of the DOX is retained in the CD-DETA and CD-DETA/NO over a period of 2 hours. Over that same period, 70% of the NO is retained in the CD-DETA/NO-DOX. It is found that at the pH of tumor tissue (5.4) 80% of the DOX is released from the CD-DETA and CD-DETA/NO over a period of 2 hours and 90% of the NO. The profile of release of DOX from CD-DETA and CD-DETA/NO is substantially the same.

The anticancer capabilities of the CD-DETA-DOX and from CD-DETA/NO-DOX are then tested using A549 cells. It is found that the IC50 CD-DETA-DOX is four times as high as that for CD-DETA/NO-DOX, demonstrating a synergistic effect of the CD-DETA/NO-DOX for the treatment of cancer.

Example 8: In Vivo Testing of CD-DETA/NO-DOX

This is a prophetic example. Additional studies are carried out to determine whether the differences in efficacy of DOX and CD-DETA/NO-DOX against lung cancer tumors in vivo. 30 patients ranging in age from 40 to 50 years old and suffering from non-small cell lung cancer are divided into three groups of 10. The control group receives liposomal DOX via inhalation using a nebulizer, the first experimental group receives CD-DETA/NO via inhalation using a nebulizer, and the second experimental group receives CD-DETA/NO-DOX via inhalation using a nebulizer. Over the course of 12 months, cancer progress is monitored in each of the patient groups. It is found that, in the control group, 20% of patients are in remission with only 40% showing a reduction in tumor size. In the first experimental group 10% of the patients are in remission and 30% show reduced tumor size. In the second experimental group, 80% of the patients are in remission and the remaining 20% show reduced tumor size. The results demonstrate synergistic activity of CD-DETA/NO and DOX versus DOX or CD-DETA/NO alone. Surprisingly, CD-DETA/NO has some antitumor activity by itself. Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic.

Some embodiments have been described in connection with the accompanying drawings. Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in other implementations.

Conditional language used herein, such as, among others, "can," "could," "might," "may," "e.g.," and the like, unless specifically stated otherwise or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Further, while illustrative embodiments have been described, any embodiments having equivalent elements, modifications, omissions, and/or combinations are also within the scope of this disclosure. Moreover, although certain aspects, advantages, and novel features are described herein, not necessarily all such advantages may be achieved in accordance with any particular embodiment. For example, some embodiments within the scope of this disclosure achieve one advantage, or a group of advantages, as taught herein without necessarily achieving other advantages taught or suggested herein. Further, some embodiments may achieve different advantages than those taught or suggested herein.

In summary, various embodiments and examples of antimicrobial compounds have been disclosed. This disclosure extends beyond the specifically disclosed embodiments and examples to other alternative embodiments and/or other uses of the embodiments, as well as to certain modifications and equivalents thereof. Moreover, this disclosure expressly contemplates that various features and aspects of the disclosed embodiments can be combined with, or substituted for, one another. Accordingly, the scope of this disclosure should not be limited by the particular disclosed embodiments described above, but should be determined by a fair reading of the claims.

What is claimed is:

1. A functionalized cyclodextrin represented by the following structure:

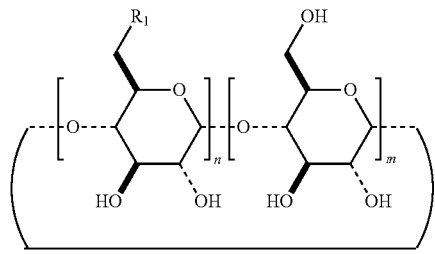

Formula III wherein
n is an integer selected from 1 to 8;
m is an integer from 0 to 7;
each instance of $R_1$ is represented by —$X^1$—$((CH_2)_{f'}X^2)_{g'}((CH_2)_q X^3)_r$—$(CH_2)_{h'}$H;
wherein
each of f', q, g', r, and h' is independently selected from an integer from 0 to 4;
each instance of $X^1$, $X^2$, or $X^3$ is independently selected from O, NH, or a nitric oxide donating substituent; and at least one instance of $X^1$, $X^2$, or $X^3$ in said functionalized cyclodextrin is

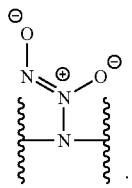

2. The functionalized cyclodextrin of claim 1, wherein at least one instance of $R_1$ is represented by one of the following:

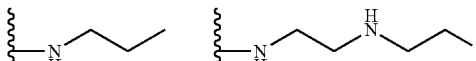

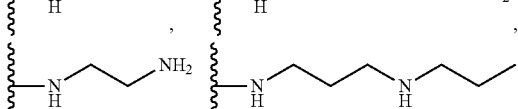

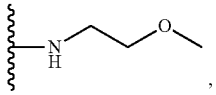

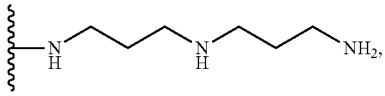

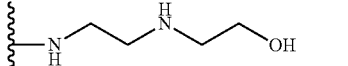

, and

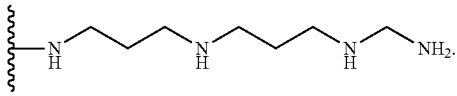

3. The functionalized cyclodextrin of claim 1, wherein at least one instance of $R_1$ is represented by one of the following:

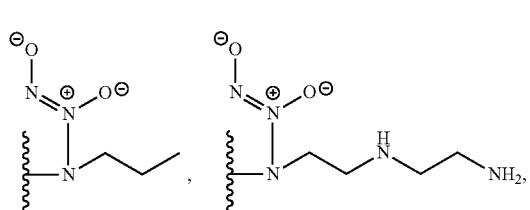

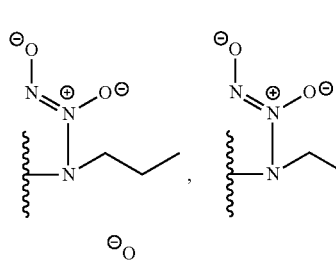

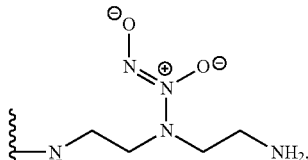

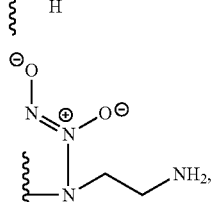

,

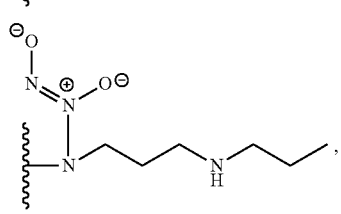

,

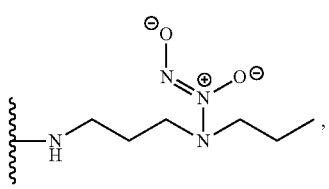

,

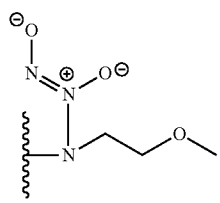

,

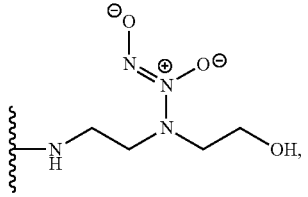

,

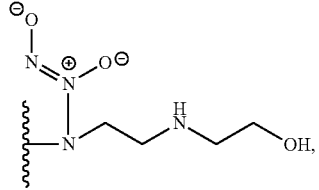

,

-continued

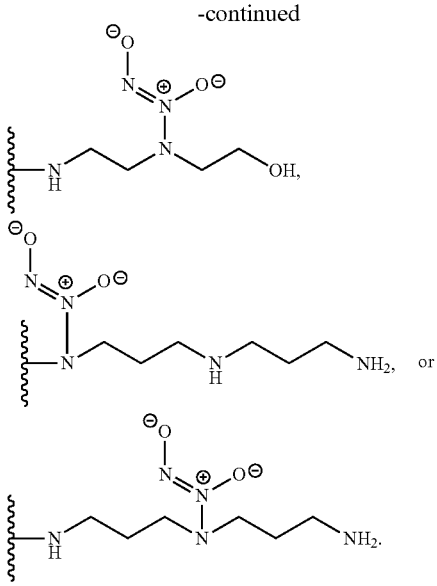

4. The functionalized cyclodextrin of claim 1, wherein n is an integer selected from 6, 7, and 8.

5. The functionalized cyclodextrin of claim 4, wherein m is 0.

6. The functionalized cyclodextrin of claim 3, wherein at least one instance of $R_1$ is represented by one of the following:

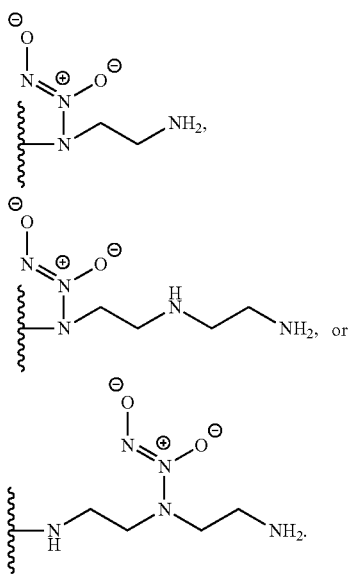

7. The functionalized cyclodextrin of claim 1, wherein n is 1 and m is 6.

8. The functionalized cyclodextrin of claim 1, wherein n is 7 and m is 0.

9. The functionalized cyclodextrin of claim 1, wherein said functionalized cyclodextrin has a total releasable nitric oxide storage of at least 0.5 µmol of NO per milligram of functionalized cyclodextrin as determined in aqueous buffer at pH 7.4 and 37° C.

10. The functionalized cyclodextrin of claim 1, wherein said functionalized cyclodextrin has a total releasable nitric oxide storage in a range of about 0.5 µmol to 2.5 µmol of NO per milligram of functionalized cyclodextrin as determined in aqueous buffer at pH 7.4 and 37° C.

11. The functionalized cyclodextrin of claim 1, wherein said functionalized cyclodextrin has a half-life for nitric oxide release in a range of between about 0.7-4.2 hours as determined in aqueous buffer at pH 7.4 and 37° C.

12. The functionalized cyclodextrin of claim 1, wherein said functionalized cyclodextrin has a half-life for nitric oxide release over about 1 hour as determined in aqueous buffer at pH 7.4 and 37° C.

13. The functionalized cyclodextrin of claim 1, wherein said functionalized cyclodextrin has a total NO release after 4 hours in a range of between about 0.3-2.0 µmol of NO per milligram of the functionalized cyclodextrin as determined in aqueous buffer at pH 7.4 and 37° C.

14. A composition comprising the functionalized cyclodextrin of claim 1 and a pharmaceutically acceptable carrier.

15. A functionalized cyclodextrin comprising: at least one ring unit of Formula I:

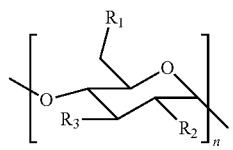

Formula I wherein n is an integer selected from 1 to 8;

$R_2$ and $R_3$ are independently selected from the group consisting of —OH, —O—$((CH_2)_tO)_{u'}$—H, —O—$((CH_2)_tO)_{u'}$—$(CH_2)_vH$, —O—$(C_{1-5}$ alkyl), —NH—$((CH_2)_cNH)_d$—H, —NH—$((CH_2)_cNH)_{d'}$—$(CH_2)_eH$, —$X^1$—$((CH_2)_fX^2)_g$—$(CH_2)_hH$, and —$X^1$—$((CH_2)_fX^2)_g$—$((CH_2)_qX^3)_r$—$(CH_2)_hH$;

$R_1$ is selected from the group consisting of —$X^1$—$((CH_2)_fX^2)_g$—$(CH_2)_h$ H and —$X^1$—$((CH_2)_fX^2)_{g'}$—$((CH_2)_hH$;

wherein each of c, c', d, d', e, f, f', g, g', h, h', q, r, t, t', u, u', and v is independently selected from an integer from 0 to 10;

$X^1$, $X^2$, and $X^3$ are independently selected from O, S, NH, or a nitric oxide donating substituent; wherein at least one of $X^1$, $X^2$, and $X^3$ is said nitric oxide donating substituent represented by the following structure:

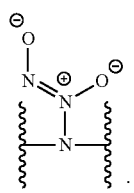

16. The functionalized cyclodextrin of claim 15, selected from the group consisting of:

117
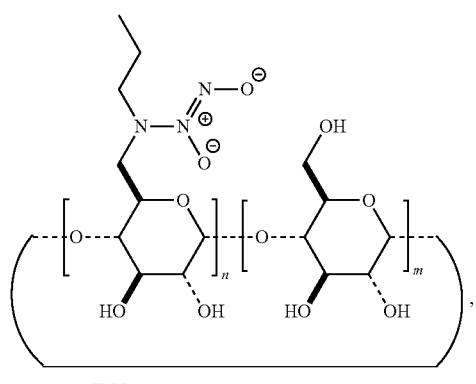
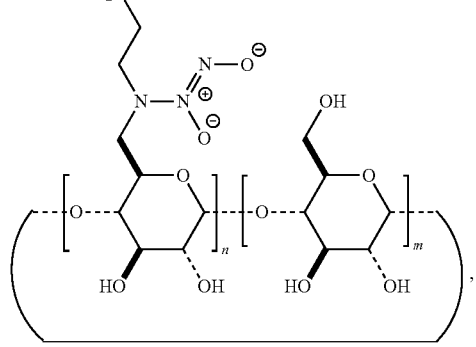
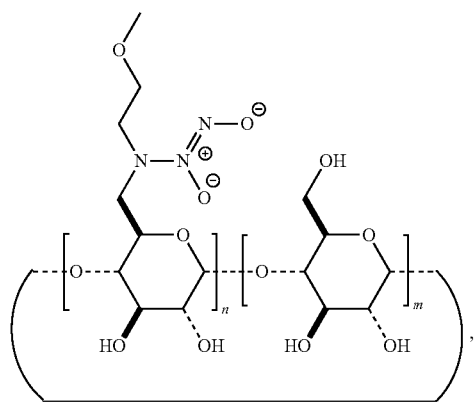
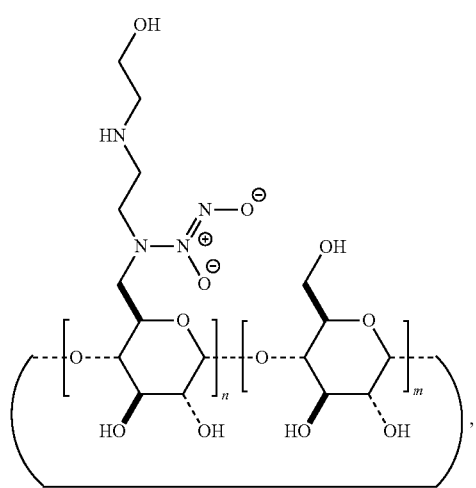
118
-continued
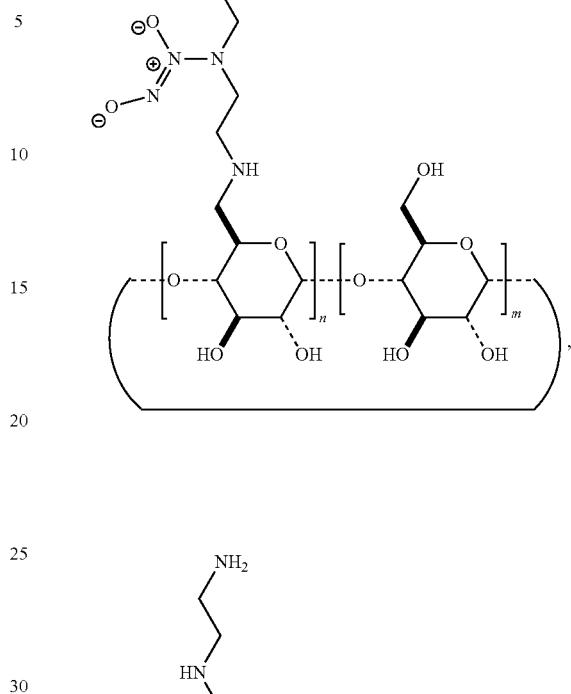
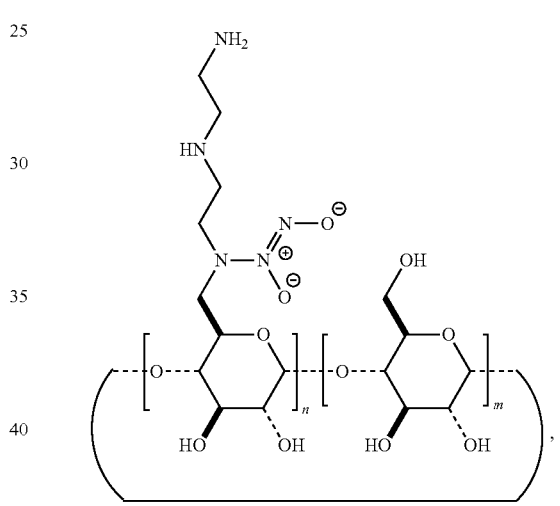
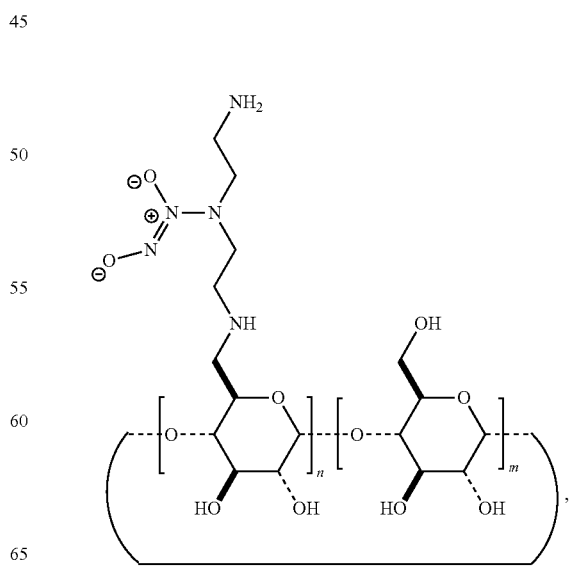

119
-continued
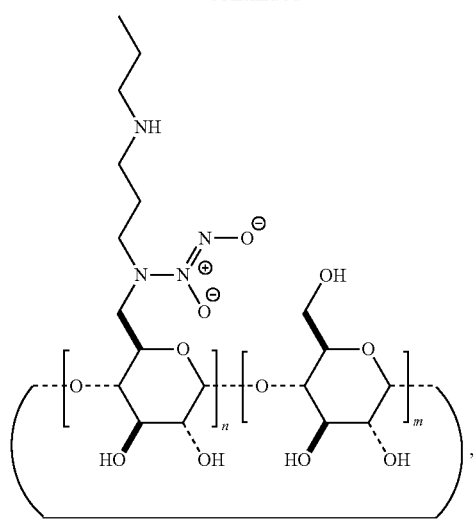
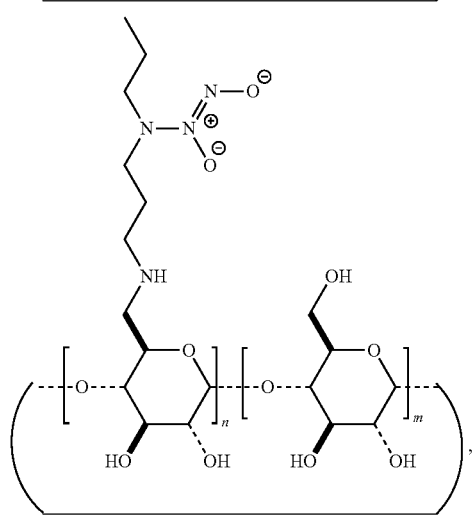
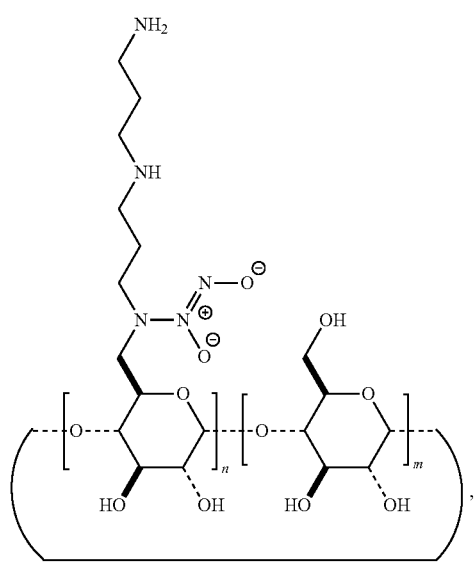
120
-continued
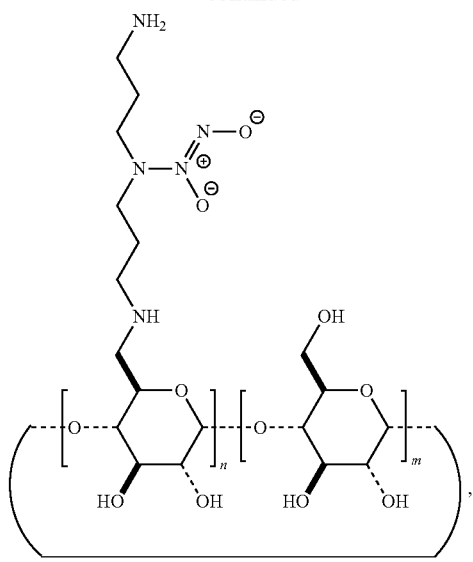
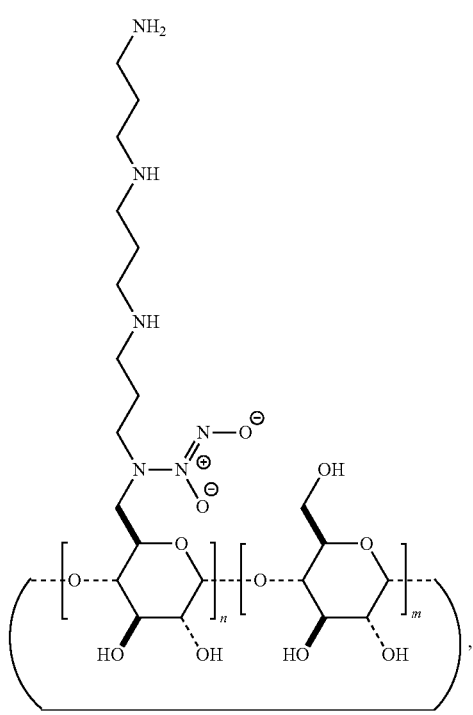

-continued

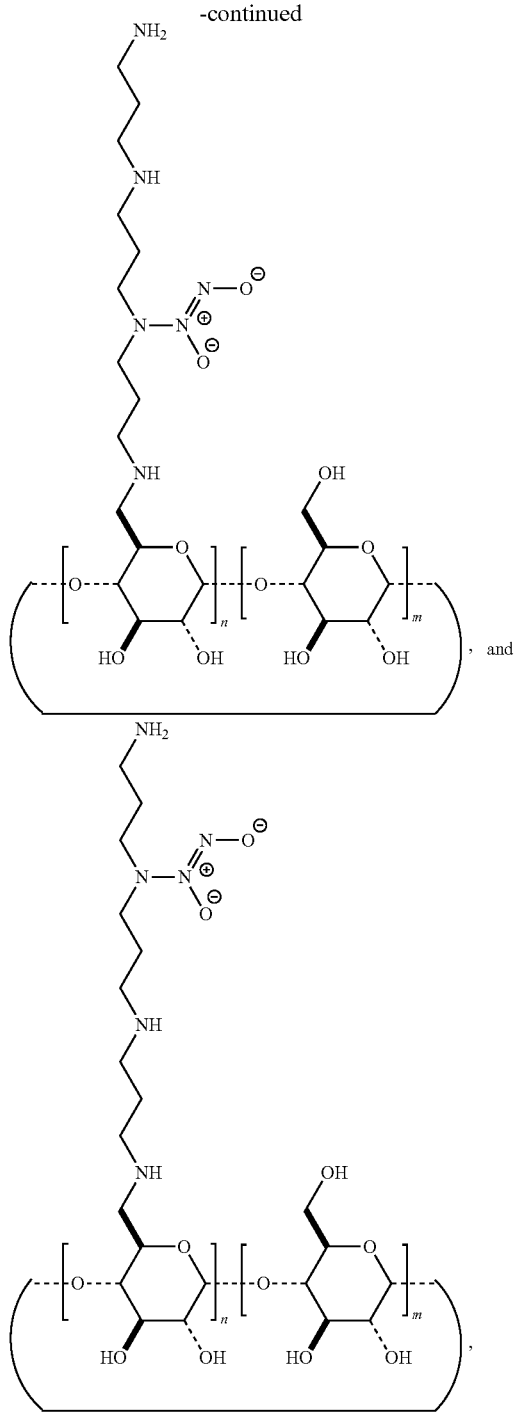

wherein, m is an integer from 0 to 7.

17. The functionalized cyclodextrin of claim 15, wherein $R_2$ and $R_3$ are —OH.

18. The functionalized cyclodextrin of claim 15, wherein said functionalized cyclodextrin has a total releasable nitric oxide storage of at least 0.5 μmol of NO per milligram of functionalized cyclodextrin as determined in aqueous buffer at pH 7.4 and 37° C.

19. The functionalized cyclodextrin of claim 18, wherein said functionalized cyclodextrin has a total releasable nitric oxide storage in a range of about 0.5 μmol to 2.5 μmol of NO per milligram of functionalized cyclodextrin as determined in aqueous buffer at pH 7.4 and 37° C.

20. The functionalized cyclodextrin of claim 19, wherein said functionalized cyclodextrin has a total releasable nitric oxide storage in a range of about 1.0 μmol to 2.5 μmol of NO per milligram of functionalized cyclodextrin as determined in aqueous buffer at pH 7.4 and 37° C.

21. The functionalized cyclodextrin of claim 15, wherein said functionalized cyclodextrin has a half-life for nitric oxide release in a range of between about 0.1-24 hours as determined in aqueous buffer at pH 7.4 and 37° C.

22. The functionalized cyclodextrin of claim 21, wherein said functionalized cyclodextrin has a half-life for nitric oxide release in a range of between about 0.7-4.2 hours as determined in aqueous buffer at pH 7.4 and 37° C.

23. The functionalized cyclodextrin of claim 8, wherein $X^1$ is

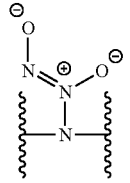

f' is 2, $X^2$ is 0, g' is 1, and q, r, and h' are each 0.

* * * * *